(12) United States Patent
Andrew et al.

(10) Patent No.: US 9,221,756 B2
(45) Date of Patent: Dec. 29, 2015

(54) PYRROLE DERIVATIVES

(71) Applicant: University of Leicester, Leicester (GB)

(72) Inventors: Peter William Andrew, Leicester (GB); Rana Lonnen, Leicester (GB); Fritz-Frieder Frickel, Deidesheim (DE); Simon Christopher Hirst, Nottingham (GB); Mark William Davies, Nottingham (GB); Daniel Hamza, Nottingham (GB)

(73) Assignee: University of Leicester, Leicester (GB)

( * ) Notice: Subject to any disclaimer, the term of this patent is extended or adjusted under 35 U.S.C. 154(b) by 0 days.

(21) Appl. No.: 14/360,365

(22) PCT Filed: Dec. 5, 2012

(86) PCT No.: PCT/GB2012/053022
§ 371 (c)(1),
(2) Date: May 23, 2014

(87) PCT Pub. No.: WO2013/083975
PCT Pub. Date: Jun. 13, 2013

(65) Prior Publication Data
US 2014/0309193 A1    Oct. 16, 2014

(30) Foreign Application Priority Data
Dec. 5, 2011 (EP) .................................. 11191986

(51) Int. Cl.
| | | |
|---|---|---|
| *C07D 207/00* | (2006.01) | |
| *C07D 207/36* | (2006.01) | |
| *C07D 401/04* | (2006.01) | |
| *C07D 401/12* | (2006.01) | |
| *C07D 403/04* | (2006.01) | |
| *C07D 407/04* | (2006.01) | |
| *C07D 413/04* | (2006.01) | |
| *C07D 417/04* | (2006.01) | |
| *C07C 229/18* | (2006.01) | |
| *C07C 237/06* | (2006.01) | |
| *C07C 229/42* | (2006.01) | |
| *C07C 237/20* | (2006.01) | |
| *C07D 207/38* | (2006.01) | |
| *C07D 401/14* | (2006.01) | |
| *C07F 9/572* | (2006.01) | |

(52) U.S. Cl.
CPC ............ *C07D 207/36* (2013.01); *C07C 229/18* (2013.01); *C07C 229/42* (2013.01); *C07C 237/06* (2013.01); *C07C 237/20* (2013.01); *C07D 207/38* (2013.01); *C07D 401/04* (2013.01); *C07D 401/12* (2013.01); *C07D 401/14* (2013.01); *C07D 403/04* (2013.01); *C07D 407/04* (2013.01); *C07D 413/04* (2013.01); *C07D 417/04* (2013.01); *C07F 9/5725* (2013.01)

(58) Field of Classification Search
CPC ..... C07D 207/12; C07D 207/36; A61K 31/40; A61K 31/4015; A61K 31/455
USPC ............................................. 548/541; 514/91
See application file for complete search history.

(56) References Cited

U.S. PATENT DOCUMENTS

| | | |
|---|---|---|
| 3,224,939 A | 12/1965 | Hoehn et al. |
| 3,427,305 A | 2/1969 | Chinn |
| 4,637,829 A | 1/1987 | Schurter et al. |
| 4,707,177 A | 11/1987 | Schurter et al. |
| 5,019,130 A | 5/1991 | Flood |
| 5,451,597 A | 9/1995 | Bovy et al. |
| 5,484,937 A | 1/1996 | Bovy et al. |
| 5,698,581 A | 12/1997 | Kleeman et al. |
| 5,714,489 A | 2/1998 | Lubisch et al. |
| 5,852,017 A | 12/1998 | Lubisch et al. |
| 5,902,719 A | 5/1999 | Baba et al. |
| 5,910,504 A | 6/1999 | Hutchinson |
| 6,780,950 B2 * | 8/2004 | Cho et al. ..................... 526/258 |

(Continued)

FOREIGN PATENT DOCUMENTS

| | | |
|---|---|---|
| CA | 2068004 | 11/1992 |
| CN | 101018547 | 8/2007 |

(Continued)

OTHER PUBLICATIONS

Varea, T., A. Grancha, and G. Asensio "A simple and efficient route to 1,4-diketones from squaric acid" Tetrahedron (1995), 51(45), pp. 12373-12382.*

Dallacker, F., V. Mues "On the preparation of 3, 4-Methylenedioxy thiophene, furan and pyrrole derivatives" Chem. Reports (1975), 108: pp. 569-575.*

Arzanlou et al., Allicin from garlic neutralizes the hemolytic activity of intra- and extracellular pneumolysin O in vitro, Toxicon, 2011, pp. 540-545, vol. 57.

Byeon et al., Ferulic acid and benzothiazole dimer derivatives with high binding affinity to β-amyloid fibrils, Bioorganic & Medicinal Chemistry Letters, 2007, pp. 4022-4025, vol. 17.

(Continued)

*Primary Examiner* — James O Wilson
*Assistant Examiner* — Sagar Patel
(74) *Attorney, Agent, or Firm* — Dentons US LLP

(57) ABSTRACT

There are provided inter alia compounds of formula (I) wherein $R^1$, $R^2$, $R^3$, $R^{4a}$ and $R^{4b}$ are as defined in the specification and their use in therapy, especially in the treatment of bacterial (e.g. pneumococcal) infections.

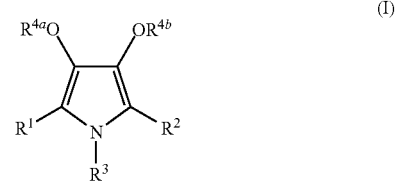

24 Claims, 9 Drawing Sheets

(56) References Cited

U.S. PATENT DOCUMENTS

| | | | |
|---|---|---|---|
| 6,803,379 B2 | 10/2004 | Fernandez-Pol et al. | |
| 8,691,982 B2 | 4/2014 | Meijer et al. | |
| 2002/0103243 A1 | 8/2002 | Takeyama et al. | |
| 2003/0225155 A1 | 12/2003 | Fernandez-Pol et al. | |
| 2004/0059134 A1 | 3/2004 | Vaysse-Ludot et al. | |
| 2004/0167204 A1 | 8/2004 | Fernandez-Pol et al. | |
| 2008/0096920 A1 | 4/2008 | Belvedere et al. | |
| 2009/0005410 A1 | 1/2009 | Charvat et al. | |
| 2010/0317568 A1* | 12/2010 | DeGoey et al. | 514/4.2 |

FOREIGN PATENT DOCUMENTS

| | | |
|---|---|---|
| CN | 101853963 | 10/2010 |
| DE | 4217952 | 12/1993 |
| DE | 4445088 | 6/1996 |
| DE | 19745776 | 4/1998 |
| DE | 19718742 | 11/1998 |
| EP | 0159966 | 4/1985 |
| EP | 0538231 | 4/1993 |
| EP | 0579066 | 1/1994 |
| EP | 0676395 | 10/1995 |
| EP | 1074551 | 2/2001 |
| EP | 1389626 | 2/2004 |
| EP | 1403265 | 3/2004 |
| EP | 2602248 | 12/2011 |
| EP | 2486925 | 8/2012 |
| GB | 1311336 | 3/1973 |
| JP | H 10181212 | 7/1998 |
| JP | 2000086713 | 3/2000 |
| JP | 2000280621 | 10/2000 |
| JP | 2000280621 A * | 10/2000 |
| JP | 2006193433 | 7/2006 |
| WO | WO 92-11255 | 7/1992 |
| WO | WO 94-17059 | 8/1994 |
| WO | WO 96-18770 | 6/1996 |
| WO | WO 96-23788 | 8/1996 |
| WO | WO 96/33994 | 10/1996 |
| WO | WO 97-47299 | 12/1997 |
| WO | WO 97-48786 | 12/1997 |
| WO | WO 99-21851 | 5/1999 |
| WO | WO 99-41244 | 8/1999 |
| WO | WO 01-09093 | 2/2001 |
| WO | WO 02-083665 | 10/2002 |
| WO | WO 03-013509 | 2/2003 |
| WO | WO 03-057212 | 7/2003 |
| WO | WO 03-078396 | 9/2003 |
| WO | WO 2004-101531 | 11/2004 |
| WO | WO 2006-020004 | 2/2006 |
| WO | WO 2006-023462 | 3/2006 |
| WO | WO 2006-032173 | 3/2006 |
| WO | WO 2007-009389 | 1/2007 |
| WO | WO 2007-027878 | 3/2007 |
| WO | WO 2007-127137 | 11/2007 |
| WO | WO 2008-011551 | 1/2008 |
| WO | WO 2008-019139 | 2/2008 |
| WO | WO 2008-062469 | 5/2008 |
| WO | WO 2009-035553 | 3/2009 |
| WO | WO 2009-038847 | 3/2009 |
| WO | WO 2009-073973 | 6/2009 |
| WO | WO 2009-117734 | 9/2009 |
| WO | WO 2010-048207 | 4/2010 |
| WO | WO 2010-103473 | 9/2010 |
| WO | WO 2010-103486 | 9/2010 |
| WO | WO 2011/043480 | 4/2011 |
| WO | WO 2013-033240 | 3/2013 |

OTHER PUBLICATIONS

Cockeran et al., Pneumolysin as a vaccine and drug target in the prevention and treatment of invasive pneumococcal disease, Arch Immunol. Ther. Exp., 2005, pp. 189-198, vol. 53.
Damaso et al., New Approaches for the Treatment of Pneumococcal Diseases, 6th International Symposium on Pneumococcus and Pneumococcal Diseases, Jun. 2008, Iceland, 3 pages.
De Mouilpied, The Condensation of Phenylglycinoacetic Esters in Presence of Sodium Alkyloxides, J. Chem. Soc. Trans., 1905, pp. 435-450, vol. 87.
Elassar et al., Synthesis, characterisation and bioactivity of polysubstituted 1-(4-(1H-pyrrol-1-yl)phenyl)-1H-pyrrole derivatives, J. Chem. Res., 2012, pp. 328-332, vol. 36, No. 6, Caesar Accession No. 1971, Caplus Accession No. 2012:1056084, abstract, 1 page.
El-Rachkidy et al., High throughput screening for small molecules that inhibit the haemolytic activity of pneumolysin, 6th International Symposium on Pneumococcus and Pneumococcal Diseases, Jun. 2008, Iceland, 3 pages.
Hirst et al., Relative Roles of Pneumolysin and Hydrogen Peroxide from *Streptococcus pneumonia* in Inhibition of Ependymal Ciliary Beat Frequency, Infection and Immunity, Mar. 2000, pp. 1557-1562, vol. 68, No. 3.
Hirst et al., *Streptococcus pneumonia*-Induced Inhibition of Rat Ependymal Cilia is Attenuated by Antipneumolysin Antibody, Infection and Immunity, 2004, pp. 6694-6698, vol. 72, No. 11.
International Search Report dated Jul. 9, 2013 in International Application PCT/GB201/053022 filed Dec. 5, 2012, 10 pages.
Johnson et al., Synthesis of Pyrrole Compounds from Imido Acids, N-Phenyl-α, β-Dicarbethoxy-β, β'-Diketopyrrolidine, J. Am. Chem. Soc., 1911, pp. 745-755, vol. 33.
Johnson et al., Morbidity and mortality of pneumococcal meningitis and serotypes of causative strains prior to introduction of the 7-valent conjugant pneumococcal vaccine in England, Journal of Infection, 2007, pp. 394-399, vol. 55.
Lee et al., Synthesis and characterization of polar functional group substituted mono- and bis-(o-carboranyl)-1,3,5-triazine derivatives, Tetrahedron Letters, 2008, pp. 159-164, vol. 49 No. 1.
Marquart et al., Cholesterol as Treatment for Pneumococcal Keratitis: Cholesterol-Specific Inhibition of Pneumolysin in the Cornea, Investigative Ophthalmology & Visual Science, 2007, pp. 2661-2666, vol. 48, No. 6.
Molyneux et al., Dexamethasone treatment in childhood bacterial meningitis in Malawi: a randomised controlled trial, Lancet, 2002, pp. 211-218, vol. 360.
Ngwendson et al., A Zn(II) ion selective fluorescence sensor that is not affected by Cd(II), Tetrahedron Letters, 2007, pp. 7316-7319, vol. 48.
Sorm et al., Conjugated systems obtained by reaction of cyclic amides with dehydrogenation and dehydration agents-III Mesoionic compounds: Anhydro Dihydroxides of 1,4-Disubstituted-3,5-bis(Arylthio)-2,6-Dihydroxy-Pyrazinium, Tetrahedron, 1972, pp. 603-610, vol. 28.
Sun et al., Influence of N-substituent and solvent on internal conversion in 1-aminonaphthalenes, Spectrochimica Acta. Part A, 2007, pp. 220-224, vol. 68, No. 2.
Tatsuta et al., Synthesis and Biological Evaluation of Neopyrrolomycin Analogs, The Journal of Antibiotics, Feb. 1994, pp. 262-265, vol. 47, No. 2.
Varea et al., A simple and Efficient Route to 1,4-Diketones from Squaric Acid, Tetrahedron, 1995, pp. 12373-12382, vol. 51, No. 45.
Watson et al., Sterol Structural Requirements for Inhibition of Streptolysin O Activity, Biochem. J., 1974, pp. 95-98, vol. 140.
Winter et al., A Role for Pneumolysin but Not Neuraminidase in the Hearing Loss and Cochlear Damage Induced by Experimental Pneumococcal Meningitis in Guinea Pigs, Infection and Immunity, 1997, pp. 4411-4418, vol. 65, No. 11.
Witzenrath et al., Phosphodiesterase 2 inhibition diminished acute lung injury in murine pneumococcal pneumonia, Critical Care Med., 2009, pp. 584-590, vol. 37, No. 2.
Written Opinion in corresponding International Application PCT/GB2012/053022 filed on May 12, 2012, entered on Jun. 5, 2014, 12 pages.
Los et al., Role of Pore-Forming Toxins in Bacterial Infectious Diseases, Microbiol. Mol. Biol. Rev., 2013, pp. 173-207, vol. 77, No. 2.
Branstrom et al. XP-002726996 abstract, database accession No. 2013:348502, Mar. 7, 2013, 1 page. (corresponding WO 2013/033240, previously cited).
Chinese Office Action received on Jun. 26, 2015 in related Chinese Application No. 201280060023, English Translation, 8 pages.

(56) References Cited

OTHER PUBLICATIONS

Dallacker et al., Zur Darstellung von 3,4-Methylendioxythiophen-, -furan- und -pyrrol-Abkömmlingen, Chem. Ber., 1975, pp. 569-575, vol. 108 (in German).
Dallacker et al., Zur Darstellung von 3,4-Methylendioxythiophen-, -furan- und -pyrrol-Abkömmlingen, Chem. Ber., 1975, pp. 569-575, vol. 108 (in English, machine translation, 9 pages).
Dimroth et al., Ein Neuer Weg Zum Aufbau Des Pyrrol-Ringsystems, Justus Liebigs Annalen der Chemie, 1961, pp. 102-124, vol. 639 (in German).
Dimroth et al., Ein Neuer Weg Zum Aufbau des Pyrrol-Ringsystems, Justus Liebigs Annalen der Chemie, 1961, pp. 102-124, vol. 639 (in English, machine translation, 23 pages).
Dyatkina et al., XP002726995 abstract, database accession No. 1224, Jul. 17, 2003, 1 page. (corresponding WO 2003/057212, previously cited).
Euler et al., Bis-Reduktone aus 3.4-Dihydroxy-dicarbansäure-(2.5)-estern des Furans, Thiophens, N-Phenyl-pyrrols und Selenophens, Hoppe-Seyler's Xeitschrift fuer Physiologische Chemie, 1956, pp. 49-55, vol. 306 (in German).
Euler et al., Bis-Reduktone aus 3.4-Dihydroxy-dicarbansaure-(2.5)-estern des Furans, Thiophens, N-Phenyl-pyrrols und Selenophens, Hoppe-Seyler's Xeitschrift fuer Physiologische Chemie, 1956, pp. 49-55, vol. 306 (in English, machine translation, 7 pages).
International Search Report and Written Opinion dated Jul. 23, 2014 in related International Application No. PCT/GB2014/051723 filed Jun. 4, 2014, 10 pages.
International Search Report and Written Opinion dated Jul. 23, 2014 in related International Application No. PCT/GB2014/051725 filed Jun. 4, 2014, 11 pages.
International Search Report and Written Opinion dated Jul. 30, 2014 in related International Application PCT/GB2014/051720 filed Jun. 4, 2014, 12 pages.
International Search Report and Written Opinion dated Sep. 5, 2014 in related International Application No. PCT/GB2014/051728 filed Jun. 4, 2014, 10 pages.
International Search Report and Written Opinion dated Nov. 6, 2014 in related International Application No. PCT/GB2014/0517744 filed Jun. 5, 2014, 18 pages.
STN Registry Database Reference No. 654052-34-2, ACS, Feb. 25, 2004, 1 page.
Wo 2011/043480 published Apr. 14, 2011, 104 pages. (in English, machine translation).
El-Rachkidy et al., P1-135 High throughput screening for small molecules that inhibit the haemolytic activity of pneumolysin, 6th International Symposium on Pneumococci and Pneumococcal Diseases, Jun. 8-12, 2008, Reykjavik, Iceland, poster abstract, 2 pages.
Damaso et al., P1-137 New Approaches for the Treatment of Pneumococcal Diseases, 6th International Symposium on Pneumococci and Pneumococcal Diseases, Jun. 8-12, 2008, Reykjavik, Iceland, poster abstract, 2 pages.

\* cited by examiner

PYRROLE DERIVATIVES

CROSS REFERENCE TO RELATED APPLICATIONS

The present application claims the benefit of PCT International Application No. PCT/GB2012/053022, filed 05 Dec. 2012; which claims the benefit of EP application Ser. No. 11191986.6, filed 05 Dec. 2011, all of which are incorporated herein by reference in their entireties.

FIELD OF THE INVENTION

The invention relates to compounds which are cytolysin inhibitors and their use in therapy, including in pharmaceutical combinations, especially in the treatment of bacterial, e.g. pneumococcal, infections.

BACKGROUND OF THE INVENTION

*Streptococcus pneumoniae* (pneumococcus) is one of the most potent human pathogens, affecting over 10 million people worldwide, of all age groups, in particular young children, the elderly and the immunocompromised. It is a leading causative agent of serious, often fatal diseases, such as pneumonia, bacteraemia and meningitis. It is also responsible of other less serious, but nevertheless debilitating diseases such as otitis media and keratitis.

Even after decades of using antibiotics and steroids as adjunctive to antibiotics the mortality and morbidity from pneumococcal diseases remains very high in the developed world and alarmingly high in the developing world. Nearly 20% of hospitalised patients still die despite antibiotic killing of the pneumococcus, while many survivors of pneumococcal meningitis suffer severe neurological handicaps, including cognitive impairment, vision and hearing loss, hence imposing huge distress on patients and their families and a very significant cost to healthcare systems. Today, infection with pneumococcus remains a major global public health problem that is widely recognised by leaders in the field and by health organisations, including the WHO.

One of the leading factors for this consistently high mortality and morbidity that is not addressed by the current standard therapy, is the toxaemia resulting from the release of toxic pneumococcal products, the most important of which is the pneumococcal toxin pneumolysin. This toxin is a major player in pneumococcal virulence and is the primary direct and indirect cause of toxaemia.

Pneumolysin belongs to the family of cholesterol dependent cytolysins (CDCs), which bind to cholesterol containing membranes and generate large pores that have lethal and sub-lethal effects on the affected cells. In the bacterium, the toxin pneumolysin is cytoplasmic and is mainly released from the pneumococcus after its lysis. Consequently, under the effect of lytic antibiotics, a large bolus of toxin is released, compounding the toxaemia. Thus, even if treatment with antibiotics is successful in clearing the bacteria from the patients, the subsequent release of the toxin is detrimental and can be fatal or cause long-term handicaps.

This toxaemia constitutes a substantial unmet medical need that is internationally recognised. Currently, corticosteroids, principally dexamethasone, are used as an adjunctive to antibiotic therapy for pneumococcal meningitis. However, even when dexamethasone is used, significant mortality and morbidity are seen and the widespread use of dexamathasone is still debated due to its non-specific effect, limited clinical impact and in some cases its detrimental effect in increasing neuronal apoptosis in meningitis [Lancet (2002) 360 211-218]. Therefore, the present state of the art is not adequate for the efficient treatment of invasive pneumococcal diseases.

There is considerable evidence substantiating the validity of pneumolysin as a therapeutic target. In the laboratories of the inventors it has been demonstrated that, using a mouse pneumonia model, a mutated strain of *S. pneumoniae* (PLN-A) that does not produce pneumolysin is no longer lethal, causes substantially less bacteraemia and exhibits a significant reduction in the severity of pulmonary inflammation. Other evidence obtained in a rat meningitis model, has shown that infection with the pneumolysin-negative mutant was markedly less severe than with wild-type pneumococci, with no observed damage to the ciliated epithelium of the brain and no apoptosis of the cells surrounding the epithelium [J. Infect, (2007) 55 394-399]. In pneumococcal meningitis in guinea pigs, wild-type pneumococci induced severe cochlear damage and hearing loss, while infection with PLN-A left the organ of Corti intact [Infect. Immun. (1997) 65 4411-4418]. An ex vivo model using cultured ciliated brain epithelial cells, enabled recreation of the in vivo situation, where cells lining the brain ventricles are exposed to *S. pneumoniae*. Both intact and antibiotic-killed wild-type pneumococci induced damage to the epithelial cells in culture and significantly impaired ciliary beating; effects not seen with PLN-A [Infect. Immun. (2000) 68 1557-1562]. This damaging effect of antibiotic-lysed pneumococci on the cultured ependymal cells is clearly caused by the toxin pneumolysin released from the antibiotic-lysed bacteria, as this damage was abolished in the presence of anti-pneumolysin antibodies [Infect. Immun. (2004) 72 6694-6698]. This finding supports the strategy that antibiotic-induced toxaemia is prevented by combination with anti-pneumolysin agents.

Evidence for the significant involvement of pneumolysin in pneumococcal infections and the substantial improvement of the disease prognosis in the absence of pneumolsyin, has led to the conclusion that pneumolysin constitutes a potential therapeutic target to develop new treatments for pneumococcal diseases. Previous research has shown the ability of cholesterol to inhibit pneumolysin [Biochem. J. (1974) 140 95-98], however, this inhibition is merely due to the fact that cholesterol is a natural cellular receptor of pneumolysin that is required for the pore formation in the target cell membrane. The topical application of cholesterol on the cornea of rabbits demonstrated a positive therapeutic effect in pneumococcal keratitis [Invest. Ophthalmol. Vis. Sci. (2007) 48 2661-2666]. This indicates the involvement of pneumolysin in pneumococcal keratitis and the therapeutic benefit obtained following its inhibition. However, cholesterol is not considered as a therapeutic agent for the treatment of pneumococcal diseases and has not been clinically used in patients. Another pneumolysin inhibitor, Allicin, a component in garlic extract, has been previously found to inhibit the haemolytic activity of pneumolysin in vitro [Toxicon (2011) 57 540-545]. This compound is a cysteine inhibitor that irreversibly binds to the reactive thiol group of the toxin. Compounds exhibiting such a property are unfavourable as drug candidates because of their potential unspecific binding to other cysteine-containing proteins in the body.

There remains a need to provide inhibitors of cytolysins, such as pneumolysin, which are suitable for use in the treatment of bacterial infections.

The present invention provides compounds that specifically inhibit the direct toxic effect of pneumolysin and other cholesterol dependent cytolysins that are pivotal in the virulence of their respective hosts. The compounds of the invention have no structural similarity to Allicin and do not bind covalently to the reactive thiol groups of the toxins.

Certain N-phenyl substituted pyrroles are known, however their use as pharmaceuticals in particular for the treatment of bacterial infections had not been suggested. The compounds diethyl 3,4-dihydroxy-1-(4-methoxyphenyl)-1H-pyrrole-2,5-dicarboxylate (CAS 654052-34-3) and diethyl 3,4-dihydroxy-1-phenyl-1H-pyrrole-2,5-dicarboxylate (CAS 55932-13-3) are commercially available. The compounds dimethyl 3,4-dihydroxy-1-(4-bromophenyl)-1H-pyrrole-2,5-dicarboxylate (CAS 1087699-40-8), dimethyl 3,4-dihydroxy-1-(4-chlorophenyl)-1H-pyrrole-2,5-dicarboxylate (CAS 1082655-47-7), di-tert-butyl 3,4-dihydroxy-1-(4-nitrophenyl)-1H-pyrrole-2,5-dicarboxylate (CAS 110332-46-2) and dimethyl 3,4-dihydroxy-1-(4-methoxyphenyl)-1H-pyrrole-2,5-dicarboxylate (CAS 101090-98-6) are described in Justus Liebigs Annalen der Chemie (1961), 639, 102-24. The compounds dimethyl 3,4-dihydroxy-1-phenyl-1H-pyrrole-2,5-dicarboxylate (CAS 7803-73-8) and dimethyl 3,4-bis(acetyloxy)-1-phenyl-1H-pyrrole-2,5-dicarboxylate (CAS 7342-22-5) are described in Hoppe-Seyler's Zeitschrift fuer Physiologische Chemie (1956), 306, 49-55. The compound diethyl 3,4-bis(acetyloxy)-1-phenyl-1H-pyrrole-2,5-dicarboxylate (CAS 55932-14-4) is disclosed in Chemische Berichte (1975), 108(2), 569-75.

The compounds of the present invention also prevent stimulation of host-derived toxic effects induced by pneumolysin and other cholesterol dependent cytolysins. Thus these compounds may be used as single agents or as adjunct to antibiotics, to prevent or attenuate pneumolysin-induced toxicity and its anti-host effects seen during infections caused e.g. by S. pneumoniae.

SUMMARY OF THE INVENTION

According to the invention, there is provided a compound of formula (I):

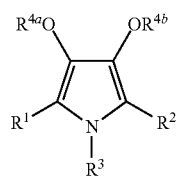

wherein:
$R^1$ and $R^2$ are independently selected from —C(O)NR$^5$R$^6$, —C(O)OR$^7$, CN, —C(O)R$^7$, —C(O)NHC(O)R$^7$, —NO$_2$, —SO$_3$R$^7$, —SO$_2$R$^7$, —SOR$^7$, —SO$_2$NR$^5$R$^6$, —SO$_2$NH—C(O)OR$^8$, —POR$^{21}$R$^{22}$ and optionally substituted phenyl or heteroaryl;
$R^3$ is optionally substituted phenyl;
$R^{4a}$ and $R^{4b}$ are independently selected from hydrogen; $C_1$-$C_6$ alkyl which alkyl group may optionally be substituted by hydroxyl, COOR$^{12}$ or CONR$^{13}$R$^{14}$; aryl and —$C_1$-$C_3$ alkylaryl in which said aryl groups may be optionally substituted;
$R^5$ and $R^6$ are independently selected from:
  (a) hydrogen,
  (b) $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —$C_1$-$C_3$ alkyl-$C_3$-$C_{10}$ cycloalkyl, —$C_1$-$C_3$ alkyl-$C_5$-$C_{10}$ cycloalkenyl or —$C_1$-$C_3$ alkylheterocyclyl, or R$^5$ and R$^6$ together with the N to which they are attached may form a 5- or 6-membered heterocyclic ring optionally containing a further heteroatom selected from O, S and NR$^9$, in which any of the aforementioned R$^5$ and R$^6$ groups may be optionally substituted by a group selected from cyano, $C_1$-$C_6$ alkoxy, $C_1$-$C_6$ fluoroalkoxy, $C_1$-$C_6$ alkyl, $C_1$-$C_6$ fluoroalkyl and —C(O)NR$^a$R$^b$, where R$^a$ and R$^b$ are independently selected from hydrogen and $C_1$-$C_6$ alkyl, and any of the aforementioned R$^5$ and R$^6$ groups may be optionally substituted by one or more halogen atoms, and
  (c) aryl, heteroaryl, $C_1$-$C_3$ alkylaryl and —$C_1$-$C_3$ alkylheteroaryl, said aryl and heteroaryl groups being optionally substituted;
$R^7$ is selected from:
  (a) $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —$C_1$-$C_3$ alkyl-$C_3$-$C_{10}$ cycloalkyl, —$C_1$-$C_3$ alkyl-$C_5$-$C_{10}$ cycloalkenyl or —$C_1$-$C_3$ alkylheterocyclyl, in which any of the aforementioned R$^7$ groups may be optionally substituted by a group selected from cyano, $C_1$-$C_6$ alkoxy, $C_1$-$C_6$ fluoroalkoxy, $C_1$-$C_6$ alkyl, $C_1$-$C_6$ fluoroalkyl and —C(O)NR$^a$R$^b$, where R$^a$ and R$^b$ are independently selected from hydrogen and $C_1$-$C_6$ alkyl, and any of the aforementioned R$^7$ groups may be optionally substituted by one or more halogen atoms, and
  (b) aryl, heteroaryl, $C_1$-$C_3$ alkylaryl and —$C_1$-$C_3$ alkylheteroaryl, said aryl and heteroaryl groups being optionally substituted;
$R^8$ is $C_1$-$C_6$ alkyl;
$R^9$ is hydrogen, $C_1$-$C_6$ alkyl; —C(O)R$^{10}$ or —C(O)OR$^{11}$;
$R^{10}$ is $C_1$-$C_6$ alkyl;
$R^{11}$ is $C_1$-$C_6$ alkyl;
$R^{12}$ is $C_1$-$C_6$ alkyl;
$R^{13}$ is hydrogen or $C_1$-$C_6$ alkyl;
$R^{14}$ is hydrogen or $C_1$-$C_6$ alkyl; and
$R^{21}$ and $R^{22}$ are independently selected from $C_1$-$C_6$ alkyl and $C_1$-$C_6$ hydroxyalkyl;
or a pharmaceutically acceptable prodrug derivative thereof, or a pharmaceutically acceptable salt or solvate thereof;
provided that the compound is not:
  a) diethyl 3,4-dihydroxy-1-(4-methoxyphenyl)-1H-pyrrole-2,5-dicarboxylate;
  b) diethyl 3,4-dihydroxy-1-phenyl-1H-pyrrole-2,5-dicarboxylate;
  c) dimethyl 3,4-dihydroxy-1-(4-bromophenyl)-1H-pyrrole-2,5-dicarboxylate;
  d) dimethyl 3,4-dihydroxy-1-(4-chlorophenyl)-1H-pyrrole-2,5-dicarboxylate;
  e) di-tert-butyl 3,4-dihydroxy-1-(4-nitrophenyl)-1H-pyrrole-2,5-dicarboxylate;
  f) dimethyl 3,4-dihydroxy-1-(4-methoxyphenyl)-1H-pyrrole-2,5-dicarboxylate;
  g) dimethyl 3,4-dihydroxy-1-phenyl-1H-pyrrole-2,5-dicarboxylate;
  h) diethyl 3,4-bis(acetyloxy)-1-phenyl-1H-pyrrole-2,5-dicarboxylate; or
  i) dimethyl 3,4-bis(acetyloxy)-1-phenyl-1H-pyrrole-2,5-dicarboxylate.

The compounds of formula (I) including the compounds which are the subject of provisos a) to i) have therapeutic activity. In a further aspect, the present invention provides a compound of formula (I) without provisos a) to i) for use as a medicament.

Figure 1:
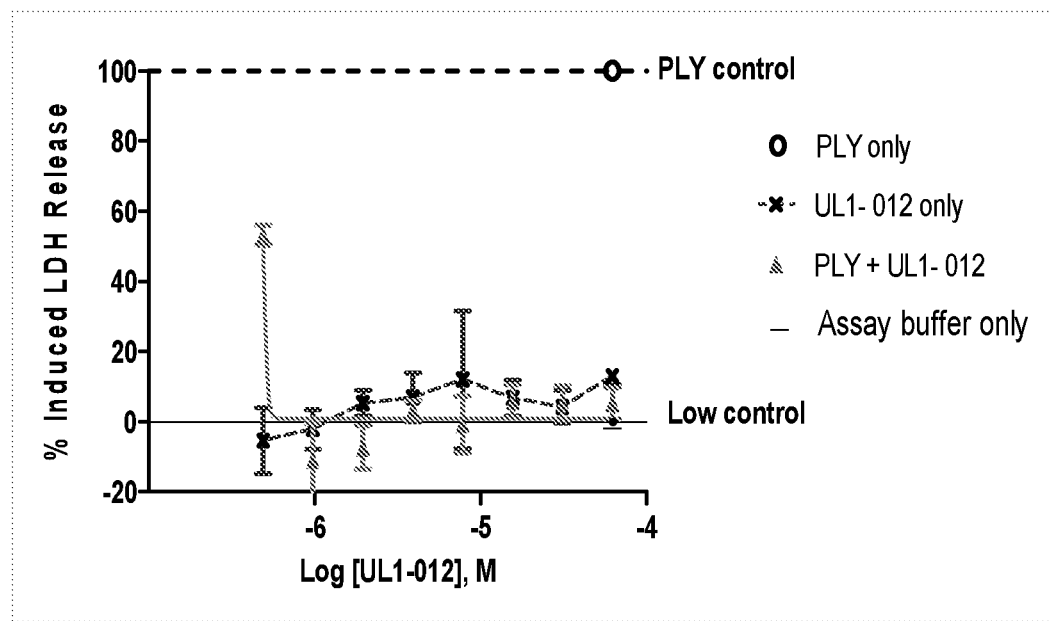
FIG. 1 shows the in vitro inhibition of pneumolysin-induced LDH release by the compound UL1-012 using A549 human lung epithelial cells.

DETAILED DESCRIPTION OF THE INVENTION $R^1$ and $R^2$ may be independently selected from —C(O)NR$^5$R$^6$, —C(O)OR$^7$, CN, —C(O)R$^7$, —C(O)NHC(O)R$^7$, —NO$_2$, —SO$_3$R$^7$, —SO$_2$R$^7$, —SOR$^7$, —SO$_2$NR$^5$R$^6$, —SO$_2$NH—C(O)OR$^8$ and optionally substituted phenyl or heteroaryl; for example $R^1$ and $R^2$ may be independently selected from —C(O)NR$^5$R$^6$, —C(O)OR$^7$, CN, —C(O)R$^7$, —C(O)NHC(O)R$^7$, —SO$_3$R$^7$, —SO$_2$R$^7$, —SOR$^7$, —SO$_2$NR$^5$R$^6$, —SO$_2$NH—C(O)OR$^8$ and optionally substituted phenyl or heteroaryl. $R^1$ and $R^2$ are preferably independently selected from —C(O)NR$^5$R$^6$, —C(O)OR$^7$, CN, —C(O)R$^7$, —C(O)NHC(O)R$^7$ and —SO$_2$NH—C(O)OR$^8$; more preferably $R^1$ and $R^2$ are independently selected from —C(O)NR$^5$R$^6$, —C(O)OR$^7$ and CN; even more preferably $R^1$ and $R^2$ are independently selected from —C(O)NR$^5$R$^6$ and —C(O)OR$^7$.

$R^1$ is preferably —C(O)NR$^5$R$^6$.

In one embodiment $R^2$ is —C(O)NR$^5$R$^6$. In another embodiment $R^2$ is —C(O)OR$^7$. Thus in one embodiment $R^1$ is —C(O)NR$^5$R$^6$ and $R^2$ is —C(O)NR$^5$R$^6$ and in another embodiment $R^1$ is —C(O)NR$^5$R$^6$ and $R^2$ is —C(O)OR$^7$.

When $R^1$ and $R^2$ are both —C(O)NR$^5$R$^6$ they may be same or different, preferably they are the same.

In an alternative embodiment $R^1$ and $R^2$ are both —C(O)OR$^7$ and they may be same or different, preferably they are the same.

$R^3$ is preferably substituted phenyl.

Suitable optional substituents for $R^3$ include 1 or more, e.g. 1, 2 or 3, substituents (e.g. 1 substituent) independently selected from halo, cyano, hydroxyl, $C_1$-$C_6$ alkoxy, $C_1$-$C_6$ hydroxyalkoxy, $C_1$-$C_6$ fluoroalkoxy, $C_1$-$C_6$ alkyl, $C_1$-$C_6$ fluoroalkyl, —C(O)NR$^a$R$^b$, where R$^a$ and R$^b$ are independently selected from hydrogen and $C_1$-$C_6$ alkyl; —O—R$^{15}$ wherein $R^{15}$ is —(CH$_2$)$_x$—P(O)(OR$^{23}$)$_2$ (where x is 0, 1, 2, 3 or 4 and $R^{23}$ is independently selected from hydrogen and $C_1$-$C_3$ alkyl), —(CH$_2$)$_y$—S(O)$_2$Me (where y is 1, 2, 3 or 4), —$C_1$-$C_6$ alkylheterocyclyl which heterocyclyl group may be optionally substituted e.g. by $C_1$-$C_3$ alkyl, —$C_1$-$C_6$ alkylphenyl which phenyl group may be optionally substituted e.g. by $C_1$-$C_3$ alkoxy, or phenyl or 5- or 6-membered heteroaryl which phenyl or heteroaryl group may optionally be substituted by a group e.g. selected from $C_1$-$C_4$ alkyl and halo; or —(O(CH$_2$)$_z$)$_p$OR$^{24}$, where each z, which may be the same or different, represents 2 or 3, p represents 1, 2, 3, 4 or 5 and $R^{24}$ is hydrogen or $C_1$-$C_3$ alkyl; or two adjacent carbon atoms within $R^3$ may be linked by —O—CH$_2$—O—.

When $R^{15}$ is —$C_1$-$C_6$ alkylheterocyclyl, particular heterocyclyl groups which may be mentioned include 5- or 6-membered, monocyclic non-aromatic ring systems, containing up to two heteroatoms selected from N, O and S. Such rings are suitably linked to —$C_1$-$C_6$ alkyl via an N atom. Examples of heterocyclic rings include morpholine, piperazine, and the like, which may be optionally substituted e.g. by $C_1$-$C_3$ alkyl, such as methyl. Further examples of heterocyclic rings include piperidine and pyrrolidine.

A group of suitable optional substituents for $R^3$ which may be mentioned include 1, 2 or 3 substituents selected from halo, cyano, $C_1$-$C_6$ alkoxy, $C_1$-$C_6$ fluoroalkoxy, $C_1$-$C_6$ alkyl, $C_1$-$C_6$ fluoroalkyl and —C(O)NR$^a$R$^b$, where R$^a$ and R$^b$ are independently selected from hydrogen and $C_1$-$C_6$ alkyl. In addition, when $R^3$ is substituted phenyl, said phenyl may be provided with a single substituent —O—R$^{15}$ wherein $R^{15}$ is selected from phenyl and 5- or 6-membered heteroaryl which phenyl or heteroaryl group may optionally be substituted by a group selected from $C_1$-$C_4$ alkyl and halo.

Preferred optional substituents for $R^3$ include 1 or more, e.g. 1, 2 or 3, substituents (e.g. 1 substituent) independently selected from $C_1$-$C_6$ alkoxy; —O—R$^{15}$ wherein $R^{15}$ is —(CH$_2$)$_x$—P(O)(OR$^{23}$)$_2$, where x is 0, 1, 2, 3 or 4 and $R^{23}$ is independently selected from hydrogen and $C_1$-$C_3$ alkyl or $R^{15}$ is —(CH$_2$)$_y$—S(O)$_2$Me where y is 1, 2, 3 or 4; and —(O(CH$_2$)$_z$)$_p$OR$^{24}$, where each z, which may be the same or different, represents 2 or 3, p represents 1, 2, 3, 4 or 5 and $R^{24}$ is hydrogen or $C_1$-$C_3$ alkyl.

Suitable optional substituents for $R^3$ are described in further detail below.

When $R^3$ is substituted phenyl, it preferably has a substituent in the meta or para position relative to the pyrrole ring, more preferably it has a substituent in the para position relative to the pyrrole ring. Alternatively, when $R^3$ is substituted phenyl it may have a substituent in the ortho position relative to the pyrrole ring. In one embodiment, $R^3$ is phenyl substituted by a single substituent. In another embodiment, $R^3$ is phenyl substituted by two substituents. When $R^3$ is substituted phenyl having 2 substituents, these may, for example, be in the meta and para positions relative to the pyrrole ring. In another embodiment, $R^3$ is phenyl substituted by three substituents. When $R^3$ is substituted phenyl having 3 substituents, these may, for example, be in the 3, 4 and 5 positions relative to the pyrrole ring.

For example, $R^3$ may represent phenyl bearing a para substituent selected from F, Cl, I, cyano, OCH$_3$, OCH$_2$CH$_3$, OCH$_2$CH$_2$CH$_3$, CF$_3$, OCF$_3$, CON(CH$_3$)$_2$, O-phenyl, methyl, ethyl, isopropyl, t-butyl, hydroxyl, —OP(O)(OH)$_2$, —(O(CH$_2$)$_2$)$_p$OMe where p is 1, 2, 3 or 4,3-morpholinopropoxy, 3-(4-methylpiperazin-1-yl)propoxy, 3-(diethoxyphosphoryl)propoxy, —(O(CH$_2$)$_3$)—P(O)(OH)$_2$, 3-(methylsulfonyl)propoxy, and 4-methoxybenzyloxy. In a further group of compounds that may be mentioned $R^3$ may represent phenyl bearing a para substituent selected from F, Cl, I, OCH$_3$, $OCH_2CH_3$, $OCH_2CH_2CH_3$, $CF_3$, $OCF_3$, $CON(CH_3)_2$, O-phenyl, methyl, ethyl, isopropyl and t-butyl. A particular $R^3$ group which may be mentioned is phenyl bearing a para $OCH_3$ substituent.

For example, $R^3$ may represent phenyl bearing an ortho substituent which is $OCH_3$.

For example, $R^3$ may represent phenyl bearing a meta substituent which is O-phenyl or $OCH_3$.

For example, $R^3$ may represent phenyl substituted in the meta position by I and in the para position by $OCH_3$, or phenyl substituted in the meta position by $OCH_3$ and in the para position by $OCH_3$, or phenyl linked in the meta and para positions by —O—$CH_2$—O—.

For example, $R^3$ may represent phenyl substituted in the ortho position by $OCH_3$ and in the para position by $OCH_3$.

For example, $R^3$ may represent phenyl substituted in the 3, 4 and 5 positions by $OCH_3$, or phenyl substituted in the 3 and 5 positions by F and in the para position by $OCH_2CH_3$.

Hence a particularly suitable substituent for the phenyl of $R^3$ is $OCH_3$, especially in the para position. Further particularly suitable substituents for $R^3$ include —O—$R^{15}$ wherein $R^{15}$ is as defined above and —$(O(CH_2)_z)_p OR^{24}$, where z, p and $R^{24}$ are as defined above, especially in the para position.

When an alkyl group or $R^{4a}$ and/or $R^{4b}$ is substituted by hydroxyl, $COOR^{12}$ or $CONR^{13}R^{14}$, examples of $R^{4a}$ and/or $R^{4b}$ groups include —$CH_2COOt$-butyl, $CH_2CONH_2$ and $CH_2CH_2OH$.

$R^{4a}$ and $R^{4b}$ may be independently selected from hydrogen; $C_1$-$C_6$ alkyl which alkyl group may optionally be substituted by hydroxyl, $COOR^{12}$ or $CONR^{13}R^{14}$; and —$C_1$-$C_3$ alkylaryl in which said aryl groups may be optionally substituted. $R^{4a}$ and $R^{4b}$ are preferably independently selected from hydrogen, $C_1$-$C_6$ alkyl, aryl and —$C_1$-$C_3$ alkylaryl in which aryl may be optionally substituted.

For example $R^{4a}$ and $R^{4b}$ are preferably independently selected from hydrogen, $C_1$-$C_6$ alkyl and —$C_1$-$C_3$ alkylaryl in which aryl may be optionally substituted. $R^{4a}$ and $R^{4b}$ are more preferably hydrogen or —$C_1$-$C_3$ alkylaryl, e.g. benzyl. Most preferably $R^{4a}$ and $R^{4b}$ are hydrogen.

$R^5$ and $R^6$ are preferably independently selected from hydrogen, $C_1$-$C_6$ alkyl e.g. methyl, ethyl, or propyl, aryl e.g. phenyl, or $C_1$-$C_3$ alkylaryl, e.g. benzyl in which said aryl may be optionally substituted, or $R^5$ and $R^6$ together with the N to which they are attached may form a 5- or 6-membered heterocyclic ring optionally containing a further heteroatom selected from O, S and $NR^9$, e.g. morpholine, piperidine or piperazine (optionally N substituted with an $R^9$ group).

In one embodiment of the invention one of $R^5$ and $R^6$ is hydrogen. Preferably at least one of $R^5$ and $R^6$ is not hydrogen, more preferably both of $R^5$ and $R^6$ are not hydrogen.

Specific —$NR^5R^6$ groups of interest include $NMe_2$, NHethyl, —N-morpholinyl and N-piperidinyl, especially $NMe_2$.

$R^7$ is preferably $C_1$-$C_6$ alkyl e.g. methyl, ethyl, propyl or butyl, such as iso-propyl or tert-butyl.

$R^8$ is preferably methyl.

$R^9$ is preferably hydrogen, methyl, $COCH_3$ or —CO-t-butyl.

$R^{10}$ is preferably methyl.

$R^{11}$ is preferably methyl.

$R^{12}$ is preferably methyl.

$R^{13}$ is preferably H or methyl.

$R^{14}$ is preferably H or methyl.

In an embodiment $R^{15}$ is —$(CH_2)_x$—$P(O)(OR^{23})_2$ or —$(CH_2)_y$—$S(O)_2Me$.

In an embodiment $R^{15}$ group is optionally substituted phenyl, e.g. unsubstituted phenyl.

In an embodiment $R^{15}$ is —$C_1$-$C_6$ alkylheterocyclyl which heterocyclyl group may be optionally substituted e.g. by $C_1$-$C_3$ alkyl.

$R^{21}$ are $R^{22}$ are preferably independently selected from $C_1$-$C_6$ alkyl, e.g. methyl.

$R^{23}$ is preferably hydrogen, methyl or ethyl.

$R^{24}$ is preferably $C_1$-$C_3$ alkyl, e.g. methyl.

x is preferably 0, 1, 2, 3 or 4.

y is preferably 1, 2 or 3.

z is preferably 2.

p is preferably 2, 3, 4 or 5.

Prodrug derivatives of compounds of the invention will break down after administration to a subject to form an active compound of formula (I) in vivo. Prodrug derivatives of compounds of the invention may have some intrinsic biological activity (e.g. as pneumolysin inhibitors) however typically they have little or no such intrinsic activity.

Prodrug derivatives of the compounds of formula (I) include ester prodrug derivatives. Ester prodrug derivatives include carboxylate ester, sulfamate ester, phosphate ester and carbamate ester derivatives, preferably carboxylate ester, sulfamate ester or phosphate ester derivatives, more preferably carboxylate ester or phosphate ester derivatives, even more preferably carboxylate ester derivatives. Examples of ester prodrug derivatives thus include compounds of formula (I) wherein one or both of $R^{4a}$ and $R^{4b}$ are independently selected from —$C(O)R^{16}$, —$SO_2NH_2$, —$PO(OR^{19})(OR^{20})$, —$CHR^{26}$—$OPO(OR^{19})(OR^{20})$ (where $R^{26}$ is hydrogen or $C_1$-$C_6$ alkyl), and —$C(O)NR^{17}R^{18}$, wherein $R^{16}$, $R^{17}$, $R^{18}$, $R^{19}$ and $R^{20}$ are independently selected from:

(a) $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —$C_1$-$C_3$ alkyl-$C_3$-$C_{10}$ cycloalkyl, —$C_1$-$C_3$ alkyl-$C_5$-$C_{10}$ cycloalkenyl or —$C_1$-$C_3$ alkylheterocyclyl, or $R^{17}$ and $R^{18}$ together with the N to which they are attached may form a 5- or 6-membered heterocyclic ring optionally containing a further heteroatom selected from O, S and $NR^{25a}R^{25b}$ where $R^{25a}$ is hydrogen, $C_1$-$C_6$ alkyl, —$CH_2$—$OPO(OR^{19})(OR^{20})$ or a 5- or 6-membered heterocyclic ring, and $R^{25b}$ is absent or $C_1$-$C_6$ alkyl; and in which any of the aforementioned $R^{16}$, $R^{17}$ or $R^{18}$ groups may be optionally substituted by one or more groups, e.g. one group, selected from cyano, —$OPO(OR^{19})(OR^{20})$, —$(O(CH_2)_z)_r OR^{24}$ (wherein each z, which may be the same or different, represents 2 or 3, r represents an integer selected from 1 to 20, e.g. 7 to 12, and $R^{24}$ is hydrogen, $C_1$-$C_3$ alkyl or —$PO(OR^{19})(OR^{20})$), $C_1$-$C_6$ alkoxy, $C_1$-$C_6$ fluoroalkoxy, $C_1$-$C_6$ alkyl, $C_1$-$C_6$ fluoroalkyl and —$C(O)NR^aR^b$, where $R^a$ and $R^b$ are independently selected from hydrogen and $C_1$-$C_6$ alkyl, and any of the aforementioned $R^{16}$, $R^{17}$ or $R^{18}$ groups may be optionally substituted by one or more halogen atoms; and (b) aryl, heteroaryl, $C_1$-$C_3$ alkylaryl and —$C_1$-$C_3$ alkylheteroaryl, said aryl and heteroaryl groups being optionally substituted;

or $R^{18}$, $R^{19}$ and $R^{20}$ may independently represent hydrogen.

Optional substituents for phenyl, aryl and heteroaryl groups within the definitions of $R^1$, $R^2$, $R^3$, $R^{4a}$, $R^{4b}$, $R^5$, $R^6$, $R^7$, $R^{16}$, $R^{17}$, $R^{18}$, $R^{19}$ and $R^{20}$ are suitably selected from hydroxyl, halo, cyano, —$(CHR^{26})_q$—$OPO(OR^{19})(OR^{20})$ wherein q represents 0 or 1 (said group not being substituted by another $R^{19}$ or $R^{20}$ containing group), $C_1$-$C_6$ alkoxy or $C_1$-$C_6$ fluoroalkoxy, e.g. $C_1$-$C_3$ alkoxy or $C_1$-$C_3$ fluoroalkoxy such as methoxy, ethoxy or trifluoromethoxy, $C_1$-$C_6$ alkyl or $C_1$-$C_6$ fluoroalkyl, e.g. $C_1$-$C_3$ alkyl or $C_1$-$C_3$ fluoroalkyl such as methyl or trifluoromethyl, and —$C(O)NR^aR^b$, where $R^a$ and $R^b$ are independently selected from hydrogen and $C_1$-$C_6$ alkyl e.g. $C_1$-$C_3$ alkyl such as methyl; and also when two adjacent hydroxyl substituents are present they may optionally be connected by a methylene group to form an acetal. Another possible optional substituent is —$SF_5$. Said aryl and heteroaryl groups, if substituted, may be substituted by 1, 2 or 3, preferably 1 or 2, more preferably 1 substituent.

Optional substituents for the $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —$C_1$-$C_3$ alkyl-$C_3$-$C_{10}$ cycloalkyl, —$C_1$-$C_3$ alkyl-$C_5$-$C_{10}$ cycloalkenyl, —$C_1$-$C_3$ alkylheterocyclyl or heterocyclic ring groups of $R^5$, $R^6$, $R^7$, $R^{16}$, $R^{17}$, $R^{18}$, $R^{19}$ and $R^{20}$ include substituents selected from cyano, —$OPO(OR^{19})(OR^{20})$ (said group not being substituted by another $R^{19}$ or $R^{20}$ containing group), $C_1$-$C_6$ alkoxy or $C_1$-$C_6$ fluoroalkoxy, e.g. $C_1$-$C_3$ alkoxy or $C_1$-$C_3$ fluoroalkoxy such as methoxy, ethoxy or trifluoromethoxy, $C_1$-$C_6$ alkyl or $C_1$-$C_6$ fluoroalkyl, e.g. $C_1$-$C_3$ alkyl or $C_1$-$C_3$ fluoroalkyl such as methyl or trifluoromethyl, and —$C(O)NR^aR^b$, where $R^a$ and $R^b$ are independently selected from hydrogen and $C_1$-$C_6$ alkyl e.g. $C_1$-$C_3$ alkyl such as methyl. Optional substituents for the groups $R^5$, $R^6$ and $R^7$ also include one or more (e.g. 1, 2, or 3) halogen atoms e.g. F or Cl atoms (especially F atoms).

$R^{16}$ preferably represents $C_1$-$C_6$ alkyl or $C_3$-$C_{10}$ cycloalkyl in which either of the aforementioned groups may be optionally substituted (and is preferably substituted) by a group selected from —$OPO(OR^{19})(OR^{20})$ and —$(O(CH_2)_z)_rOR^{24}$, where each z, which may be the same or different, represents 2 or 3, r represents an integer selected from 1 to 20, e.g. 7 to 12, and $R^{24}$ is hydrogen, $C_1$-$C_3$ alkyl or —$PO(OR^{19})(OR^{20})$.

Alternatively, $R^{16}$ preferably represents phenyl optionally substituted (and is preferably substituted) by —$(CHR^{26})_q$—$OPO(OR^{19})(OR^{20})$ wherein q represents 0 or 1.

$R^{17}$ preferably represents $C_1$-$C_6$ alkyl e.g. methyl. $R^{18}$ preferably represents $C_1$-$C_6$ alkyl e.g. methyl. Alternatively, $R^{17}$ and $R^{18}$ together with the N to which they are attached may form a 5- or 6-membered heterocyclic ring optionally containing a further heteroatom selected from O, S and $NR^{25a}$ where $R^{25a}$ is hydrogen, $C_1$-$C_6$ alkyl, —$CH_2$—$OPO(OR^{19})(OR^{20})$ or a 5- or 6-membered heterocyclic ring.

$R^{19}$ is preferably hydrogen, methyl or ethyl, especially hydrogen.

$R^{20}$ is preferably hydrogen, methyl or ethyl, especially hydrogen.

$R^{25a}$ is preferably hydrogen or methyl.

$R^{25b}$ is preferably absent.

$R^{26}$ is preferably hydrogen or methyl, more preferably methyl.

In one embodiment q represents 0. In another embodiment q represents 1.

In one embodiment one of $R^{4a}$ and $R^{4b}$ represents a prodrug derivative group as defined above.

In another embodiment both of $R^{4a}$ and $R^{4b}$ represent a prodrug group as defined above. When only one of $R^{4a}$ and $R^{4b}$ represents a prodrug derivative group as defined above the other of $R^{4a}$ and $R^{4b}$ is preferably hydrogen.

In one embodiment both of $R^{4a}$ and $R^{4b}$ are independently selected from —$C(O)R^{16}$, —$SO_2NH_2$, —$PO(OR^{19})(OR^{20})$, —$CHR^{26}$—$OPO(OR^{19})(OR^{20})$ where $R^{26}$ is hydrogen or $C_1$-$C_6$ alkyl, and —$C(O)NR^{17}R^{18}$. In a further embodiment one of $R^{4a}$ and $R^{4b}$ is selected from —$C(O)R^{16}$, —$SO_2NH_2$, —$PO(OR^{19})(OR^{20})$, —$CHR^{26}$—$OPO(OR^{19})(OR^{20})$ where $R^{26}$ is hydrogen or $C_1$-$C_6$ alkyl, and —$C(O)NR^{17}R^{18}$; and the other of $R^{4a}$ and $R^{4b}$ is hydrogen.

One or both of $R^{4a}$ and $R^{4b}$ are preferably independently selected from —$C(O)R^{16}$.

When the prodrug is a carboxylate ester prodrug, e.g. wherein one or both of $R^{4a}$ and $R^{4b}$ are —$C(O)R^{16}$, the carbon atom adjacent to the C(O) moiety is preferably a tertiary or quaternary carbon atom.

Specific examples of prodrug derivatives include compounds of formula (I) wherein one or both of $R^{4a}$ and $R^{4b}$ are independently selected from —$SO_2NH_2$, —$PO(OH)_2$, —$CH_2$—$PO(OH)_2$, —$PO(OEt)_2$, —$CON$-$(4$-N-piperidinyl-piperidine), —$COt$-butyl, —$CO$isopropyl, —$CON$—(N-methyl)piperazine, —$CON$-piperazine, —$CON(CH_3)_2$, $COCH_3$, —$CO$—$(CH_2)_2$—$OMe$, —$CO(CH_2)_2$—$(O(CH_2)_2)_p$ OMe where p is 1 to 12, —$CO$—$CMe_2$-$CH_2$—$(O(CH_2)_3)_p$ OMe where p is 1 to 12, —$CO$—$CMe_2$-$CH_2$—$(O(CH_2)_2)_p$ O—$PO(OH)_2$ where p is 1 to 12, —$CO$—$CMe_2$-$CH_2$—$(O(CH_2)_2)_pO$—$PO(OH)_2$ where p is 1 to 12, —$CO$-(4-phosphonoxymethylbenzene) and —$CO$-(4-phosphonoxymethylcyclohexane); wherein when only one of $R^{4a}$ and $R^{4b}$ represents a prodrug derivative group as defined above the other of $R^{4a}$ and $R^{4b}$ is hydrogen. A group of specific examples of prodrug derivatives include compounds of formula (I) wherein $R^{4a}$ and $R^{4b}$ are independently selected from —$SO_2NH_2$, —$PO(OH)_2$, —$CON$-(4-N-piperidinyl-piperidine), —$COt$-butyl, —$CO$isopropyl, —$CON$—(N-methyl)piperazine, —$CON(CH_3)_2$ and $COCH_3$.

While the preferred groups for each variable have generally been listed above separately for each variable, preferred compounds of this invention include those in which several or each variable in formula (I) is selected from the preferred, more preferred or particularly listed groups for each variable. Therefore, this invention is intended to include all combinations of preferred, more preferred and particularly listed groups.

The molecular weight of the compounds of the invention is preferably less than 2000, more preferably less than 1000, even more preferably less than 800, for example less than 600.

Particular compounds of the invention include the following:

$N^2,N^2,N^5,N^5$-tetraethyl-1-(4-fluorophenyl)-3,4-dihydroxy-1H-pyrrole-2,5-dicarboxamide;

1-(4-ethoxyphenyl)-$N^2,N^2,N^5,N^5$-tetraethyl-3,4-dihydroxy-1H-pyrrole-2,5-dicarboxamide;

$N^2,N^2,N^5,N^5$-tetraethyl-3,4-dihydroxy-1-(4-methoxyphenyl)-1H-pyrrole-2,5-dicarboxamide;

(3,4-dihydroxy-1-(4-methoxyphenyl)-1H-pyrrole-2,5-diyl)bis(morpholinomethanone);

3,4-dihydroxy-1-(4-methoxyphenyl)-$N^2,N^2,N^5,N^5$-tetramethyl-1H-pyrrole-2,5-dicarboxamide;

(1-(4-fluorophenyl)-3,4-dihydroxy-1H-pyrrole-2,5-diyl)bis(morpholinomethanone);

1-(4-fluorophenyl)-3,4-dihydroxy-$N^2,N^5$-dimethyl-$N^2,N^5$-diphenyl-1H-pyrrole-2,5-dicarboxamide;

1-(4-fluorophenyl)-3,4-dihydroxy-$N^2,N^2,N^5,N^5$-tetramethyl-1H-pyrrole-2,5-dicarboxamide;

di-tert-butyl 4,4'-(1-(4-fluorophenyl)-3,4-dihydroxy-1H-pyrrole-2,5-dicarbonyl)bis(piperazine-1-carboxylate);

1,1'-(4,4'-(1-(4-fluorophenyl)-3,4-dihydroxy-1H-pyrrole-2,5-dicarbonyl)bis(piperazine-4,1-diyl))diethanone;

(1-(4-fluorophenyl)-3,4-dihydroxy-1H-pyrrole-2,5-diyl)bis(piperidin-1-ylmethanone);

ethyl 5-(dimethylcarbamoyl)-3,4-dihydroxy-1-(4-methoxyphenyl)-1H-pyrrole-2-carboxylate;

1-(4-fluorophenyl)-3,4-dihydroxy-$N^2,N^5$-diisopropyl-$N^2,N^5$-dimethyl-1H-pyrrole-2,5-dicarboxamide;

$N^2,N^5$-dibenzyl-1-(4-fluorophenyl)-3,4-dihydroxy-$N^2,N^5$-dimethyl-1H-pyrrole-2,5-dicarboxamide;

di-tert-butyl 4,4'-(3,4-dihydroxy-1-(4-methoxyphenyl)-1H-pyrrole-2,5-dicarbonyl)bis(piperazine-1-carboxylate);

(3,4-dihydroxy-1-(4-methoxyphenyl)-1H-pyrrole-2,5-diyl) bis(piperazin-1-ylmethanone);

1-(4-fluorophenyl)-3,4-dihydroxy-$N^2,N^2,N^5,N^5$-tetraisopropyl-1H-pyrrole-2,5-dicarboxamide;

(3,4-dihydroxy-1-(4-methoxyphenyl)-1H-pyrrole-2,5-diyl) bis(piperidin-1-ylmethanone);

3,4-dihydroxy-1-(2-methoxyphenyl)-$N^2,N^2,N^5,N^5$-tetramethyl-1H-pyrrole-2,5-dicarboxamide;

(3,4-dihydroxy-1-(2-methoxyphenyl)-1H-pyrrole-2,5-diyl) bis(morpholinomethanone);

1-(4-ethoxyphenyl)-3,4-dihydroxy-$N^2,N^2,N^5,N^5$-tetramethyl-1H-pyrrole-2,5-dicarboxamide;

(1-(4-ethoxyphenyl)-3,4-dihydroxy-1H-pyrrole-2,5-diyl)bis(morpholinomethanone);

(3,4-dihydroxy-1-(4-(trifluoromethyl)phenyl)-1H-pyrrole-2,5-diyl)bis(morpholinomethanone);

$N^2$-ethyl-3,4-dihydroxy-1-(4-methoxyphenyl)-$N^5,N^5$-dimethyl-1H-pyrrole-2,5-dicarboxamide;

3,4-dihydroxy-1-(4-methoxyphenyl)-N,N-dimethyl-5-(piperidine-1-carbonyl)-1H-pyrrole-2-carboxamide;

3,4-dihydroxy-1-(4-methoxyphenyl)-N,N-dimethyl-5-(morpholine-4-carbonyl)-1H-pyrrole-2-carboxamide;

3,4-dihydroxy-1-(4-methoxyphenyl)-N,N-dimethyl-5-(4-methylpiperazine-1-carbonyl)-1H-pyrrole-2-carboxamide;

3,4-dihydroxy-$N^2, N^2,N^5, N^5$-tetramethyl-1-(4-(trifluoromethyl)phenyl)-1H-pyrrole-2,5-dicarboxamide;

1-(4-(dimethylcarbamoyl)phenyl)-3,4-dihydroxy-$N^2, N^2, N^5, N^5$-tetramethyl-1H-pyrrole-2,5-dicarboxamide;

tert-butyl (5-(dimethylcarbamoyl)-3,4-dihydroxy-1-(4-methoxyphenyl)-1H-pyrrol-2-yl)sulfonylcarbamate;

5-cyano-3,4-dihydroxy-1-(4-methoxyphenyl)-N,N-dimethyl-1H-pyrrole-2-carboxamide;

ethyl 5-(dimethylcarbamoyl)-1-(4-fluorophenyl)-3,4-dihydroxy-1H-pyrrole-2-carboxylate;

1,1'-(4,4'-(3,4-dihydroxy-1-(4-methoxyphenyl)-1H-pyrrole-2,5-dicarbonyl)bis(piperazine-4,1-diyl))diethanone;

3,4-dihydroxy-1-(4-methoxyphenyl)-1H-pyrrole-2,5-dicarbonitrile;

isopropyl 5-(dimethylcarbamoyl)-3,4-dihydroxy-1-(4-methoxyphenyl)-1H-pyrrole-2-carboxylate;

tert-butyl 5-(dimethylcarbamoyl)-3,4-dihydroxy-1-(4-methoxyphenyl)-1H-pyrrole-2-carboxylate;

ethyl 3,4-dihydroxy-1-(4-methoxyphenyl)-5-(4-methylpiperazine-1-carbonyl)-1H-pyrrole-2-carboxylate;

ethyl 5-(dibutylcarbamoyl)-3,4-dihydroxy-1-(4-methoxyphenyl)-1H-pyrrole-2-carboxylate;

ethyl 5-cyano-1-(4-fluorophenyl)-3,4-dihydroxy-1H-pyrrole-2-carboxylate;

ethyl 3,4-dihydroxy-1-(4-methoxyphenyl)-5-(morpholine-4-carbonyl)-1H-pyrrole-2-carboxylate;

ethyl 5-(diethylcarbamoyl)-3,4-dihydroxy-1-(4-methoxyphenyl)-1H-pyrrole-2-carboxylate;

ethyl 5-(dimethylcarbamoyl)-3,4-dihydroxy-1-(4-iodophenyl)-1H-pyrrole-2-carboxylate;

ethyl 5-(dimethylcarbamoyl)-3,4-dihydroxy-1-(3-iodo-4-methoxyphenyl)-1H-pyrrole-2-carboxylate;

3,4-bis(benzyloxy)-1-(4-ethoxyphenyl)-$N^2, N^2, N^5, N^5$-tetraethyl-1H-pyrrole-2,5-dicarboxamide;

3,4-bis(benzyloxy)-$N^2, N^2, N^5, N^5$-tetraethyl-1-(4-methoxyphenyl)-1H-pyrrole-2,5-dicarboxamide;

3,4-bis(benzyloxy)-1-(4-methoxyphenyl)-$N^2, N^2,N^5, N^5$-tetramethyl-1H-pyrrole-2,5-dicarboxamide;

di-tert-butyl 4,4'-(3,4-bis(benzyloxy)-1-(4-methoxyphenyl)-1H-pyrrole-2,5-dicarbonyl)bis(piperazine-1-carboxylate);

(3,4-bis(benzyloxy)-1-(4-methoxyphenyl)-1H-pyrrole-2,5-diyl)bis(piperidin-1-ylmethanone);

3,4-bis(benzyloxy)-1-(2-methoxyphenyl)-$N^2, N^2, N^5, N^5$-tetramethyl-1H-pyrrole-2,5-dicarboxamide;

(3,4-bis(benzyloxy)-1-(2-methoxyphenyl)-1H-pyrrole-2,5-diyl)bis(morpholinomethanone);

3,4-bis(benzyloxy)-1-(4-ethoxyphenyl)-$N^2, N^2, N^5, N^5$-tetramethyl-1H-pyrrole-2,5-dicarboxamide;

(3,4-bis(benzyloxy)-1-(4-ethoxyphenyl)-1H-pyrrole-2,5-diyl)bis(morpholinomethanone);

3,4-bis(benzyloxy)-$N^2, N^2,N^5, N^5$-tetramethyl-1-(4-(trifluoromethyl)phenyl)-1H-pyrrole-2,5-dicarboxamide;

3,4-bis(benzyloxy)-$N^2$-ethyl-1-(4-methoxyphenyl)-$N^5,N^5$-dimethyl-1H-pyrrole-2,5-dicarboxamide;

3,4-bis(benzyloxy)-1-(4-methoxyphenyl)-N,N-dimethyl-5-(4-methylpiperazine-1-carbonyl)-1H-pyrrole-2-carboxamide;

3,4-bis(benzyloxy)-1-(4-methoxyphenyl)-N,N-dimethyl-5-(piperidine-1-carbonyl)-1H-pyrrole-2-carboxamide;

3,4-bis(benzyloxy)-1-(4-methoxyphenyl)-N,N-dimethyl-5-(morpholine-4-carbonyl)-1H-pyrrole-2-carboxamide;

1,1'-(4,4'-(3,4-bis(benzyloxy)-1-(4-methoxyphenyl)-1H-pyrrole-2,5-dicarbonyl)bis(piperazine-4,1-diyl))diethanone;

ethyl 3,4-bis(benzyloxy)-5-cyano-1-(4-fluorophenyl)-1H-pyrrole-2-carboxylate;

3,4-bis(benzyloxy)-5-cyano-1-(4-fluorophenyl)-N,N-dimethyl-1H-pyrrole-2-carboxamide;

ethyl 3,4-bis(benzyloxy)-5-(dimethylcarbamoyl)-1-(4-iodophenyl)-1H-pyrrole-2-carboxylate;

3,4-bis(benzyloxy)-1-(4-methoxyphenyl)-1H-pyrrole-2,5-dicarboxamide;

3,4-dihydroxy-1-(4-methoxyphenyl)-1H-pyrrole-2,5-dicarboxamide;

3,4-bis(benzyloxy)-$N^2,N^5$-diethyl-1-(4-methoxyphenyl)-1H-pyrrole-2,5-dicarboxamide;

3,4-bis(benzyloxy)-1-(4-fluorophenyl)-1H-pyrrole-2,5-dicarboxamide;

1-(4-fluorophenyl)-3,4-dihydroxy-1H-pyrrole-2,5-dicarboxamide;

1-(4-ethoxyphenyl)-3,4-dihydroxy-1H-pyrrole-2,5-dicarboxamide;

1-(4-ethoxyphenyl)-$N^2,N^5$-diethyl-3,4-dihydroxy-1H-pyrrole-2,5-dicarboxamide;

ethyl 3,4-bis(benzyloxy)-5-carbamoyl-1-(4-methoxyphenyl)-1H-pyrrole-2-carboxylate;

ethyl 5-carbamoyl-3,4-dihydroxy-1-(4-methoxyphenyl)-1H-pyrrole-2-carboxylate;

ethyl 3,4-bis(benzyloxy)-5-(2-methoxyphenyl)-1-(4-methoxyphenyl)-1H-pyrrole-2-carboxylate;

ethyl 3,4-bis(benzyloxy)-1-(4-methoxyphenyl)-5-(pyridin-2-yl)-1H-pyrrole-2-carboxylate;

ethyl 3,4-dihydroxy-1-(4-methoxyphenyl)-5-(pyridin-2-yl)-1H-pyrrole-2-carboxylate;

ethyl 3,4-bis(benzyloxy)-1-(4-methoxyphenyl)-5-(pyridin-4-yl)-1H-pyrrole-2-carboxylate;

ethyl 3,4-bis(benzyloxy)-1-(4-methoxyphenyl)-5-(pyridin-3-yl)-1H-pyrrole-2-carboxylate;

ethyl 5-(4-ethylthiazol-2-yl)-3,4-dihydroxy-1-(4-methoxyphenyl)-1H-pyrrole-2-carboxylate;

ethyl 3,4-bis(benzyloxy)-1-(4-methoxyphenyl)-5-(5-methyl-1,3,4-oxadiazol-2-yl)-1H-pyrrole-2-carboxylate;

ethyl 3,4-bis(benzyloxy)-5-(5-ethyl-1,3,4-oxadiazol-2-yl)-1-(4-methoxyphenyl)-1H-pyrrole-2-carboxylate;

ethyl 3,4-dihydroxy-1-(4-methoxyphenyl)-5-(2H-tetrazol-5-yl)-1H-pyrrole-2-carboxylate;

ethyl 3,4-bis(benzyloxy)-1-(4-methoxyphenyl)-5-(2H-tetrazol-5-yl)-1H-pyrrole-2-carboxylate;
diethyl 3,4-dihydroxy-1-(4-methoxyphenyl)-1H-pyrrole-2,5-dicarboxylate (this compound is not novel per se);
diethyl 3,4-dihydroxy-1-phenyl-1H-pyrrole-2,5-dicarboxylate (this compound is not novel per se);
diethyl 1-(4-fluorophenyl)-3,4-dihydroxy-1H-pyrrole-2,5-dicarboxylate;
diethyl 3,4-dihydroxy-1-(3-methoxyphenyl)-1H-pyrrole-2,5-dicarboxylate;
diethyl 3,4-dihydroxy-1-(4-(trifluoromethoxy)phenyl)-1H-pyrrole-2,5-dicarboxylate;
diethyl 3,4-dihydroxy-1-(4-isopropylphenyl)-1H-pyrrole-2,5-dicarboxylate;
diethyl 3,4-dihydroxy-1-(4-phenoxyphenyl)-1H-pyrrole-2,5-dicarboxylate;
diethyl 1-(4-ethoxyphenyl)-3,4-dihydroxy-1H-pyrrole-2,5-dicarboxylate;
diethyl 1-(4-ethylphenyl)-3,4-dihydroxy-1H-pyrrole-2,5-dicarboxylate;
diethyl 3,4-dihydroxy-1-(p-tolyl)-1H-pyrrole-2,5-dicarboxylate;
diethyl 1-(3,4-dimethoxyphenyl)-3,4-dihydroxy-1H-pyrrole-2,5-dicarboxylate;
diethyl 1-(4-chlorophenyl)-3,4-dihydroxy-1H-pyrrole-2,5-dicarboxylate;
diethyl 3,4-dihydroxy-1-(4-(trifluoromethyl)phenyl)-1H-pyrrole-2,5-dicarboxylate;
diethyl 3,4-dihydroxy-1-(3,4,5-trimethoxyphenyl)-1H-pyrrole-2,5-dicarboxylate;
diethyl 1-(2,4-dimethoxyphenyl)-3,4-dihydroxy-1H-pyrrole-2,5-dicarboxylate;
diethyl 3,4-dihydroxy-1-(4-propoxyphenyl)-1H-pyrrole-2,5-dicarboxylate;
diethyl 1-(4-ethoxy-3,5-difluorophenyl)-3,4-dihydroxy-1H-pyrrole-2,5-dicarboxylate;
diethyl 3,4-dihydroxy-1-(3-phenoxyphenyl)-1H-pyrrole-2,5-dicarboxylate;
diethyl 1-(benzo[d][1,3]dioxol-5-yl)-3,4-dihydroxy-1H-pyrrole-2,5-dicarboxylate;
diisopropyl 3,4-dihydroxy-1-(4-methoxyphenyl)-1H-pyrrole-2,5-dicarboxylate;
2-ethyl 5-isopropyl 3,4-dihydroxy-1-(4-methoxyphenyl)-1H-pyrrole-2,5-dicarboxylate;
di-tert-butyl 3,4-dihydroxy-1-(4-methoxyphenyl)-1H-pyrrole-2,5-dicarboxylate;
diethyl 3,4-dihydroxy-1-(2-methoxyphenyl)-1H-pyrrole-2,5-dicarboxylate;
diethyl 1-(4-cyanophenyl)-3,4-dihydroxy-1H-pyrrole-2,5-dicarboxylate;
diethyl 1-(4-fluorophenyl)-3-hydroxy-4-(2-hydroxyethoxy)-1H-pyrrole-2,5-dicarboxylate;
diethyl 3-hydroxy-4-(2-hydroxyethoxy)-1-(4-methoxyphenyl)-1H-pyrrole-2,5-dicarboxylate;
diethyl 3-(2-(tert-butoxy)-2-oxoethoxy)-1-(4-fluorophenyl)-4-hydroxy-1H-pyrrole-2,5-dicarboxylate;
diethyl 3-(benzyloxy)-4-(2-(tert-butoxy)-2-oxoethoxy)-1-(4-methoxyphenyl)-1H-pyrrole-2,5-dicarboxylate;
diethyl 3-(2-amino-2-oxoethoxy)-1-(4-fluorophenyl)-4-hydroxy-1H-pyrrole-2,5-dicarboxylate;
diethyl 3-(2-(tert-butoxy)-2-oxoethoxy)-4-hydroxy-1-(4-methoxyphenyl)-1H-pyrrole-2,5-dicarboxylate;
diethyl 3-(2-amino-2-oxoethoxy)-4-hydroxy-1-(4-methoxyphenyl)-1H-pyrrole-2,5-dicarboxylate;
diethyl 1-(4-(tert-butyl)phenyl)-3,4-dihydroxy-1H-pyrrole-2,5-dicarboxylate; and
diethyl 3,4-dihydroxy-1-(3-iodo-4-methoxyphenyl)-1H-pyrrole-2,5-dicarboxylate;
or a pharmaceutically acceptable prodrug derivative of any one thereof, or a pharmaceutically acceptable salt or solvate of any one thereof.

Further particular compounds of the invention include the following:
5-acetyl-3,4-dihydroxy-1-(4-methoxyphenyl)-N,N-dimethyl-1H-pyrrole-2-carboxamide;
ethyl 5-(dimethylcarbamoyl)-3,4-dihydroxy-1-(4-(2-methoxyethoxy)phenyl)-1H-pyrrole-2-carboxylate;
ethyl 3-((diethoxyphosphoryl)oxy)-5-(dimethylcarbamoyl)-4-hydroxy-1-(4-methoxyphenyl)-1H-pyrrole-2-carboxylate;
ethyl 1-(4-(2,5,8,11-tetraoxamidecan-13-yloxy)phenyl)-5-(dimethylcarbamoyl)-3,4-dihydroxy-1H-pyrrole-2-carboxylate;
ethyl 3,4-dihydroxy-1-(4-methoxyphenyl)-5-(methylcarbamoyl)-1H-pyrrole-2-carboxylate;
ethyl 5-(dimethylcarbamoyl)-3,4-dihydroxy-1-(4-hydroxyphenyl)-1H-pyrrole-2-carboxylate;
ethyl 5-(dimethylcarbamoyl)-3,4-dihydroxy-1-(4-(phosphonooxy)phenyl)-1H-pyrrole-2-carboxylate;
ethyl 5-(dimethylcarbamoyl)-3,4-dihydroxy-1-(4-(3-morpholinopropoxy)phenyl)-1H-pyrrole-2-carboxylate;
ethyl 5-(dimethylcarbamoyl)-3,4-dihydroxy-1-(4-(3-(4-methylpiperazin-1-yl)propoxy)phenyl)-1H-pyrrole-2-carboxylate;
ethyl 1-(4-(3-(diethoxyphosphoryl)propoxy)phenyl)-5-(dimethylcarbamoyl)-3,4-dihydroxy-1H-pyrrole-2-carboxylate;
(3-(4-(2-(dimethylcarbamoyl)-5-(ethoxycarbonyl)-3,4-dihydroxy-1H-pyrrol-1-yl)phenoxy)propyl)phosphonic acid;
ethyl 5-(dimethylcarbamoyl)-3,4-dihydroxy-1-(4-(3-(methylsulfonyl)propoxy)phenyl)-1H-pyrrole-2-carboxylate;
neopentyl 5-(dimethylcarbamoyl)-3,4-dihydroxy-1-(4-methoxyphenyl)-1H-pyrrole-2-carboxylate;
2,6-dimethylcyclohexyl 5-(dimethylcarbamoyl)-3,4-dihydroxy-1-(4-methoxyphenyl)-1H-pyrrole-2-carboxylate;
cyclopentyl 5-(dimethylcarbamoyl)-3,4-dihydroxy-1-(4-methoxyphenyl)-1H-pyrrole-2-carboxylate;
5-(dimethylphosphoryl)-3,4-dihydroxy-1-(4-methoxyphenyl)-N,N-dimethyl-1H-pyrrole-2-carboxamide;
diethyl 3,4-dihydroxy-1-(4-(2-methoxyethoxy)phenyl)-1H-pyrrole-2,5-dicarboxylate;
diethyl 3,4-dihydroxy-1-(4-(2-(2-(2-methoxyethoxy)ethoxy)ethoxy)phenyl)-1H-pyrrole-2,5-dicarboxylate;
diethyl 1-(4-(2,5,8,11-tetraoxamidecan-13-yloxy)phenyl)-3,4-dihydroxy-1H-pyrrole-2,5-dicarboxylate;
diethyl 3,4-dihydroxy-1-(4-(3-morpholinopropoxy)phenyl)-1H-pyrrole-2,5-dicarboxylate; and
diethyl 3,4-dihydroxy-1-(4-((4-methoxybenzyl)oxy)phenyl)-1H-pyrrole-2,5-dicarboxylate;
or a pharmaceutically acceptable prodrug derivative of any one thereof, or a pharmaceutically acceptable salt or solvate of any one thereof.

Particular prodrug derivatives of the compounds of the invention include the following:
2-(dimethylcarbamoyl)-5-(ethoxycarbonyl)-1-(4-methoxyphenyl)-1H-pyrrole-3,4-diyl diacetate;
ethyl 5-(dimethylcarbamoyl)-3,4-bis((dimethylcarbamoyl)oxy)-1-(4-methoxyphenyl)-1H-pyrrole-2-carboxylate;
2-(dimethylcarbamoyl)-5-(ethoxycarbonyl)-1-(4-methoxyphenyl)-1H-pyrrole-3,4-diyl bis(4-methylpiperazine-1-carboxylate);

2-(dimethylcarbamoyl)-5-(ethoxycarbonyl)-1-(4-methoxyphenyl)-1H-pyrrole-3,4-diyl bis([1,4'-bipiperidine]-1'-carboxylate);
ethyl 5-(dimethylcarbamoyl)-4-((dimethylcarbamoyl)oxy)-3-hydroxy-1-(4-methoxyphenyl)-1H-pyrrole-2-carboxylate;
2-(dimethylcarbamoyl)-5-(ethoxycarbonyl)-1-(4-methoxyphenyl)-1H-pyrrole-3,4-diyl bis(2-methylpropanoate);
2-(dimethylcarbamoyl)-5-(ethoxycarbonyl)-1-(4-methoxyphenyl)-1H-pyrrole-3,4-diyl bis(2,2-dimethylpropanoate);
ethyl 5-(dimethylcarbamoyl)-3-hydroxy-1-(4-methoxyphenyl)-4-(sulfamoyloxy)-1H-pyrrole-2-carboxylate;
ethyl 5-(dimethylcarbamoyl)-3-hydroxy-1-(4-methoxyphenyl)-4-(phosphonooxy)-1H-pyrrole-2-carboxylate; and
2-(dimethylcarbamoyl)-5-(ethoxycarbonyl)-4-hydroxy-1-(4-methoxyphenyl)-1H-pyrrol-3-yl [1,4'-bipiperidine]-1'-carboxylate;
or a pharmaceutically acceptable salt or solvate of any one thereof.

Further particular prodrug derivatives of the compounds of the invention include the following:
ethyl 3,4-bis((diethoxyphosphoryl)oxy)-5-(dimethylcarbamoyl)-1-(4-methoxyphenyl)-1H-pyrrole-2-carboxylate;
ethyl 3-((diethoxyphosphoryl)oxy)-5-(dimethylcarbamoyl)-4-hydroxy-1-(4-methoxyphenyl)-1H-pyrrole-2-carboxylate;
ethyl 4-((diethoxyphosphoryl)oxy)-5-(dimethylcarbamoyl)-3-hydroxy-1-(4-methoxyphenyl)-1H-pyrrole-2-carboxylate;
2-(dimethylcarbamoyl)-5-(ethoxycarbonyl)-1-(4-(2-(2-(2-methoxyethoxy)ethoxy)ethoxy)phenyl)-1H-pyrrole-3,4-diyl bis(2-methylpropanoate);
2-(dimethylcarbamoyl)-5-(ethoxycarbonyl)-1-(4-methoxyphenyl)-1H-pyrrole-3,4-diyl bis(3-methoxypropanoate);
2-(dimethylcarbamoyl)-5-(ethoxycarbonyl)-1-(4-methoxyphenyl)-1H-pyrrole-3,4-diyl bis(3-(2-methoxyethoxy)propanoate);
2-(dimethylcarbamoyl)-5-(ethoxycarbonyl)-1-(4-methoxyphenyl)-1H-pyrrole-3,4-diyl bis(3-(2-methoxyethoxy)-2,2-dimethylpropanoate);
ethyl 5-(dimethylcarbamoyl)-3-hydroxy-1-(4-methoxyphenyl)-4-((phosphonooxy)methoxy)-1H-pyrrole-2-carboxylate;
2-(dimethylcarbamoyl)-5-(ethoxycarbonyl)-1-(4-methoxyphenyl)-1H-pyrrole-3,4-diyl bis(3-(2-(2-methoxyethoxy)ethoxy)-2,2-dimethylpropanoate);
2,5-bis(dimethylcarbamoyl)-1-(4-methoxyphenyl)-1H-pyrrole-3,4-diyl bis(2-methylpropanoate);
ethyl 5-(dimethylcarbamoyl)-4-hydroxy-1-(4-methoxyphenyl)-3-((phosphonooxy)methoxy)-1H-pyrrole-2-carboxylate;
2-(dimethylcarbamoyl)-5-(ethoxycarbonyl)-1-(4-methoxyphenyl)-1H-pyrrole-3,4-diyl bis(2,2-dimethyl-3-(2-(2-(phosphonooxy)ethoxy)ethoxy)propanoate);
2-(dimethylcarbamoyl)-5-(ethoxycarbonyl)-1-(4-methoxyphenyl)-1H-pyrrole-3,4-diyl bis(2,2-dimethyl-3-(3-(phosphonooxy)propoxy)propanoate);
2-(dimethylcarbamoyl)-5-(ethoxycarbonyl)-1-(4-methoxyphenyl)-1H-pyrrole-3,4-diyl bis(25,25-dimethyl-2,5,8,11,14,17,20,23-octaoxahexacosan-26-oate);
2,5-bis(dimethylcarbamoyl)-1-(4-methoxyphenyl)-1H-pyrrole-3,4-diyl bis(25,25-dimethyl-2,5,8,11,14,17,20,23-octaoxahexacosan-26-oate);
2,5-bis(dimethylcarbamoyl)-1-(4-methoxyphenyl)-1H-pyrrole-3,4-diyl bis(2,2-dimethyl-3-(2-(2-(phosphonooxy)ethoxy)ethoxy)propanoate);
2-(dimethylcarbamoyl)-5-(isopropoxycarbonyl)-1-(4-methoxyphenyl)-1H-pyrrole-3,4-diyl bis(2,2-dimethyl-3-(2-(2-(phosphonooxy)ethoxy)ethoxy)propanoate);
2,5-bis(dimethylcarbamoyl)-1-(4-methoxyphenyl)-1H-pyrrole-3,4-diyl bis(piperidine-4-carboxylate);
2,5-bis(dimethylcarbamoyl)-1-(4-methoxyphenyl)-1H-pyrrole-3,4-diyl bis(4-((phosphonooxy)methyl)benzoate); and
(1R,1'R,4R,4'R)-2,5-bis(dimethylcarbamoyl)-1-(4-methoxyphenyl)-1H-pyrrole-3,4-diyl bis(4-((phosphonooxy)methyl)cyclohexanecarboxylate);
or a pharmaceutically acceptable salt or solvate of any one thereof.

Particular compound of the invention and prodrugs which may be mentioned include those designated as compounds UL1-004, UL1-005, UL1-012, UL1-024, UL1-028, UL1-035, UL1-049, UL1-070, UL1-089, UL1-098, UL1-106, UL1-109, UL1-111, UL1-114, UL1-115, UL1-116, UL1-117, UL1-118, UL1-120, UL1-121, UL1-122, UL1-124, UL1-126 and UL2-001, in Table 1 below.

Alkyl as used herein refers to straight chain or branched chain alkyl, such as, without limitation, methyl, ethyl, propyl, iso-propyl, butyl, and tert-butyl. In one embodiment alkyl refers to straight chain alkyl in another embodiment alkyl refers to branched chain alkyl. Alkenyl and alkynyl should be interpreted accordingly.

Fluoroalkyl groups are as described above for alkyl, but may have one or more hydrogen atoms replaced by fluoro. Examples of fluoroalkyl groups include —$CH_2F$, —$CHF_2$ and —$CF_3$.

Cycloalkyl as used herein refers to a cyclic alkyl group, containing 3-10 carbon atoms, optionally branched, for example cyclobutyl, cyclopentyl, cyclohexyl or cycloheptyl. A branched example is 2-methylcyclopentyl. Cycloalkenyl refers to a cyclic alkenyl group containing typically 5-10 carbon atoms, for example cyclopentyl, cyclohexenyl or cycloheptenyl. Cycloalkyl and cycloalkenyl groups may for example be monocyclic or bicyclic (including spirocyclic) but are suitably monocyclic.

Alkoxy as used herein refers to straight or branched chain alkoxy, for example methoxy, ethoxy, propoxy, butoxy. Alkoxy as used herein also extends to embodiments in which the oxygen atom is located within the alkyl chain, for example —$CH_2OCH_3$. In one embodiment the alkoxy is linked through oxygen to the remainder of the molecule. In one embodiment the disclosure relates to straight chain alkoxy.

Halo includes fluoro, chloro, bromo or iodo, in particular fluoro, chloro or bromo, especially fluoro or chloro.

Heterocyclyl as used herein includes 4- to 10-membered mono or bicyclic non-aromatic ring systems, e.g. 4- to 7-membered monocyclic saturated rings, containing up to three heteroatoms selected from N, O and S. Examples of heterocyclic rings include oxetane, tetrahydrofuran, tetrahydropyran, oxepane, oxocane, thietane, tetrahydrothiophene, tetrahydrothiopyran, thiepane, thiocane, azetidine, pyrrolidine, piperidine, azepane, azocane, [1,4]dioxane, oxazolidine, piperazine, and the like a further example is morpholine. Other examples of heterocyclic rings include the oxidised forms of the sulfur-containing rings. Thus, tetrahydrothiophene-1-oxide, tetrahydrothiophene-1,1-dioxide, tetrahydrothiopyran-1-oxide and tetrahydrothiopyran-1,1-dioxide are also considered to be heterocyclic rings.

Aryl as used herein includes $C_6$-$C_{14}$ mono or bicyclic groups having 1 or 2 rings wherein at least one ring is aromatic, including phenyl, naphthyl, 5,6,7,8-tetrahydronaphthyl and the like, such as phenyl and napthyl particularly phenyl.

Heteroaryl as used herein includes 5- to 10-membered aromatic mono or bicyclic ring systems comprising one or more, (for example 1, 2, 3 or 4) heteroatoms independently selected from O, N and S. Examples of heteroaryl groups include pyrrole, furan, thiophene, oxazole, thiazole, isothiazole, oxadiazole, tetrazole, imidazole, pyrazole, isoxazole, pyridine, pyridazine, pyrimidine, pyrazine, benzothiophene, benzofuran, 1, 2, 3-triazole and 1, 2, 4-triazole. In a bicyclic ring system the definition of heteroaryl will be satisfied if at least one ring contains a heteroatom and at least one ring is aromatic. The heteroaryl may be linked to the remainder of the molecule through a carbocyclic ring or a ring comprising a heteroatom.

Examples of salts of the compounds of formula (I) include all pharmaceutically acceptable salts prepared from pharmaceutically acceptable non-toxic bases or acids. Salts derived from bases include, for example, potassium and sodium salts and the like. Salts derived from acids, include those derived from inorganic and organic acids such as, for example, hydrochloric, methanesulfonic, sulfuric and p-toluenesulfonic acid and the like.

Examples of solvates include hydrates.

The compounds described herein may include one or more chiral centers, and the disclosure extends to include racemates, enantiomers and stereoisomers resulting therefrom. In one embodiment one enantiomeric form is present in a substantially purified form that is substantially free of the corresponding enantiomeric form.

The invention also extends to all polymorphic forms of the compounds of formula (I).

The invention also extends to isotopically-labelled compounds of formula (I) in which one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^2$H, $^3$H, $^{11}$C, $^{14}$C and $^{18}$F. Isotopically labelled compounds of formula (I) may be prepared by carrying out the synthetic methods described below and substituting an isotopically labelled reagent or intermediate for a non-isotopically labelled reagent or intermediate.

The invention extends to all tautomeric forms of the compounds illustrated herein (particularly enol-keto tautomers). For example whereas formula (I) illustrates in some embodiments (e.g. when $R^{4a}$ and/or $R^{4b}$ represents H) an enol form, the corresponding keto form is also embraced as part of the invention. The same applies to other structures herein which illustrate enol or keto forms of compounds. Similarly, the disclaimed compounds are disclaimed in all their tautomeric forms.

Compounds of the invention may be prepared by the following methods or by methods analogous thereto or by using conventional methods known to a skilled person:

A general method for preparing compounds of formula (I) in which $R^{4a}$ and $R^{4b}$ represent hydrogen is shown below in Scheme A:

Scheme A

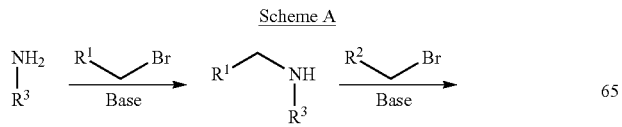

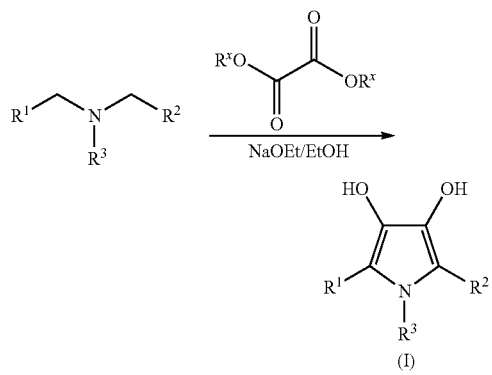

In the third step shown in Scheme A, $R^x$ typically represents $C_1$-$C_6$alkyl such as methyl or ethyl.

A method for preparing certain compounds of formula (I) in which $R^1$ is —C(O)NR$^5$R$^6$, $R^2$ is —C(O)OR$^7$ and $R^{4a}$ and $R^{4b}$ represent hydrogen is shown below in Scheme B:

Scheme B

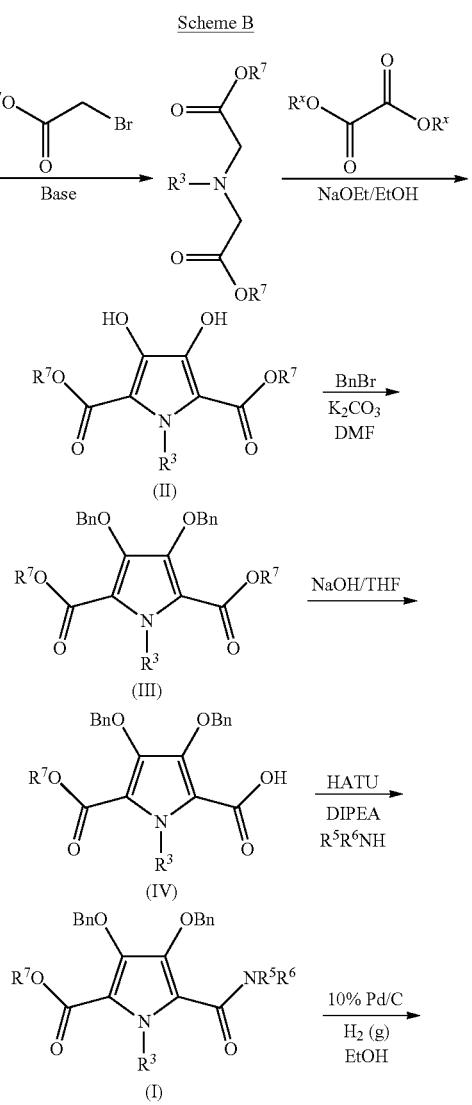

-continued

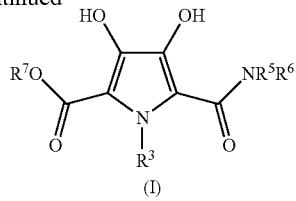
(I)

In the second step shown in Scheme B, $R^x$ typically represents $C_1$-$C_6$alkyl such as methyl or ethyl.

An alternative method for preparing certain compounds of formula (I) in which $R^1$ is —C(O)NR$^5$R$^6$, $R^2$ is —C(O)OR$^7$ and $R^{4a}$ and $R^{4b}$ represent hydrogen is shown below in Scheme C:

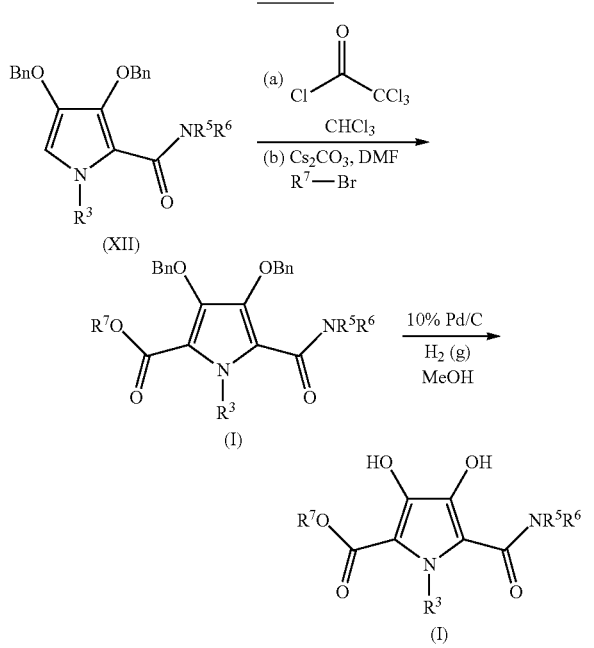

A method for preparing certain compounds of formula (I) in which $R^1$ is —C(O)NHR$^6$, $R^2$ is C(O)NR$^5$R$^6$ and $R^{4a}$ and $R^{4b}$ represent hydrogen is shown below in Scheme D:

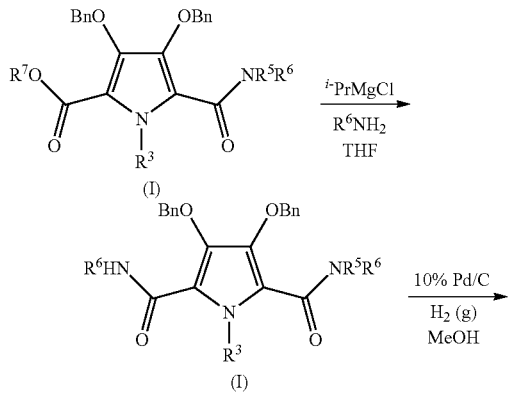

-continued

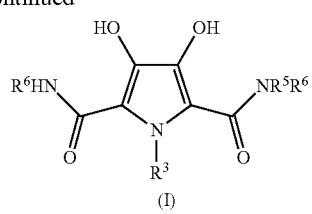
(I)

A method for preparing certain compounds of formula (I) in which $R^1$ is —C(O)NR$^5$R$^6$, $R^2$ is C(O)NR$^5$R$^6$ and $R^{4a}$ and $R^{4b}$ represent hydrogen is shown below in Scheme E:

Scheme E

A method for preparing certain compounds of formula (I) in which $R^1$ is —CN, $R^2$ is C(O)NR$^5$R$^6$ and $R^{4a}$ and $R^{4b}$ represent hydrogen is shown below in Scheme F:

Scheme F

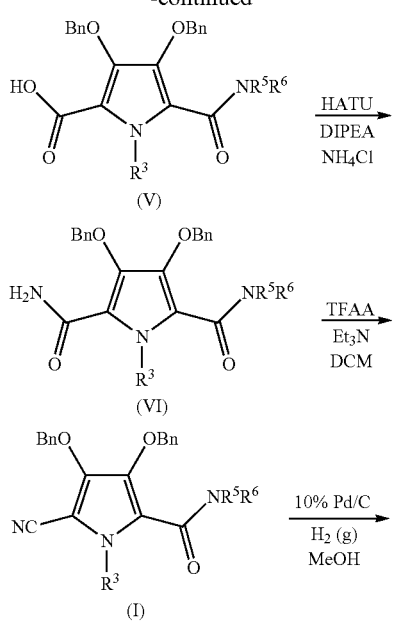

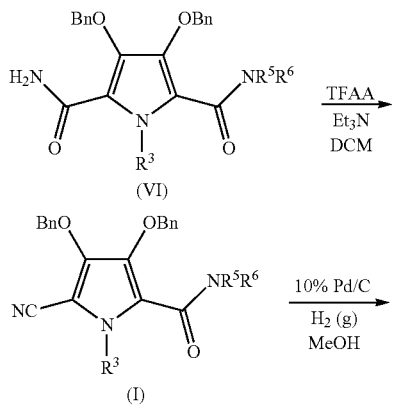

A method for preparing certain compounds of formula (I) in which $R^1$ is —C(O)OR$^7$, $R^2$ is CN and $R^{4a}$ and $R^{4b}$ represent hydrogen is shown below in Scheme G:

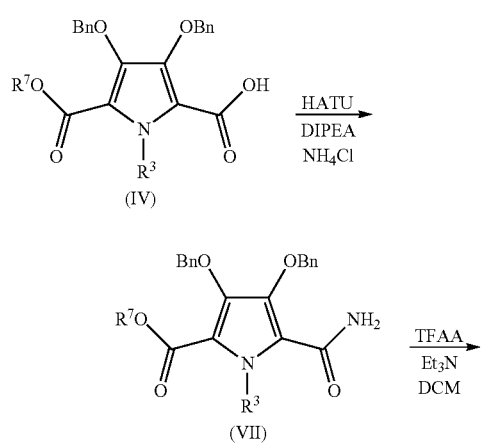

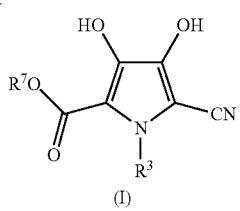

A method for preparing certain compounds of formula (I) in which $R^1$ is —SO$_2$NH—C(O)OR$^8$, $R^2$ is C(O)NR$^5$R$^6$ and $R^{4a}$ and $R^{4b}$ represent hydrogen is shown below in Scheme H:

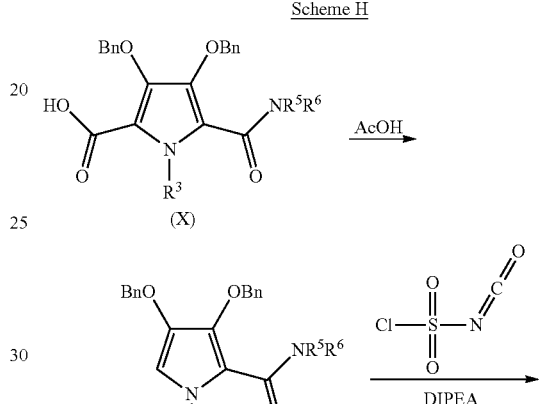

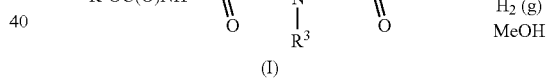

A method for preparing certain compounds of formula (I) in which $R^1$ is —CN, $R^2$ is —CN and $R^{4a}$ and $R^{4b}$ represent hydrogen is shown below in Scheme I:

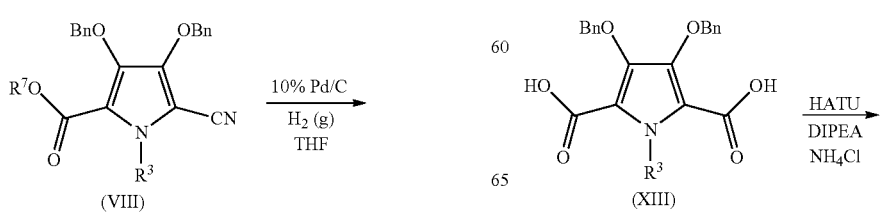

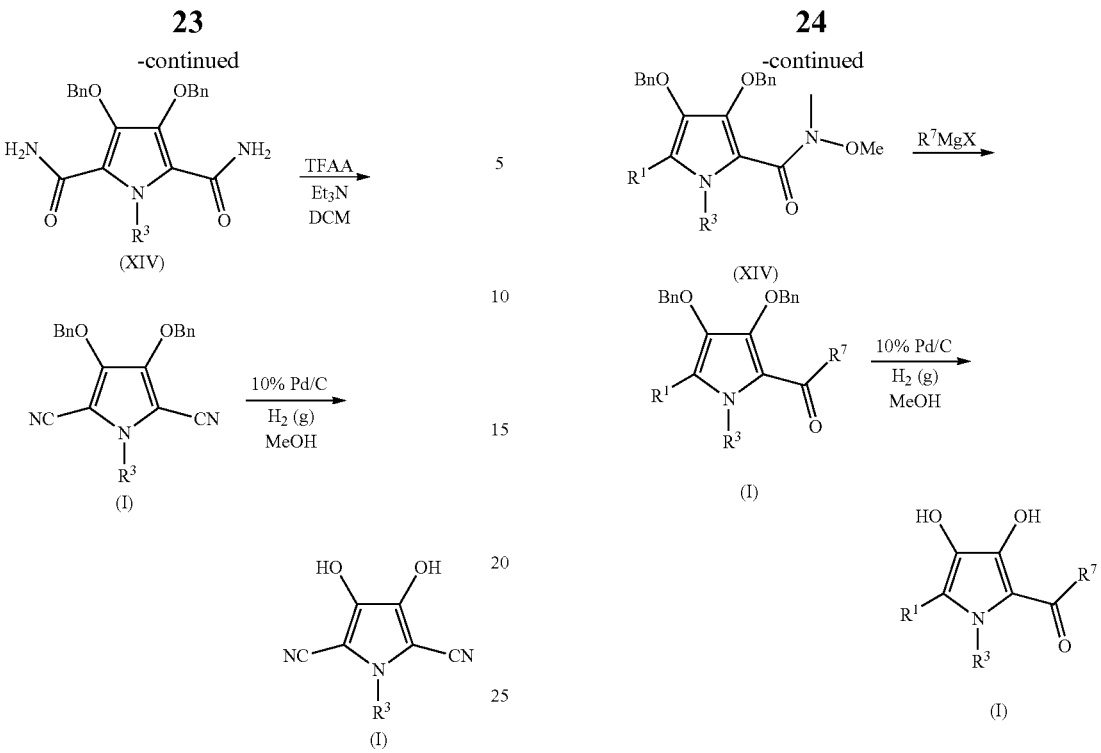

A method for preparing certain compounds of formula (I) in which $R^{4a}$ and $R^{4b}$ represent groups other than hydrogen is shown below in Scheme J:

Scheme J

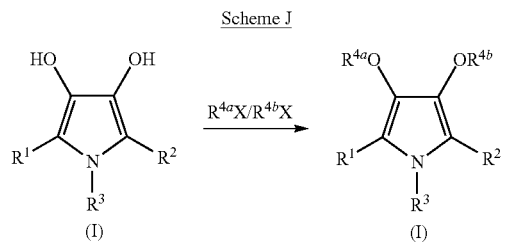

Scheme J may be adapted to convert one or both hydroxyl groups to $OR^{4a}$ and/or $OR^{4b}$ depending on the molar excess of reagent(s) employed. When $R^{4a}$ and $R^{4b}$ are different, it may be necessary to employ a protection strategy to incorporate one and then the other group. This process is also suitable for preparing prodrug derivatives of compounds of formula (I).

A method for preparing certain compounds of formula (I) where $R^2$ is —C(O)$R^7$ and $R^{4a}$ and $R^{4b}$ represent H is shown below in Scheme K:

Scheme K

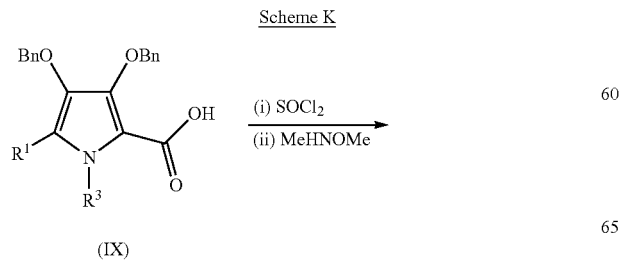

A method for preparing certain compounds of formula (I) where $R^2$ is aryl/heteroaryl is shown below in Scheme L:

Scheme L

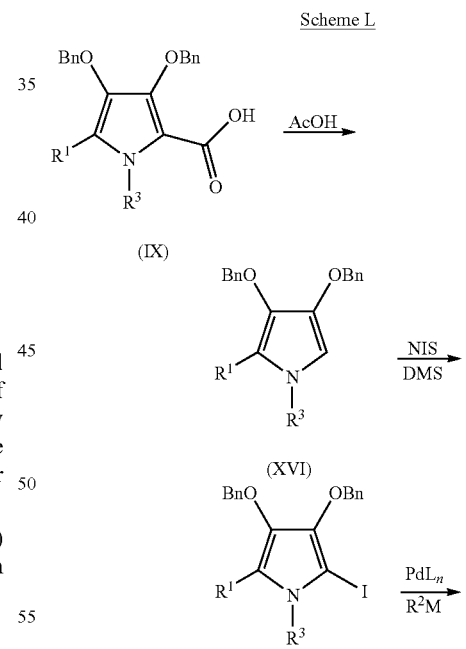

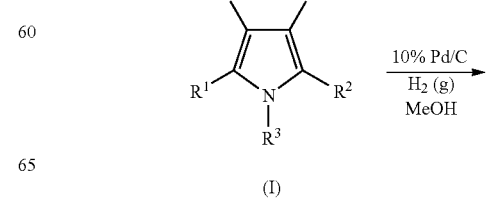

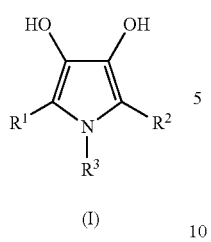

(I)

Compounds where R² is —POR²¹R²² may be prepared by reaction of a compound of formula (XVII) shown above with a compound of formula POR²¹R²²Cl, followed by deprotection.

A method for preparing certain compounds of formula (I) where R¹ is —C(O)OR⁷ and R² is a thiazole containing group and R⁴ᵃ and R⁴ᵇ represent H is shown below in Scheme M:

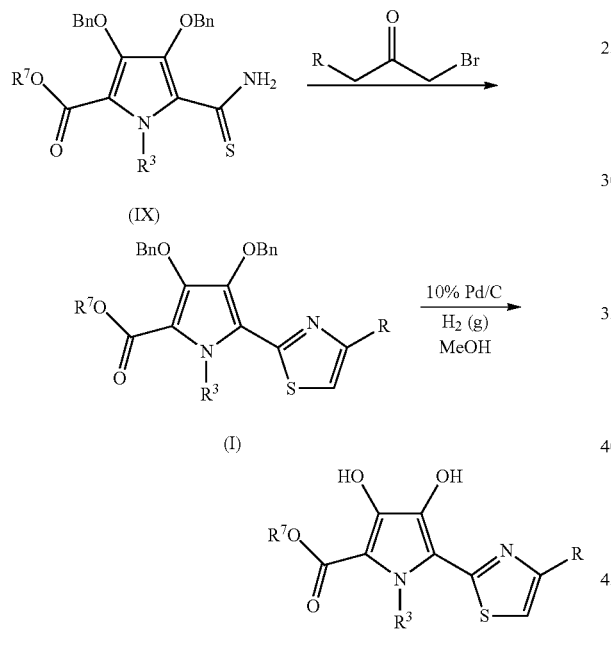

A method for preparing certain compounds of formula (I) where R¹ is —C(O)OR⁷, R² is tetrazole and R⁴ᵃ and R⁴ᵇ represent H is shown below in Scheme N:

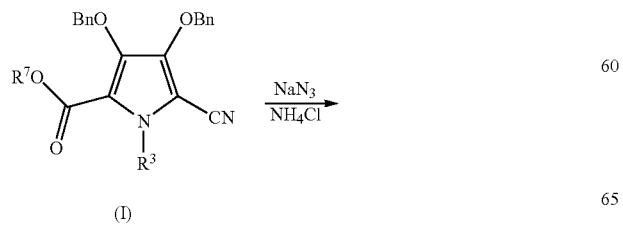

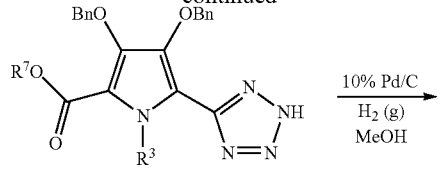

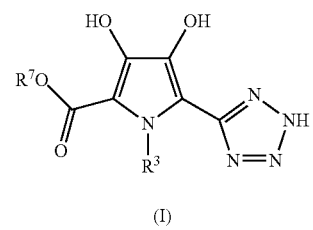

(I)

A method for preparing certain compounds of formula (I) where R¹ is —C(O)OR⁷ and R² is a oxadiazole containing group and R⁴ᵃ and R⁴ᵇ represent H is shown below in Scheme O:

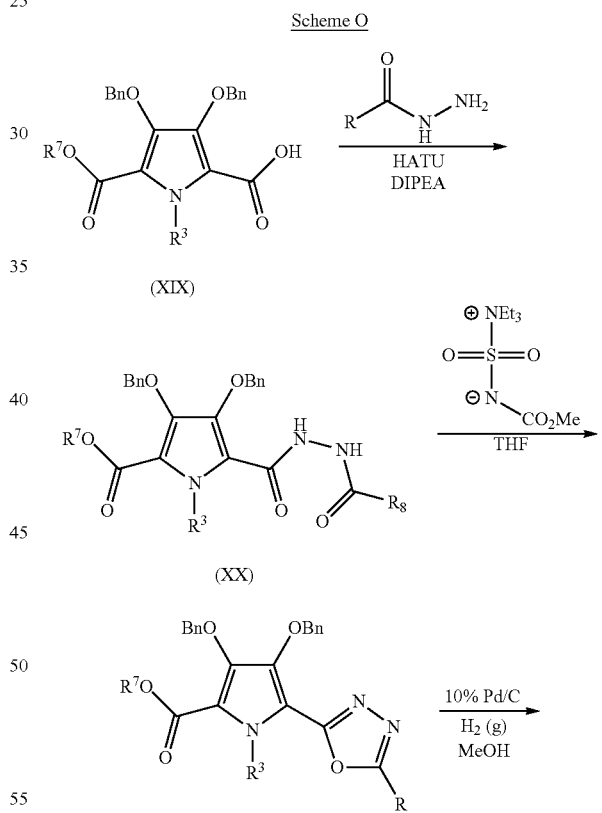

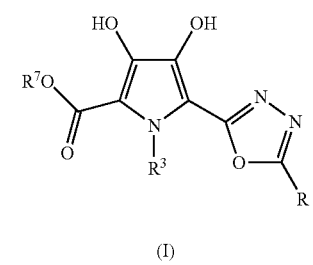

(I)

In the above Schemes A to O the general conditions for performing the reactions specified will be well known to a skilled person.

Compounds of formula (I) may be converted to different compounds of formula (I) by the above methods and/or by conventional methods.

For example the skilled person will be familiar with standard procedures for converting carboxylic acids to esters, amides, carbamates and ureas and for converting amines to amides and sulphonamides.

Thus compounds of formula (I) in which $R^1$ and/or $R^2$ represents —C(O)NHC(O)$R^7$ may be prepared by reaction of a compound of formula (I) in which $R^1$ and/or $R^2$ represents —C(O)NH$_2$ with a compound of formula $R^7$C(O)L wherein L represents a leaving group, such as halogen.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; $4^{th}$ Rev Ed., 2006, ISBN-10: 0471697540.

Any novel intermediates, such as those defined above, may be of use in the synthesis of compounds of formula (I) and are therefore also included within the scope of the invention.

Thus according to a further aspect of the invention there is provided a compound of formula (II):

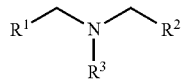

(II)

wherein $R^1$ and $R^2$ are as defined above for the compounds of formula (I), and $R^3$ is phenyl substituted by 1 or more, e.g. 1, 2 or 3, substituents (e.g. 1 substituent) independently selected from halo, cyano, hydroxyl, $C_1$-$C_6$ alkoxy, $C_1$-$C_6$ hydroxyalkoxy, $C_1$-$C_6$ fluoroalkoxy, $C_1$-$C_6$ alkyl, $C_1$-$C_6$ fluoroalkyl, —C(O)NR$^a$R$^b$, where R$^a$ and R$^b$ are independently selected from hydrogen and $C_1$-$C_6$ alkyl; —O—$R^{15}$ wherein $R^{15}$ is —(CH$_2$)$_x$—P(O)(OR$^{23}$)$_2$, where x is 0, 1, 2, 3 or 4 and $R^{23}$ is independently selected from hydrogen and $C_1$-$C_3$ alkyl, —(CH$_2$)$_y$—S(O)$_2$Me where y is 1, 2, 3 or 4, —$C_1$-$C_6$ alkyl-heterocyclyl which heterocyclyl group may be optionally substituted by $C_1$-$C_3$ alkyl, —$C_1$-$C_6$ alkylphenyl which phenyl group may be optionally substituted by $C_1$-$C_3$ alkoxy, or phenyl or 5- or 6-membered heteroaryl which phenyl or heteroaryl group may optionally be substituted by a group selected from $C_1$-$C_4$ alkyl and halo; or —(O(CH$_2$)$_z$)$_p$OR$^{24}$, where each z, which may be the same or different, represents 2 or 3, p represents 1, 2, 3, 4 or 5 and $R^{24}$ is hydrogen or $C_1$-$C_3$ alkyl; or two adjacent carbon atoms within $R^3$ may be linked by —O—CH$_2$—O—, or a salt or protected derivative thereof;
provided that when $R^5$ or $R^6$ is optionally substituted aryl, said aryl is optionally substituted by 1, 2 or 3 groups selected from hydroxyl, halo, cyano, $C_1$-$C_6$ alkoxy or $C_1$-$C_6$ fluoroalkoxy, $C_1$-$C_6$ alkyl or $C_1$-$C_6$ fluoroalkyl, and —C(O)NR$^a$R$^b$, where R$^a$ and R$^b$ are independently selected from hydrogen and $C_1$-$C_6$ alkyl; or when two adjacent hydroxyl substituents are present they may optionally be connected by a methylene group to form an acetal;

and provided that the compound is not:
a) methyl 2-((2-oxo-2-(phenylamino)ethyl)(phenyl)amino)acetate;
b) methyl 2-((4-methoxyphenyl)(2-oxo-2-(phenylamino)ethyl)amino)acetate;
c) ethyl 2-(phenyl(tosylmethyl)amino)acetate;
d) ethyl 2-((cyanomethyl)(3,4-dichlorophenyl)amino)acetate;
e) methyl 2-((cyanomethyl)(p-tolyl)amino)acetate;
f) ethyl 2-(mesityl(2-oxopropyl)amino)acetate;
g) dimethyl 2,2'-((3-bromophenyl)azanediyl)diacetate; or
h) dimethyl-2,2'-((4-iodophenyl)azanediyl)diacetate.

The specific compounds disclaimed from the definition of formula (II) above are found in CAS as follows: methyl 2-((2-oxo-2-(phenylamino)ethyl)(phenyl)amino)acetate (CAS 862699-62-5), methyl 2-((4-methoxyphenyl)(2-oxo-2-(phenylamino)ethyl)amino)acetate (CAS 862699-57-8), ethyl 2-(phenyl(tosylmethyl)amino)acetate (CAS 1129284-66-7), ethyl 2-((cyanomethyl)(3,4-dichlorophenyl)amino)acetate (CAS 1003878-20-3), methyl 2-((cyanomethyl)(p-tolyl)amino)acetate (CAS 100134-88-1) and ethyl 2-(mesityl(2-oxopropyl)amino)acetate (CAS 935758-17-1); or otherwise as follows: dimethyl 2,2'-((3-bromophenyl)azanediyl)diacetate and dimethyl 2,2'((4-iodophenyl)azanediyl)diacetate (International Patent Application WO2006/020004).

Compounds of formula (II) which may be mentioned in particular are those in which $R^1$ is —C(O)NR$^5$R$^6$ and $R^2$ is —C(O)NR$^5$R$^6$ or wherein $R^1$ is —C(O)NR$^5$R$^6$ and $R^2$ is —C(O)OR$^7$.

According to a further aspect of the invention there is provided a compound of formula (II):

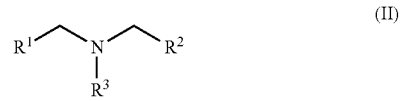

(II)

wherein $R^1$ is —C(O)NR$^5$R$^6$ and $R^2$ is —C(O)NR$^5$R$^6$ or wherein $R^1$ is —C(O)NR$^5$R$^6$ and $R^2$ is —C(O)OR$^7$, and $R^3$, $R^5$ and $R^6$ are as defined above for the compounds of formula (I), or a salt or protected derivative thereof;
provided that when $R^5$ or $R^6$ is optionally substituted aryl, said aryl is optionally substituted by 1, 2 or 3 groups selected from hydroxyl, halo, cyano, $C_1$-$C_6$ alkoxy or $C_1$-$C_6$ fluoroalkoxy, $C_1$-$C_6$ alkyl or $C_1$-$C_6$ fluoroalkyl, and —C(O)NR$^a$R$^b$, where R$^a$ and R$^b$ are independently selected from hydrogen and $C_1$-$C_6$ alkyl; or when two adjacent hydroxyl substituents are present they may optionally be connected by a methylene group to form an acetal;
and provided that the compound is not:
a) methyl 2-((2-oxo-2-(phenylamino)ethyl)(phenyl)amino)acetate; or
b) methyl 2-((4-methoxyphenyl)(2-oxo-2-(phenylamino)ethyl)amino)acetate.

Any preferences or examples of specific groups for $R^1$, $R^2$, $R^3$, $R^5$, $R^6$, R$^a$ and R$^b$ as described above for the compounds of formula (I) also apply to the definitions of $R^1$, $R^2$, $R^3$, $R^5$, $R^6$, R$^a$ and R$^b$ in the compounds of formula (II).

Particular compounds of formula (II) include those mentioned in the examples.

There is also provided a process for preparing compounds of formula (I) in which $R^{4a}$ and $R^{4b}$ represent H which comprises reacting a compound of formula (II) with a compound of formula R$^x$OCOCOOR$^x$ in which R$^x$ represents $C_1$-$C_6$ alkyl. This process is typically performed in a polar protic solvent such as ethanol in the presence of a strong base such as sodium ethoxide.

Compounds of formula (I) without provisos a) to i) are referred to below as "compounds of the invention".

As indicated above the compounds of the invention are useful for treatment of bacterial infections caused by bacteria producing pore-forming toxins, such as cholesterol dependent cytolysins.

In particular the compounds of the invention are useful for the treatment of toxaemia associated with bacterial infections.

For such use the compounds of the invention will generally be administered in the form of a pharmaceutical composition.

Further, the present invention provides a pharmaceutical composition comprising a compound of formula (I) without provisos a) to i) optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. intravitreal, pulmonary or intranasal administration, particularly in the form of eye drops, powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in *Remington's Pharmaceutical Sciences,* 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Pharmaceutical compositions of the invention may optionally include one or more anti-oxidants (e.g. ascorbic acid or metabisulfate and salts thereof).

The compounds of the invention are inhibitors of the cholesterol-dependent cytolysin, pneumolysin, produced by the bacterium *Streptococcus pneumoniae*. They also inhibit Streptolysin O (SLO) produced by Group A Streptococci and Perfringolysin O (PFO) produced by *Clostridium perfringens*. They are also expected to inhibit other members of the closely related cholesterol-dependent cytolysins, examples of which include, but are not limited to, Listeriolysin O (LLO) produced by *Listeria monocytogenes*, Anthrolysin O (ALO) produced by *Bacillus anthracis* and Suilysin (SLY) produced by *Streptococcus suis*.

The compounds of the invention are useful for the treatment of bacterial infections, e.g. pneumococcal infections including the associated toxaemia where the pneumolysin toxin has been demonstrated to play a pivotal role in the diseases produced. Such diseases include, but are not limited to, pneumococcal pneumonia, pneumococcal meningitis, pneumococcal septicaemia/bacteraemia, pneumococcal keratitis and pneumococcal otitis media. The compounds of the invention are also useful for the treatment of pneumococcal infections associated with other conditions. Such conditions include (without limitation) cystic fibrosis and chronic obstructive pulmonary disease (COPD). For example, *S pneumoniae* has been isolated from patients with COPD and is believed to be an exacerbatory factor in this disease.

The compounds of the invention are useful for the treatment of infections caused by group A Streptococci (GAS), including but not limited to, invasive group A Streptococcal diseases, where the toxin Streptolysin O (SLO) has been demonstrated to play a crucial role in the pathogenesis of systemic GAS diseases.

The compounds of the invention are useful for the treatment of infections caused by *Clostridium perfringens* including, but not limited to, gas gangrene, characterized by myonecrosis, septic shock and death, where the toxin Perfringolysin O has been demonstrated to be a major virulence factor in the pathogenesis of this disease.

The compounds of the invention are useful for the treatment of infections caused by *Bacillus anthracis*, where the cholesterol dependent cytolysin Anthrolysin O (ALO) plays an essential role in gastrointestinal (GI) anthrax, and contributes to the pathogenesis of inhalational anthrax.

The compounds of the invention are useful for the treatment of other diseases caused by Gram positive bacteria, producing cholesterol-dependent cytolysins, examples of which include, but are not limited to:

Porcine meningitis, septicaemia/bacteraemia and septic shock caused by *Streptococcus suis* which produces a cholesterol dependent cytolysin, Suilysin, involved in the pathogenesis of diseases by *S. suis*.

Encephalitis, enteritis, meningitis, septicaemia/bacteraemia and pneumonia caused by *Listeria monocytogenes* where the cholesterol dependent cytolysin, listeriolosin O (LLO), plays an important role in the pathogensis of the above diseases.

The compounds of the invention may well also be useful for the inhibition of other bacterial pore-forming toxins, such as the RTX family of toxins, which are essential in the virulence of their host. Examples include, but are not limited to, pneumonia and septicaemia/bacteraemia caused by *Staphylococcus aureus*, which produces the pore-forming toxin staphylococcal α-hemolysis and peritonitis caused by pathogenic *Escherichia coli* which produces the pore forming toxin α-hemolysin.

Thus the invention provides:

A compound of the invention for use in the treatment of bacterial infections caused by bacteria producing pore-forming toxins, wherein the bacterial infection is caused by *Streptococcus* spp. (e.g. *Streptococcus pneumoniae*, Group A Streptococci or *Streptococcus suis*), *Clostridium* spp. (e.g. *Clostridium perfringens*), *Listeria* spp. (e.g. *Listeria monocytogenes*) or *Bacillus* spp. (e.g. *Bacillus anthracis*);

A compound of the invention for the treatment of bacterial infection which is caused by *Streptococcus pneumonia*;

A compound of the invention for use in the treatment of pneumococcal pneumonia, pneumococcal meningitis, pneumococcal septicaemia/bacteraemia, pneumococcal keratitis or pneumococcal otitis media; and A compound of the invention for the treatment of conditions selected from gas gangrene, gastrointestinal anthrax, inhalational anthrax, porcine meningitis, encephalitis, septicaemia/bacteraemia and pneumonia which are caused by bacteria other than pneumococcus.

The compounds of the invention may be used to treat either humans or animals, such as domestic animals or livestock, e.g. pigs, cows, sheep, horses etc, and references to pharmaceutical compositions should be interpreted to cover compositions suitable for either human or animal use.

Thus, in a further aspect, the present invention provides a compound of formula (I) without provisos a) to i) for use in the treatment of the above mentioned conditions.

In a further aspect, the present invention provides a compound of formula (I) without provisos a) to i) for the manufacture of a medicament for the treatment of the above mentioned conditions.

In a further aspect, the present invention provides a method of treatment of the above mentioned conditions which comprises administering to a subject in need thereof an effective amount of a compound of formula (I) without provisos a) to i) or a pharmaceutical composition thereof.

The word "treatment" is intended to embrace prophylaxis as well as therapeutic treatment.

The compounds of the invention may be used either alone or in combination with further therapeutically active ingredients. Thus compounds of the invention may be administered in combination, simultaneously, sequentially or separately, with further therapeutically active ingredients either together in the same formulation or in separate formulations and either via the same route or via a different route of administration. The compounds of the invention may thus be administered in combination with one or more other active ingredients suitable for treating the above mentioned conditions. For example, possible combinations for treatment include combinations with antimicrobial agents, e.g. antibiotic agents, including natural, synthetic and semisynthetic antimicrobial agents. Examples of antibiotic agents include β-lactams including, but not limited to, penicillin, benzylpenicillin, amoxicillin and all generations thereof; β-lactams in combination with β-lactamase inhibitors including, but not limited to, clavulanic acid and sulbactam; cephalosporins including, but not limited to, cefuroxime, cefotaxime and ceftriaxone; fluoroquinolones including, but not limited to, levofloxacin and moxifloxacin; tetracyclines including, but not limited to, doxycycline; macrolides including, but not limited to, erythromycin and clarithromycin; lipopeptide antibiotics including, but not limited to, daptomycin; aminoglycosides including, but not limited to, kanamycin and gentamicin; glycopeptide antibiotics, including but not limited to, vancomycin; lincosamides including, but not limited to, clindamycin and lincomycin; rifamycins including, but not limited to, rifampicin; and chloramphenicol.

Further combinations include combinations with immunomodulatory agents, such as anti-inflammatory agents.

Immunomodulatory agents can include for example, agents which act on the immune system, directly or indirectly, by stimulating or suppressing a cellular activity of a cell in the immune system, for example, T-cells, B-cells, macrophages, or antigen presenting cells, or by acting upon components outside the immune system which, in turn, stimulate, suppress, or modulate the immune system, for example, hormones, receptor agonists or antagonists and neurotransmitters, other immunomodulatory agents can include immunosuppressants or immunostimulants. Anti-inflammatory agents include, for example, agents which treat inflammatory responses, tissue reaction to injury, agents which treat the immune, vascular or lymphatic systems or combinations thereof. Examples of anti-inflammatory and immunomodulatory agents include, but are not limited to, interferon derivatives such as betaseron, β-interferon, prostane derivatives such as iloprost and cicaprost, corticosteroids such as prednisolone, methylprednisolone, dexamethasone and fluticasone, COX2 inhibitors, immunsuppressive agents such as cyclosporine A, FK-506, methoxsalene, thalidomide, sulfasalazine, azathioprine and methotrexate, lipoxygenase inhibitors, leukotriene antagonists, peptide derivatives such as ACTH and analogs, soluble TNF (tumor necrosis factor)-receptors, TNF-antibodies, soluble receptors of interleukines, other cytokines and T-cell-proteins, antibodies against receptors of interleukins, other cytokines and T-cell-proteins. Further anti-inflammatory agents include non-steroidal anti-inflammatory drugs (NSAID's). Examples of NSAID's include sodium cromoglycate, nedocromil sodium, phosphodiesterase (PDE) inhibitors e.g. theophylline, PDE4 inhibitors or mixed PDE3/PDE4 inhibitors, leukotriene antagonists, inhibitors of leukotriene synthesis such as montelukast, iNOS inhibitors, tryptase and elastase inhibitors, beta-2 integrin antagonists and adenosine receptor agonists or antagonists such as adenosine 2a agonists, cytokine antagonists e.g. chemokine antagonists, such as CCR3 antagonists, or inhibitors of cytokine synthesis, and 5-lipoxygenase inhibitors.

Thus an aspect of the invention provides a compound of formula (I) without provisos a) to i) in combination with one or more further active ingredients, for example one or more of the active ingredients described above.

Another aspect of the invention provides a pharmaceutical composition comprising a compound of formula (I) without provisos a) to i) optionally in combination with one or more pharmaceutically acceptable adjuvants, diluents or carriers and comprising one or more other therapeutically active ingredients.

Similarly, another aspect of the invention provides a combination product comprising:
(A) a compound of formula (I) without provisos a) to i); and
(B) another therapeutic agent, wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of the present invention and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of formula (I) without provisos a) to i) in admixture with a pharmaceutically acceptable adjuvant, diluent or carrier; and
(ii) a pharmaceutical formulation including another therapeutic agent, in admixture with a pharmaceutically-acceptable adjuvant, diluent or carrier;
which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

The other therapeutic agent (i.e. component (B) above) may be, for example, any of the agents e.g. antimicrobial or immunomodulatory agents mentioned above.

The combination product (either a combined preparation or kit-of-parts) of this aspect of the invention may be used in the treatment or prevention of any of the conditions mentioned above.

The compounds of formula (I) without provisos a) to i) may also be provided for use, e.g. with instructions for use, in combination with one or more further active ingredients.

Thus a further aspect of the invention provides a compound of formula (I) without provisos a) to i) for use in combination with one or more further active ingredients, for example one or more of the active ingredients described above.

The compound of formula (I) without provisos a) to i) for use in this aspect of the invention may be used in the treatment or prevention of any of the conditions mentioned above.

The invention will now be described by reference to the following examples which are for illustrative purposes and are not to be construed as a limitation of the scope of the present invention.

EXAMPLES

Abbreviations
AcOH glacial acetic acid
aq. aqueous
Bn benzyl
br broad
Boc tert-butoxycarbonyl
COPD chronic obstructive pulmonary disease
d doublet
DCM dichloromethane
DIPEA N,N-diisopropylethylamine
DMAP 4-dimethylaminopyridine
DMF N,N-dimethylformamide
DMSO dimethylsulfoxide
EtOAc ethyl acetate
h hour(s)
HATU N,N,N',N'-tetramethyl-O-(7-azabenzothazol-1-yl)uronium $PF_6$
HPLC high performance liquid chromatography
m multiplet
MeCN acetonitrile
MeOH methanol
min minute(s)
NMR nuclear magnetic resonance
quin. quintet
RT room temperature
s singlet
sat. saturated
SAX solid supported strong cation exchange resin
sept. septet
sext. sextet
t triplet
TFAA trifluoroacetic acid anhydride
THF tetrahydrofuran General Procedures All starting materials and solvents were obtained from commercial sources or prepared according to literature conditions.

Hydrogenations were performed either on a Thales H-cube flow reactor or with a suspension of the catalyst under a balloon of hydrogen.

Column chromatography was performed on pre-packed silica (230-400 mesh, 40-63 μM) cartridges.

Analytical Methods

Reverse Phase High Performance Liquid Chromatography:

Agilent Zorbax Extend RRHT column 1.8 μm (4.6×30 mm) flow rate 2.5 mL/min eluting with a $H_2O$-MeCN gradient containing 0.1% v/v formic acid employing UV detection at 215 and 254 nm.

$^1H$ NMR Spectroscopy:

NMR spectra were recorded using a Bruker Avance III 400 MHz instrument, using either residual non-deuterated solvent or tetra-methylsilane as reference.

Chemical Synthesis:

The compounds of formula (I) were prepared using the following general methods:

Example A $N^2,N^2,N^5,N^5$-Tetraethyl-3,4-dihydroxy-1-(4-methoxyphenyl)-1H-pyrrole-2,5-dicarboxamide (UL1-003)

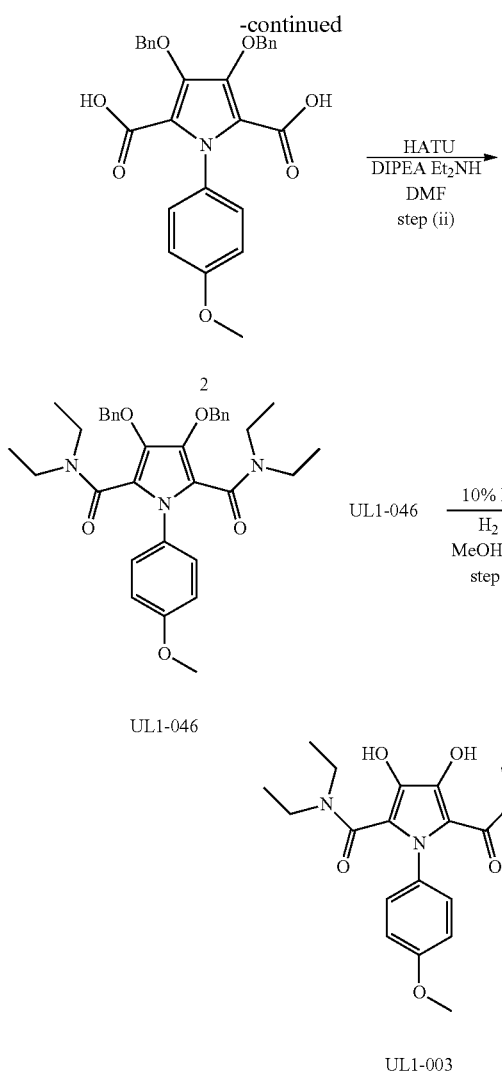

HATU (803 mg, 2.11 mmol) followed by diethylamine (219 μL, 2.11 mmol). The reaction mixture was stirred at RT for 1 h and then partitioned between Et$_2$O (50 mL) and sat. NaOAc (aq.) (30 mL). The organic phase was washed succesively with sat. NaOAc (aq.) (20 mL), sat. NaHCO$_3$ (aq.) (20 mL) and brine (2×20 mL), dried (MgSO$_4$), filtered and concentrated in vacuo to afford the crude product. The residue was purified by silica gel chromatography (12 g, 30% EtOAc/isohexane) to afford 3,4-bis(benzyloxy)-N$^2$,N$^2$,N$^5$,N$^5$-tetraethyl-1-(4-methoxyphenyl)-1H-pyrrole-2,5-dicarboxamide (UL1-046) (201 mg, 41%) as a yellow solid: m/z 584 (M+H)$^+$ (ES$^+$). $^1$H NMR (400 MHz, DMSO-d$_6$) δ: 7.47-7.22 (m, 10H), 7.09-6.99 (m, 2H), 6.94-6.76 (m, 2H), 4.97 (s, 4H), 3.74 (s, 3H), 3.29-3.03 (m, 8H), 0.98-0.71 (m, 12H).

Step (iii): N$^2$,N$^2$,N$^5$,N$^5$-Tetraethyl-3,4-dihydroxy-1-(4-methoxyphenyl)-1H-pyrrole-2,5-dicarboxamide (UL1-003)

A solution of 3,4-bis(benzyloxy)-N$^2$,N$^2$,N$^5$,N$^5$-tetraethyl-1-(4-methoxyphenyl)-1H-pyrrole-2,5-dicarboxamide UL1-046 (50 mg, 0.086 mmol) in methanol/DCM (4 mL/4 mL) was passed through a Thales 'H-cube' cartridge (10% Pd/C) at a flow rate of 1 mL/min at 25° C. under H$_2$ (full H$_2$ mode). The output was concentrated in vacuo to afford N$^2$,N$^2$,N$^5$,N$^5$-tetraethyl-3,4-dihydroxy-1-(4-methoxyphenyl)-1H-pyrrole-2,5-dicarboxamide (UL1-003) (32 mg, 93%) as a light yellow solid: m/z 404 (M+H)$^+$ (ES$^+$); 402 (M−H)$^-$ (ES$^-$). $^1$H NMR (400 MHz, DMSO-d$_6$) δ 8.26 (s, 2H), 6.96-6.88 (m, 2H), 6.87-6.81 (m, 2H), 3.72 (s, 3H), 3.27 (q, J=7.1 Hz, 8H), 0.96 (t, J=7.0 Hz, 12H).

Example B

Ethyl 5-(dimethylcarbamoyl)-3,4-dihydroxy-1-(4-methoxyphenyl)-1H-pyrrole-2-carboxylate (UL1-012)

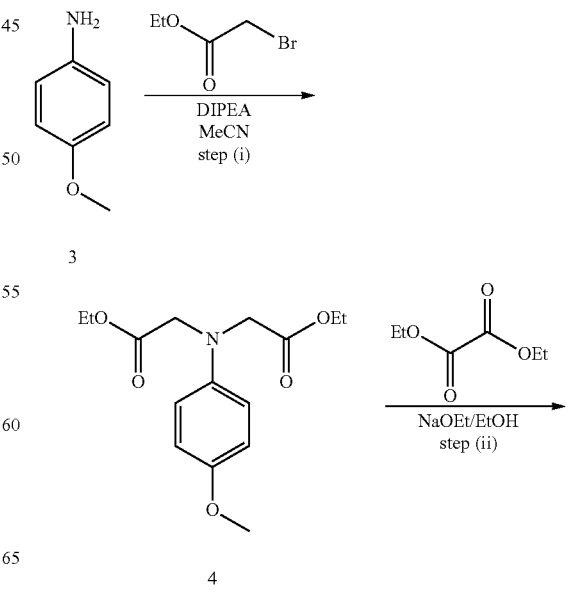

Step (i): 3,4-Bis(benzyloxy)-1-(4-methoxyphenyl)-1H-pyrrole-2,5-dicarboxylic acid (2)

A mixture of diethyl 3,4-bis(benzyloxy)-1-(4-methoxyphenyl)-1H-pyrrole-2,5-dicarboxylate (1) (2.8 g, 5.29 mmol), 2M NaOH (aq.) (26.4 mL, 52.9 mmol), in ethanol (12 mL) and THF (20 mL) was stirred at 60° C. for 72 h. After cooling to RT, the mixture was acidified with 6M HCl (aq.) and the resulting precipitate was collected by filtration, washed with water (5 mL), and Et$_2$O (5 mL) to afford 4-bis(benzyloxy)-1-(4-methoxyphenyl)-1H-pyrrole-2,5-dicarboxylic acid (2) (1.94 g, 67%) as an off-white solid: m/z 474 (M+H)$^+$ (ES$^+$); 472 (M−H)$^-$ (ES$^-$). $^1$H NMR (400 MHz, DMSO-d$_6$) δ 12.61 (s, 2H), 7.46-7.40 (m, 4H), 7.39-7.29 (m, 6H), 7.16-7.07 (m, 2H), 6.92-6.84 (m, 2H), 5.07 (s, 4H), 3.78 (s, 3H).

Step (ii): 3,4-Bis(benzyloxy)-N$^2$,N$^2$,N$^5$,N$^5$-tetraethyl-1-(4-methoxyphenyl)-1H-pyrrole-2,5-dicarboxamide (UL-046)

To a solution of 4-bis(benzyloxy)-1-(4-methoxyphenyl)-1H-pyrrole-2,5-dicarboxylic acid (2) (400 mg, 0.85 mmol) and DIPEA (386 μL, 2.11 mmol) in DMF (4 mL) was added

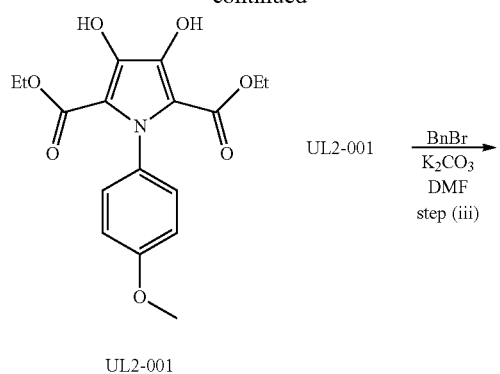
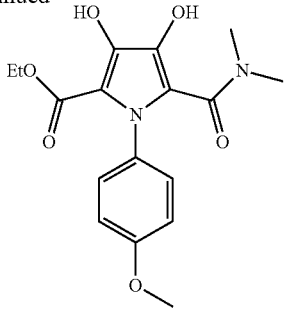
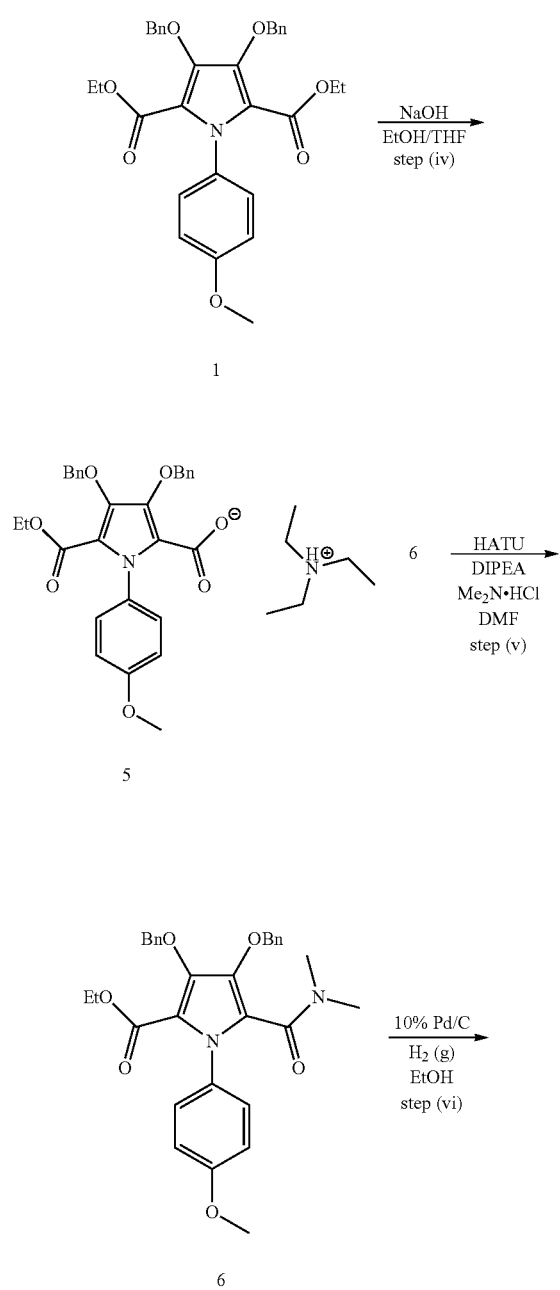

Step (i): Diethyl 2,2'-((4-methoxyphenyl)azanediyl)diacetate (4)

Ethyl 2-bromoacetate (146 mL, 1.3 mol) was added dropwise to a stirred solution of 4-methoxyaniline (3) (75 g, 0.61 mol) and DIPEA (265 mL, 1.5 mol) in MeCN (300 mL). The reaction mixture was stirred at 60° C. for 16 h and then partitioned between 2 M HCl (aq.) (500 mL), and EtOAc (300 mL), the aqueous phase was extracted with EtOAc (300 mL) and the combined organics were washed succesively with 2 M HCl (aq.) (2×300 mL), water (500 mL), and brine (500 mL), dried (MgSO$_4$), filtered and solvents removed in vacuo to give diethyl 2,2'-((4-methoxyphenyl)azanediyl)diacetate (4) (180 g, 100%) as a purple oil: m/z 296 (M+H)$^+$ (ES$^+$). $^1$H NMR (400 MHz, CDCl$_3$) δ 6.82-6.78 (m, 2H), 6.64-6.59 (m, 2H), 4.19 (q, J=7.1 Hz, 4H), 4.10 (s, 4H), 3.74 (s, 3H), 1.27 (t, J=7.1 Hz, 6H).

Step (ii): Diethyl 3,4-dihydroxy-1-(4-methoxyphenyl)-1H-pyrrole-2,5-dicarboxylate (UL2-001)

Diethyl oxalate (83 ml, 0.61 mol) was added dropwise to a stirred solution of diethyl 2,2'4-(4-methoxyphenyl)azanediyl)diacetate (4) (180 g, 0.61 mol) in NaOEt (21% by wt in EtOH) (506 ml, 1.3 mol), the mixture was stirred at 100° C. for 1 h. The reaction was quenched with acetic acid (210 ml, 3.7 mol) and the resulting suspension was poured into iced water (1 L), the resulting off-white solid collected by vacuum filtration. The crude product was recrystallised from hot EtOH (3.5 L) to give diethyl 3,4-dihydroxy-1-(4-methoxyphenyl)-1H-pyrrole-2,5-dicarboxylate (UL2-001) (152 g, 71%) as a white solid: m/z 350 (M+H)$^+$ (ES$^+$); 348 (M−H)$^-$ (ES$^-$). $^1$H NMR (400 MHz, DMSO-d$_6$) δ 8.64 (s, 2H), 7.13-7.01 (m, 2H), 6.92-6.81 (m, 2H), 3.99 (q, J=7.1 Hz, 4H), 3.78 (s, 3H), 0.99 (t, J=7.1 Hz, 6H).

Step (iii): Diethyl 3,4-bis(benzyloxy)-1-(4-methoxyphenyl)-1H-pyrrole-2,5-dicarboxylate (1)

Benzyl bromide (42.6 ml, 358 mmol) was added dropwise to a stirred suspension of 3,4-dihydroxy-1-(4-methoxyphenyl)-1H-pyrrole-2,5-dicarboxylate (UL2-001) (50 g, 143 mmol) and K$_2$CO$_3$ (49.5 g, 358 mmol) in DMF (1 L), the reaction mixture was stirred at 60° C. for 4 h. After cooling to RT the reaction mixture was poured into ether (500 mL) and washed with brine (3×250 mL), dried (MgSO$_4$), filtered and concentrated in vacuo to afford a bright yellow solid. The crude product was triturated with isohexane to give diethyl 3,4-bis(benzyloxy)-1-(4-methoxyphenyl)-1H-pyrrole-2,5-dicarboxylate (1) (64.8 g, 85%) as a white solid: m/z 530

(M+H)⁺ (ES⁺). ¹H NMR (400 MHz, DMSO-d₆) δ: 7.48-7.29 (m, 10H), 7.17-7.09 (m, 2H), 6.95-6.87 (m, 2H), 5.09 (s, 4H), 3.99 (q, J=7.1 Hz, 4H), 3.80 (s, 3H), 0.99 (t, J=7.1 Hz, 6H).

Step (iv): Triethylammonium 3,4-bis(benzyloxy)-5-(ethoxycarbonyl)-1-(4-methoxyphenyl)-1H-pyrrole-2-carboxylate (5)

To a solution of diethyl 3,4-bis(benzyloxy)-1-(4-methoxyphenyl)-1H-pyrrole-2,5-dicarboxylate (1) (39.6 g, 74.8 mmol) in THF/EtOH (300/50 mL) was added NaOH (3.07 g, 77 mmol) as a solution in water (20 mL). The reaction was stirred at 50° C. for 16 h. Triethylamine was added (30 mL, 215 mmol) and the volatiles were removed in vacuo. The residue was purified by silica gel chromatography (50% isohexane:DCM (+2% Et₃N), then 20% MeOH/EtOAc (+2% Et₃N)) to afford triethylammonium 3,4-bis(benzyloxy)-5-(ethoxycarbonyl)-1-(4-methoxyphenyl)-1H-pyrrole-2-carboxylate (5) (39.3 g, 83%) as a yellow oil: m/z 502 (M+H)⁺ (ES⁺); 500 (M−H)⁻ (ES⁻). ¹H NMR (400 MHz, DMSO-d₆) δ: 7.51-7.26 (m, 10H), 7.11-7.05 (m, 2H), 6.92-6.83 (m, 2H), 5.09 (s, 2H), 5.06 (s, 2H), 3.95 (q, J=7.1 Hz, 2H), 3.79 (s, 3H), 2.85-2.62 (m, 6H), 1.08-0.92 (m, 12H).

Step (v): Ethyl 3,4-bis(benzyloxy)-5-(dimethylcarbamoyl)-1-(4-methoxyphenyl)-1H-pyrrole-2-carboxylate (6)

To a solution of triethylammonium 3,4-bis(benzyloxy)-5-(ethoxycarbonyl)-1-(4-methoxyphenyl)-1H-pyrrole-2-carboxylate (5) (10.84 g, 17.99 mmol) in DMF (150 mL), at 0° C. was added HATU (10.26 g, 27.0 mmol), dimethylamine hydrochloride (2.93 g, 36.0 mmol) and DIPEA (18.8 ml, 108 mmol). The reaction mixture was stirred at RT for 16 h and partitioned between EtOAc (500 mL) and 1M HCl (aq.) (250 mL). The organic phase was washed successively with 1M HCl (aq.) (250 mL), sat. NaHCO₃ (aq.) (2×250 mL), and brine (2×250 mL), dried (MgSO₄), filtered and concentrated in vacuo to afford ethyl 3,4-bis(benzyloxy)-5-(dimethylcarbamoyl)-1-(4-methoxyphenyl)-1H-pyrrole-2-carboxylate (6) (7.62 g, 79%) as a light yellow oil, that solidified on standing: m/z 529 (M+H)⁺ (ES⁺). ¹H NMR (400 MHz, DMSO-d₆) δ: 7.51-7.21 (m, 10H), 7.14-7.03 (m, 2H), 6.94-6.84 (m, 2H), 5.12 (s, 2H), 4.96 (s, 2H), 4.00 (q, J=7.1 Hz, 2H), 3.77 (s, 3H), 2.70 (s, 6H), 1.00 (t, J=7.1 Hz, 6H).

Step (vi): Ethyl 5-(dimethylcarbamoyl)-3,4-dihydroxy-1-(4-methoxyphenyl)-1H-pyrrole-2-carboxylate (UL1-012)

Ethyl 3,4-bis(benzyloxy)-5-(dimethylcarbamoyl)-1-(4-methoxyphenyl)-1H-pyrrole-2-carboxylate (6) (1.03 g, 1.94 mmol) was dissolved in EtOH and then treated with 10% Pd/C (37 mg). The reaction mixture was purged with N₂ for 5 min then Hydrogen gas was bubbled through the mixture with stirring at RT for 1.5 h. The mixture was filtered through Celite and concentrated in vacuo. The residual yellow solid was triturated with Et₂O to afford ethyl 5-(dimethylcarbamoyl)-3,4-dihydroxy-1-(4-methoxyphenyl)-1H-pyrrole-2-carboxylate (UL1-012) (602 mg, 89%) as a white solid: m/z 349 (M+H)⁺ (ES⁺), 347 (M−H)⁻ (ES⁻). 1H NMR (400 MHz, DMSO-d₆) δ: 8.60 (s, 1H), 8.46 (s, 1H), 7.08-7.01 (m, 2H), 6.90-6.82 (m, 2H), 4.00 (q, J=7.0 Hz, 2H), 3.76 (s, 3H), 2.83 (br s, 6H), 0.99 (t, J=7.1 Hz, 6H).

Example C

N²-Ethyl-3,4-dihydroxy-1-(4-methoxyphenyl)-N⁵,N⁵-dimethyl-1H-pyrrole-2,5-dicarboxamide (UL1-024)

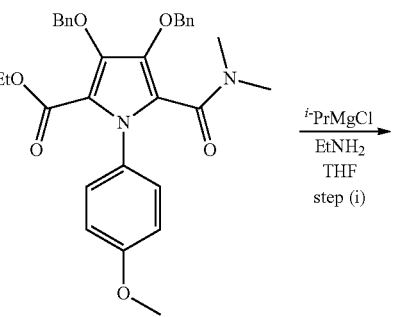

6

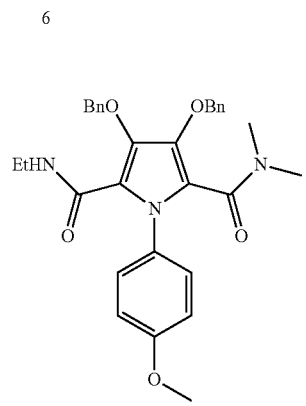

UL1-055

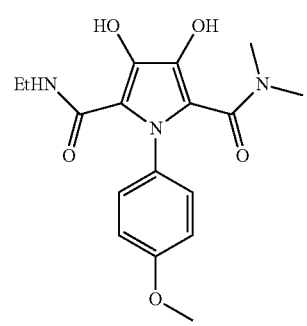

UL1-024

Step (i): 3,4-Bis(benzyloxy)-N²-ethyl-1-(4-methoxyphenyl)-N⁵,N⁵-dimethyl-1H-pyrrole-2,5-dicarboxamide (UL1-055)

To a stirred suspension of ethyl 3,4-bis(benzyloxy)-5-(dimethylcarbamoyl)-1-(4-methoxyphenyl)-1H-pyrrole-2- carboxylate (6) (200 mg, 0.38 mmol) and ethylamine hydrochloride (61.7 mg, 0.75 mmol) in THF (2 mL) was added isopropylmagnesium chloride (2 M in THF) (757 μL, 1.51 mmol) and the reaction stirred at RT for 2 h, further portions of ethylamine hydrochloride (120 mg, 1.5 mmol) and isopropylmagnesium chloride (2 M in THF) (1.5 mL, 3.0 mmol) were added and the reaction stirred for 16 h at RT. The reaction mixture was partitioned between sat. NH$_4$Cl solution (aq.) (5 mL) and EtOAc (20 mL) the aqueous was further acidified with 1 M HCl (5 mL). The organic layer was separated and washed with brine (25 mL), dried (MgSO$_4$), filtered and concentrated in vacuo to afford crude product. The residue was purified by silica gel chromatography (25 g, 30-80% EtOAc in isohexane) to afford 3,4-bis(benzyloxy)-N$^2$-ethyl-1-(4-methoxyphenyl)-N$^5$,N$^5$-dimethyl-1H-pyrrole-2,5-dicarboxamide (UL1-055) (192 mg, 95%) as a yellow oil: m/z 528 (M+H)$^+$ (ES$^+$). $^1$H NMR (400 MHz, CDCl$_3$) δ: 7.44-7.30 (m, 10H), 7.20-7.09 (m, 2H), 7.06-6.97 (m, 1H), 6.89-6.80 (m, 2H), 5.20 (s, 2H), 5.07 (s, 2H), 3.79 (s, 3H), 3.25-3.14 (m, 2H), 2.79 (s, 3H), 2.72 (s, 3H), 0.97 (t, J=7.3 Hz, 3H).

Step (ii) N$^2$-Ethyl-3,4-dihydroxy-1-(4-methoxyphenyl)-N$^5$,N$^5$-dimethyl-1H-pyrrole-2,5-dicarboxamide (UL1-024)

A solution of 3,4-bis(benzyloxy)-N$^2$-ethyl-1-(4-methoxyphenyl)-N$^5$,N$^5$-dimethyl-1H-pyrrole-2,5-dicarboxamide (UL1-055) (118 mg, 0.22 mmol) in methanol (4.5 mL) was passed through a Thales 'H-cube' cartridge (10% Pd/C) at a flow rate of 1 mL/min at 30° C. under H$_2$ (full H$_2$ mode). The output was concentrated in vacuo to afford N$^2$-ethyl-3,4-dihydroxy-1-(4-methoxyphenyl)-N$^5$,N$^5$-dimethyl-1H-pyrrole-2,5-dicarboxamide (UL1-024) (66 mg, 82%) as a brown solid: m/z 348 (M+H)$^+$ (ES$^+$); 346 (M−H)$^-$ (ES$^-$). $^1$H NMR (400 MHz, DMSO-d$_6$) δ: 9.44 (s, 1H), 8.42 (s, 1H), 7.10-7.03 (m, 1H), 7.02-6.97 (m, 2H), 6.86-6.77 (m, 2H), 3.75 (s, 3H), 3.14-3.06 (m, 2H), 2.81 (br s, 6H), 0.97 (t, J=7.2 Hz, 3H).

Example D isopropyl 5-(dimethylcarbamoyl)-3,4-dihydroxy-1-(4-methoxyphenyl)-1H-pyrrole-2-carboxylate (UL1-035)

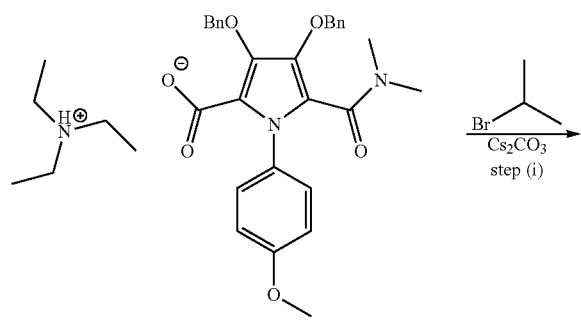

7

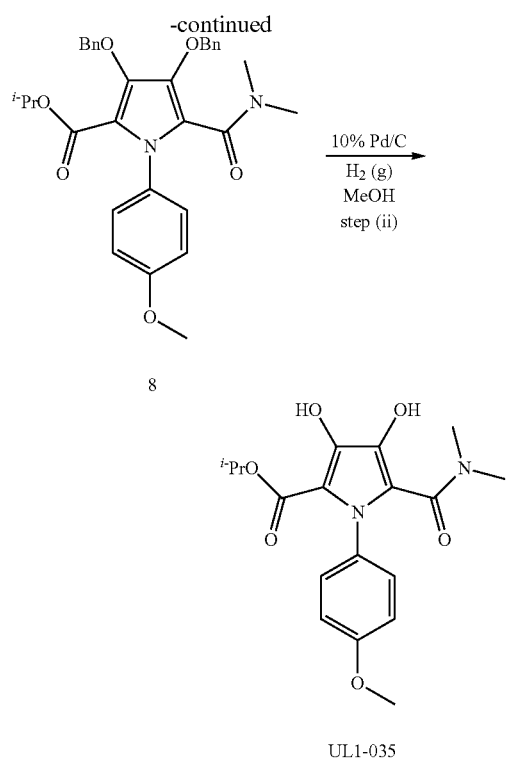

Step (i): Isopropyl 3,4-bis(benzyloxy)-5-(dimethylcarbamoyl)-1-(4-methoxyphenyl)-1H-pyrrole-2-carboxylate (8)

To a stirred suspension of triethylammonium 3,4-bis(benzyloxy)-5-(dimethylcarbamoyl)-1-(4-methoxyphenyl)-1H-pyrrole-2-carboxylate (7) [prepared as example B-step (iv) using ethyl 3,4-bis(benzyloxy)-5-(dimethylcarbamoyl)-1-(4-methoxyphenyl)-1H-pyrrole-2-carboxylate (6) as starting material] (360 mg, 0.60 mmol) and Cs$_2$CO$_3$ (429 mg, 1.32 mmol) in DMF (3 mL) was added 2-bromopropane (197 μL, 2.10 mmol) and the reaction stirred at 40° C. for 2 h then partitioned between EtOAc (50 mL) and water (20 mL). The organic was separated and washed with water (2×50 mL), brine (2×50 mL), dried (MgSO$_4$), filtered and concentrated in vacuo to afford a yellow oil. The residue was purified by silica gel chromatography (40 g, 20-60% EtOAc in isohexane) to afford isopropyl 3,4-bis(benzyloxy)-5-(dimethylcarbamoyl)-1-(4-methoxyphenyl)-1H-pyrrole-2-carboxylate (8) (108 mg, 33%) as a yellow oil: $^1$H NMR (400 MHz, DMSO-d$_6$) δ: 7.51-7.43 (m, 2H), 7.43-7.28 (m, 8H), 7.19-7.05 (m, 2 H), 6.96-6.84 (m, 2H), 5.13 (s, 2H), 4.96 (s, 2H), 4.85 (sept., J=6.2 Hz, 1H), 3.78 (s, 3H), 2.72 (s, 3H), 2.71 (s, 3H), 1.10 (d, J=6.2 Hz, 6H).

Step (ii): Isopropyl 5-(dimethylcarbamoyl)-3,4-dihydroxy-1-(4-methoxyphenyl)-1H-pyrrole-2-carboxylate (UL1-035)

A solution of isopropyl 3,4-bis(benzyloxy)-5-(dimethylcarbamoyl)-1-(4-methoxyphenyl)-1H-pyrrole-2-carboxylate (8) (130 mg, 0.240 mmol) in methanol (5 mL) was passed through a Thales 'H-cube' cartridge (10% Pd/C) at a flow rate of 1 mL/min at 30° C. under H$_2$ (full H$_2$ mode). The output was concentrated in vacuo to afford isopropyl 5-(dimethylcarbamoyl)-3,4-dihydroxy-1-(4-methoxyphenyl)-1H-pyrrole-2-carboxylate (UL1-035) (69 mg, 79%) as a white solid: m/z 363 (M+H)$^+$ (ES$^+$); 361 (M–H)$^-$ (ES$^-$). $^1$H NMR (400 MHz, DMSO-d$_6$) δ: 8.60 (s, 1H), 8.42 (s, 1H), 7.10-6.99 (m, 2H), 6.91-6.82 (m, 2H), 4.83 (sept., J=6.2 Hz, 1H), 3.77 (s, 3H), 2.83 (br s, 6H), 0.96 (d, J=6.2 Hz, 6H).

Example E tert-Butyl (5-(dimethylcarbamoyl)-3,4-dihydroxy-1-(4-methoxyphenyl)-1H-pyrrol-2-yl)sulfonylcarbamate (UL1-030)

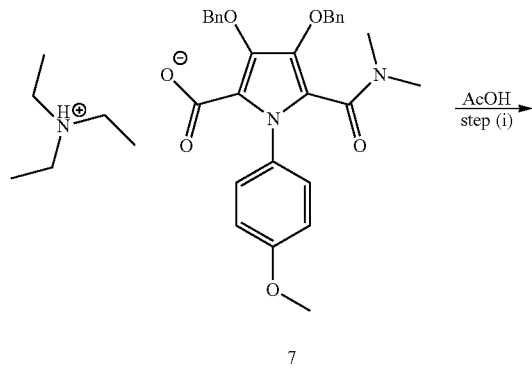

7

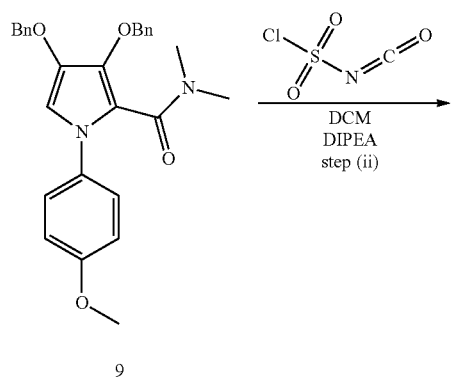

9

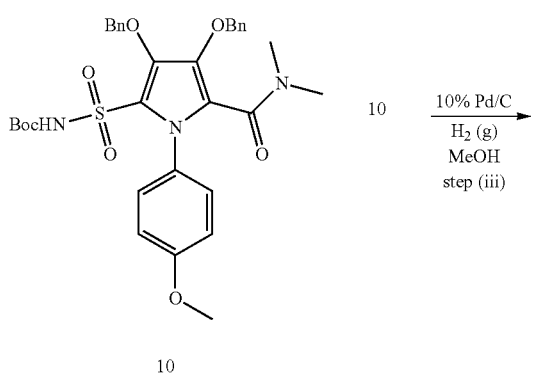

10

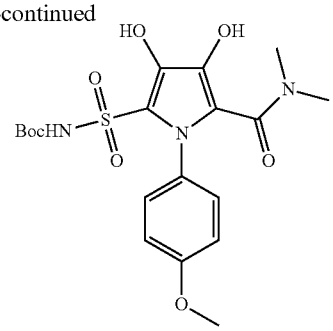

UL1-030

Step (i): 3,4-Bis(benzyloxy)-1-(4-methoxyphenyl)-N,N-dimethyl-1H-pyrrole-2-carboxamide (9)

A solution of triethylammonium 3,4-bis(benzyloxy)-5-(dimethylcarbamoyl)-1-(4-methoxyphenyl)-1H-pyrrole-2-carboxylate (7) (3.5 g, 6.70 mmol) in acetic acid (100 mL) was stirred at RT for 4 h and then 110° C. for 1 h. The volatiles were removed in vacuo and the crude material partitioned between EtOAc (100 mL) and 1M NaOH (aq.) (20 mL)/brine (50 mL), the organic layer was then dried (MgSO$_4$), filtered and concentrated in vacuo to afford 3,4-bis(benzyloxy)-1-(4-methoxyphenyl)-N,N-dimethyl-1H-pyrrole-2-carboxamide (9) (3.05 g, 100%) as a yellow oil: m/z 457 (M+H)$^+$ (ES$^+$).

Step (ii): tert-Butyl (3,4-bis(benzyloxy)-5-(dimethylcarbamoyl)-1-(4-methoxyphenyl)-1H-pyrrol-2-yl)sulfonylcarbamate (10)

To a solution of chlorosulfonyl isocyanate (70.9 μL, 0.82 mmol) at −5° C. in anhydrous DCM (4 mL) was added tert-butanol (solution in 0.5 mL anhydrous DCM) (81 μL, 0.85 mmol) dropwise over 5 min and the reaction stirred at −5° C. for 15 min. After this time, DIPEA (296 μL, 1.70 mmol) was added dropwise. After 15 min a solution of 3,4-bis(benzyloxy)-1-(4-methoxyphenyl)-N,N-dimethyl-1H-pyrrole-2-carboxamide (9) (310 mg, 0.68 mmol) in DCM (1 mL) was added and the reaction was allowed to warm to RT and stirred for 16 h. The reaction was partitioned between water (10 mL) and DCM (20 mL) and the organic washed with 1 M HCl (aq.) (2×20 mL), and brine (10 mL), dried (MgSO$_4$), filtered and solvent removed in vacuo to afford crude product. The residue was purified by silica gel chromatography (40 g, 0-4% MeOH in DCM) to afford tert-butyl (3,4-bis(benzyloxy)-5-(dimethylcarbamoyl)-1-(4-methoxyphenyl)-1H-pyrrol-2-yl)sulfonylcarbamate (10) (166 mg, 35%) as a colourless oil: m/z 636 (M+H)$^+$ (ES$^+$); 634 (M–H)$^-$ (ES$^-$).

Step (iii): tert-Butyl (5-(dimethylcarbamoyl)-3,4-dihydroxy-1-(4-methoxyphenyl)-1H-pyrrol-2-yl) sulfonylcarbamate (UL1-030)

tert-Butyl (3,4-bis(benzyloxy)-5-(dimethylcarbamoyl)-1-(4-methoxyphenyl)-1H-pyrrol-2-yl)sulfonyl carbamate (10) (166 mg, 0.26 mmol) in methanol (2.5 mL) was passed through a Thales 'H-cube' cartridge (10% Pd/C) at a flow rate of 1 mL/min at 30° C. under H$_2$ (full H$_2$ mode). The output was concentrated in vacuo to afford tert-butyl (5-(dimethylcarbamoyl)-3,4-dihydroxy-1-(4-methoxyphenyl)-1H-pyrrol-2-yl)sulfonylcarbamate (UL1-030) (65 mg, 52%) as a yellow solid: m/z 456 (M+H)$^+$ (ES$^+$); 454 (M–H)$^-$ (ES$^-$). $^1$H NMR (400 MHz, DMSO-d$_6$) δ: 11.04 (s, 1H), 8.75 (s, 1H), 8.35 (s, 1H), 7.07-7.00 (m, 2H), 6.92-6.86 (m, 2H), 3.77 (s, 3H), 2.80 (br s, 6H), 1.35 (s, 9H).

Example F

5-Cyano-3,4-dihydroxy-1-(4-methoxyphenyl)-N,N-dimethyl-1H-pyrrole-2-carboxamide (UL1-031)

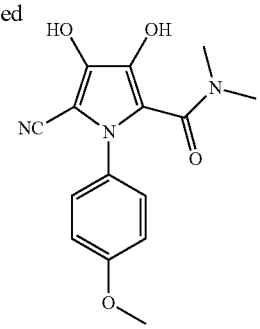

UL1-031

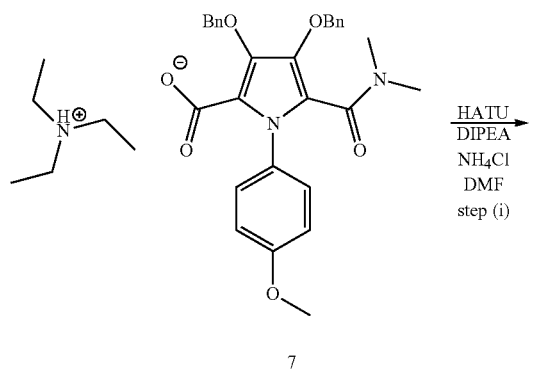

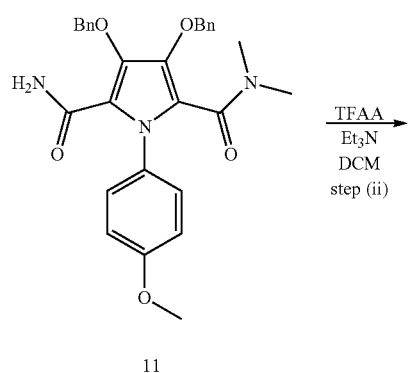

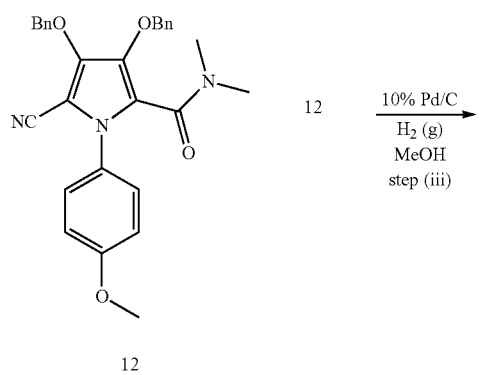

Step (i): 3,4-Bis(benzyloxy)-1-(4-methoxyphenyl)-N$^2$,N$^2$-dimethyl-1H-pyrrole-2,5-dicarboxamide (11)

3,4-Bis(benzyloxy)-1-(4-methoxyphenyl)-N$^2$,N$^2$-dimethyl-1H-pyrrole-2,5-dicarboxamide (11) was prepared using the same procedure as Example B step (iv) except using triethylammonium 3,4-bis(benzyloxy)-5-(dimethylcarbamoyl)-1-(4-methoxyphenyl)-1H-pyrrole-2-carboxylate (7) (570 mg, 0.76 mmol) and ammonium chloride (405 mg, 7.58 mmol) to afford 3,4-bis(benzyloxy)-1-(4-methoxyphenyl)-N$^2$,N$^2$-dimethyl-1H-pyrrole-2,5-dicarboxamide (11) as yellow oil: m/z 500 (M+H)$^+$ (ES$^+$).

Step (ii): 3,4-Bis(benzyloxy)-5-cyano-1-(4-methoxyphenyl)-N,N-dimethyl-1H-pyrrole-2-carboxamide (12)

Trifluoroacetic anhydride (27.0 μL, 0.19 mmol) was added dropwise to a stirred solution of 3,4-bis(benzyloxy)-1-(4-methoxyphenyl)-N$^2$,N$^2$-dimethyl-1H-pyrrole-2,5-dicarboxamide (11) (88 mg, 0.18 mmol) and triethylamine (74.3 μL, 0.53 mmol) in DCM (4 mL) at 0° C. The reaction mixture was stirred for 1 h before and trifluoroacetic anhydride (27.0 μL, 0.19 mmol) was added and the mixture allowed to warm to RT. The reaction was partitioned between sat. NaHCO$_3$ (aq.) (5 mL) and DCM (5 mL) the organic layer was separated and volatiles removed in vacuo to afford 4-bis(benzyloxy)-5-cyano-1-(4-methoxyphenyl)-N,N-dimethyl-1H-pyrrole-2-carboxamide (12) (85 mg, 100%), as a yellow oil: m/z 482 (M+H)$^+$ (ES$^+$).

Step (iii): 5-Cyano-3,4-dihydroxy-1-(4-methoxyphenyl)-N,N-dimethyl-1H-pyrrole-2-carboxamide (UL1-031)

4-Bis(benzyloxy)-5-cyano-1-(4-methoxyphenyl)-N,N-dimethyl-1H-pyrrole-2-carboxamide (12) (85 mg, 0.17 mmol) in methanol (2 mL) was passed through a Thales 'H-cube' cartridge (10% Pd/C) at a flow rate of 1.5 mL/min at 25° C. under H$_2$ (full H$_2$ mode). The output was concentrated in vacuo to afford 5-cyano-3,4-dihydroxy-1-(4-methoxyphenyl)-N,N-dimethyl-1H-pyrrole-2-carboxamide (UL1-031) (11 mg, 21%) as a yellow solid: m/z 302 (M+H)$^+$ (ES$^+$); 300

(M-H)⁻ (ES⁻). ¹H NMR (400 MHz, DMSO-d₆) δ: 9.80 (s, 1H), 8.80 (s, 1H), 7.21-7.11 (m, 2H), 7.03-6.93 (m, 2H), 3.79 (s, 3H), 2.88 (br s, 6H).

Example G 3,4-Dihydroxy-1-(4-methoxyphenyl)-1H-pyrrole-2,5-dicarbonitrile (UL1-034)

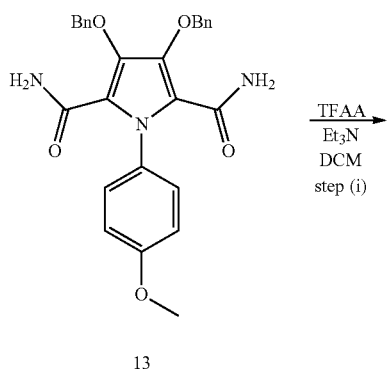

13

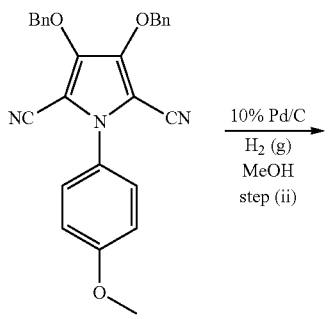

14

Step (i): 3,4-Bis(benzyloxy)-1-(4-methoxyphenyl)-1H-pyrrole-2,5-dicarbonitrile (14)

To a stirred solution of 3,4-bis(benzyloxy)-1-(4-methoxyphenyl)-1H-pyrrole-2,5-dicarboxamide (13) [prepared using the same procedure as Example A step (ii) using ammonium chloride] (267 mg, 0.57 mmol) and triethylamine (710 μL, 5.10 mmol) in DCM (8 mL) at 0° C. was added trifluoroacetic anhydride (240 μL, 1.70 mmol) and the reaction allowed to warm to RT over 30 min. The reaction mixture was partitioned between DCM (50 mL) and 1 M HCl (aq.) (30 mL), the organic was washed with 1 M HCl (aq.) (20 mL), sat. NaHCO₃ (aq.) (30 mL), and brine (20 mL), dried (MgSO₄), filtered and volatiles removed in vacuo to afford a yellow solid. The crude residue was purified by silica gel chromatography (40 g, 0-50% EtOAc in isohexane) to afford 3,4-bis(benzyloxy)-1-(4-methoxyphenyl)-1H-pyrrole-2,5-dicarbonitrile (14) (240 mg, 97%) as a pale yellow solid: ¹H NMR (400 MHz, DMSO-d₆) δ: 7.47-7.27 (m, 10H), 7.30-7.20 (m, 2H), 7.05-6.91 (m, 2H), 5.26 (s, 4H), 3.79 (s, 3H).

Step (ii): 3,4-Dihydroxy-1-(4-methoxyphenyl)-1H-pyrrole-2,5-dicarbonitrile (UL1-034)

3,4-Bis(benzyloxy)-1-(4-methoxyphenyl)-1H-pyrrole-2,5-dicarbonitrile (14) (70 mg, 0.16 mmol) in THF (5 mL) was passed through a Thales 'H-cube' cartridge (10% Pd/C) at a flow rate of 1.5 mL/min at 25° C. under H₂ (full H₂ mode). The output was concentrated in vacuo to afford the crude product. The compound was purified by preparative HPLC (C-18 column, 21.2 mm i.d.×100 mm, 5 micron particle size, gradient 5-95% MeCN in 0.1% aqueous formic acid over 16 min) to afford 3,4-dihydroxy-1-(4-methoxyphenyl)-1H-pyrrole-2,5-dicarbonitrile (UL1-034) (6 mg, 14%) as a yellow powder: m/z 254 (M-H)⁻ (ES⁻). ¹H NMR (400 MHz, DMSO-d₆) δ: 7.44-7.36 (m, 2H), 7.14-7.05 (m, 2H).

Example H

Ethyl 5-cyano-1-(4-fluorophenyl)-3,4-dihydroxy-1H-pyrrole-2-carboxylate (UL1-039)

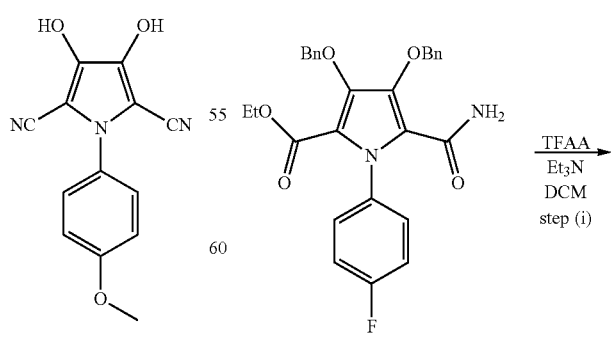

15

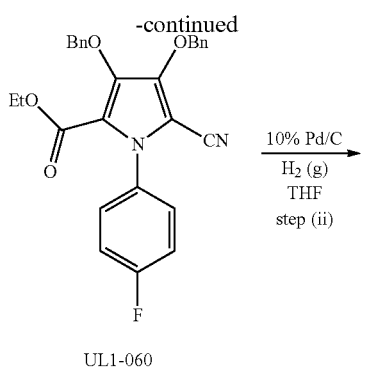

UL1-060 to afford ethyl 5-cyano-1-(4-fluorophenyl)-3,4-dihydroxy-1H-pyrrole-2-carboxylate (UL1-039) (18 mg, 29% yield) as a white solid: m/z 291 (M+H)$^+$ (ES$^+$); 289 (M−H)$^−$ (ES$^−$). $^1$H NMR (400 MHz, DMSO-d$_6$) δ: 10.14 (s, 1H), 8.99 (s, 1H), 7.44-7.36 (m, 2H), 7.35-7.26 (m, 2H), 4.05 (q, J=7.1 Hz, 2H), 1.01 (t, J=7.1 Hz, 3H).

Example I tert-Butyl 5-(dimethylcarbamoyl)-3,4-dihydroxy-1-(4-methoxyphenyl)-1H-pyrrole-2-carboxylate (UL1-036)

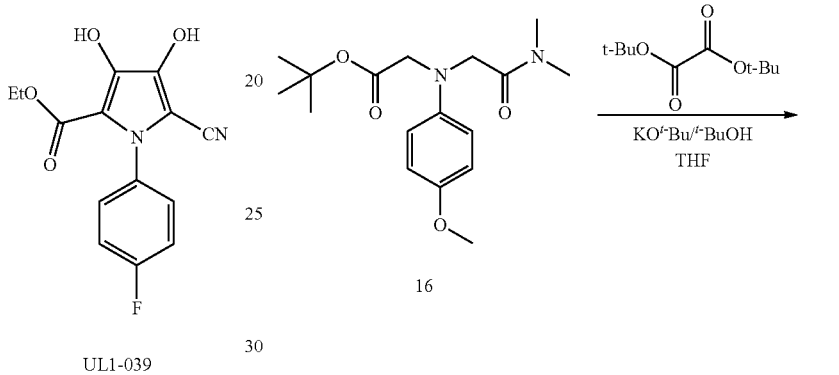

UL1-039

16

UL1-036

Step (i): Ethyl 3,4-bis(benzyloxy)-5-cyano-1-(4-fluorophenyl)-1H-pyrrole-2-carboxylate (UL1-060)

To a stirred solution of ethyl 3,4-bis(benzyloxy)-5-carbamoyl-1-(4-fluorophenyl)-1H-pyrrole-2-carboxylate (15) (1.1 g, 2.25 mmol) [prepared using the same procedure as Example B step (v) using triethylammonium 3,4-bis(benzyloxy)-5-(dimethylcarbamoyl)-1-(4-fluorophenyl)-1H-pyrrole-2-carboxylate and ammonium chloride] and triethylamine (1.26 mL, 9.0 mmol) in DCM (60 mL) at 0° C. was added trifluoroacetic anhydride (0.48 mL 3.38 mmol). The reaction mixture was allowed to warm to RT and partitioned between 1M HCl (aq.) (25 mL) and DCM (50 mL) the organic layer was washed with 1M HCl (aq.), and sat. NaHCO$_3$ (aq.) (25 mL), dried (MgSO$_4$), filtered and the volatiles removed in vacuo to afford the crude product. The crude residue was purified by silica gel chromatography (40 g, 0-20% EtOAc in isohexane) to afford ethyl 3,4-bis(benzyloxy)-5-cyano-1-(4-fluorophenyl)-1H-pyrrole-2-carboxylate (UL1-060) (1.01 g, 94%) as yellow solid: m/z 471 (M+H)$^+$ (ES$^+$). $^1$H NMR (400 MHz, DMSO-d$_6$) δ: 7.57-7.27 (m, 14H), 5.27 (s, 2H), 5.11 (s, 2H), 4.05 (q, J=7.1 Hz, 2H), 1.00 (t, J=7.1 Hz, 3H).

Step (ii): Ethyl 5-cyano-1-(4-fluorophenyl)-3,4-dihydroxy-1H-pyrrole-2-carboxylate (UL1-039)

Ethyl 3,4-bis(benzyloxy)-5-cyano-1-(4-fluorophenyl)-1H-pyrrole-2-carboxylate (UL1-060) (102 mg, 0.22 mmol) in THF (5 mL) was passed through a Thales 'H-cube' cartridge (10% Pd/C) at a flow rate of 1.5 mL/min at 20° C. under H$_2$ (full H$_2$ mode). The output was concentrated in vacuo to afford the crude product. The crude residue was purified by silica gel chromatography (4 g, 0-35% EtOAc in isohexane)

To a solution of tert-butyl 2-((2-(dimethylamino)-2-oxoethyl)(4-methoxyphenyl)amino)acetate (16) (1.98 g, 6.14 mmol) and di-tert-butyl oxalate (1.37 g, 6.76 mmol) in anhydrous tert-butanol (6 mL) was added potassium tert-butoxide (20 wt. % in THF) (10.77 ml, 15.35 mmol) and the reaction was stirred at 100° C. for 1.5 h, di-tert-butyl oxalate (300 mg, 1.5 mmol), potassium tert-butoxide (20 wt. % in THF) (4 mL, 5.71 mmol), THF (10 mL), and tert-butanol (4 mL) were added and the mixture stirred for a further 1 h. The mixture was allowed to cool to RT and acetic acid (4 ml, 69.9 mmol) added, the mixture was poured on to ice-cold water (50 mL) and the resulting precipitate was collected by vacuum filtration and recrystallised from hot ethanol to afford tert-butyl 5-(dimethylcarbamoyl)-3,4-dihydroxy-1-(4-methoxyphenyl)-1H-pyrrole-2-carboxylate (UL1-036) (890 mg, 37%) as a white powder: m/z 377 (M+H)$^+$ (ES$^+$); 375 (M−H)$^−$ (ES$^−$). $^1$H NMR (400 MHz, DMSO-d$_6$) δ: 8.62 (s, 1H), 8.45 (s, 1H), 7.12-6.99 (m, 2H), 6.94-6.81 (m, 2H), 3.76 (s, 3H), 2.83 (br s, 6H), 1.17 (s, 9H).

Example J

2-(Dimethylcarbamoyl)-5-(ethoxycarbonyl)-1-(4-methoxyphenyl)-1H-pyrrole-3,4-diyl diacetate (UL1-044)

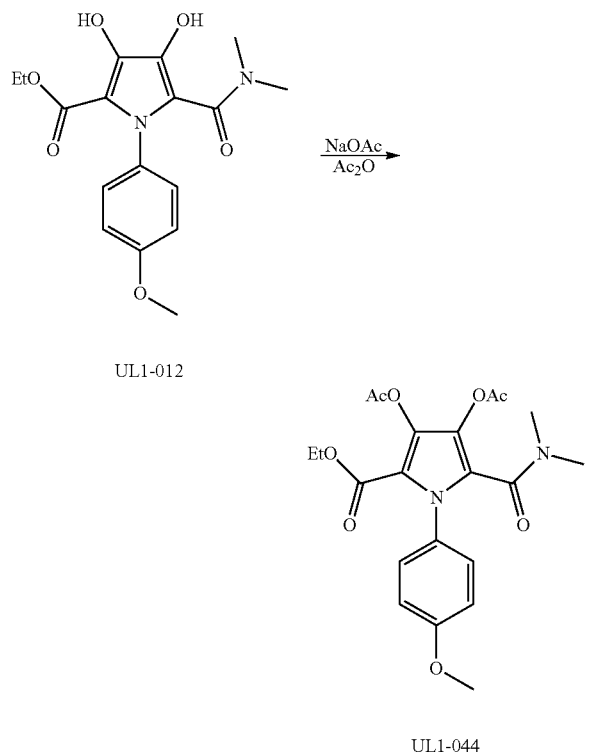

To a suspension of ethyl 5-(dimethylcarbamoyl)-3,4-dihydroxy-1-(4-methoxyphenyl)-1H-pyrrole-2-carboxylate (UL1-012) (120 mg, 0.35 mmol) in acetic anhydride (1 mL, 10.6 mmol) was added NaOAc (90 mg, 1.06 mmol), the suspension was stirred at 100° C. for 2 h. The reaction mixture was partitioned between DCM (25 mL) and iced water (25 mL), dried (MgSO$_4$), filtered and volatiles removed in vacuo to afford a colourless oil. Trituration of the colourless oil from Et$_2$O gave 2-(dimethylcarbamoyl)-5-(ethoxycarbonyl)-1-(4-methoxyphenyl)-1H-pyrrole-3,4-diyl diacetate (UL1-044) (80 mg, 52%) as a white solid: m/z 433 (M+H)$^+$ (ES$^+$). $^1$H NMR (400 MHz, DMSO-d$_6$) δ: 7.27-7.11 (2H, m), 7.00-6.88 (2H, m), 4.00 (q, J=7.1 Hz, 2H), 3.79 (s, 3H), 2.79 (s, 3H), 2.71 (s, 3H), 2.26 (s, 6H) 1.05 (t, J=7.1 Hz, 3H).

Example K

Ethyl 5-(dimethylcarbamoyl)-3,4-dihydroxy-1-(4-methoxyphenyl)-1H-pyrrole-2-carboxylate (UL1-012)

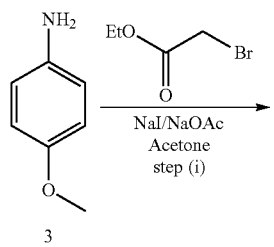

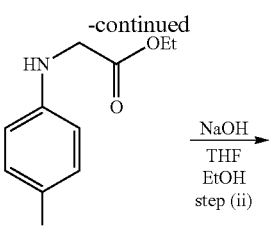

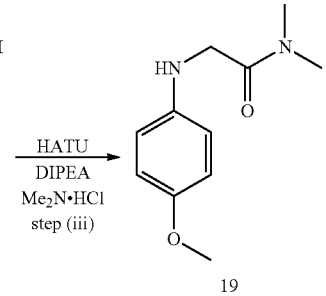

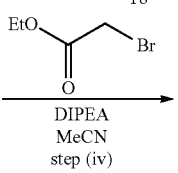

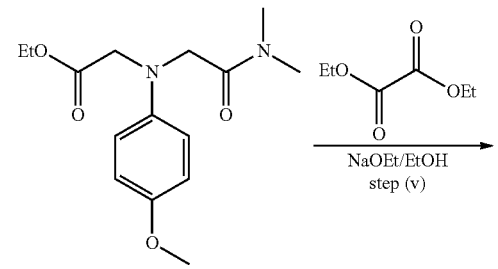

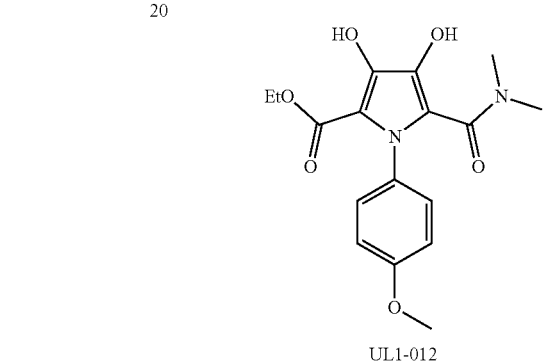

Step (i): Ethyl 2-((4-methoxyphenyl)amino)acetate (17)

To a solution of sodium iodide (122 g, 0.81 mol) and sodium acetate trihydrate (221 g, 1.62 mol) in water (200 mL) was added 4-methoxyaniline (3) (100 g, 0.81 mol) followed by ethyl 2-bromoacetate (90 mL, 812 mmol) the reaction was stirred at 90° C. for 3 h. The reaction mixture was cooled to RT and partitioned with EtOAc (1 L), the organic phase was separated, washed with water (400 mL), 1 M HCl (aq.) (3×500 mL), and the organic phase discarded. The combined acidic extracts were cooled to 0° C. and solid NaOH was added to pH 14 and the aqueous phase was extracted with EtOAc (3×400 mL). The combined organics were washed with brine (250 mL), dried (MgSO$_4$), filtered and solvents removed in vacuo to give ethyl 2-((4-methoxyphenyl)amino) acetate (17) (128 g, 75%) as a purple oil that crystallised on standing: m/z 210 (M+H)$^+$ (ES$^+$). $^1$H NMR (400 MHz, DMSO-d$_6$) δ: 6.75-6.69 (m, 2H), 6.55-6.46 (m, 2H), 3.99 (t, J=6.5 Hz, 1H), 4.10 (q, J=7.1 Hz, 2H), 3.82 (d, J=6.5 Hz, 2H), 3.63 (s, 3H), 1.19 (t, J=7.1 Hz, 3H).

Step (ii): 2-((4-Methoxyphenyl)amino)acetic acid (18)

2M NaOH (aq.) (149 mL, 0.30 mol) was added dropwise to a stirred solution of ethyl 2-((4-methoxyphenyl)amino)acetate (17) (59.2 g, 0.28 mol) in EtOH/THF (300 mL/80 mL). The reaction was stirred at 40° C. for 3 h. The mixture was diluted with water (100 mL) and phosphoric acid (85% wt in water) (35.9 g, 0.31 mol) was added to pH 3. The resulting brown precipitate was collected by filtration and washed with water (100 mL) and dried under vacuum to give 2-((4-methoxyphenyl)amino)acetic acid (18) (45.5 g, 84%) as a brown solid: m/z 182 (M+H)$^+$ (ES$^+$); 180 (M–H)$^-$ (ES$^-$). $^1$H NMR (400 MHz, DMSO-d$_6$) δ: 6.78-6.64 (m, 2H), 6.55-6.44 (m, 2H), 3.74 (s, 2H), 3.64 (s, 3H).

Step (iii): 2-((4-Methoxyphenyl)amino)-N,N-dimethylacetamide (19)

To a stirred suspension of 2-((4-methoxyphenyl)amino) acetic acid (18) (45 g, 0.25 mol) and dimethylamine hydrochloride (40.5 g, 0.5 mol) in acetonitrile (1 L) at 0° C., was added DIPEA (174 ml, 0.99 mol) followed by HATU (99 g, 0.26 mol). The reaction mixture was stirred at RT for 1 h, and then partitioned between EtOAc (1 L) and 5% NaH$_2$PO$_4$ (aq.) (250 mL), the organic layer was washed with sat. NaHCO$_3$ (aq.) (3×300 mL), and 3M HCl (aq.) (4×250 mL). The combined acidic extracts were cooled to 0° C. and solid NaOH was added to pH 14 and the aqueous phase was extracted with EtOAc (3×400 mL), the combined organics were washed with brine (500 mL) dried (MgSO$_4$), filtered and solvents removed in vacuo to give 2-((4-methoxyphenyl)amino)-N,N-dimethylacetamide (19) (37.1 g, 71%) as a brown solid: m/z 209 (M+H)$^+$ (ES$^+$). $^1$H NMR (400 MHz, DMSO-d$_6$) δ: 6.74-6.70 (m, 2H), 6.65-6.59 (m, 2H), 5.10 (br s, 1H), 3.81 (s, 2H), 3.64 (s, 3H), 3.01 (s, 3H), 2.87 (s, 3H).

Step (iv): Ethyl 2-((2-(dimethylamino)-2-oxoethyl) (4-methoxyphenyl)amino)acetate (20)

To a stirred solution of 2-(4-methoxyphenylamino)-N,N-dimethylacetamide (19) (10.7 g, 51.2 mmol) in MeCN (80 mL) and DIPEA (13.4 ml, 77 mmol) was added ethyl bromoacetate (6.84 ml, 61.4 mmol) the reaction was stirred at 60° C. for 16 h. The volatiles were removed in vacuo, and the crude mixture was dissolved in EtOAc (150 mL), washed with 1M HCl (aq.) (150 mL), brine (150 mL), dried (MgSO$_4$), filtered and solvents removed in vacuo to afford a purple oil. The residue was purified by silica gel chromatography (120 g, 60-100% EtOAc in isohexane) to afford ethyl 2-((2-(dimethylamino)-2-oxoethyl)(4-methoxyphenyl)amino)acetate (X) (12.9 g, 85%) as a purple oil: m/z 295.4 (M+H)$^+$ (ES$^+$). $^1$H NMR (400 MHz, DMSO-d$_6$) δ: 6.81-6.71 (m, 2H), 6.60-6.47 (m, 2H), 4.24-3.96 (m, 6H), 3.66 (s, 3H), 2.99 (br s, 3H), 2.83 (br s, 3H), 1.19 (t, J=7.1 Hz, 3H).

Step (v): Ethyl 5-(dimethylcarbamoyl)-3,4-dihydroxy-1-(4-methoxyphenyl)-1H-pyrrole-2-carboxylate (UL1-012)

Diethyl oxalate (2.54 ml, 18.6 mmol) was added dropwise to a stirred solution of ethyl 2-((2-(dimethylamino)-2-oxoethyl)(4-methoxyphenyl)amino)acetate (20) (5.21 g, 17.7 mmol) in NaOEt (21% by wt in EtOH) (27.8 ml, 74.3 mol), the mixture was stirred at 85° C. for 1.5 h. The reaction was quenched with acetic acid (10.1 ml, 177 mmol) and the resulting suspension was poured into iced water (200 mL), and extracted with EtOAc (3×100 mL), combined organics were washed with brine (200 mL), dried (MgSO$_4$), filtered and solvents removed in vacuo to afford a brown oil. The residue was purified by silica gel chromatography (80 g, 0-10% MeOH (+1% NH$_3$) in DCM) to afford ethyl 5-(dimethylcarbamoyl)-3,4-dihydroxy-1-(4-methoxyphenyl)-1H-pyrrole-2-carboxylate (UL1-012) (3.64 g, 53%) as a white solid: m/z 349 (M+H)$^+$ (ES$^+$), 347 (M–H)$^-$ (ES$^-$). $^1$H NMR (400 MHz, DMSO-d$_6$) δ: 8.60 (s, 1H), 8.46 (s, 1H), 7.08-7.01 (m, 2H), 6.90-6.82 (m, 2H), 4.00 (q, J=7.0 Hz, 2H), 3.76 (s, 3H), 2.83 (br s, 6H), 0.99 (t, J=7.1 Hz, 6H).

Example L

Diisopropyl 3,4-dihydroxy-1-(4-methoxyphenyl)-1H-pyrrole-2,5-dicarboxylate (U L2-020) and 2-ethyl 5-isopropyl 3,4-dihydroxy-1-(4-methoxyphenyl)-1H-pyrrole-2,5-dicarboxylate (UL2-021)

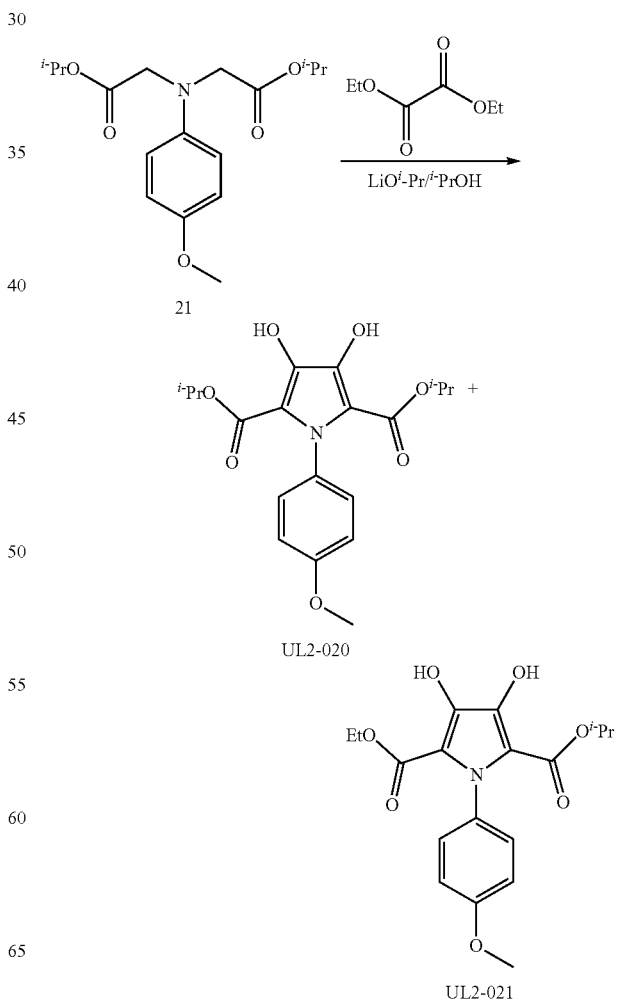

Lithium isopropoxide (2M in THF) (10.4 mL, 20.8 mmol) was added to a mixture of diisopropyl 2,2'-((4-methoxyphenyl)azanediyl)diacetate (21) (2.69 g, 8.32 mmol) [prepared using the same procedure as Example B step (i) using isopropyl 2-bromoacetate] and diethyl oxalate (1.13 mL, 8.32 mmol), the mixture was stirred at 65° C. for 16 h. A further portion of lithium isopropoxide (2M in THF) (5.2 ml, 10.4 mmol) was added and the reaction stirred at 65° C. for 3 h. The reaction was quenched with acetic acid (5 mL) and the volatiles removed in vacuo, the crude product was took up in EtOAc (100 mL) and partitioned with water (100 mL), the aqueous was washed with EtOAc (2×100 mL) combined organics were washed with brine (150 mL), dried (MgSO$_4$), filtered and solvents removed in vacuo to afford a brown oil. The crude product was recrystallised from hot $^i$-PrOH (50 mL), to provide a white solid. The solid was purified by silica gel chromatography (12 g, 0-50% EtOAc in isohexane) to afford diisopropyl 3,4-dihydroxy-1-(4-methoxyphenyl)-1H-pyrrole-2,5-dicarboxylate (UL2-020) (21 mg, 1%) as a white solid: m/z 378 (M+H)$^+$ (ES$^+$). $^1$H NMR (400 MHz, DMSO-d$_6$) δ: 8.62 (s, 2H), 7.12-7.01 (m, 2H), 6.93-6.84 (m, 2H), 4.80 (sept., J=6.3 Hz, 2H), 3.78 (s, 3H), 0.95 (d, J=6.2 Hz, 12H).

Impure fractions were combined and purified by preparative HPLC (C-18, 5 μm, 21.2×50 mm column, 5-95% MeCN in Water 0.1% Formic Acid) to afford 2-ethyl 5-isopropyl 3,4-dihydroxy-1-(4-methoxyphenyl)-1H-pyrrole-2,5-dicarboxylate (UL2-021) (22 mg, 1%) as a white solid: m/z 364 (M+H)$^+$ (ES$^+$). $^1$H NMR (400 MHz, DMSO-d$_6$) δ: 8.66 (s, 1H), 8.62 (s, 1H), 7.09-7.03 (m, 2H), 6.90-6.85 (m, 2H), 4.80 (sept., J=6.2 Hz, 1H), 3.98 (q, J=7.1 Hz, 2H), 3.77 (s, 3H), 1.00 (t, J=7.1 Hz, 3H), 0.93 (d, J=6.2 Hz, 6H).

Example M

Diethyl 3-(2-(benzyloxy)ethoxy)-1-(4-fluorophenyl)-4-hydroxy-1H-pyrrole-2,5-dicarboxylate (UL2-025)

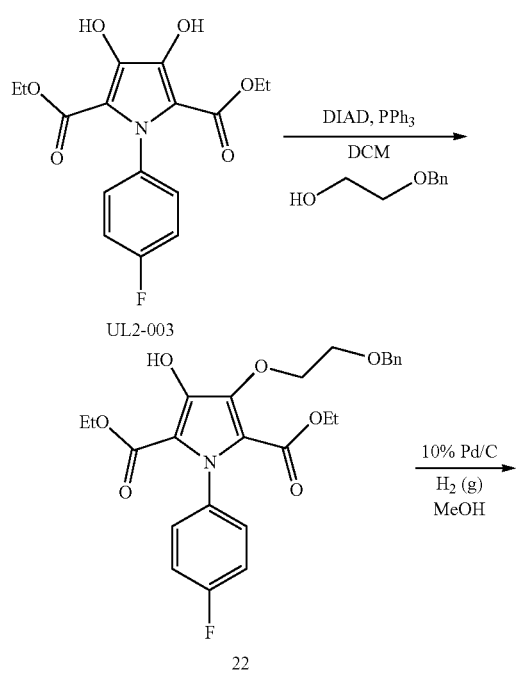

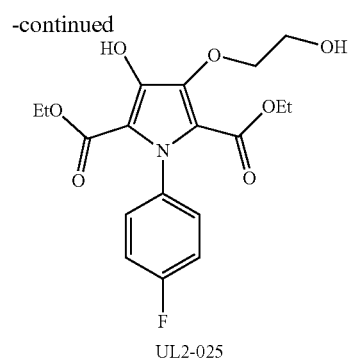

Step (i) Diethyl 3-(2-(benzyloxy)ethoxy)-1-(4-fluorophenyl)-4-hydroxy-1H-pyrrole-2,5-dicarboxylate (22)

Diisopropyl azodicarboxylate (317 μL, 1.63 mmol) was added to a solution of diethyl 1-(4-fluorophenyl)-3,4-dihydroxy-1H-pyrrole-2,5-dicarboxylate (UL2-003) (500 mg, 1.48 mmol), 2-(benzyloxy)ethanol (232 μL, 1.63 mmol) and triphenylphosphine (428 mg, 1.63 mmol) in DCM (5 ml), at 0° C. The reaction mixture was allowed to warm to RT and stirred for 1 h. The reaction was washed with water (5 mL) and the phases separated using a phase separation cartridge, the organic was concentrated in vacuo to afford a yellow oil. The residue was purified by silica gel chromatography (80 g, 0-25% EtOAc in isohexane) to afford diethyl 3-(2-(benzyloxy)ethoxy)-1-(4-fluorophenyl)-4-hydroxy-1H-pyrrole-2,5-dicarboxylate (22) (122 mg, 17%) as a yellow oil: m/z 472 (M+H)$^+$ (ES$^+$); 470 (M−H)$^−$ (ES$^−$). $^1$H NMR (400 MHz, DMSO-d$_6$) δ: 8.70 (s, 1H), 7.38-7.26 (m, 5H), 7.24-7.12 (m, 4H), 4.54 (s, 2H), 4.27-4.16 (m, 2H), 4.09-3.89 (m, 4H), 3.78-3.71 (m, 2H), 1.01-0.94 (m, 6H).

Step (ii) Diethyl 1-(4-fluorophenyl)-3-hydroxy-4-(2-hydroxyethoxy)-1H-pyrrole-2,5-dicarboxylate (UL2-025)

A solution of diethyl 3-(2-(benzyloxy)ethoxy)-1-(4-fluorophenyl)-4-hydroxy-1H-pyrrole-2,5-dicarboxylate (22) (122 mg, 0.26 mmol) in MeOH (120 ml) was passed through a Thales 'H-cube' cartridge (10% Pd/C) at a flow rate of 1 mL/min at 30° C. under H$_2$ (full H$_2$ mode). The output was concentrated in vacuo to afford diethyl 3-(2-(benzyloxy)ethoxy)-1-(4-fluorophenyl)-4-hydroxy-1H-pyrrole-2,5-dicarboxylate (UL2-025) (122 mg, 85%) as a pale yellow oil: m/z 382 (M+H)$^+$ (ES$^+$), 380 (M−H)$^−$ (ES$^−$). $^1$H NMR (400 MHz, DMSO-d$_6$) δ: 8.94 (br s, 1H), 7.29-7.22 (m, 2H), 7.21-7.14 (m, 2H), 5.01 (br s, 1H), 4.08-3.97 (m, 6H), 3.73-3.65 (m, 2H), 1.02 (t, J=7.1 Hz, 3H), 0.99 (t, J=7.1 Hz, 3H).

Example N

Diethyl 3-(2-amino-2-oxoethoxy)-4-hydroxy-1-(4-methoxyphenyl)-1H-pyrrole-2,5-dicarboxylate (UL2-031)

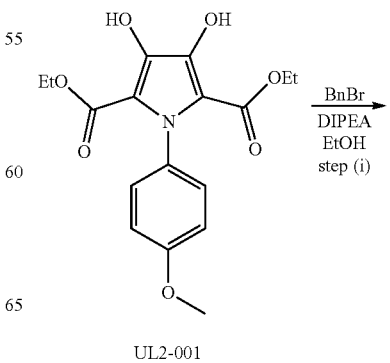

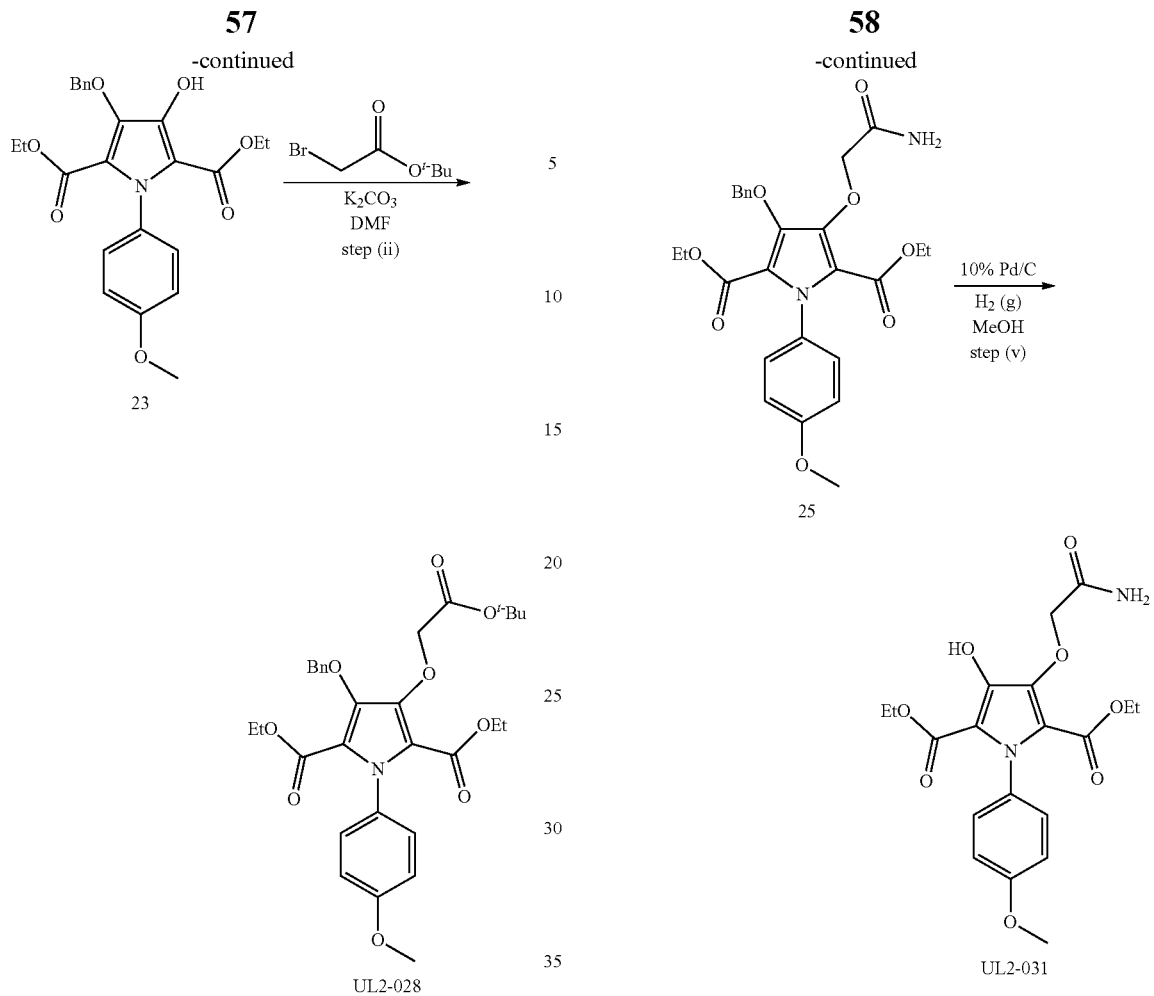

Step (i): Diethyl 3-(benzyloxy)-4-hydroxy-1-(4-methoxyphenyl)-1H-pyrrole-2,5-dicarboxylate (23)

Benzyl bromide (2.13 ml, 17.9 mmol) was added dropwise to a suspension of DIPEA (3.12 mL, 17.9 mmol) and diethyl 3,4-dihydroxy-1-(4-methoxyphenyl)-1H-pyrrole-2,5-dicarboxylate (UL2-001) (5 g, 14.3 mmol) in EtOH (200 mL). The reaction mixture was stirred at 50° C. for 18 h. Additional benzyl bromide (0.85 mL, 7.20 mmol) and DIPEA (1.25 mL, 7.20 mmol) were added and the reaction stirred at 60° C. for 24 h, after which further portions of benzyl bromide (0.85 ml, 7.20 mmol) and DIPEA (1.25 mL, 7.20 mmol) were added and the reaction mixture stirred at 60° C. for 24 h. The reaction mixture was allowed to cool to RT, and partitioned between EtOAc (200 mL) and sat. NaHCO$_3$ (aq.) (200 mL), the organic layer was separated and washed with sat. NaHCO$_3$ (aq.) (2×200 mL) dried (MgSO$_4$), filtered and solvents removed in vacuo to give an orange oil. The residue was purified by silica gel chromatography (80 g, 0-100% EtOAc in isohexane) to afford a yellow solid. The product was recrystallised from EtOH (100 mL) to afford diethyl 3-(benzyloxy)-4-hydroxy-1-(4-methoxyphenyl)-1H-pyrrole-2,5-dicarboxylate (23) (2.89 g, 37%) as a pale yellow solid: m/z 440 (M+H)$^+$ (ES$^+$). $^1$H NMR (400 MHz, DMSO-d$_6$) δ: 8.82 (s, 1H), 7.52-7.30 (m, 5H), 7.16-7.03 (m, 2H), 6.94-6.83 (m, 2H), 5.09 (s, 2H), 4.10-3.91 (m, 4H), 3.79 (s, 3H), 1.02-0.92 (m, 6H).

Step (ii): Diethyl 3-(benzyloxy)-4-(2-(tert-butoxy)-2-oxoethoxy)-1-(4-methoxyphenyl)-1H-pyrrole-2,5-dicarboxylate (UL2-028)

tert-Butyl 2-bromoacetate (0.55 ml, 3.41 mmol) was added dropwise to a stirred solution of diethyl 3-(benzyloxy)-4-hydroxy-1-(4-methoxyphenyl)-1H-pyrrole-2,5-dicarboxylate (23) (1.0 g, 2.28 mmol) and $K_2CO_3$ (0.63 g, 4.55 mmol) in DMF (20 mL). The reaction mixture was stirred at RT for 18 h, and partitioned between EtOAc (200 mL) and sat. $NaHCO_3$ (aq.) (200 mL), the organic layer was separated and washed with sat. $NaHCO_3$ (aq.) (2×200 mL), dried ($MgSO_4$), filtered and solvents removed in vacuo to give a yellow oil. The residue was purified by silica gel chromatography (120 g, 0-20% EtOAc in isohexane) to afford diethyl 3-(benzyloxy)-4-(2-(tert-butoxy)-2-oxoethoxy)-1-(4-methoxyphenyl)-1H-pyrrole-2,5-dicarboxylate (UL2-028) (912 mg, 72%) as a pale yellow oil: m/z 554 (M+H)$^+$ (ES$^+$). $^1$H NMR (400 MHz, DMSO-$d_6$) δ: 7.49-7.44 (m, 2H), 7.43-7.31 (m, 3H), 7.15-7.08 (m, 2H), 6.94-6.88 (m, 2H), 5.12 (s, 2H), 4.59 (s, 2H), 4.02-3.94 (m, 4H), 3.79 (s, 3H), 1.40 (s, 9H), 1.02 (t, J=7.1 Hz, 3H), 0.97 (t, J=7.1 Hz, 3H).

Step (iii): 2-((4-(benzyloxy)-2,5-Bis(ethoxycarbonyl)-1-(4-methoxyphenyl)-1H-pyrrol-3-yl)oxy)acetic acid (24)

Diethyl 3-(benzyloxy)-4-(2-(tert-butoxy)-2-oxoethoxy)-1-(4-methoxyphenyl)-1H-pyrrole-2,5-dicarboxylate (UL2-028) (250 mg, 0.45 mmol) was dissolved in 4 M HCl in dioxane (2.5 mL, 10.0 mmol), and the reaction mixture was stirred at RT for 2 h, volatiles were removed in vacuo and the product was azeotroped with toluene (2×5 mL) to afford 2-((4-(benzyloxy)-2,5-bis(ethoxycarbonyl)-1-(4-methoxyphenyl)-1H-pyrrol-3-yl)oxy)acetic acid (24) (216 mg, 87%) as a yellow oil: m/z 498 (M+H)$^+$ (ES$^+$); 496 (M–H)$^-$ (ES$^-$).

Step (iv): Diethyl 3-(2-amino-2-oxoethoxy)-4-(benzyloxy)-1-(4-methoxyphenyl)-1H-pyrrole-2,5-dicarboxylate (25)

HATU (153 mg, 0.40 mmol) was added to a stirred solution 2-((4-(benzyloxy)-2,5-bis(ethoxycarbonyl)-1-(4-methoxyphenyl)-1H-pyrrol-3-yl)oxy)acetic acid (24) (100 mg, 0.20 mmol), DIPEA (176 µL, 1.00 mmol), and $NH_4Cl$ (53.8 mg, 1.00 mmol) in THF (2 mL) at 0° C. The reaction mixture was stirred at 0° C. for 20 min and then at RT for 2 h volatiles were removed in vacuo, dissolved in EtOAc (30 mL) and washed with 1 M HCl (3×30 mL), sat. $NaHCO_3$ (aq.) (3×30 mL) and brine (30 mL), dried ($MgSO_4$), filtered and solvents removed in vacuo to give a yellow oil. The product was purified by silica gel chromatography (12 g, 0-100% EtOAc in isohexane) to afford diethyl 3-(2-amino-2-oxoethoxy)-4-(benzyloxy)-1-(4-methoxyphenyl)-1H-pyrrole-2,5-dicarboxylate (25) (66 mg, 66%) as a white solid: m/z 497 (M+H)$^+$ (ES$^+$). $^1$H NMR (400 MHz, DMSO-$d_6$) δ: 7.58 (br s, 1H), 7.51 (br s, 1H), 7.49-7.44 (m, 2H), 7.43-7.33 (m, 3H), 7.17-7.09 (m, 2H), 6.95-6.86 (m, 2H), 5.10 (s, 2H), 4.46 (s, 2H), 4.00 (q, J=7.1 Hz, 2H), 3.98 (q, J=7.1 Hz, 2H), 3.79 (s, 3H), 0.97 (t, J=7.1 Hz, 3H), 0.96 (t, J=7.1 Hz, 3H).

Step (v): Diethyl 3-(2-amino-2-oxoethoxy)-4-hydroxy-1-(4-methoxyphenyl)-1H-pyrrole-2,5-dicarboxylate (UL2-031)

Diethyl 3-(2-amino-2-oxoethoxy)-4-(benzyloxy)-1-(4-methoxyphenyl)-1H-pyrrole-2,5-dicarboxylate (25) (66 mg, 0.133 mmol) in MeOH (66 mL) was passed through a Thales 'H-cube' cartridge (10% Pd/C) at a flow rate of 1 mL/min at 20° C. under $H_2$ (full $H_2$ mode). The output was concentrated in vacuo to afford a yellow oil. The residue was purified by silica gel chromatography (4 g, 0-100% EtOAc in isohexane) to afford diethyl 3-(2-amino-2-oxoethoxy)-4-hydroxy-1-(4-methoxyphenyl)-1H-pyrrole-2,5-dicarboxylate (UL2-031) (25 mg, 46%) as a white solid: m/z 407 (M+H)$^+$ (ES$^+$); 405 (M–H)$^-$ (ES$^-$). $^1$H NMR (400 MHz, DMSO-$d_6$) δ: 9.61 (s, 1H), 7.82-7.63 (m, 2H), 7.10-7.06 (m, 2H), 6.93-6.84 (m, 2H), 4.49 (s, 2H), 4.03-3.93 (m, 4H), 3.79 (s, 3H), 1.05-0.94 (m, 6H).

Example O

Ethyl 5-(dimethylcarbamoyl)-3,4-bis((dimethylcarbamoyl)oxy)-1-(4-methoxyphenyl)-1H-pyrrole-2-carboxylate (UL1-063)

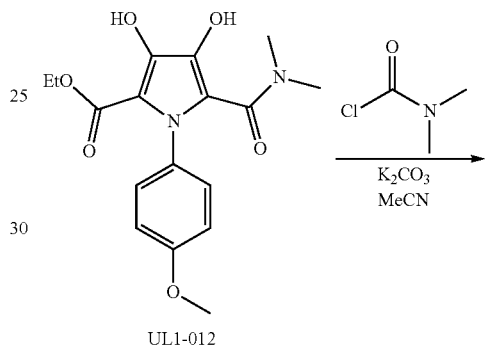

UL1-012

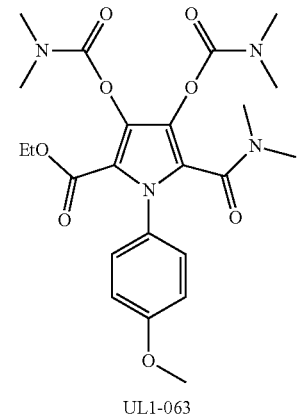

UL1-063

Dimethylcarbamic chloride (160 µL, 1.74 mmol) was added dropwise to a stirred suspension of ethyl 5-(dimethylcarbamoyl)-3,4-dihydroxy-1-(4-methoxyphenyl)-1H-pyrrole-2-carboxylate (UL1-012) (202 mg, 0.58 mmol) and $K_2CO_3$ (240 mg, 1.74 mmol) in MeCN (4 mL). The resulting mixture was stirred at 80° C. for 16 h then partitioned between sat. $NaHCO_3$ (aq.) (10 mL) and $Et_2O$ (10 mL) the aqueous layer was extracted with $Et_2O$ (2×10 mL), the combined organics were washed with 10% NaOH (aq.) (2×10 mL), water (2×10 mL) and brine (2×10 mL), dried ($MgSO_4$), filtered and solvents removed in vacuo to give an orange oil. Trituration of the oil with isohexane provided ethyl 5-(dimethylcarbamoyl)-3,4-bis((dimethylcarbamoyl)oxy)-1-(4-methoxyphenyl)-1H-pyrrole-2-carboxylate (UL1-063) (40 mg, 14%) as a cream solid: m/z 491 (M+H)⁺ (ES⁺). ¹H NMR (400 MHz, DMSO-d₆) δ: 7.21-7.11 (m, 2H), 6.98-6.88 (m, 2H), 4.00 (q, J=7.1 Hz, 2H), 3.79 (s, 3H), 3.01 (s, 3H), 2.96 (s, 3H), 2.90 (s, 3H), 2.88 (s, 3H), 2.80 (s, 3H), 2.70 (s, 3H), 1.05 (t, J=7.1 Hz, 3H).

7.06 (m, 2H), 6.95-6.86 (m, 2H), 4.00 (q, J=7.1 Hz, 2H), 3.77 (s, 3H), 2.98 (s, 3H), 2.88 (s, 3H), 2.78 (s, 3H), 2.69 (s, 3H), 1.00 (t, J=7.1 Hz, 3H).

Example P

Ethyl 5-(dimethylcarbamoyl)-4-((dimethylcarbamoyl)oxy)-3-hydroxy-1-(4-methoxyphenyl)-1H-pyrrole-2-carboxylate (UL1-066)

Example Q

Ethyl 5-(dimethylcarbamoyl)-3-hydroxy-1-(4-methoxyphenyl)-4-(sulfamoyloxy)-1H-pyrrole-2-carboxylate (UL1-068)

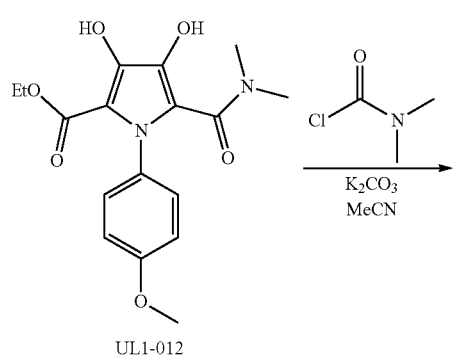

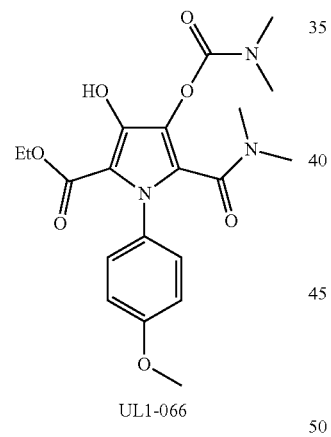

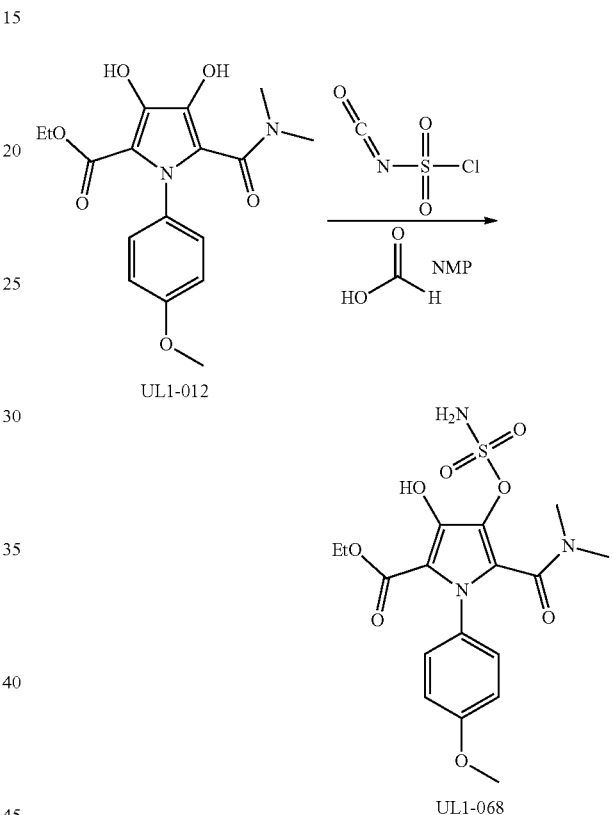

Dimethylcarbamic chloride (163 μL, 1.77 mmol) was added dropwise to a stirred suspension of ethyl 5-(dimethylcarbamoyl)-3,4-dihydroxy-1-(4-methoxyphenyl)-1H-pyrrole-2-carboxylate (UL1-012) (494 mg, 1.42 mmol) and K₂CO₃ (255 mg, 1.85 mmol) in MeCN (8 mL). The resulting mixture was stirred at RT for 24 h then partitioned between water (30 mL) and DCM (20 mL) the aqueous layer was extracted with DCM (2×20 mL), the combined organics were dried (MgSO₄), filtered and solvents removed in vacuo to give an orange oil. The residue was purified by silica gel chromatography (12 g, 0-10% MeOH (+1% NH₃) in DCM) to afford ethyl 5-(dimethylcarbamoyl)-4-((dimethylcarbamoyl)oxy)-3-hydroxy-1-(4-methoxyphenyl)-1H-pyrrole-2-carboxylate (UL1-066) (35 mg, 6%) as a white solid: m/z 420 (M+H)⁺ (ES⁺). ¹H NMR (400 MHz, DMSO-d₆) δ: 8.85 (s, 1H), 7.16-

Formic acid (165 μL, 4.31 mmol) was added dropwise to neat sulfurisocyanatidic chloride (374 μL, 4.31 mmol) at 0° C. with stirring. The reaction mixture allowed to warm to RT and stirred for 2 h, after which a solution of ethyl 5-(dimethylcarbamoyl)-3,4-dihydroxy-1-(4-methoxyphenyl)-1H-pyrrole-2-carboxylate (UL1-012) (0.5 g, 1.44 mmol) in NMP (3 mL) was added dropwise. The reaction mixture was stirred at 0° C. for 30 min and allowed to warm to RT and stirred for a further 2 h. The reaction mixture was partitioned with brine (30 mL) and EtOAc (25 mL), the aqueous layer was extracted with EtOAc (2×25 mL) the combined organics were dried (MgSO₄), filtered and solvents removed in vacuo to give a yellow oil. The compound was purified by preparative HPLC (C-18 column, 21.2 mm i.d.×100 mm, 5 micron particle size, gradient 5-95% MeCN in 0.1% aqueous formic acid over 16 min) to afford ethyl 5-(dimethylcarbamoyl)-3-hydroxy-1-(4-methoxyphenyl)-4-(sulfamoyloxy)-1H-pyrrole-2-carboxylate (UL1-068) (76 mg, 12%) as a white solid: m/z 428 (M+H)⁺ (ES⁺); 426 (M−H)⁻ (ES⁻). ¹H NMR (400 MHz, DMSO-d₆) δ: 8.87 (s, 1H), 7.92 (s, 2H), 7.16-7.08 (m, 2H), 6.96-6.88 (m, 2H), 4.03 (q, J=7.1 Hz, 2H), 3.79 (s, 3H), 2.75 (s, 3H), 2.67 (s, 3H), 1.02 (t, J=7.1 Hz, 3H).

Example R

Ethyl 5-(dimethylcarbamoyl)-3-hydroxy-1-(4-methoxyphenyl)-4-(phosphonooxy)-1H-pyrrole-2-carboxylate (UL1-070)

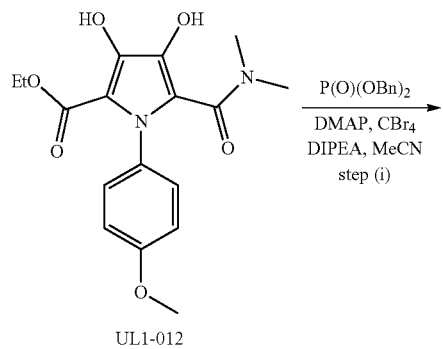

UL1-012

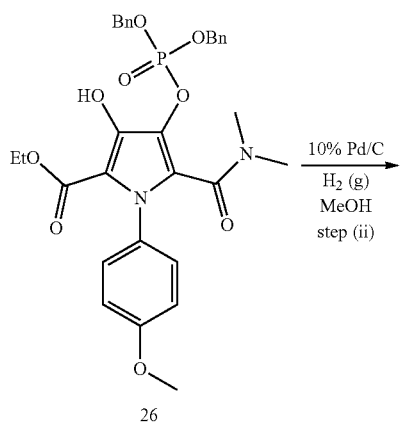

26

Step (i): Ethyl 4-((bis(benzyloxy)phosphoryl)oxy)-5-(dimethylcarbamoyl)-3-hydroxy-1-(4-methoxyphenyl)-1H-pyrrole-2-carboxylate (26)

Perbromomethane (286 mg, 0.86 mmol) and N-ethyl-N-isopropylpropan-2-amine (376 μL, 2.15 mmol) were added successively to a solution of N,N-dimethylpyridin-4-amine (8.8 mg, 0.07 mmol) and ethyl 5-(dimethylcarbamoyl)-3,4-dihydroxy-1-(4-methoxyphenyl)-1H-pyrrole-2-carboxylate (UL1-012) (250 mg, 0.72 mmol) in MeCN (3 mL) at −10° C. The reaction mixture was allowed to stir for 30 min and bis(phenoxymethyl)phosphine oxide (166 μL, 0.75 mmol) was added, the reaction was allowed to slowly warm to 0° C. and stirred for 1 h. The reaction was quenched with 5% $NaH_2PO_4$ (aq.) (20 mL) and extracted with EtOAc (3×25 mL). The combined organics were washed with brine (50 mL), dried ($MgSO_4$), filtered and solvents removed in vacuo. The crude residue was purified by silica gel chromatography (40 g, 0-4% MeOH in DCM) to afford an orange oil. The compound was purified by preparative HPLC (C-18 column, 21.2 mm i.d.×100 mm, 5 micron particle size, gradient 5-95% MeCN in 0.1% aqueous formic acid over 16 min) to afford ethyl 4-((bis(benzyloxy)phosphoryl)oxy)-5-(dimethylcarbamoyl)-3-hydroxy-1-(4-methoxyphenyl)-1H-pyrrole-2-carboxylate (26) (228 mg, 51%) as a pale yellow solid: m/z 609 $(M+H)^+$ $(ES^+)$; 607 $(M-H)^-$ $(ES^-)$.

Step (ii): Ethyl 5-(dimethylcarbamoyl)-3-hydroxy-1-(4-methoxyphenyl)-4-(phosphonooxy)-1H-pyrrole-2-carboxylate (UL1-070)

A solution of ethyl 4-((bis(benzyloxy)phosphoryl)oxy)-5-(dimethylcarbamoyl)-3-hydroxy-1-(4-methoxyphenyl)-1H-pyrrole-2-carboxylate (26) (225 mg, 0.37 mmol) in MeOH (10 mL) was passed through a Thales 'H-cube' cartridge (10% Pd/C) at a flow rate of 1 mL/min at 30° C. under $H_2$ (full $H_2$ mode). The output was concentrated in vacuo to afford ethyl 5-(dimethylcarbamoyl)-3-hydroxy-1-(4-methoxyphenyl)-4-(phosphonooxy)-1H-pyrrole-2-carboxylate (UL1-070) (151 mg, 94%) as a pale yellow solid: m/z 429 $(M+H)^+$ $(ES^+)$; 427 $(M-H)^-$ $(ES^-)$, $^1$H NMR (400 MHz, DMSO-$d_6$) δ: 7.11-7.03 (m, 2H), 6.93-6.85 (m, 2H), 3.99 (q, J=7.1 Hz, 2H), 3.77 (s, 3H), 2.82 (s, 3H), 2.71 (s, 3H), 1.02 (t, J=7.1 Hz, 3H).

Example S

Ethyl 3,4-dihydroxy-1-(4-methoxyphenyl)-5-(pyridin-2-yl)-1H-pyrrole-2-carboxylate (UL1-083)

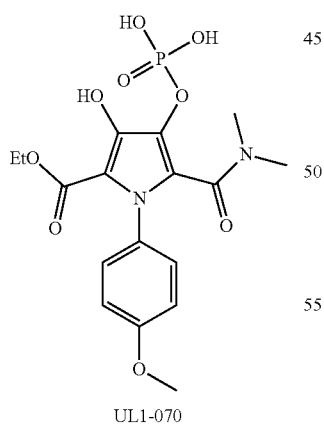

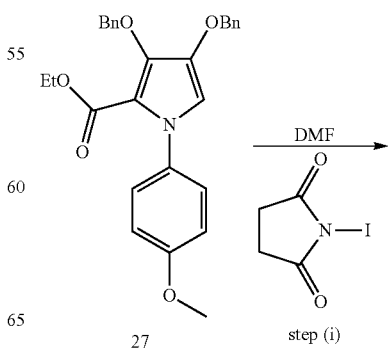

27　　step (i)

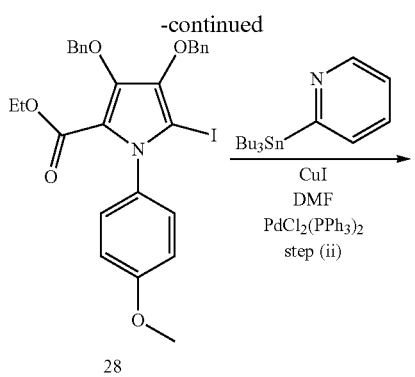

28

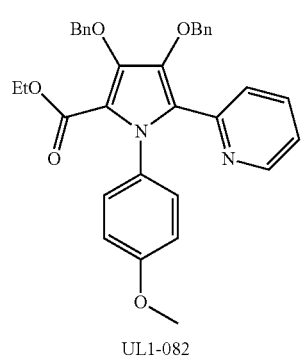

UL1-082

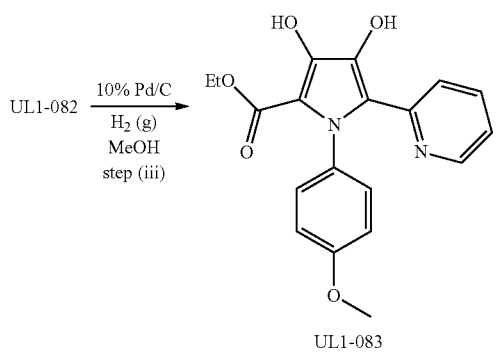

UL1-083

Step (i): Ethyl 3,4-bis(benzyloxy)-5-iodo-1-(4-methoxyphenyl)-1H-pyrrole-2-carboxylate (28)

N-Iodosuccinimide (1.77 g, 7.57 mmol) was added to a solution of ethyl 3,4-bis(benzyloxy)-1-(4-methoxyphenyl)-1H-pyrrole-2-carboxylate (27) [prepared using the same procedure as Example E step (i) using (5) as starting material] (3.0 g, 6.56 mmol) in DMF (60 mL) and stirred at 0° C. for 10 min. The mixture was partitioned between sat. $Na_2S_2O_3$ (aq.) (100 mL) and $Et_2O$ (250 mL), the organic layer was separated and washed with sat. $Na_2S_2O_3$ (aq.) (100 mL), brine (100 mL) dried ($MgSO_4$), filtered and solvents removed in vacuo. The crude residue was purified by silica gel chromatography (120 g, 0-40% $Et_2O$ in isohexane) to afford ethyl 3,4-bis(benzyloxy)-5-iodo-1-(4-methoxyphenyl)-1H-pyrrole-2-carboxylate (28) (2.92 g, 76%) as a white solid: m/z 584 (M+H)$^+$ (ES$^+$). $^1$H NMR (400 MHz, DMSO-$d_6$) δ: 7.51-7.29 (m, 10 H), 7.14-7.05 (m, 2H), 7.03-6.92 (m, 2H), 5.12 (s, 2H), 5.00 (s, 2H), 3.97 (q, J=7.1 Hz, 2H) 3.82 (s, 3H), 0.99 (t, J=7.1 Hz, 3H).

Step (ii): Ethyl 3,4-bis(benzyloxy)-1-(4-methoxyphenyl)-5-(pyridin-2-yl)-1H-pyrrole-2-carboxylate (UL1-082)

To a solution of ethyl 3,4-bis(benzyloxy)-5-iodo-1-(4-methoxyphenyl)-1H-pyrrole-2-carboxylate (28) (300 mg, 0.51 mmol) in DMF (5 mL) was added 2-(tributylstannyl)pyridine (280 μL, 0.87 mmol), copper(I) iodide (19.6 mg, 0.10 mmol) and dichlorobis(triphenylphosphine)palladium (II) (36.1 mg, 0.05 mmol). The mixture was heated in a microwave at 140° C. for 30 min, AcOH (2 mL) was added and the crude product was loaded onto a column of SCX (5 g). The column was washed with MeOH and then the product was eluted with 1% $NH_3$ in MeOH. The resultant mixture was concentrated in vacuo and the residue was purified by silica gel chromatography (12 g, 20-100% EtOAc in isohexane) to afford ethyl 3,4-bis(benzyloxy)-1-(4-methoxyphenyl)-5-(pyridin-2-yl)-1H-pyrrole-2-carboxylate (UL1-082) (231 mg, 83%) as a pale yellow oil: m/z 535 (M+H)$^+$ (ES$^+$). $^1$H NMR (400 MHz, DMSO-$d_6$) δ: $^1$H NMR (400 MHz, DMSO-$d_6$) δ: 8.47-8.40 (m, 1H), 7.71-7.63 (m, 1H), 7.54-7.47 (m, 2H), 7.45-7.16 (m, 10H), 7.12-7.03 (m, 2H), 6.83-6.76 (m, 2H), 5.18 (s, 2H), 4.96 (s, 2H), 4.02 (q, J=7.1 Hz, 2H), 3.72 (s, 3H), 1.03 (t, J=7.1 Hz, 3H).

Step (iii): Ethyl 3,4-dihydroxy-1-(4-methoxyphenyl)-5-(pyridin-2-yl)-1H-pyrrole-2-carboxylate (UL1-083)

A solution of ethyl 3,4-bis(benzyloxy)-1-(4-methoxyphenyl)-5-(pyridin-2-yl)-1H-pyrrole-2-carboxylate (UL1-082) (146 mg, 0.273 mmol) in MeOH/THF (9:1; 20 mL) was passed through a Thales 'H-cube' cartridge (10% Pd/C) at a flow rate of 1 mL/min at 30° C. under $H_2$ (full $H_2$ mode). The output was concentrated in vacuo and the resulting oil was purified by silica gel chromatography (12 g, 0-2% MeOH in DCM) to afford ethyl 3,4-dihydroxy-1-(4-methoxyphenyl)-5-(pyridin-2-yl)-1H-pyrrole-2-carboxylate (UL1-083) (86 mg, 89%) as a pale orange solid: m/z 355 (M+H)$^+$ (ES$^+$). $^1$H NMR (400 MHz, DMSO-$d_6$) δ: 10.84 (s, 1H), 8.62 (s, 1H), 8.56-8.47 (m, 1H), 7.67-7.55 (m, 1H), 7.26-7.12 (m, 3H), 7.01-6.89 (m, 2H), 6.62-6.49 (m, 1H), 4.01 (q, J=7.1 Hz, 2H), 3.80 (s, 3H), 1.02 (t, J=7.1 Hz, 3H).

Example T

Ethyl 5-(4-ethylthiazol-2-yl)-3,4-dihydroxy-1-(4-methoxyphenyl)-1H-pyrrole-2-carboxylate (UL1-086)

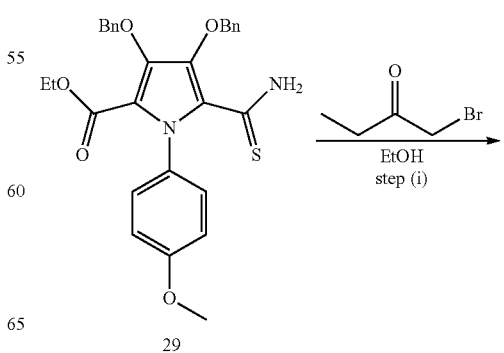

29

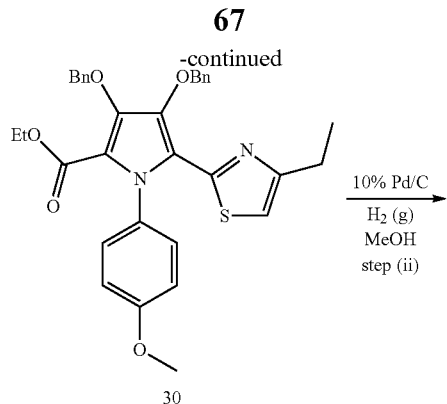

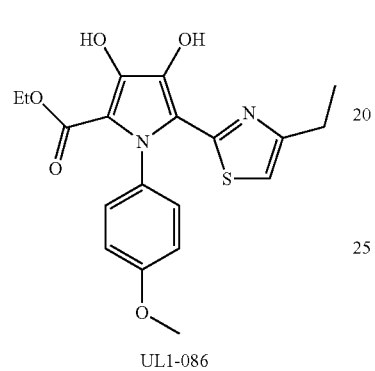

UL1-086

Step (i): Ethyl 3,4-bis(benzyloxy)-5-(4-ethylthiazol-2-yl)-1-(4-methoxyphenyl)-1H-pyrrole-2-carboxylate (30)

A solution of 1-bromobutan-2-one (24 μL, 0.21 mmol) and ethyl 3,4-bis(benzyloxy)-5-carbamothioyl-1-(4-methoxyphenyl)-1H-pyrrole-2-carboxylate (29) [prepared under standard conditions from UL1-079 and Lawesson reagent] (100 mg, 0.19 mmol) in EtOH (4 mL) was heated at 80° C. for 45 min. The volatiles were removed in vacuo and the product was purified by silica gel chromatography (12 g cartridge, 0-25% EtOAc in isohexane) to afford ethyl 3,4-bis(benzyloxy)-5-(4-ethylthiazol-2-yl)-1-(4-methoxyphenyl)-1H-pyrrole-2-carboxylate (30) (82 mg, 75%) as a yellow oil: m/z 569 (M+H)+ (ES+).

Step (ii) Ethyl 5-(4-ethylthiazol-2-yl)-3,4-dihydroxy-1-(4-methoxyphenyl)-1H-pyrrole-2-carboxylate (UL1-086)

A solution of ethyl 3,4-bis(benzyloxy)-5-(4-ethylthiazol-2-yl)-1-(4-methoxyphenyl)-1H-pyrrole-2-carboxylate (30) (70 mg, 0.12 mmol) in MeOH/THF (3:1; 5 mL) was passed through a Thales 'H-cube' cartridge (10 Pd/C) at a flow rate of 1 mL/min at 40° C. under $H_2$ (full $H_2$ mode). The output was concentrated in vacuo and the resulting oil was purified by silica gel chromatography (12 g, 0-20% EtOAc in isohexane) to afford ethyl 5-(4-ethylthiazol-2-yl)-3,4-dihydroxy-1-(4-methoxyphenyl)-1H-pyrrole-2-carboxylate (UL1-086) (30 mg, 63%) as an off-white solid: m/z 389 (M+H)+ (ES+). $^1$H NMR (400 MHz, DMSO-$d_6$) δ: $^1$H NMR (400 MHz, DMSO-d6) δ: 9.82 (s, 1H), 8.68 (s, 1H), 7.28-7.19 (m, 2H), 7.06-7.03 (m, 1H), 7.03-6.97 (m, 2H), 4.00 (q, J=7.1 Hz, 2H), 3.82 (s, 3H), 2.67 (q, J=7.5 Hz, 2H), 1.16 (t, J=7.5 Hz, 3H), 0.99 (t, J=7.1 Hz, 3H).

Example U

Ethyl 3,4-bis(benzyloxy)-1-(4-methoxyphenyl)-5-(5-methyl-1,3,4-oxadiazol-2-yl)-1H-pyrrole-2-carboxylate (UL1-087)

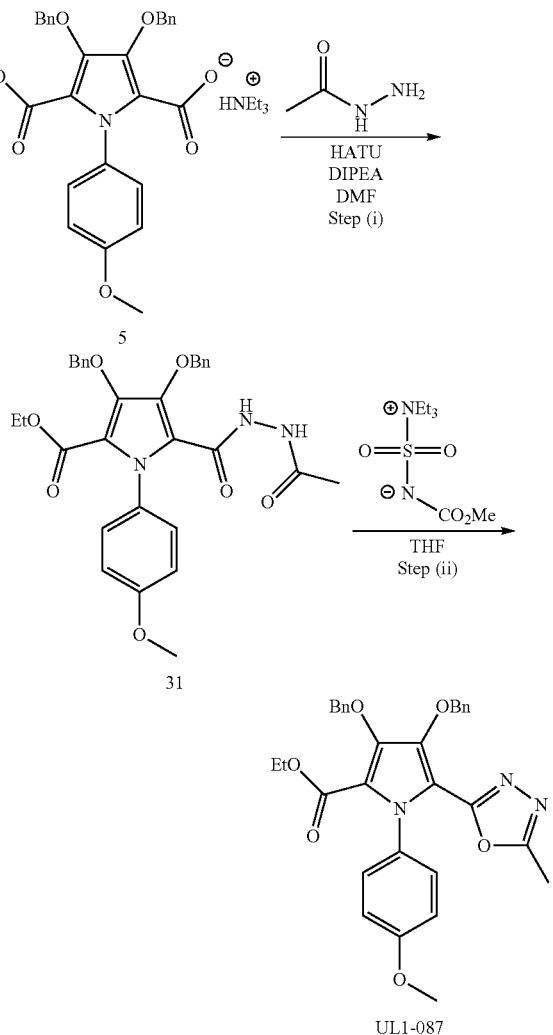

UL1-087

Step (i): Ethyl 5-(2-acetylhydrazinecarbonyl)-3,4-bis(benzyloxy)-1-(4-methoxyphenyl)-1H-pyrrole-2-carboxylate (31)

HATU (739 mg, 1.94 mmol) was added to a solution of triethylammonium 3,4-bis(benzyloxy)-5-(ethoxycarbonyl)-1-(4-methoxyphenyl)-1H-pyrrole-2-carboxylate (5) (325 mg, 0.65 mmol), DIPEA (566 μL, 3.24 mmol) and acetohydrazide (53 mg, 0.71 mmol) in DMF (5 mL) at 0° C. The mixture was stirred for 30 min and allowed to warm to RT. The reaction was partitioned between water (10 mL) and Et$_2$O (30 mL) and NH$_4$OAc (aq.) (20 mL) was added, the organic layer was separated and washed with sat. NaHCO$_3$ (aq.) (20 mL), brine (20 mL), dried (MgSO₄), filtered and solvents removed in vacuo. The product was purified by silica gel chromatography (40 g, 0-80% EtOAc in isohexane) to afford ethyl 5-(2-acetylhydrazinecarbonyl)-3,4-bis(benzyloxy)-1-(4-methoxyphenyl)-1H-pyrrole-2-carboxylate (31) (196 mg, 100%) as a colourless oil: m/z 558 (M+H)⁺ (ES⁺).

Step (ii): Ethyl 3,4-bis(benzyloxy)-1-(4-methoxyphenyl)-5-(5-methyl-1,3,4-oxadiazol-2-yl)-1H-pyrrole-2-carboxylate (UL1-087)

A solution of ethyl 3,4-bis(benzyloxy)-1-(4-methoxyphenyl)-5-(2-acetylhydrazinecarbonyl)-1H-pyrrole-2-carboxylate (31) (155 mg, 0.56 mmol) and Burgess reagent (132 mg, 0.56 mmol) were dissolved in THF (2 mL). The mixture was heated in a microwave at 100° C. for 30 min and the volatiles removed in vacuo. The crude product was purified by silica gel chromatography (12 g, 0-30% EtOAc in isohexane) to afford ethyl 3,4-bis(benzyloxy)-1-(4-methoxyphenyl)-5-(5-methyl-1,3,4-oxadiazol-2-yl)-1H-pyrrole-2-carboxylate (UL1-087) (115 mg, 77%) as a colourless oil: m/z 540 (M+H)⁺ (ES⁺). ¹H NMR (400 MHz, DMSO-d₆) δ: 7.51-7.46 (m, 2H), 7.43-7.31 (m, 8H), 7.18-7.12 (m, 2H), 6.93-6.87 (m, 2H), 5.17 (s, 2H), 5.07 (s, 2H), 4.02 (q, J=7.1 Hz, 2H), 3.78 (s, 3H), 2.35 (s, 3H), 1.01 (t, J=7.1 Hz, 3H).

Example V

Ethyl 3,4-dihydroxy-1-(4-methoxyphenyl)-5-(2H-tetrazol-5-yl)-1H-pyrrole-2-carboxylate (UL1-089)

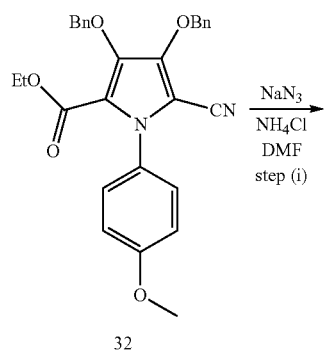

32

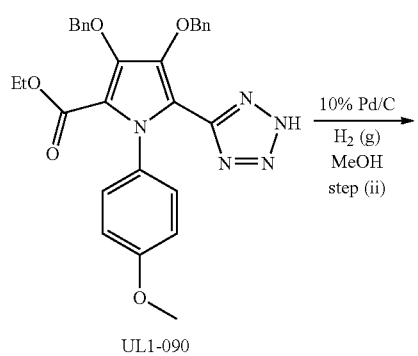

UL1-090

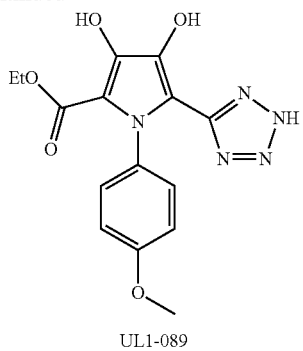

UL1-089

Step (i): Ethyl 3,4-bis(benzyloxy)-1-(4-methoxyphenyl)-5-(2H-tetrazol-5-yl)-1H-pyrrole-2-carboxylate (UL1-090)

A solution of ethyl 3,4-bis(benzyloxy)-5-cyano-1-(4-methoxyphenyl)-1H-pyrrole-2-carboxylate (32) [prepared using the same procedure as Example H step (i) using UL1-079 as starting material] (400 mg, 0.83 mmol), NH₄Cl (222 mg, 4.14 mmol) and sodium azide (269 mg, 4.14 mmol) were dissolved in DMF (4 mL). The reaction mixture was heated in a microwave at 120° C. for 2 h, partitioned between EtOAc (15 mL) and water (15 mL). The organic layer was separated and washed with water (3×15 mL), dried (MgSO₄), filtered and solvents removed in vacuo. The product was purified by silica gel chromatography (40 g, 0-40% MeOH in DCM/2.5% Et₃N) to afford the triethylammonium salt of (UL1-090). The salt was dissolved in DCM (10 mL) and the organic layer was washed with 1M HCl (aq.) (10 mL), brine (10 mL), sat. NaHCO₃ (aq.) (10 mL), brine (10 mL), dried (MgSO₄), filtered and solvents removed in vacuo to afford ethyl 3,4-bis(benzyloxy)-1-(4-methoxyphenyl)-5-(2H-tetrazol-5-yl)-1H-pyrrole-2-carboxylate (UL1-090) (150 mg, 34%) as a white solid: m/z 526 (M+H)⁺ (ES⁺); 524 (M−H)⁻ (ES⁻). ¹H NMR (400 MHz, DMSO-d₆) δ: 7.51-7.45 (m, 2H), 7.42-7.25 (m, 8H), 7.10-7.03 (m, 2H), 6.83-6.76 (m, 2H), 5.15 (s, 2H), 4.95 (s, 2H), 4.00 (q, J=7.1 Hz, 2H), 3.74 (s, 3H), 1.00 (t, J=7.1 Hz, 3H).

Step (ii): Ethyl 3,4-dihydroxy-1-(4-methoxyphenyl)-5-(2H-tetrazol-5-yl)-1H-pyrrole-2-carboxylate (UL1-089)

A solution of ethyl 3,4-bis(benzyloxy)-1-(4-methoxyphenyl)-5-(2H-tetrazol-5-yl)-1H-pyrrole-2-carboxylate (UL1-090) (85 mg, 0.16 mmol) in MeOH (6 mL) was passed through a Thales 'H-cube' cartridge (10% Pd/C) at a flow rate of 1 mL/min at 40° C. under H₂ (full H₂ mode). The output was concentrated in vacuo. The crude material was dissolved in DCM (5 mL) and washed with 1M HCl (aq.), brine (5 mL), sat. NaHCO₃ (aq.) (5 mL), the basic aqueous layer was acidified with 1M HCl (aq.) (5 mL) and washed with DCM (2×5 mL), the combined organics were dried (MgSO₄), filtered and solvents removed in vacuo to afford ethyl 3,4-dihydroxy-1-(4-methoxyphenyl)-5-(2H-tetrazol-5-yl)-1H-pyrrole-2-carboxylate (UL1-089) (45 mg, 79%) as a white solid: m/z 346 (M+H)⁺ (ES⁺); 344 (M−H)⁻ (ES⁻). ¹H NMR (400 MHz, DMSO-$d_6$) δ: 9.30 (br s, 1H), 8.67 (s, 1H), 7.10-7.05 (m, 2H), 6.87-6.81 (m, 2H), 4.02 (q, J=7.1 Hz, 2H), 3.76 (s, 3H), 0.99 (t, J=7.1 Hz, 3H).

Example W

5-Acetyl-3,4-dihydroxy-1-(4-methoxyphenyl)-N,N-dimethyl-1H-pyrrole-2-carboxamide (UL1-091)

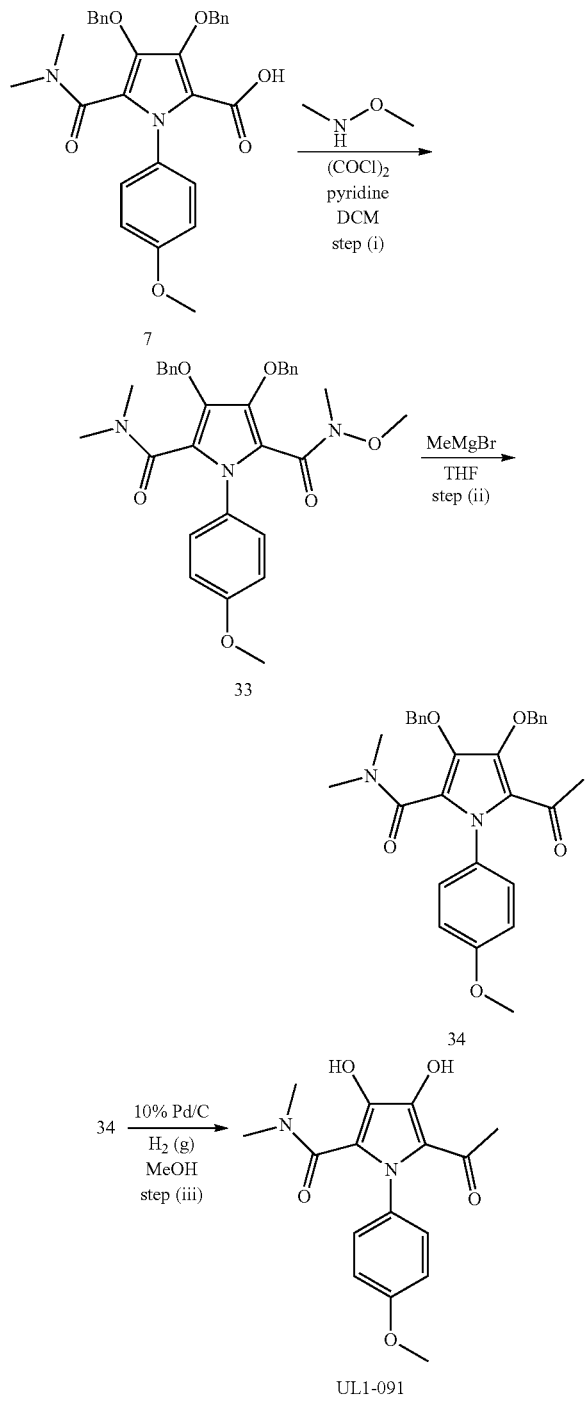

Step (i): 3,4-Bis(benzyloxy)-$N^2$-methoxy-1-(4-methoxyphenyl)-$N^2,N^5,N^5$-trimethyl-1H-pyrrole-2,5-dicarboxamide (33)

(COCl)$_2$ (560 µL, 6.39 mmol) was added dropwise to a stirred solution of 3,4-bis(benzyloxy)-5-(dimethylcarbamoyl)-1-(4-methoxyphenyl)-1H-pyrrole-2-carboxylic acid (7) (1.6 g, 3.20 mmol) in DCM (20 mL) at 0° C., followed by 2 drops of DMF. The reaction mixture was stirred at RT for 5 h, concentrated in vacuo and the resulting residue was dissolved in DCM (15 mL). N,O-dimethylhydroxylamine was added (215 mg, 3.52 mmol) followed by pyridine (620 µL, 7.67 mmol), and the reaction allowed to stir at RT for 18 h. The mixture was diluted with DCM (25 mL) and water (50 mL), the organic layer was separated and washed with water (2×25 mL), brine (25 mL), dried (MgSO$_4$), filtered and concentrated in vacuo. The product was purified by silica gel chromatography (40 g, 0-80% EtOAc in isohexane) to afford 3,4-bis(benzyloxy)-$N^2$-methoxy-1-(4-methoxyphenyl)-$N^2,N^5,N^5$-trimethyl-1H-pyrrole-2,5-dicarboxamide (33) (505 mg, 22%) as a colourless oil. m/z 544 (M+H)$^+$ (ES$^+$).

Step (ii): 5-Acetyl-3,4-bis(benzyloxy)-1-(4-methoxyphenyl)-N,N-dimethyl-1H-pyrrole-2-carboxamide (34)

Methylmagnesium bromide (3 M in Et$_2$O) (294 µL, 0.88 mmol) was added dropwise to a stirred solution of 3,4-bis(benzyloxy)-$N^2$-methoxy-1-(4-methoxyphenyl)-$N^2,N^5,N^5$-trimethyl-1H-pyrrole-2,5-dicarboxamide (33) (320 mg, 0.59 mmol) in THF (1 mL) at 0° C. The reaction mixture was allowed to warm to RT and stirred for 20 h. The reaction mixture was cooled to −10° C. and 1 M HCl (aq.) (10 mL) was added. The aqueous layer was extracted with DCM (3×10 mL). The combined organic phases were washed with water (20 mL), brine (20 mL), dried (MgSO$_4$), filtered and concentrated in vacuo to give a yellow oil.

The product was purified by silica gel chromatography (40 g, 0-100% EtOAc in isohexane) to afford 5-acetyl-3,4-bis(benzyloxy)-1-(4-methoxyphenyl)-N,N-dimethyl-1H-pyrrole-2-carboxamide (34) (110 mg, 38%) as a yellow oil: m/z 499 (M+H)$^+$ (ES$^+$). $^1$H NMR (400 MHz, DMSO-$d_6$) δ: 7.46-7.33 (m, 10H), 7.05-7.03 (m, 2H), 6.88-6.86 (m, 2H), 5.25 (s, 2H), 5.01 (s, 2H), 3.77 (s, 3H), 2.71 (s, 6H), 2.26 (s, 3H).

Step (iii): 5-Acetyl-3,4-dihydroxy-1-(4-methoxyphenyl)-N,N-dimethyl-1H-pyrrole-2-carboxamide (UL1-091)

A solution of 5-acetyl-3,4-bis(benzyloxy)-1-(4-methoxyphenyl)-N,N-dimethyl-1H-pyrrole-2-carboxamide (34) (100 mg, 0.20 mmol) in MeOH (5 mL) was passed through a Thales 'H-cube' cartridge (10% Pd/C) at a flow rate of 1 mL/min at 20° C. under H$_2$ (full H$_2$ mode). The output was concentrated in vacuo. The crude compound was purified by preparative HPLC (C-18 column, 21.2 mm i.d.×100 mm, 5 micron particle size, gradient 5-95% MeCN in 0.1% aq. formic acid over 16 min) to afford 5-acetyl-3,4-dihydroxy-1-(4-methoxyphenyl)-N,N-dimethyl-1H-pyrrole-2-carboxamide (UL1-091) (45 mg, 70%) as a pale yellow solid: m/z 319 (M+H)$^+$ (ES$^+$), 317 (M−H)$^-$ (ES$^-$). $^1$H NMR (400 MHz, DMSO-d$_6$) δ: 9.77 (s, 1H), 8.57 (s, 1H), 7.09-7.07 (m, 2H), 6.88-6.86 (m, 2H), 3.77 (s, 3H), 2.81 (br s, 6H), 2.05 (s, 3H).

Example X

Ethyl 3,4-bis((diethoxyphosphoryl)oxy)-5-(dimethylcarbamoyl)-1-(4-methoxyphenyl)-1H-pyrrole-2-carboxylate (UL1-092)

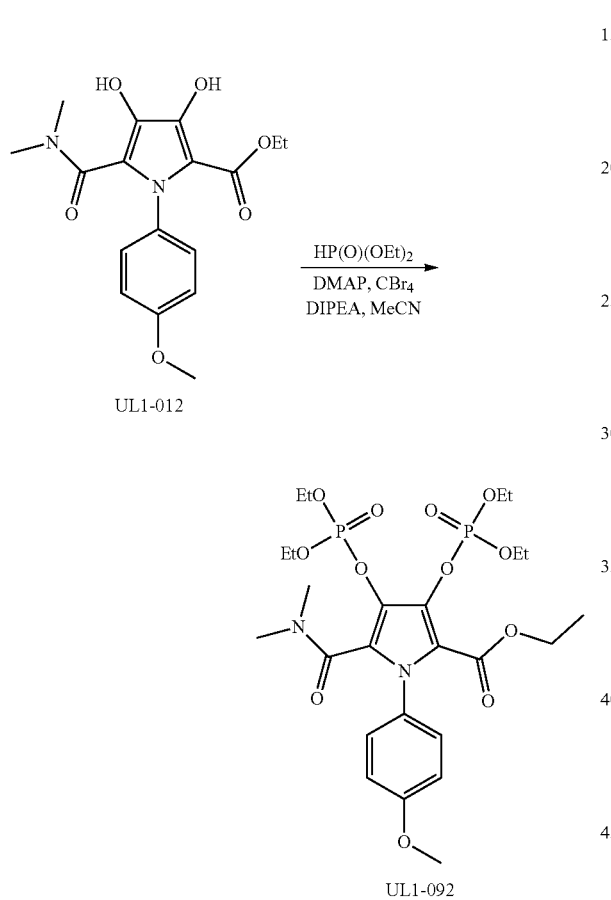

Perbromomethane (207 mg, 0.62 mmol) and DIPEA (131 µL, 0.75 mmol) were added successively to a solution of DMAP (3.05 mg, 0.03 mmol) and ethyl 5-(dimethylcarbamoyl)-3,4-dihydroxy-1-(4-methoxyphenyl)-1H-pyrrole-2-carboxylate (UL1-012) (87 mg, 0.25 mmol) in MeCN (3 mL) at −10° C. The reaction mixture was allowed to stir for 30 min and diethyl phosphite (166 µL, 0.75 mmol) added, the reaction was allowed to warm slowly to RT and stirred for 3 h. The reaction was quenched with 5% NaH$_2$PO$_4$ (aq.) (20 mL) and extracted with EtOAc (3×25 mL). The combined organics were washed with brine (50 mL), dried (MgSO$_4$), filtered and concentrated in vacuo. The crude residue was purified by silica gel chromatography (40 g, 0-4% MeOH in DCM) to afford an orange oil. The compound was further purified by preparative HPLC (C-18 column, 21.2 mm i.d.×100 mm, 5 micron particle size, gradient 5-95% MeCN in 0.1% aq. formic acid over 16 min) to afford ethyl 3,4-bis((diethoxyphosphoryl)oxy)-5-(dimethylcarbamoyl)-1-(4-methoxyphenyl)-1H-pyrrole-2-carboxylate (UL1-092) (35 mg, 22%) as a yellow oil: m/z 621 (M+H)$^+$ (ES$^+$). $^1$H NMR (400 MHz, DMSO-d$_6$) δ: 7.18-7.15 (m, 2H), 6.97-6.94 (m, 2H), 4.22-4.02 (m, 10H), 3.79 (s, 3H), 2.75 (s, 3H), 2.71 (s, 3H), 1.31-1.24 (m, 12H), 1.07 (t, J=7.2 Hz, 3H).

Example Y

Ethyl 5-(dimethylcarbamoyl)-3,4-dihydroxy-1-(4-hydroxyphenyl)-1H-pyrrole-2-carboxylate (UL1-100)

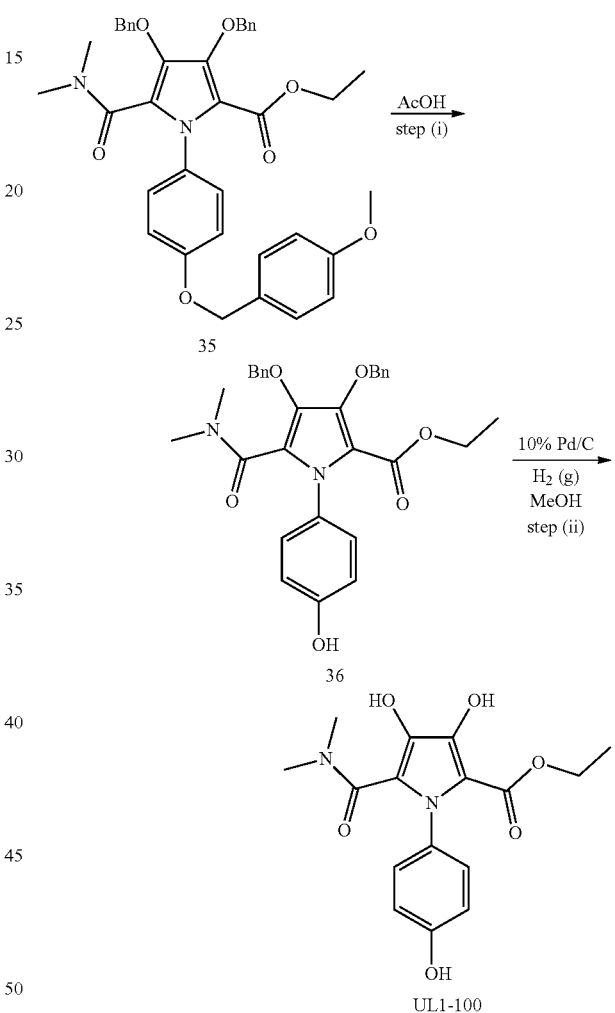

Step (i): Ethyl 3,4-bis(benzyloxy)-5-(dimethylcarbamoyl)-1-(4-hydroxyphenyl)-1H-pyrrole-2-carboxylate (36)

A solution of ethyl 3,4-bis(benzyloxy)-5-(dimethylcarbamoyl)-1-(4-((4-methoxybenzyl)oxy)phenyl)-1H-pyrrole-2-carboxylate (35) [prepared using the same procedure as Example B except 4-((4-methoxybenzyl)oxy)aniline used in step (i)] (46 mg, 0.07 mmol) in AcOH (5 mL) was stirred at 105° C. for 18 h. The volatiles were removed in vacuo and the residue was purified by silica gel chromatography (4 g, 0-10% MeOH in DCM) to afford ethyl 3,4-bis(benzyloxy)-5-(dimethylcarbamoyl)-1-(4-hydroxyphenyl)-1H-pyrrole-2-carboxylate (36) (35 mg, 91%) as a yellow solid: m/z 515 (M+H)$^+$ (ES$^+$). $^1$H NMR (400 MHz, DMSO-d$_6$) δ: 9.63 (1H, s), 7.47-7.42 (m, 2H), 7.41-7.29 (m, 8H), 6.99-6.91 (m, 2H), 6.73-6.66 (m, 2H), 5.10 (s, 2H), 4.95 (s, 2H), 3.99 (q, J=7.1 Hz, 2H), 2.69 (s, 3H), 2.67 (s, 3H), 1.00 (t, J=7.1 Hz, 3H).

Step (ii): Ethyl 5-(dimethylcarbamoyl)-3,4-dihydroxy-1-(4-hydroxyphenyl)-1H-pyrrole-2-carboxylate (UL1-100)

A solution of ethyl 3,4-bis(benzyloxy)-5-(dimethylcarbamoyl)-1-(4-hydroxyphenyl)-1H-pyrrole-2-carboxylate (36) (30 mg, 0.06 mmol) in MeOH (2 mL) was passed through a Thales 'H-cube' cartridge (10% Pd/C) at a flow rate of 1 mL/min at 25° C. under $H_2$ (full $H_2$ mode). The output was concentrated in vacuo, and a solid was collected by filtration after trituration with isohexane to afford ethyl 5-(dimethylcarbamoyl)-3,4-dihydroxy-1-(4-hydroxyphenyl)-1H-pyrrole-2-carboxylate (UL1-100) (11 mg, 56%) as a yellow solid: m/z 335 $(M+H)^+$ $(ES^+)$, 333 $(M-H)^-$ $(ES^-)$. $^1$H NMR (400 MHz, DMSO-$d_6$) δ: 9.50 (s, 1H), 8.54 (s, 1H), 8.42 (s, 1H), 6.94-6.86 (m, 2H), 6.69-6.62 (m, 2H), 3.99 (q, J=7.0 Hz, 2H), 2.81 (br s, 6H), 0.98 (t J=7.0 Hz, 3H).

Example Z

Ethyl 5-(dimethylcarbamoyl)-3,4-dihydroxy-1-(4-(3-morpholinopropoxy)phenyl)-1H-pyrrole-2-carboxylate (UL1-102)

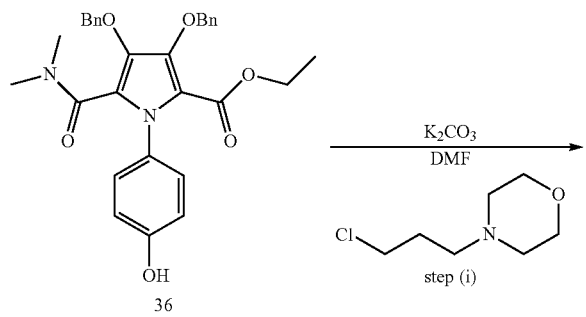

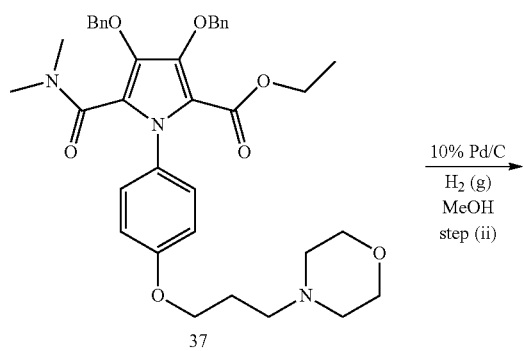

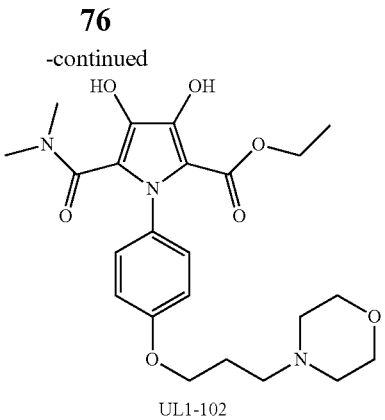

Step (i): Ethyl 3,4-bis(benzyloxy)-5-(dimethylcarbamoyl)-1-(4-(3-morpholinopropoxy)phenyl)-1H-pyrrole-2-carboxylate (37)

A solution of ethyl 3,4-bis(benzyloxy)-5-(dimethylcarbamoyl)-1-(4-hydroxyphenyl)-1H-pyrrole-2-carboxylate (36) (45 mg, 0.09 mmol), 4-(3-chloropropyl)morpholine hydrochloride (19 mg, 0.10 mmol) and $K_2CO_3$ (25 mg, 0.18 mmol) in DMF (1 mL) was stirred at 60° C. for 18 h. The reaction mixture was partitioned between EtOAc (10 mL) and water (5 mL), the organic layer was separated and washed with brine (5 mL), dried ($MgSO_4$), filtered and concentrated in vacuo. The residue was dissolved in MeOH (2 mL) and loaded onto a column of SCX (5 g). The column was washed with MeOH and then the product was eluted with 1% $NH_3$ in MeOH, removal of the solvents in vacuo afforded ethyl 3,4-bis(benzyloxy)-5-(dimethylcarbamoyl)-1-(4-(3-morpholinopropoxy)phenyl)-1H-pyrrole-2-carboxylate (37) (32 mg, 57%) as a yellow oil: m/z 642 $(M+H)^+$ $(ES^+)$. $^1$H NMR (400 MHz, DMSO-$d_6$) δ: 7.47-7.42 (m, 2H), 7.41-7.30 (m, 8H), 7.10-7.05 (m, 2H), 6.99-6.91 (m, 2H), 5.11 (s, 2H), 4.96 (s, 2H), 4.04-3.95 (m, 4H), 3.59-3.52 (m, 5H), 2.72-2.67 (m, 6H), 2.44-2.38 (m, 3H), 2.37-2.32 (m, 5H), 1.92-1.81 (m, 2H), 1.00 (t, J=7.0 Hz, 3H).

Step (ii): Ethyl 5-(dimethylcarbamoyl)-3,4-dihydroxy-1-(4-(3-morpholinopropoxy)phenyl)-1H-pyrrole-2-carboxylate (UL1-102)

A solution of ethyl 3,4-bis(benzyloxy)-5-(dimethylcarbamoyl)-1-(4-(3-morpholinopropoxy)phenyl)-1H-pyrrole-2-carboxylate (37) (105 mg, 0.16 mmol) in MeOH (4 mL) was passed through a Thales 'H-cube' cartridge (10% Pd/C) at a flow rate of 1 mL/min at 25° C. under $H_2$ (full $H_2$ mode). The output was concentrated in vacuo, and a solid was collected by filtration after trituration with isohexane to afford ethyl 5-(dimethylcarbamoyl)-3,4-dihydroxy-1-(4-(3-morpholinopropoxy)phenyl)-1H-pyrrole-2-carboxylate (UL1-102) (20 mg, 25%) as a yellow solid: m/z 462 $(M+H)^+$ $(ES^+)$, 460 $(M-H)^-$ $(ES^-)$. $^1$H NMR (400 MHz, DMSO-$d_6$) δ: 8.58 (s, 1H), 8.44 (s, 1H), 7.05-6.99 (m, 2H), 6.86-6.82 (m, 2H), 4.03-3.95 (m, 4H), 3.61-3.53 (m, 4H), 2.82 (br s, 6H), 2.45-2.34 (m, 6H), 1.93-1.81 (m, 2H), 0.98 (t, J=7.0 Hz, 3H).

Example A1

2-(Dimethylcarbamoyl)-5-(ethoxycarbonyl)-1-(4-methoxyphenyl)-1H-pyrrole-3,4-diyl bis(3-methoxypropanoate) (UL1-104)

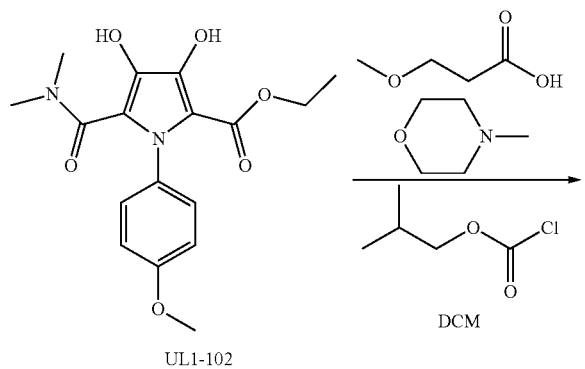

δ: 7.24-7.15 (m, 2H), 6.98-6.89 (m, 2H), 4.00 (q, J=7.1 Hz, 2H), 3.79 (s, 3H), 3.65-3.59 (m, 4H), 3.27 (s, 3H), 3.25 (s, 3H), 2.82 (s, 3H), 2.78 (t, J=6.0 Hz, 4H), 2.71 (s, 3H), 1.05 (t, J=7.1 Hz, 3H).

Example B1

2-(Dimethylcarbamoyl)-5-(ethoxycarbonyl)-1-(4-methoxyphenyl)-1H-pyrrole-3,4-diyl bis(3-(2-methoxyethoxy)-2,2-dimethylpropanoate) (UL1-108)

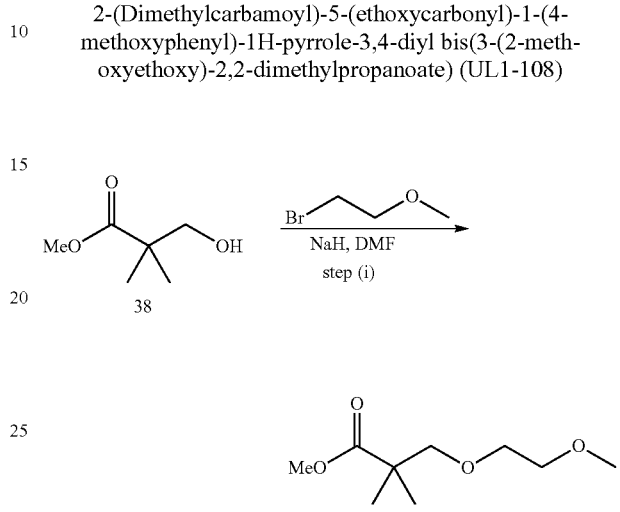

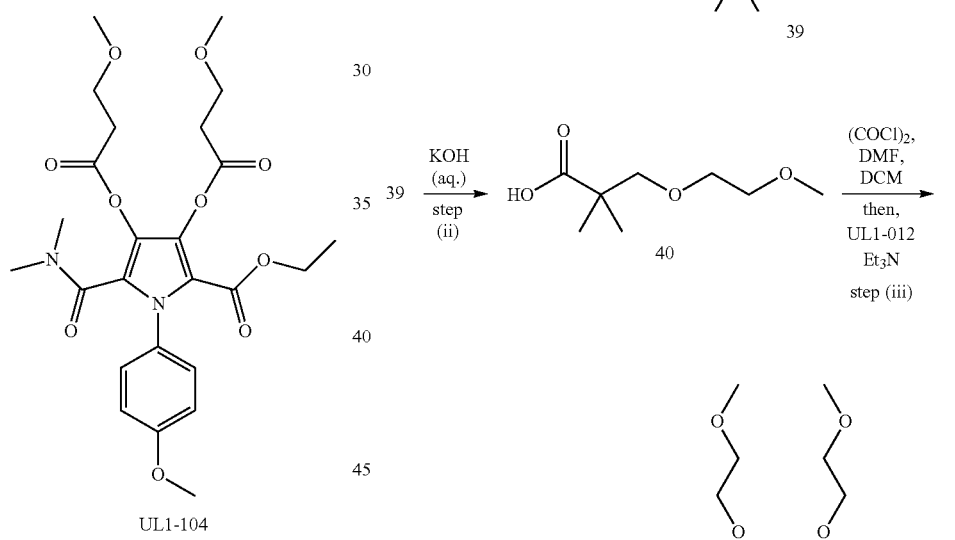

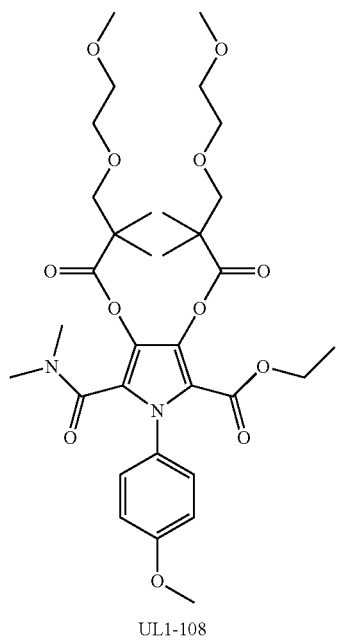

Isobutyl chloroformate (410 µL, 3.16 mmol) was added dropwise to a stirred solution of 3-methoxypropanoic acid (297 µL, 3.16 mmol) and 4-methylmorpholine (790 µL, 7.18 mmol) in DCM (20 mL) at −15° C. and the reaction mixture was allowed to stir for 20 min. A solution of ethyl 5-(dimethylcarbamoyl)-3,4-dihydroxy-1-(4-methoxyphenyl)-1H-pyrrole-2-carboxylate (UL1-012) (0.5 g, 1.44 mmol) in DCM (20 mL) was added, and the reaction allowed to warm to RT and stirred for 18 h. The solvents were removed in vacuo, and the mixture was partitioned between DCM (30 mL) and 1 M HCl (aq.) (10 mL), the organic layer was separated and washed with sat. NaHCO$_3$ (aq.) (10 mL), dried (MgSO$_4$), filtered and concentrated in vacuo. The crude residue was purified by silica gel chromatography (40 g, 50-70% EtOAc in isohexane) to afford 2-(dimethylcarbamoyl)-5-(ethoxycarbonyl)-1-(4-methoxyphenyl)-1H-pyrrole-3,4-diyl bis(3-methoxypropanoate) (UL1-104) (300 mg, 39%) as a yellow oil: m/z 521 (M+H)$^+$ (ES$^+$). $^1$H NMR (400 MHz, DMSO-d$_6$)

Step (i): Methyl 3-(2-methoxyethoxy)-2,2-dimethylpropanoate (39)

Sodium hydride (60% wt in oil) (3.14 g, 78 mmol) was added to a stirred solution of methyl 3-hydroxy-2,2-dimethylpropanoate (5 mL, 39.2 mmol) in DMF (5.6 mL) at 0° C., after 5 min 1-bromo-2-methoxyethane (7.4 mL, 78 mmol) was added dropwise, and the reaction mixture was allowed to stir for 3 h. The reaction was quenched with sat. $NH_4Cl$ (aq.) (30 mL) and the aqueous layer was extracted with DCM (2×50 mL), the combined organic layers were dried ($MgSO_4$), filtered and concentrated in vacuo. The crude oil was dissolved in EtOAc (125 mL) and washed with water (3×40 mL), dried ($MgSO_4$), filtered and concentrated in vacuo. The material was purified by vacuum distillation (68-69° C., 4.4 mbar) to afford methyl 3-(2-methoxyethoxy)-2,2-dimethylpropanoate (39) (1.83 g, 25%) as a colourless oil: $^1$H NMR (400 MHz, $CDCl_3$) δ: 3.68 (s, 3H), 3.60-3.58 (m, 2H), 3.52-3.50 (m, 2H), 3.49 (s, 2H), 3.37 (s, 3H), 1.19 (s, 6H).

Step (ii): 3-(2-Methoxyethoxy)-2,2-dimethylpropanoic acid (40)

A suspension of methyl 3-(2-methoxyethoxy)-2,2-dimethylpropanoate (39) (1.83 g, 9.62 mmol) and KOH (2.16 g, 38.5 mmol) in water (20 mL) was stirred at RT for 3 days. The aqueous layer was washed with DCM (3×20 mL) and acidified to pH 1-2 with 6 M HCl (aq.) and extracted with DCM (3×20 mL). The combined organics were dried ($MgSO_4$), filtered and concentrated in vacuo to afford 3-(2-methoxyethoxy)-2,2-dimethylpropanoic acid (40) (1.62 g, 96%) as colourless oil: $^1$H NMR (400 MHz, $CDCl_3$) δ: 3.67-3.65 (m, 2H), 3.56-3.54 (m, 2H), 3.51 (s, 2H), 3.38 (s, 3H), 1.23 (s, 6H).

Step (iii): 2-(Dimethylcarbamoyl)-5-(ethoxycarbonyl)-1-(4-methoxyphenyl)-1H-pyrrole-3,4-diyl bis(3-(2-methoxyethoxy)-2,2-dimethylpropanoate) (UL1-108)

DMF (2.2 μL, 0.03 mmol) was added to a stirred solution of 3-(2-methoxyethoxy)-2,2-dimethylpropanoic acid (40) (500 mg, 2.84 mmol) followed by a solution of $(COCl)_2$ (0.25 mL, 2.85 mmol) in DCM (11.4 mL), the reaction mixture was allowed to stir for 1 h. To this mixture was added ethyl 5-(dimethylcarbamoyl)-3,4-dihydroxy-1-(4-methoxyphenyl)-1H-pyrrole-2-carboxylate (UL1-012) (450 mg, 1.29 mmol), followed by $Et_3N$ (900 μL, 6.45 mmol) and the reaction allowed to stir for 45 min. The reaction was then filtered, and the filtrate concentrated in vacuo. The crude residue was purified by silica gel chromatography (40 g, 0-3% MeOH in DCM) to afford 2-(dimethylcarbamoyl)-5-(ethoxycarbonyl)-1-(4-methoxyphenyl)-1H-pyrrole-3,4-diyl bis(3-(2-methoxyethoxy)-2,2-dimethylpropanoate) (UL1-108) (447 mg, 52%) as a light yellow oil: m/z 665 (M+H)$^+$. $^1$H NMR (400 MHz, DMSO-$d_6$) δ 7.23-7.15 (m, 2H), 6.98-6.89 (m, 2H), 4.02 (q, J=7.2 Hz, 2H), 3.79 (s, 3H), 3.58-3.39 (m, 12H), 3.24 (s, 3H), 3.23 (s, 3H), 2.81 (s, 3H), 2.70 (s, 3H), 1.25 (s, 6H), 1.19 (s, 6H), 1.05 (t, J=7.2 Hz, 3H).

Example C1

Ethyl 5-(dimethylcarbamoyl)-3-hydroxy-1-(4-methoxyphenyl)-4-((phosphonooxy)methoxy)-1H-pyrrole-2-carboxylate (UL1-109)

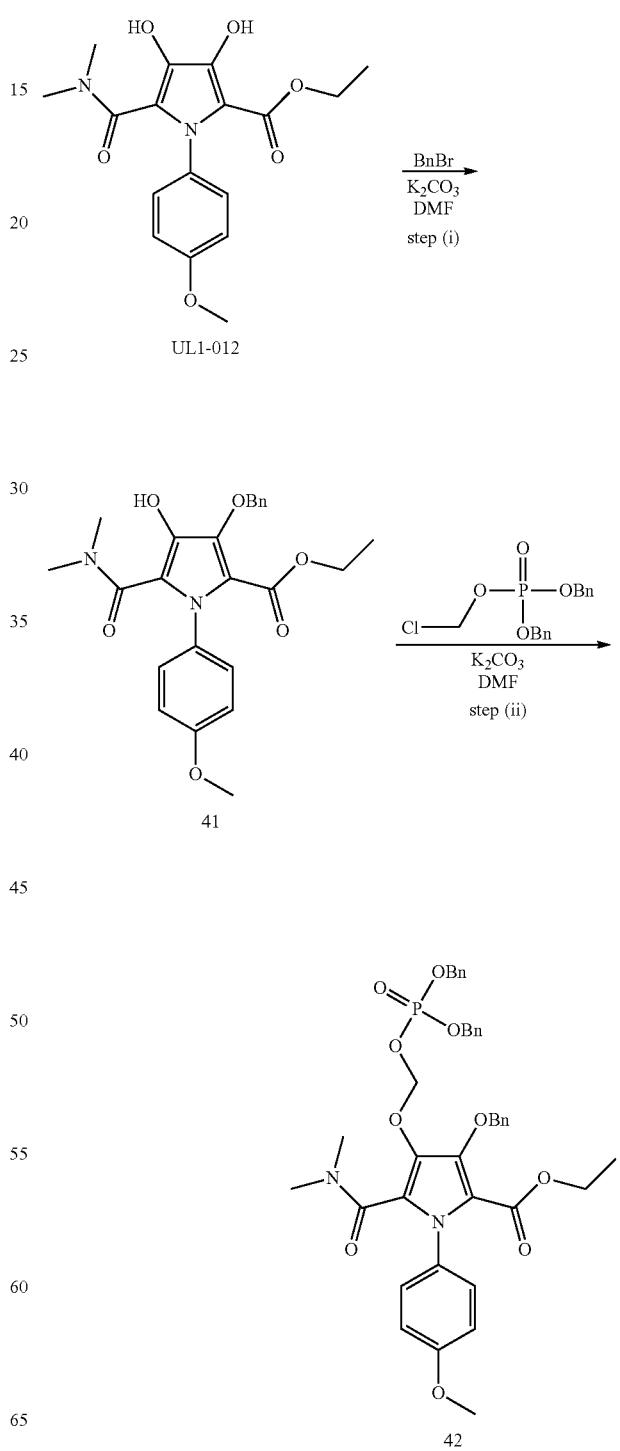

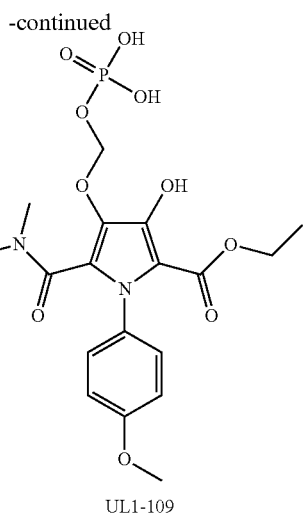

Step (i): Ethyl 3-(benzyloxy)-5-(dimethylcarbamoyl)-4-hydroxy-1-(4-methoxyphenyl)-1H-pyrrole-2-carboxylate (41)

Benzyl bromide (3.94 mL, 33.2 mmol) was added to a stirred suspension of ethyl 5-(dimethylcarbamoyl)-3,4-dihydroxy-1-(4-methoxyphenyl)-1H-pyrrole-2-carboxylate (UL1-012) (10.5 g, 30.1 mmol), potassium iodide (5.50 g, 33.2 mmol) and $K_2CO_3$ (4.58 g, 33.2 mmol) in DMF (100 mL). The reaction was allowed to stir at 80° C. for 24 h. The reaction mixture was poured into water (200 mL), washed with $Et_2O$ (2×200 mL), and the combined organic layers were washed with 1M HCl (aq.) (400 mL), brine (2×400 mL), dried ($MgSO_4$), filtered and concentrated in vacuo. The crude product was purified by silica gel chromatography (330 g, 0-50% EtOAc in toluene) to afford ethyl 3-(benzyloxy)-5-(dimethylcarbamoyl)-4-hydroxy-1-(4-methoxyphenyl)-1H-pyrrole-2-carboxylate (41) (4.36 g, 33%) as a pale yellow solid: m/z 439 (M+H)$^+$ (ES$^+$). $^1$H NMR (400 MHz, DMSO-$d_6$) δ: 8.82 (s, 1H), 7.53-7.47 (m, 2H), 7.42-7.29 (m, 3H), 7.08-7.01 (m, 2H), 6.90-6.84 (m, 2H), 5.09 (s, 2H), 3.96 (q, J=7.0 Hz, 2H), 3.76 (s, 3H), 2.82 (br s, 6H), 0.97 (t, J=7.0 Hz, 3H).

Step (ii): Ethyl 3-(benzyloxy)-4-(((bis(benzyloxy)phosphoryl)oxy)methoxy)-5-(dimethylcarbamoyl)-1-(4-methoxyphenyl)-1H-pyrrole-2-carboxylate (42)

A solution of dibenzyl(chloromethyl)phosphate (0.23 g, 0.70 mmol) in DMF (1 mL) was added dropwise to a stirred suspension of ethyl 3-(benzyloxy)-5-(dimethylcarbamoyl)-4-hydroxy-1-(4-methoxyphenyl)-1H-pyrrole-2-carboxylate (41) (0.26 g, 0.58 mmol) and $K_2CO_3$ (80 mg, 0.58 mmol) in DMF (4 mL) at 0° C., the reaction was stirred at for 1 h, then allowed to warm to RT over 16 h. A solution of dibenzyl(chloromethyl)phosphate (0.23 g, 0.70 mmol) in DMF (1 mL) and $K_2CO_3$ (80 mg, 0.58 mmol) were added and the reaction was stirred for a further 24 h. A further solution of dibenzyl(chloromethyl)phosphate (0.11 g, 0.35 mmol) in DMF (1 mL) and $K_2CO_3$ (40 mg, 0.29 mmol) were added and the reaction was stirred for a further 4 h. The reaction mixture was poured into water (20 mL) and extracted with $Et_2O$ (2×20 mL). The combined organic layers were washed with brine (3×100 mL), dried ($MgSO_4$), filtered and concentrated in vacuo. The crude product was purified by silica gel chromatography (12 g, 0-50% EtOAc in toluene) to afford ethyl 3-(benzyloxy)-4-(((bis(benzyloxy)phosphoryl)oxy)methoxy)-5-(dimethylcarbamoyl)-1-(4-methoxyphenyl)-1H-pyrrole-2-carboxylate (42) (0.10 g, 23%) as a colourless gum: m/z 729 (M+H)$^+$ (ES$^+$). $^1$H NMR (400 MHz, DMSO-$d_6$) δ: 7.36-7.30 (m, 13H), 7.09-7.05 (m, 2H), 6.88-6.92 (m, 2H), 5.49 (d, J=11.1 Hz, 2H), 5.11 (s, 2H), 5.06-4.96 (m, 2H), 4.96-5.05 (m, 4H), 4.00 (q, J=7.1 Hz, 2H), 3.77 (s, 3H), 2.72 (s, 3H), 2.65 (s, 3H), 0.99 (t, J=7.0 Hz, 3H).

Step (iii): Ethyl 5-(dimethylcarbamoyl)-3-hydroxy-1-(4-methoxyphenyl)-4-((phosphonooxy)methoxy)-1H-pyrrole-2-carboxylate (UL1-109)

A solution of ethyl 3-(benzyloxy)-4-(((bis(benzyloxy)phosphoryl)oxy)methoxy)-5-(dimethylcarbamoyl)-1-(4-methoxyphenyl)-1H-pyrrole-2-carboxylate (42) (2.17 g, 2.99 mmol) in MeOH (20 mL) was passed through a Thales 'H-cube' cartridge (10% Pd/C) at a flow rate of 1 mL/min at 40° C. under $H_2$ (full $H_2$ mode). The output was concentrated in vacuo, the residue was taken up in water (50 mL) and washed with EtOAc (50 mL), the organic layer was washed with water (2×50 mL) and the combined aqueous layers were freeze-dried to afford ethyl 5-(dimethylcarbamoyl)-3-hydroxy-1-(4-methoxyphenyl)-4-((phosphonooxy)methoxy)-1H-pyrrole-2-carboxylate (UL1-109) (720 mg, 52%) as a white solid: m/z 459 (M+H)$^+$ (ES$^+$). $^1$H NMR (400 MHz, DMSO-$d_6$) δ: 7.14-7.05 (m, 2H), 6.93-6.85 (m, 2H), 5.35-5.23 (br m, 2H), 3.99 (q, J=7.2 Hz, 2H), 3.77 (s, 3H), 2.73 (s, 3H), 2.70 (s, 3H), 1.02 (t, J=7.2 Hz, 3H).

Example D1

Ethyl 5-(dimethylcarbamoyl)-3,4-dihydroxy-1-(4-(3-(methylsulfonyl)propoxy)phenyl)-1H-pyrrole-2-carboxylate (UL1-110)

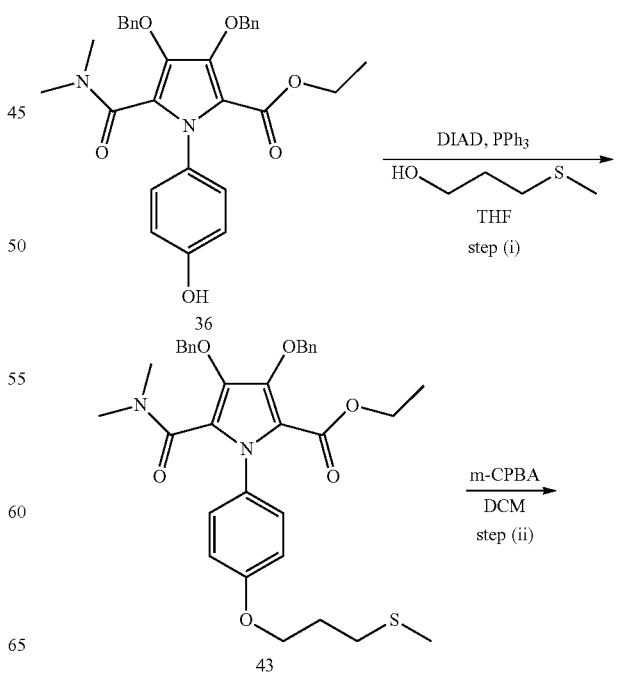

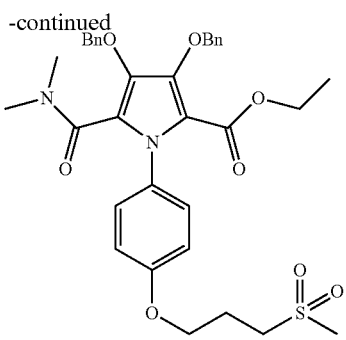

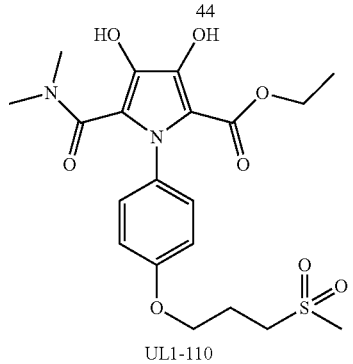

Step (i): Ethyl 3,4-bis(benzyloxy)-5-(dimethylcarbamoyl)-1-(4-(3-(methylthio)propoxy)phenyl)-1H-pyrrole-2-carboxylate (43)

To a stirred solution of ethyl 3,4-bis(benzyloxy)-5-(dimethylcarbamoyl)-1-(4-hydroxyphenyl)-1H-pyrrole-2-carboxylate (36) (350 mg, 0.68 mmol) in THF (2 mL) at 0° C. was added 3-(methylthio)propan-1-ol (84 μL, 0.82 mmol), triphenylphosphine (214 mg, 0.82 mmol), and DIAD (159 μL, 0.82 mmol). After 2 h further portions of 3-(methylthio)propan-1-ol (84 μL, 0.82 mmol), triphenylphosphine (214 mg, 0.82 mmol) and DIAD (159 μL, 0.82 mmol) were added, and the reaction mixture was allowed to stir at RT for 4 days. The reaction mixture was quenched with water (10 mL) and extracted with EtOAc (2×20 mL), the combined organics were washed with brine (30 mL), dried (MgSO₄) filtered and concentrated in vacuo. The crude product was purified by silica gel chromatography (12 g, 0-100% EtOAc in isohexane) to afford ethyl 3,4-bis(benzyloxy)-5-(dimethylcarbamoyl)-1-(4-(3-(methylthio)propoxy)phenyl)-1H-pyrrole-2-carboxylate (43) (389 mg, 85%) as a clear yellow oil: m/z 603 (M+H)⁺ (ES⁺).

Step (ii): Ethyl 3,4-bis(benzyloxy)-5-(dimethylcarbamoyl)-1-(4-(3-(methylsulfonyl)propoxy)phenyl)-1H-pyrrole-2-carboxylate (44)

To a stirred solution of ethyl 3,4-bis(benzyloxy)-5-(dimethylcarbamoyl)-1-(4-(3-(methylthio)propoxy)phenyl)-1H-pyrrole-2-carboxylate (43) (389 mg, 0.65 mmol) in DCM (8 mL) at 0° C. was added m-CPBA (445 mg, 2.58 mmol) the mixture was allowed to warm up to RT and stirred for 1 h, the reaction was quenched with sat. Na₂CO₃ (aq.) (20 mL) and extracted with DCM (3×10 mL) the combined organics were washed with brine (40 mL), passed through a phase separator, and the volatiles removed in vacuo. The crude product was purified by silica gel chromatography (12 g, 0-2% MeOH (1% NH₃) in DCM) to afford ethyl 3,4-bis(benzyloxy)-5-(dimethylcarbamoyl)-1-(4-(3-(methylsulfonyl)propoxy)phenyl)-1H-pyrrole-2-carboxylate (44) (96 mg, 23%) as a brown oil: m/z 635 (M+H)⁺ (ES⁺).

Step (iii): Ethyl 5-(dimethylcarbamoyl)-3,4-dihydroxy-1-(4-(3-(methylsulfonyl)propoxy)phenyl)-1H-pyrrole-2-carboxylate (UL1-110)

A solution of ethyl 3,4-bis(benzyloxy)-5-(dimethylcarbamoyl)-1-(4-(3-(methylsulfonyl)propoxy)phenyl)-1H-pyrrole-2-carboxylate (44) (95 mg, 0.15 mmol) in MeOH (4 mL) was passed through a Thales 'H-cube' cartridge (10% Pd/C) at a flow rate of 1 mL/min at 40° C. under H₂ (full H₂ mode). The output was concentrated in vacuo, and the compound was purified by preparative HPLC (C-18 column, 21.2 mm i.d.× 100 mm, 5 micron particle size, gradient 15-40% MeCN in 0.1% aq. formic acid over 16 min) to afford ethyl 5-(dimethylcarbamoyl)-3,4-dihydroxy-1-(4-(3-(methylsulfonyl)propoxy)phenyl)-1H-pyrrole-2-carboxylate (UL1-110) (40 mg, 58%) as a yellow solid: m/z 455 (M+H)⁺ (ES⁺); 453 (M−H)⁻ (ES⁻). ¹H NMR (400 MHz, DMSO-d₆) δ: 8.58 (s, 1H), 8.45 (s, 1H), 7.07-7.02 (m, 2H), 6.89-6.84 (m, 2H), 4.08 (t, J=7.2 Hz, 2H), 3.99 (q, J=7.1 Hz, 2H), 3.29-3.25 (m, 2H), 3.02 (s, 3H), 2.92-2.71 (br s, 6H), 2.21-2.07 (m, 2H), 0.99 (t, J=7.1 Hz, 3H).

Example E1

2,6-Dimethylcyclohexyl 5-(dimethylcarbamoyl)-3,4-dihydroxy-1-(4-methoxyphenyl)-1H-pyrrole-2-carboxylate (UL1-113)

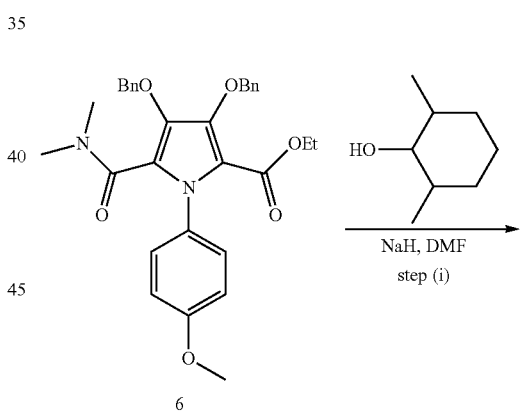

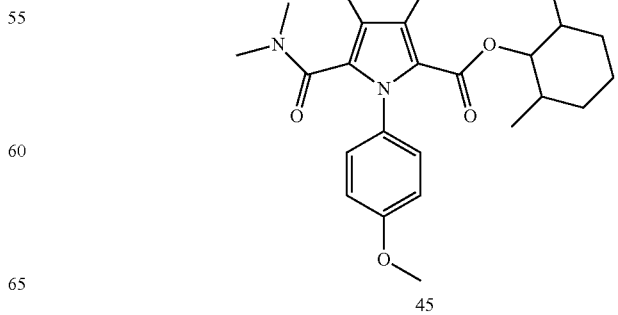

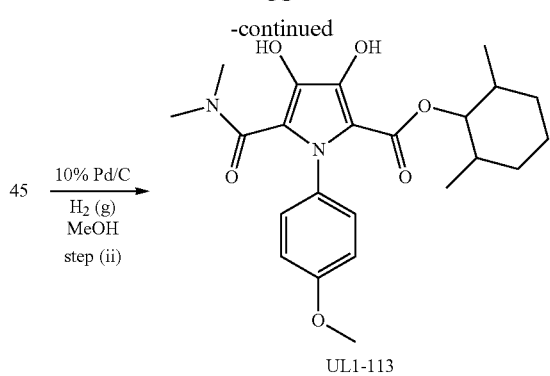

Step (i): 2,6-Dimethylcyclohexyl 3,4-bis(benzyloxy)-5-(dimethylcarbamoyl)-1-(4-methoxyphenyl)-1H-pyrrole-2-carboxylate (45)

Sodium hydride (60 wt % in oil) (78 mg, 1.95 mmol) was added to a stirred solution of 2,6-dimethylcyclohexanol (250 mg, 1.95 mmol) in DMF (1.95 mL). The mixture was heated at 60° C. for 10 min and then ethyl 3,4-bis(benzyloxy)-5-(dimethylcarbamoyl)-1-(4-methoxyphenyl)-1H-pyrrole-2-carboxylate (6) (206 mg, 0.39 mmol) was added in one portion. The reaction was allowed to stir at 70° C. for 16 h. The cooled reaction mixture was filtered through Celite, and the filtrate diluted with EtOAc (20 mL) and washed with water (3×10 mL), the organic layer was dried (MgSO$_4$), filtered and concentrated in vacuo. The crude product was purified by silica gel chromatography (12 g, 0.5% MeOH (1% NH$_3$) in DCM) to afford 2,6-dimethylcyclohexyl 3,4-bis(benzyloxy)-5-(dimethylcarbamoyl)-1-(4-methoxyphenyl)-1H-pyrrole-2-carboxylate (45) (73 mg, 20%) as a brown oil. m/z 611 (M+H)$^+$ (ES$^+$)

Step (ii): 2,6-Dimethylcyclohexyl 5-(dimethylcarbamoyl)-3,4-dihydroxy-1-(4-methoxyphenyl)-1H-pyrrole-2-carboxylate (UL1-113)

A solution of 2,6-dimethylcyclohexyl 3,4-bis(benzyloxy)-5-(dimethylcarbamoyl)-1-(4-methoxyphenyl)-1H-pyrrole-2-carboxylate (45) (73 mg, 0.12 mmol) in MeOH (6 mL) was passed through a Thales 'H-cube' cartridge (10% Pd/C) at a flow rate of 1 mL/min at 26° C. under H$_2$ (full H$_2$ mode). The output was concentrated in vacuo and the crude product was purified by preparative HPLC (Waters, Acidic (0.1% formic acid), Waters X-Select Prep-C18, 5 μm, 19×50 mm column, 5-95% MeCN in Water) to afford 2,6-dimethylcyclohexyl 5-(dimethylcarbamoyl)-3,4-dihydroxy-1-(4-methoxyphenyl)-1H-pyrrole-2-carboxylate (UL1-113) (15 mg, 29%) as a yellow solid: m/z 431 (M+H)$^+$ (ES$^+$); 429 (M−H)$^−$ (ES$^−$). $^1$H NMR (400 MHz, DMSO-d$_6$) δ: 8.67-8.40 (m, 2H), 7.15-7.05 (m, 2H), 6.91-6.85 (m, 2H), 5.05 (br s, 1H), 3.76-3.75 (m, 3H), 2.82 (br s, 6H), 1.64-0.94 (m, 6H), 0.74-0.57 (m, 6H), 0.57-0.40 (m, 2H).

Example F1

2-(Dimethylcarbamoyl)-5-(ethoxycarbonyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate) (UL1-117)

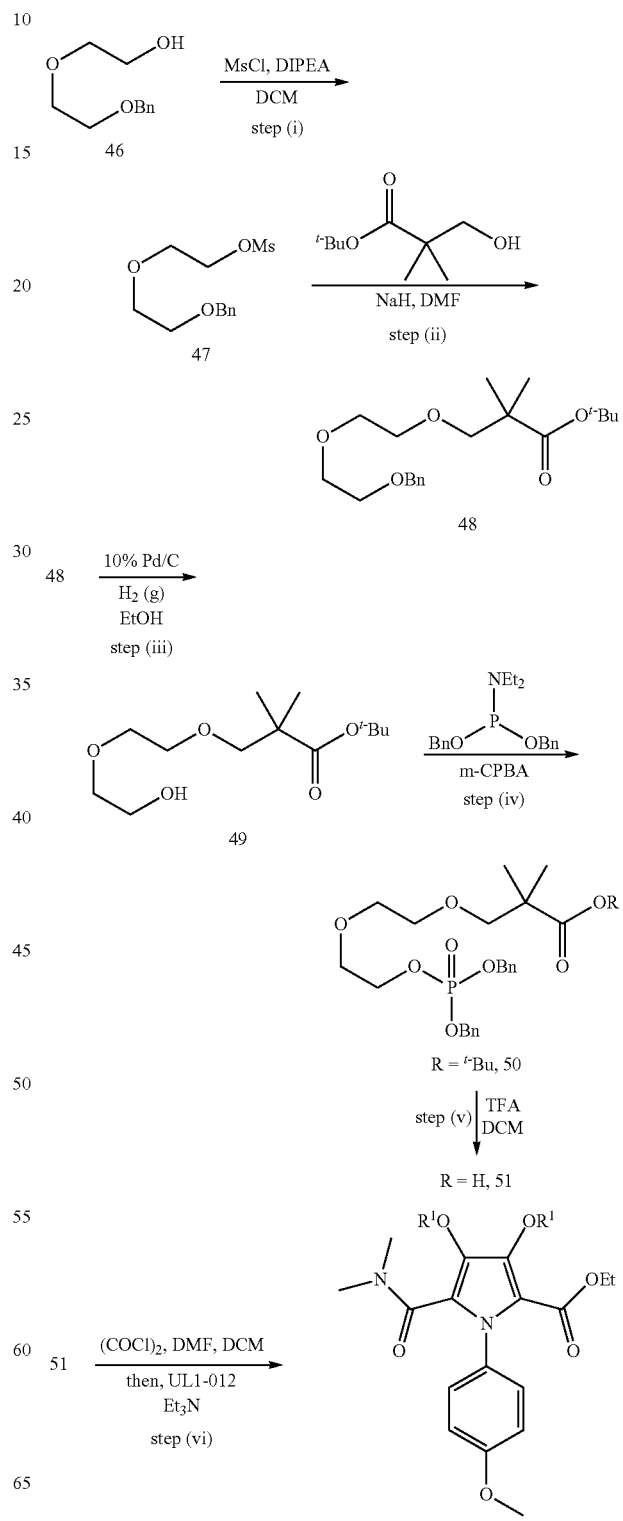

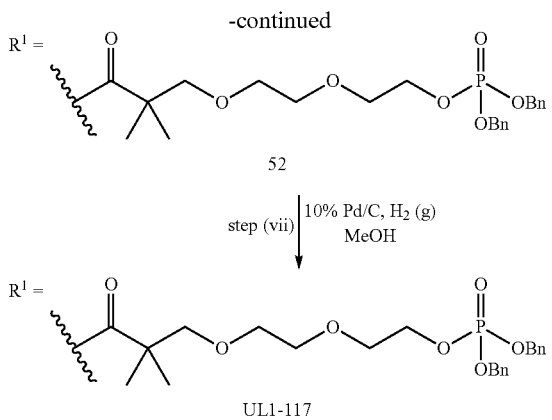

Step (i): 2-(2-(Benzyloxy)ethoxy)ethyl methanesulfonate (47)

MsCl (15.8 mL, 204 mmol) was added to a solution of 2-(2-(benzyloxy)ethoxy)ethanol (46) (25 g, 127 mmol) and Et₃N (36 mL, 255 mmol) in DCM (180 mL) at 0° C., the reaction mixture was allowed to warm up to RT and stirred for 16 h. The reaction mixture was diluted with DCM (50 mL) and washed with water (2×50 mL), 1M HCl (aq.) (2×50 mL), the organic layer was dried (MgSO₄), filtered and concentrated in vacuo to afford 2-(2-(benzyloxy)ethoxy)ethyl methanesulfonate (47) (35 g, 100%) as an orange oil: m/z 275 (M+H)⁺ (ES⁺). ¹H NMR (400 MHz, CDCl₃) δ: 7.37-7.27 (m, 5H), 4.55 (s, 2H), 4.40-4.37 (m, 2H), 3.78-3.76 (m, 2H), 3.71-3.68 (m, 2H), 3.64-3.62 (m, 2H), 3.02 (s, 3H).

Step (ii): tert-Butyl 3-(2-(2-(benzyloxy)ethoxy)ethoxy)-2,2-dimethylpropanoate (48)

To a solution of tert-butyl 3-hydroxy-2,2-dimethylpropanoate (353 mg, 2.03 mmol) and 2-(2-(benzyloxy)ethoxy)ethyl methanesulfonate (47) (500 mg, 1.82 mmol) in DMF (6 mL) at 0° C. was added NaH (60 wt % in oil) (109 mg, 2.73 mmol), and the reaction mixture was allowed to stir at RT for 30 min. The reaction was quenched with sat. NH₄Cl (aq.) (1 mL) diluted with water (20 mL) and washed with EtOAc (4×20 mL). The combined organic layers were dried (MgSO₄), filtered and concentrated in vacuo. The crude product was purified by silica gel chromatography (12 g, 0-40% Et₂O in isohexane) to afford tert-butyl 3-(2-(2-(benzyloxy)ethoxy)ethoxy)-2,2-dimethylpropanoate (48) (619 mg, 96%) as a colourless oil: m/z 375 (M+Na)⁺ (ES⁺). ¹H NMR (400 MHz, CDCl₃) δ: 7.32-7.25 (m, 5H), 4.54 (s, 2H), 3.66-3.56 (m, 8H), 3.41 (s, 2H), 1.40 (s, 8H), 1.10 (s, 6H).

Step (iii): tert-Butyl 3-(2-(2-hydroxyethoxy)ethoxy)-2,2-dimethylpropanoate (49)

A suspension of tert-butyl 3-(2-(2-(benzyloxy)ethoxy)ethoxy)-2,2-dimethylpropanoate (48) (13 g, 37 mmol) and 10% Pd/C (1.3 g) in EtOH (92 mL) were placed under 5 bar of H₂ pressure (isolated system), and stirred for 16 h. The mixture was filtered through celite and the filtrate concentrated in vacuo to afford tert-butyl 3-(2-(2-hydroxyethoxy)ethoxy)-2,2-dimethylpropanoate (49) (8.2 g, 85%) as a colourless oil: m/z 285 (M+Na)⁺ (ES⁺). ¹H NMR (400 MHz, CDCl₃) δ: 3.73-3.69 (m, 2H), 3.66-3.58 (m, 6H), 3.44 (s, 2H), 2.37 (t, J=6.2 Hz, 1H), 1.43 (s, 9H), 1.14 (s, 6H).

Step (iv): tert-Butyl 3-(2-(2-((bis(benzyloxy)phosphoryl)oxy)ethoxy)ethoxy)-2,2-dimethylpropanoate (50)

A mixture of tert-butyl 3-(2-(2-hydroxyethoxy)ethoxy)-2,2-dimethylpropanoate (49) (6.87 g, 26.2 mmol), 5-methyl-1H-tetrazole (4.40 g, 52.4 mmol), and dibenzyl diethylphosphoramidite (12.47 g, 39.3 mmol) in THF (66 mL) was allowed to stir at RT for 1.5 h. The solution was cooled to 0° C. and m-CPBA (10.85 g, 47.1 mmol) was slowly added, the mixture was allowed to stir at RT for 16 h. The reaction was diluted with DCM (200 mL) and washed with sat. NaHCO₃ (aq.) (4×100 mL), the organic layer was dried (MgSO₄), filtered and concentrated in vacuo. The crude product was purified by silica gel chromatography (220 g, 0-40% EtOAc in isohexane) to afford tert-butyl 3-(2-(2-((bis(benzyloxy)phosphoryl)oxy)ethoxy)ethoxy)-2,2-dimethylpropanoate (50) (12.2 g, 89%) as a colourless oil: m/z 545 (M+Na)⁺ (ES⁺). ¹H NMR (400 MHz, CDCl₃) δ: 7.35-7.31 (m, 10H), 5.09-5.00 (m, 4H), 4.13-4.09 (m, 2H), 3.65-3.63 (m, 2H), 3.59-3.52 (m, 4H), 3.39 (s, 2H), 1.41 (s, 9H), 1.11 (s, 6H).

Step (v): 3-(2-(2-((Bis(benzyloxy)phosphoryl)oxy)ethoxy)ethoxy)-2,2-dimethylpropanoic acid (51)

TFA (6.63 mL, 86 mmol) was added dropwise to a stirred solution of tert-butyl 3-(2-(2-((bis(benzyloxy)phosphoryl)oxy)ethoxy)ethoxy)-2,2-dimethylpropanoate (50) (4.5 g, 8.61 mmol) in DCM (43 mL) and the reaction mixture was allowed to stir at RT for 16 h then concentrated in vacuo. The crude product was dissolved in EtOAc (150 mL) and washed with 1M HCl (aq.) (50 mL), water (2×50 mL), and brine (50 mL) the organic layer was dried (MgSO₄), filtered and concentrated in vacuo to afford 3-(2-(2-((bis(benzyloxy)phosphoryl)oxy)ethoxy)ethoxy)-2,2-dimethylpropanoic acid (51) (3.98 g, 99%) as a colourless oil: m/z 467 (M+H)⁺ (ES⁺); 465 (M−H)⁻ (ES⁻). ¹H NMR (400 MHz, CDCl₃) δ: 7.36-7.31 (m, 10H), 5.12-5.03 (m, 4H), 4.14-4.09 (m, 2H), 3.69-3.64 (m, 2H), 3.60 (s, 4H), 3.47 (s, 2H), 1.20 (s, 6H).

Step (vi): 2-(Dimethylcarbamoyl)-5-(ethoxycarbonyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate) (52)

DMF (0.2 μL, 2.14 μmol) was added to a stirred solution of 3-(2-(2-((bis(benzyloxy)phosphoryl)oxy)ethoxy)ethoxy)-2,2-dimethylpropanoic acid (51) (100 mg, 0.21 mmol), followed by a solution of (COCl)₂ (19 μL, 0.22 mmol) in DCM (860 μL), the reaction mixture was allowed to stir for 45 min. To this mixture was added ethyl 5-(dimethylcarbamoyl)-3,4-dihydroxy-1-(4-methoxyphenyl)-1H-pyrrole-2-carboxylate (UL1-012) (30 mg, 0.09 mmol), the reaction mixture was cooled to 0° C. and Et₃N (60 μL, 0.43 mmol) was added, the resulting mixture was allowed to stir for 45 min. The volatiles were concentrated in vacuo, the crude was suspended in Et₂O (5 mL) filtered, concentrated in vacuo and the residue purified by silica gel chromatography (4 g, 0-2% MeOH in DCM) to afford a yellow oil. The compound was further purified by preparative HPLC (C-18 column, 19 mm i.d.×50 mm, 5 micron particle size, gradient 5-95% MeCN in 0.1% aq. formic acid over 16 min) to afford 2-(dimethylcarbamoyl)-5-(ethoxycarbonyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate) (52) (11 mg, 10%) as a colourless oil: ¹H NMR (400 MHz, CDCl₃) δ 7.40-7.30 (m, 20H), 7.25-710 (m, 2H), 3.87-6.85 (m, 2H), 5.09-4.99 (m, 8H), 4.14-4.05 (m, 6H), 3.81 (s, 3H), 3.65-3.48 (m, 16H), 2.80 (s, 3H), 2.75 (s, 3H), 1.32 (s, 6H), 1.23 (s, 6H). 1.06 (t, J=7.2 Hz, 3H).

Step (vii): 2-(Dimethylcarbamoyl)-5-(ethoxycarbonyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate) (UL1-117)

A solution of methyl 2-(dimethylcarbamoyl)-5-(ethoxycarbonyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate) (52) (10 mg, 8.03 µmol) in MeOH (4 mL) was passed through a Thales 'H-cube' cartridge (10% Pd/C) at a flow rate of 1 mL/min at 25° C. under H$_2$ (10 bar). The output was concentrated in vacuo to afford 2-(dimethylcarbamoyl)-5-(ethoxycarbonyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate) (UL1-117) (5 mg, 70%) as a white solid: m/z 885 (M+H)$^+$ (ES$^+$); 883 (M−H)$^−$ (ES$^−$). $^1$H NMR (CDCl$_3$) δ: 7.25-7.15 (m, 2H), 6.91-6.86 (m, 2H), 4.20-4.02 (m, 6H), 3.82 (s, 3H), 3.75-3.50 (m, 16H), 2.83 (s, 3H), 2.77 (s, 3H), 2.69 (br s, 4H), 1.35 (s, 6H), 1.28 (s, 6H), 1.08 (t, J=7.1 Hz, 3H).

Example G1

2-(Dimethylcarbamoyl)-5-(ethoxycarbonyl)-1-(4-methoxyphenyl)-1H-pyrrole-3,4-diyl bis(2,2-dimethyl-3-(3-(phosphonooxy)propoxy)propanoate) (UL1-118)

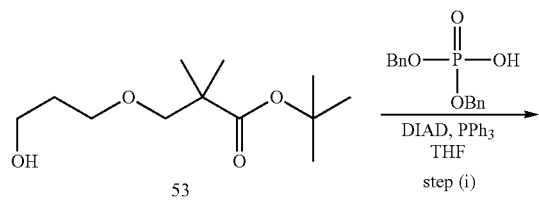

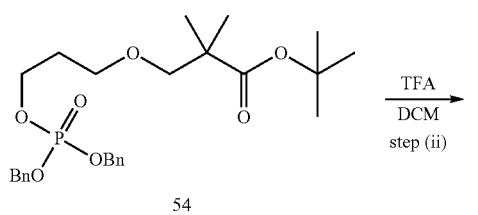

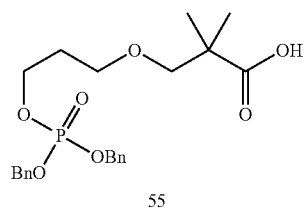

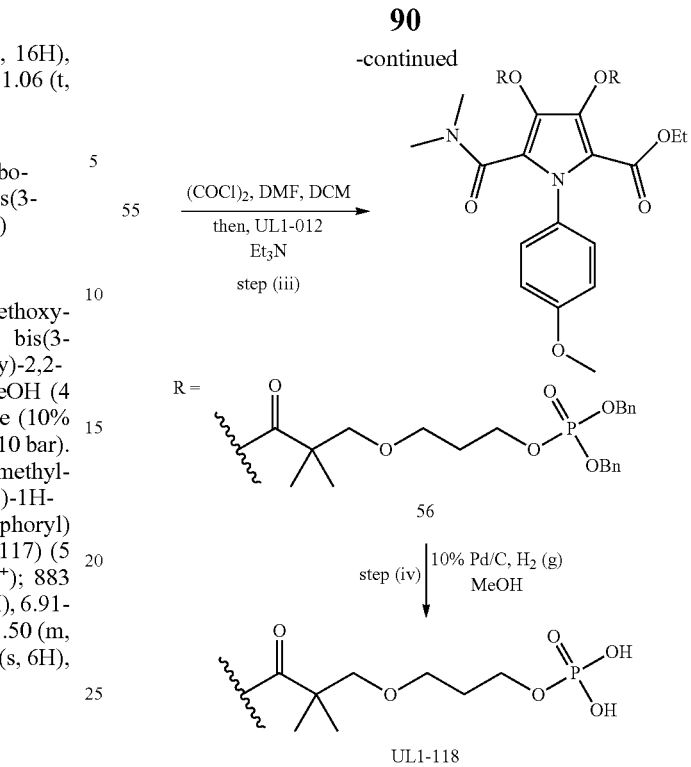

Step (i): tert-Butyl 3-(3-((bis(benzyloxy)phosphoryl)oxy)propoxy)-2,2-dimethylpropanoate (54)

DIAD (1.36 mL, 6.97 mmol) was added dropwise to a stirred solution of PPh$_3$ (76 mg, 0.30 mmol), dibenzyl phosphite (1.94 g, 6.97 mmol) and tert-butyl 3-(3-hydroxypropoxy)-2,2-dimethylpropanoate (53) (1.08 g, 4.65 mmol) [prepared using the same procedure as Example F1 steps (ii)-(iii) using 3-(benzyloxy)propyl 4-methylbenzenesulfonate in step (ii)] in THF (100 mL) at 0° C. The reaction was allowed to warm to RT and stirred for 16 h, and the volatiles were removed in vacuo. The crude product was purified by silica gel chromatography (120 g, 0-60% EtOAc in isohexane) to afford tert-butyl 3-(3-((bis(benzyloxy)phosphoryl)oxy)propoxy)-2,2-dimethylpropanoate (54) (1.76 g, 54%) as a clear colourless oil: m/z 515 (M+Na)$^+$ (ES$^+$). $^1$H NMR (400 MHz, DMSO-d$_6$) δ: 7.40-7.35 (m, 10H), 5.07-4.96 (m, 4H), 4.04-3.92 (m, 2H), 3.39 (t, J=6.2 Hz, 2H), 3.28 (s, 2H), 1.77 (quin, J=6.2 Hz, 2H), 1.35 (s, 9H), 1.02 (s, 6H).

Step (ii): 3-(3-((Bis(benzyloxy)phosphoryl)oxy)propoxy)-2,2-dimethylpropanoic acid (55)

To a stirred solution of tert-butyl 3-(3-((bis(benzyloxy)phosphoryl)oxy)propoxy)-2,2-dimethylpropanoate (54) (1.76 g, 3.57 mmol) in DCM (30 mL) was added TFA (1.38 mL, 17.9 mmol), and the reaction was allowed to stir at RT for 4 h. The volatiles were removed in vacuo and the crude product was purified by silica gel chromatography (40 g, 0-30% EtOAc in isohexane (+1% AcOH)) to afford 3-(3-((bis(benzyloxy)phosphoryl)oxy)propoxy)-2,2-dimethylpropanoic acid (55) (1.03 g, 58%) as a colourless oil: m/z 437 (M+H)$^+$ (ES$^+$); 435 (M−H)$^−$ (ES$^−$). $^1$H NMR (400 MHz, DMSO-d$_6$) δ: 7.49-7.26 (m, 10H), 5.08-4.95 (m, 4H), 4.03-3.96 (m, 2H), 3.42-3.35 (m, 2H), 3.31 (s, 2H), 1.77 (quin, J=6.2 Hz, 2H), 1.05 (s, 6H).

Step (iii): 2-(Dimethylcarbamoyl)-5-(ethoxycarbonyl)-1-(4-methoxyphenyl)-1H-pyrrole-3,4-diyl bis(3-(3-((bis(benzyloxy)phosphoryl)oxy)propoxy)-2,2-dimethylpropanoate)(56)

(COCl)$_2$ (28 μL, 0.32 mmol) was added dropwise to a stirred solution of 3-(3-((bis(benzyloxy)phosphoryl)oxy)propoxy)-2,2-dimethylpropanoic acid (55) (0.14 g, 0.32 mmol) at 0° C., followed by a solution DMF (0.25 μL, 3.2 μmol) in DCM (0.1 mL), the reaction was allowed to warm to RT and left to stir for 2.5 h. The reaction was cooled to 0° C. and a further portion of (COCl)$_2$ (28 μL, 0.32 mmol) and a solution DMF (0.25 μL, 3.2 μmol) in DCM (0.1 mL) was added and the reaction allowed to warm to RT over 4 h. The reaction was cooled to 0° C. and ethyl 5-(dimethylcarbamoyl)-3,4-dihydroxy-1-(4-methoxyphenyl)-1H-pyrrole-2-carboxylate (UL1-012) (55 mg, 0.16 mmol) was added, followed by Et$_3$N (133 μL, 0.96 mmol). The reaction was allowed to warm to RT and stirred for 16 h. The volatiles were concentrated in vacuo, the crude was suspended in EtOAc (5 mL) filtered, concentrated in vacuo and the crude product was purified by preparative HPLC (C-18 column, 19 mm i.d.×50 mm, 5 micron particle size, gradient 60-90% MeCN in water+ 0.1% aq. formic acid over 16 min) to afford 2-(dimethylcarbamoyl)-5-(ethoxycarbonyl)-1-(4-methoxyphenyl)-1H-pyrrole-3,4-diyl bis(3-(3-((bis(benzyloxy)phosphoryl)oxy)propoxy)-2,2-dimethylpropanoate) (56) (42 mg, 11%) as a pale yellow gum: m/z: no ionisation observed. $^1$H NMR (400 MHz, DMSO-d$_6$) δ: 7.37-7.32 (m, 2H), 7.18-7.11 (m, 2H), 6.95-6.89 (m, 2H), 5.06-4.95 (m, 8H), 4.05-3.95 (m, 6H) 3.78 (s, 3H), 3.45-3.36 (m, 8H), 2.76 (s, 3H), 2.66 (s, 3H), 1.80-1.75 (m, 4H), 1.23 (s, 6H), 1.13 (s, 6H), 0.98 (t, J=7.1 Hz, 3H).

Step (iv): 2-(Dimethylcarbamoyl)-5-(ethoxycarbonyl)-1-(4-methoxyphenyl)-1H-pyrrole-3,4-diyl bis(2,2-dimethyl-3-(3-(phosphonooxy)propoxy)propanoate) (UL1-118)

A solution of 2-(dimethylcarbamoyl)-5-(ethoxycarbonyl)-1-(4-methoxyphenyl)-1H-pyrrole-3,4-diyl bis(3-(3-((bis(benzyloxy)phosphoryl)oxy)propoxy)-2,2-dimethylpropanoate) (56) (37 mg, 0.03 mmol) in MeOH (4 mL) was passed through a Thales 'H-cube' cartridge (10% Pd/C) at a flow rate of 1 mL/min at 40° C. under H$_2$ (full H$_2$ mode). The output was concentrated in vacuo to afford 2-(dimethylcarbamoyl)-5-(ethoxycarbonyl)-1-(4-methoxyphenyl)-1H-pyrrole-3,4-diyl bis(2,2-dimethyl-3-(3-(phosphonooxy)propoxy)propanoate) (UL1-118) (25 mg, 95%) as a white gum: m/z 825 (M+H)$^+$ (ES$^+$); 823 (M−H)$^−$ (ES$^−$). $^1$H NMR (400 MHz, DMSO-d$_6$) δ: 7.24-7.16 (m, 2H), 6.98-6.91 (m, 2H), 4.01 (q, J=7.1 Hz, 2H), 3.90-3.81 (m, 4H), 3.79 (s, 3H), 3.51-3.43 (m, 8H), 2.82 (s, 3H), 2.70 (s, 3H), 1.86-1.73 (m, 4H), 1.25 (s, 6H), 1.19 (s, 6H), 1.01 (t, J=7.1 Hz, 3H).

Example H1

2-(Dimethylcarbamoyl)-5-(ethoxycarbonyl)-1-(4-methoxyphenyl)-1H-pyrrole-3,4-diyl bis(25,25-dimethyl-2,5,8,11,14,17,20,23-octaoxahexacosan-26-oate) (UL1-119)

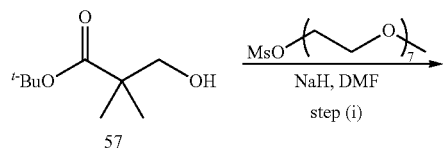

Step (i): tert-Butyl 25,25-dimethyl-2,5,8,11,14,17,20,23-octaoxahexacosan-26-oate (58)

Sodium hydride (60% wt in oil) (400 mg, 10 mmol) was added to a stirred solution of tert-butyl 3-hydroxy-2,2-dimethylpropanoate (57) (1.74 g, 10 mmol) in DMF (20 mL) at 0° C., after 30 min a solution of 2,5,8,11,14,17,20-heptaoxadocosan-22-yl methanesulfonate (2.79 g, 6.67 mmol) in DMF (10 mL) was added dropwise, and the reaction mixture was allowed to warm to RT and stirred for 16 h. The reaction was quenched with water (100 mL) and the aqueous layer was extracted with DCM (2×100 mL), the combined organic layers were washed with brine (3×100 mL), dried (MgSO$_4$), filtered and concentrated in vacuo. The crude product was purified by silica gel chromatography (120 g, 0-10% MeOH in EtOAc) to afford tert-butyl 25,25-dimethyl-2,5,8,11,14,17,20,23-octaoxahexacosan-26-oate (58) (1.59 g, 48%) as a colourless oil: $^1$H NMR (400 MHz, CDCl$_3$) δ: 3.65-3.51 (m, 32H), 3.40 (s, 2H), 3.36 (s, 3H), 1.41 (s, 9H), 1.11 (s, 6H).

Step (ii): 25,25-Dimethyl-2,5,8,11,14,17,20,23-octaoxahexacosan-26-oic acid (59)

TFA (1.5 mL, 19.3 mmol) was added dropwise to a stirred solution of tert-butyl 25,25-dimethyl-2,5,8,11,14,17,20,23-octaoxahexacosan-26-oate (58) (0.48 g, 0.97 mmol) in DCM (5 mL), and the reaction was stirred at RT for 4 h. The volatiles were removed in vacuo to afford 25,25-dimethyl-2,5,8,11,14, 17,20,23-octaoxahexacosan-26-oic acid (59) (0.49 g, 95%) as a colourless oil: $^1$H NMR (400 MHz, CDCl$_3$) δ: 3.68-3.60 (m, 26H), 3.55-3.52 (m, 2H), 3.47 (s, 2H), 3.36 (s, 3H), 1.18 (s, 6H).

Step (iii): 2-(Dimethylcarbamoyl)-5-(ethoxycarbonyl)-1-(4-methoxyphenyl)-1H-pyrrole-3,4-diyl bis(25,25-dimethyl-2,5,8,11,14,17,20,23-octaoxahexacosan-26-oate) (UL1-119)

Thionyl chloride (43 mg, 0.36 mmol) was added to a stirred solution of 25,25-dimethyl-2,5,8,11,14,17,20,23-octaoxahexacosan-26-oic acid (59) (140 mg, 0.32 mmol) in DCM (2 mL) and the reaction was stirred at RT for 2 h. The volatiles were removed in vacuo, the residue dissolved in DCM (2 mL) and added to a stirred solution of ethyl 5-(dimethylcarbamoyl)-3,4-dihydroxy-1-(4-methoxyphenyl)-1H-pyrrole-2-carboxylate (UL1-012) (50 mg, 0.14 mmol) and DIPEA (46 mg, 0.36 mmol) in DCM (3 mL) at 0° C. The reaction mixture was allowed to warm to RT and stirred for 16 h. The volatiles were concentrated in vacuo and the resulting residue was suspended in EtOAc (10 mL), filtered and the filtrate concentrated in vacuo. The crude residue was purified by silica gel chromatography (12 g, 0-3% MeOH in DCM) to give a crude oil. The product was further purified by preparative HPLC (Waters, Acidic (0.1% Formic acid), Waters X-Select Prep-C18, 5 μm, 19×50 mm column, 25-70% MeCN in water) to afford 2-(dimethylcarbamoyl)-5-(ethoxycarbonyl)-1-(4-methoxyphenyl)-1H-pyrrole-3,4-diyl bis(25,25-dimethyl-2,5,8,11,14,17,20,23-octaoxahexacosan-26-oate) (UL1-119) (52 mg, 30%) as a colourless oil: m/z 1193 (M+H)$^+$ (ES$^+$). $^1$H NMR (400 MHz, DMSO-d$_6$) δ: 7.21-7.16 (m, 2H), 6.96-6.92 (m, 2H), 4.02 (q, J=7.1 Hz, 2H), 3.79 (s, 3H), 3.58-3.46 (m, 56H), 3.43-3.40 (m, 4H), 3.23 (s, 6H), 2.82 (s, 3H), 2.70 (s, 3H), 1.25 (s, 6H), 1.19 (s, 6H), 1.02 (t, J=7.1 Hz, 3H).

Example I1

Ethyl 5-(dimethylcarbamoyl)-4-hydroxy-1-(4-methoxyphenyl)-3-((phosphonooxy)methoxy)-1H-pyrrole-2-carboxylate (UL1-115)

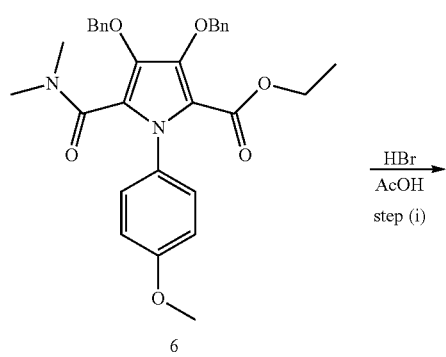

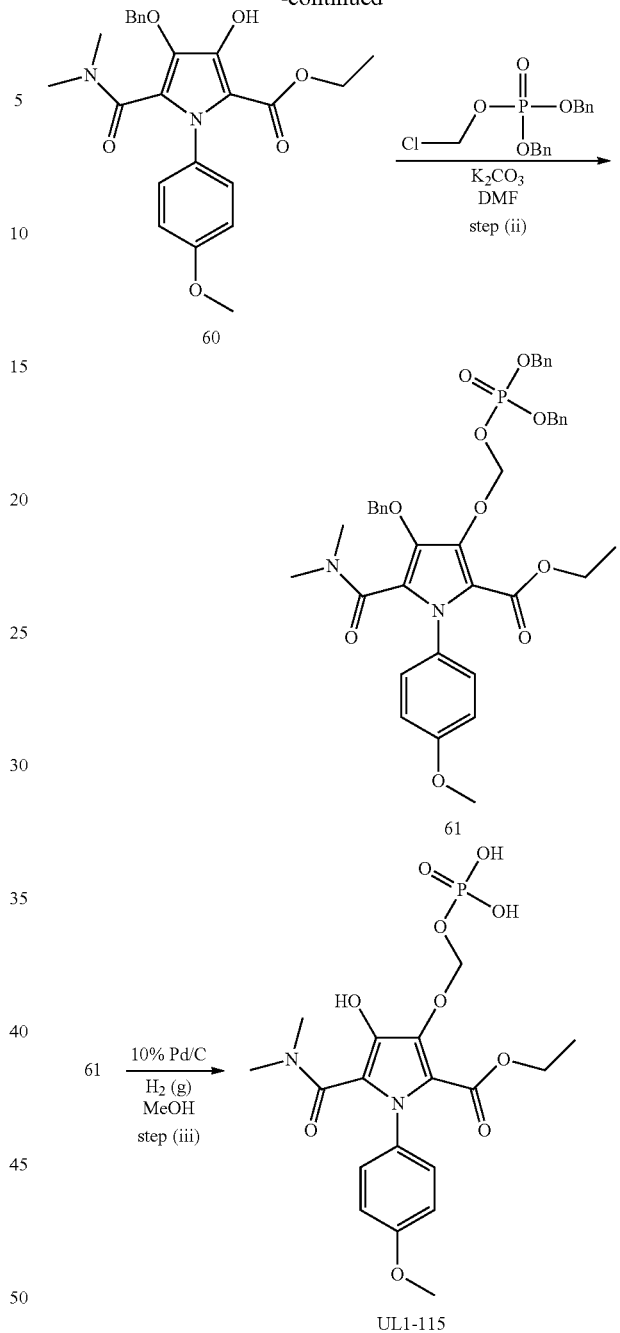

Step (i): Ethyl 4-(benzyloxy)-5-(dimethylcarbamoyl)-3-hydroxy-1-(4-methoxyphenyl)-1H-pyrrole-2-carboxylate (60)

HBr (33% in AcOH, 970 μL, 5.34 mmol) was added to a stirred solution of ethyl 3,4-bis(benzyloxy)-5-(dimethylcarbamoyl)-1-(4-methoxyphenyl)-1H-pyrrole-2-carboxylate (6) (2.82 g, 5.34 mmol) in AcOH (40 mL) and the reaction was allowed to stir for 16 h at RT. The reaction mixture was diluted with DCM (100 mL), washed with water (100 mL), brine (2×100 mL), the organic layer was dried (MgSO$_4$), filtered and concentrated in vacuo. The residue was redissolved in AcOH (40 mL) and HBr (33% in AcOH, 970 μL, 5.34 mmol) was added dropwise and the reaction was allowed to stir at RT for 40 h. The reaction mixture was diluted with DCM (100 mL), washed with water (100 mL) and brine (2×100 mL). The organic layer was dried (MgSO$_4$), filtered and concentrated in vacuo. The crude product was purified by silica gel chromatography (40 g, 0-30% EtOAc in toluene) to afford ethyl 4-(benzyloxy)-5-(dimethylcarbamoyl)-3-hydroxy-1-(4-methoxyphenyl)-1H-pyrrole-2-carboxylate (60) (1.48 g, 57%) as a colourless oil: m/z 439 (M+H)$^+$ (ES$^+$); 437 (M−H)$^−$ (ES$^−$). $^1$H NMR (400 MHz, DMSO-d$_6$) δ: 8.75 (s, 1H), 7.42-7.28 (m, 5H), 7.12-7.05 (m, 2H), 6.91-6.84 (m, 2H), 5.01 (s, 2H), 4.02 (q, J=7.1 Hz, 2H), 3.76 (s, 3H), 2.68 (s, 3H), 2.66 (s, 3H), 1.0 (t, J=7.1 Hz, 3H).

Step (ii): Ethyl 4-(benzyloxy)-3-(((bis(benzyloxy)phosphoryl)oxy)methoxy)-5-(dimethylcarbamoyl)-1-(4-methoxyphenyl)-1H-pyrrole-2-carboxylate (61)

A solution of dibenzyl(chloromethyl)phosphate (227 mg, 0.70 mmol) in DMF (1 mL) was added dropwise to a stirred suspension of ethyl 4-(benzyloxy)-5-(dimethylcarbamoyl)-3-hydroxy-1-(4-methoxyphenyl)-1H-pyrrole-2-carboxylate (60) (203 mg, 0.46 mmol) and K$_2$CO$_3$ (128 mg, 0.93 mmol) in DMF (4 mL) at 0° C., the reaction was stirred for 1 h, then allowed to warm to RT over 16 h. The reaction mixture was poured into water (50 mL), extracted with Et$_2$O (2×50 mL). The combined organic layers were washed with brine (3×100 mL), dried (MgSO$_4$), filtered and concentrated in vacuo. The crude product was purified by silica gel chromatography (40 g, 0-30% EtOAc in toluene) to afford ethyl 4-(benzyloxy)-3-(((bis(benzyloxy)phosphoryl)oxy)methoxy)-5-(dimethylcarbamoyl)-1-(4-methoxyphenyl)-1H-pyrrole-2-carboxylate (61) (178 mg, 51%) as a clear colourless oil: m/z 729 (M+H)$^+$ (ES$^+$). $^1$H NMR (400 MHz, DMSO-d$_6$) δ: 7.38-7.27 (m, 15H), 7.10-7.03 (m, 2H), 6.92-6.86 (m, 2H), 5.49 (d, J=11.1 Hz, 2H), 5.11 (s, 2H), 5.07-4.95 (m, 6H), 4.00 (q, J=7.1 Hz, 2H), 3.78 (s, 3H), 2.69 (s, 3H), 2.68 (s, 3H), 0.99 (t, J=7.0 Hz, 3H).

Step (iii): Ethyl 5-(dimethylcarbamoyl)-4-hydroxy-1-(4-methoxyphenyl)-3-((phosphonooxy)methoxy)-1H-pyrrole-2-carboxylate (UL1-115)

A solution of ethyl 4-(benzyloxy)-3-(((bis(benzyloxy)phosphoryl)oxy)methoxy)-5-(dimethylcarbamoyl)-1-(4-methoxyphenyl)-1H-pyrrole-2-carboxylate (61) (102 mg, 0.14 mmol) in MeOH (5 mL) was passed through a Thales 'H-cube' cartridge (10% Pd/C) at a flow rate of 1 mL/min at 45° C. under H$_2$ (full H$_2$ mode). The output was concentrated in vacuo to afford ethyl 5-(dimethylcarbamoyl)-4-hydroxy-1-(4-methoxyphenyl)-3-((phosphonooxy)methoxy)-1H-pyrrole-2-carboxylate (UL1-115) (61 mg, 93%) as a white solid: m/z 459 (M+H)$^+$ (ES$^+$); 457 (M−H)$^−$ (ES$^−$), $^1$H NMR (400 MHz, DMSO-d$_6$) δ: 7.11-7.05 (m, 2H), 6.91-6.84 (m, 2H), 5.45 (d, J=16 Hz, 2H), 3.98 (q, J=7.1 Hz, 2H), 3.77 (s, 3H), 2.98 (br s, 3H) 2.74 (br s, 3H), 1.01 (t, J=7.0 Hz, 3H).

Example J1

2,5-Bis(dimethylcarbamoyl)-1-(4-methoxyphenyl)-1H-pyrrole-3,4-diyl bis(2,2-dimethyl-3-(2-(2-(phosphonooxy)ethoxy)ethoxy)propanoate) (UL1-121)

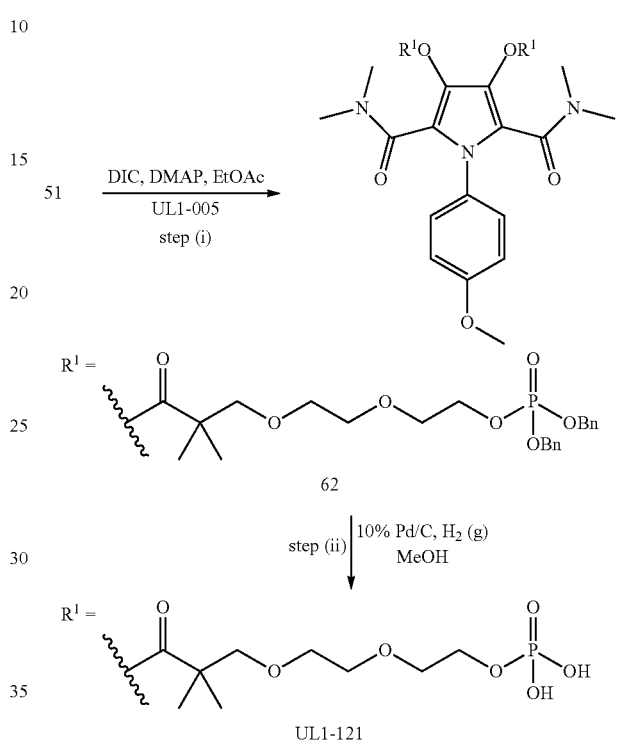

Step (i): 2,5-Bis(dimethylcarbamoyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate)(62)

DIC (160 mg, 1.27 mmol) was added to a solution of 3,4-dihydroxy-1-(4-methoxyphenyl)-N$^2$,N$^2$,N$^5$,N$^5$-tetramethyl-1H-pyrrole-2,5-dicarboxamide (UL1-005) (200 mg, 0.58 mmol), 3-(2-(2-((bis(benzyloxy)phosphoryl)oxy)ethoxy)ethoxy)-2,2-dimethylpropanoic acid (51) (591 mg, 1.27 mmol), and DMAP (28 mg, 0.23 mmol) in EtOAc (4 mL) and the reaction mixture was allowed to stir at RT for 96 h. The mixture was diluted with EtOAc (150 mL) washed with 1M HCl (aq.) (50 mL), water (2×50 mL), and brine (50 mL), dried (MgSO$_4$), filtered and concentrated in vacuo. The crude residue was purified by preparative HPLC (Waters, Acidic (0.1% Formic acid), Waters X-Select Prep-C18, 5 μm, 19×50 mm column, 50-95% MeCN in water) to afford 2,5-bis(dimethylcarbamoyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate) (62) (228 mg, 32%) as a yellow solid: m/z not observed. $^1$H NMR (400 MHz, DMSO-d$_6$) δ: 7.40-7.31 (m, 20H), 7.09-7.07 (m, 2H), 6.95-6.93 (m, 2H), 5.02 (d, J=7.6 Hz, 8H), 4.08-4.04 (m, 4H), 3.77 (s, 3H), 3.58-3.56 (m, 4H), 3.56-3.47 (m, 8H), 3.44 (s, 4H), 2.72 (s, 6H), 1.13 (s, 12H).

Step (ii) 2,5-Bis(dimethylcarbamoyl)-1-(4-methoxyphenyl)-1H-pyrrole-3,4-diyl bis(2,2-dimethyl-3-(2-(2-(phosphonooxy)ethoxy)ethoxy)propanoate) (UL1-121)

A solution of 2,5-bis(dimethylcarbamoyl)-1-(4-methoxyphenyl)-1H-pyrrole-3,4-diyl bis(3-(2-(2-((bis(benzyloxy)phosphoryl)oxy)ethoxy)ethoxy)-2,2-dimethylpropanoate) (62) (278 mg, 0.22 mmol) in MeOH (112 mL) was passed through a Thales 'H-cube' cartridge (10% Pd/C) at a flow rate of 1 mL/min at 45° C. under $H_2$ (10 bar). The output was concentrated in vacuo to afford 2,5-bis(dimethylcarbamoyl)-1-(4-methoxyphenyl)-1H-pyrrole-3,4-diyl bis(2,2-dimethyl-3-(2-(2-(phosphonooxy)ethoxy)ethoxy)propanoate) (UL1-121) (175 mg, 88%) as a light yellow oil: m/z 884 $(M+H)^+$ $(ES^+)$; 882 $(M-H)^-$ $(ES^-)$. $^1H$ NMR (400 MHz, DMSO-$d_6$) δ: 7.11-7.09 (m, 2H), 6.97-6.95 (m, 2H), 3.91-3.87 (m, 4H), 3.78 (s, 3H), 3.58-3.50 (m, 16H), 2.89 (s, 6H), 2.76 (s, 6H), 1.19 (s, 12H).

Example K1

2,5-Bis(dimethylcarbamoyl)-1-(4-methoxyphenyl)-1H-pyrrole-3,4-diyl bis(piperidine-4-carboxylate) (UL1-123)

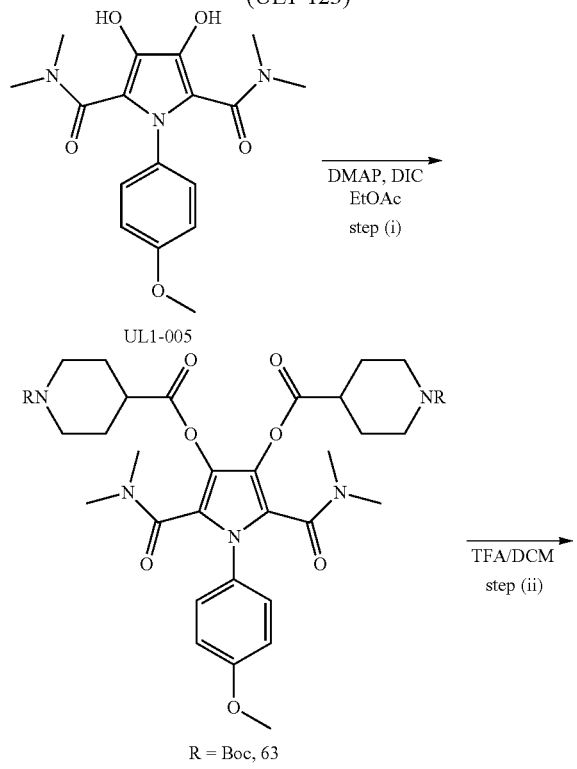

Step (i): $O^{'4},O^4$-(2,5-Bis(dimethylcarbamoyl)-1-(4-methoxyphenyl)-1H-pyrrole-3,4-diyl)1-di-tert-butyl bis(piperidine-1,4-dicarboxylate) (63)

DIC (633 µL, 4.10 mmol) was added to a solution of 3,4-dihydroxy-1-(4-methoxyphenyl)-$N^2,N^2,N^5,N^5$-tetramethyl-1H-pyrrole-2,5-dicarboxamide (UL1-005) (284 mg, 0.82 mmol), 1-(tert-butoxycarbonyl)piperidine-4-carboxylic acid (525 mg, 2.29 mmol) and DMAP (40 mg, 0.33 mmol) in EtOAc (5 mL) the reaction mixture was allowed to stir at RT for 2 h. The reaction mixture was washed with 1M HCl (aq.) (20 mL), dried ($MgSO_4$), filtered and concentrated in vacuo. The crude residue was purified by silica gel chromatography (40 g, 0-3% MeOH in DCM) to afford $O^{'4},O^4$-(2,5-bis(dimethylcarbamoyl)-1-(4-methoxyphenyl)-1H-pyrrole-3,4-diyl) 1-di-tert-butyl bis(piperidine-1,4-dicarboxylate) (63) (565 mg, 76%) as a colourless oil: 792 $(M+Na)^+$ $(ES^+)$. $^1H$ NMR (400 MHz, DMSO-$d_6$) δ: 7.12-7.08 (m, 2H), 6.98-6.93 (m, 2H), 3.88-3.81 (br m, 4H), 3.77 (s, 3H), 2.96-2.73 (m, 18H), 1.89-1.81 (br m, 4 H), 1.50-1.37 (m, 22H).

Step (ii): 4,4'-(((2,5-Bis(dimethylcarbamoyl)-1-(4-methoxyphenyl)-1H-pyrrole-3,4-diyl)bis(oxy))bis(carbonyl))bis(piperidin-1-ium) 2,2,2-trifluoroacetate (UL1-123)

TFA (1.12 mL, 14.7 mmol) was added dropwise to a solution of $O^{'4},O^4$-(2,5-bis(dimethylcarbamoyl)-1-(4-methoxyphenyl)-1H-pyrrole-3,4-diyl)1-di-tert-butyl bis(piperidine-1,4-dicarboxylate) (565 mg, 0.73 mmol) in DCM (20 mL) and the mixture was allowed to stir at RT for 2 h. The reaction was concentrated in vacuo to afford 4,4'-(((2,5-bis(dimethylcarbamoyl)-1-(4-methoxyphenyl)-1H-pyrrole-3,4-diyl)bis(oxy))bis(carbonyl))bis(piperidin-1-ium) 2,2,2-trifluoroacetate (UL1-123) (360 mg, 58%) as a white solid: m/z 570 $(M+H)^+$ $(ES^+)$. $^1H$ NMR (400 MHz, DMSO-$d_6$) δ: 8.71-8.61 (br m, 2H), 8.49-8.36 (br m, 2H), 7.13-7.08 (m, 2H), 7.00-6.95 (m, 2H), 3.78 (s, 3H), 3.33-3.25 (br m, 4H), 3.05-2.92 (m, 6H), 2.79 (br s, 6H), 2.75 (br s, 6H), 2.08-2.00 (br m, 4H), 1.82-1.69 (m, 4H).

Example L1

2,5-Bis(dimethylcarbamoyl)-1-(4-methoxyphenyl)-1H-pyrrole-3,4-diyl bis(4-((phosphonooxy)methyl)benzoate) (UL1-124)

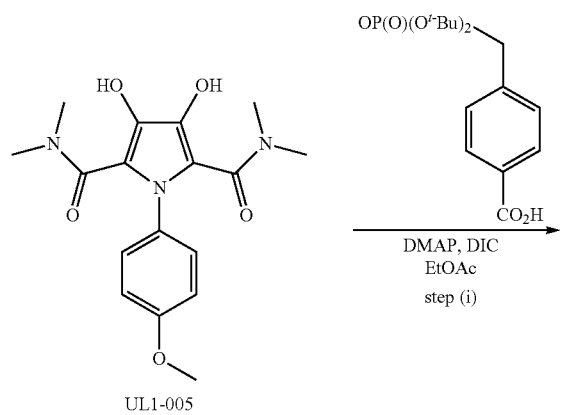

-continued

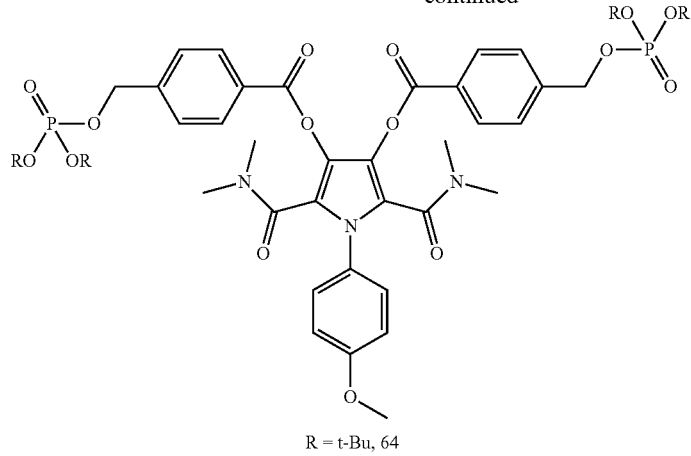

R = t-Bu, 64

TFA/DCM
step (ii)
→ R = H
UL1-124

Step (i): 2,5-Bis(dimethylcarbamoyl)-1-(4-methoxyphenyl)-1H-pyrrole-3,4-diyl bis(4-(((di-tert-butoxyphosphoryl)oxy)methyl)benzoate) (64)

DIC (633 μl, 4.10 mmol) was added to a solution of 3,4-dihydroxy-1-(4-methoxyphenyl)-$N^2,N^2,N^5,N^5$-tetramethyl-1H-pyrrole-2,5-dicarboxamide (UL1-005) (252 mg, 0.73 mmol), 4-(((di-tert-butoxyphosphoryl)oxy)methyl)benzoic acid (500 mg, 1.45 mmol) and DMAP (71.0 mg, 0.58 mmol) in EtOAc (8 mL) the reaction mixture was allowed to stir at RT for 16 h. The mixture was quenched with water (20 mL) and extracted with EtOAc (3×20 mL), the combined organics were washed with brine (100 mL), dried (MgSO$_4$), filtered and concentrated in vacuo. The crude residue was purified by silica gel chromatography (12 g, 0-5% MeOH in EtOAc) to afford 2,5-bis(dimethylcarbamoyl)-1-(4-methoxyphenyl)-1H-pyrrole-3,4-diyl bis(4-(((di-tert-butoxyphosphoryl)oxy)methyl)benzoate) (64) (91 mg, 6%) as a yellow solid: m/z 1001 (M+H)$^+$ (ES$^+$). $^1$H NMR (400 MHz, DMSO-d$_6$) δ: 8.01-7.99 (m, 4H), 7.55-7.52 (m, 4H), 7.21-7.18 (m, 2H), 7.01-6.99 (m, 2H), 5.00 (s, 4H), 3.80 (s, 3H), 2.89 (s, 6H), 2.74 (s, 6H), 1.38 (s, 36H).

Step (ii) 2,5-Bis(dimethylcarbamoyl)-1-(4-methoxyphenyl)-1H-pyrrole-3,4-diyl bis(4-((phosphonooxy)methyl)benzoate) (UL1-124)

TFA (16 mL, 208 mmol) was added dropwise to a solution of 2,5-bis(dimethylcarbamoyl)-1-(4-methoxyphenyl)-1H-pyrrole-3,4-diyl bis(4-(((di-tert-butoxyphosphoryl)oxy)methyl)benzoate) (64) (88 mg, 0.09 mmol) in DCM (64 mL) the mixture was left to stand for 72 h, and then concentrated in vacuo to afford 2,5-bis(dimethylcarbamoyl)-1-(4-methoxyphenyl)-1H-pyrrole-3,4-diyl bis(4-((phosphonooxy)methyl)benzoate) (UL1-124) as a yellow oil: m/z 776 (M+H)$^+$ (ES$^+$); 774 (M−H)$^-$ (ES$^-$). $^1$H NMR (400 MHz, DMSO-d$_6$) δ: 8.00-7.98 (m, 4H), 7.54-7.52 (m, 4H), 7.20-7.18 (m, 2H), 7.00-6.98 (m, 2H), 4.98-4.96 (d, 4H), 3.79 (s, 3H), 2.89 (s, 6H), 2.74 (s, 6H).

Example M1

5-(Dimethylphosphoryl)-3,4-dihydroxy-1-(4-methoxyphenyl)-N,N-dimethyl-1H-pyrrole-2-carboxamide (UL1-125)

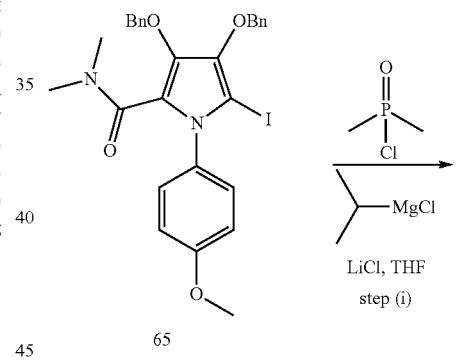

65

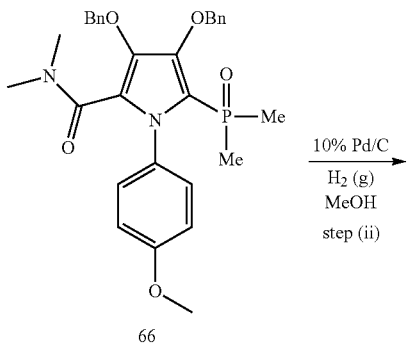

66

-continued

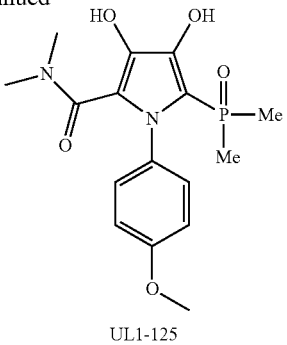

UL1-125

Step (i): 3,4-Bis(benzyloxy)-5-(dimethylphosphoryl)-1-(4-methoxyphenyl)-N,N-dimethyl-1H-pyrrole-2-carboxamide (66)

Isopropylmagnesium chloride. lithium chloride complex (1.3 M in THF, 315 µL, 0.410 mmol) was added dropwise to a stirred solution of 3,4-bis(benzyloxy)-5-iodo-1-(4-methoxyphenyl)-N,N-dimethyl-1H-pyrrole-2-carboxamide (65) [prepared using the same procedure as Example S step (i) using (9) as starting material] (211 mg, 0.36 mmol) in THF (1.2 mL) at 0° C., the reaction mixture was allowed to stir for 15 min and isopropylmagnesium chloride. lithium chloride complex (1.3 M in THF, 100 µL, 0.13 mmol) was added, and the reaction mixture was allowed to stir for a further 15 min. A solution of dimethylphosphinic chloride (61 mg, 0.54 mmol) in THF (0.6 mL) was added and the reaction allowed to warm to RT and stirred for a further 16 h. The reaction mixture was quenched with 5% AcOH in MeOH (5 mL) and the volatiles removed in vacuo. The residue was purified by silica gel chromatography (12 g, 0-5% MeOH in DCM) to afford a crude residue. The crude residue was further purified by preparative HPLC (Waters, Acidic (0.1% Formic acid), Waters X-Select Prep-C18, 5 µm, 19×50 mm column, 30-60% MeCN in water) to afford 3,4-bis(benzyloxy)-5-(dimethylphosphoryl)-1-(4-methoxyphenyl)-N,N-dimethyl-1H-pyrrole-2-carboxamide (66) (29 mg, 15%) as a colourless gum: m/z 533 (M+H)$^+$ (ES$^+$). $^1$H NMR (400 MHz, CDCl$_3$) δ: 7.44-7.28 (m, 12H), 6.92-6.87 (m, 2H), 5.22 (s, 2H), 5.05 (s, 2H), 3.82 (s, 3H), 2.76 (s, 3H), 2.63 (s, 3H), 1.41 (br d, J=13 Hz, 6H).

Step (ii): 5-(Dimethylphosphoryl)-3,4-dihydroxy-1-(4-methoxyphenyl)-N,N-dimethyl-1H-pyrrole-2-carboxamide (UL1-125)

A solution of 3,4-bis(benzyloxy)-5-(dimethylphosphoryl)-1-(4-methoxyphenyl)-N,N-dimethyl-1H-pyrrole-2-carboxamide (66) (29 mg, 0.054 mmol) in MeOH (5 mL) was passed through a Thales 'H-cube' cartridge (10% Pd/C) at a flow rate of 1 mL/min at 25° C. under H$_2$ (full H$_2$ mode). The output was concentrated in vacuo to afford 5-(dimethylphosphoryl)-3,4-dihydroxy-1-(4-methoxyphenyl)-N,N-dimethyl-1H-pyrrole-2-carboxamide (UL1-125) (13 mg, 67%) as a pale yellow solid: m/z 353 (M+H)$^+$ (ES$^+$), 351 (M−H)$^-$ (ES$^-$). $^1$H NMR (400 MHz, DMSO-d$_6$) δ: 9.35 (s, 1H), 8.55 (s, 1H), 7.23-7.14 (m, 2H), 6.96-6.88 (m, 2H), 3.77 (s, 3H), 2.86 (br s, 6H), 1.33 (s, 3H), 1.30 (s, 3H).

Example N1

(1R,1'R,4R,4'R)-2,5-Bis(dimethylcarbamoyl)-1-(4-methoxyphenyl)-1H-pyrrole-3,4-diyl bis(4-((phosphonooxy)methyl)cyclohexanecarboxylate) (UL1-126)

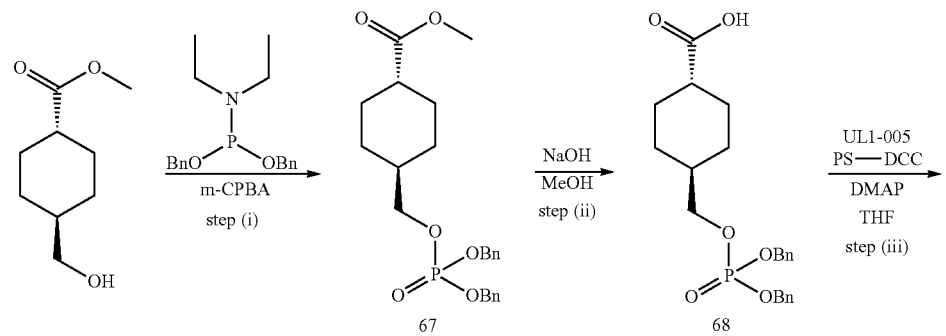

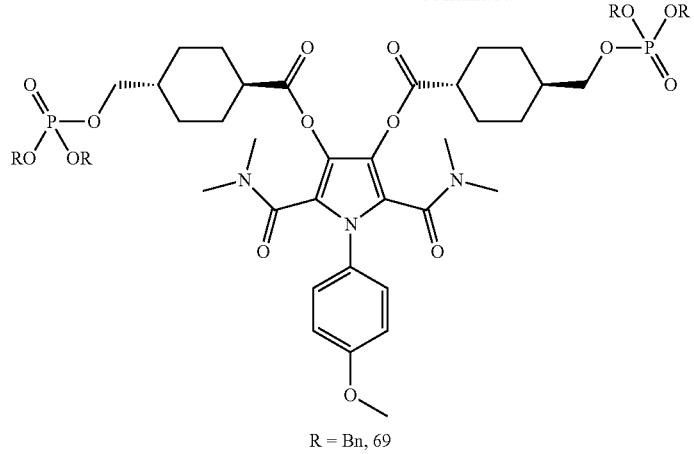
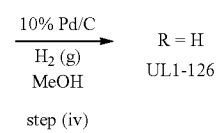

R = Bn, 69

Step (i): (1R,4R)-Methyl 4-(((bis(benzyloxy)phosphoryl)oxy)methyl)cyclohexanecarboxylate (67)

5-methyl-1H-tetrazole (4.4 g, 52.3 mmol) was added to a stirred solution of (1R,4R)-methyl 4-(hydroxymethyl)cyclohexanecarboxylate (4.5 g, 26.1 mmol) and dibenzyl diethylphosphoramidite (11.73 mL, 39.2 mmol) in THF (60 mL), after 2 h the reaction mixture was cooled to 0° C. and a solution of m-CPBA (10.5 g, 47 mmol) in THF (30 mL) was added dropwise. The reaction was allowed to warm to RT and stirred for 16 h. The volatiles were removed in vacuo and the reaction was diluted with $Et_2O$ (200 mL) and washed with sat. $NaHCO_3$ (aq.) (5×50 mL), brine (30 mL), dried ($MgSO_4$) filtered and the concentrated in vacuo. The crude residue was purified by silica gel chromatography (80 g, 0-50% $Et_2O$ in isohexane) to afford (1R,4R)-methyl 4-(((bis(benzyloxy)phosphoryl)oxy)methyl)cyclohexanecarboxylate (67) (6.35 g, 53%) as a colourless oil: m/z 433 $(M+H)^+$ $(ES^+)$. $^1H$ NMR (400 MHz, DMSO-$d_6$) δ: 7.42-7.32 (m, 10H), 5.02 (dd, J=1.0, 5.4 Hz, 4H), 3.74 (t, J=6.5 Hz, 2H), 3.58 (s, 3H), 2.20 (tt, J=12.2, 3.5 Hz, 1H), 1.90-1.83 (m, 2H), 1.70-1.62 (m, 2H), 1.26 (ddd, J=3.4, 13.1, 16.6 Hz, 2H), 0.93 (ddd, J=3.4, 13.1, 16.6 Hz, 2H).

Step (ii): (1R,4R)-4-(((Bis(benzyloxy)phosphoryl)oxy)methyl)cyclohexanecarboxylic acid (68)

NaOH (290 mg, 7.17 mmol) was added to a stirred solution of (1R,4R)-methyl 4-(((bis(benzyloxy)phosphoryl)oxy)methyl)cyclohexanecarboxylate (67) (3.1 g, 7.17 mmol) in MeOH (50 mL) and water (50 mL) and the reaction was allowed to stir for 24 h. The volatiles were removed in vacuo diluted with 1 M HCl (aq.) (20 mL) and extracted with DCM (2×100 mL), the combined organic layers were dried ($MgSO_4$), filtered and concentrated in vacuo to afford (1R,4R)-4-(((bis(benzyloxy)phosphoryl)oxy)methyl)cyclohexanecarboxylic acid (68) (2.74 g, 88%) as a white solid: m/z 419 $(M+H)^+$ $(ES^+)$; 417 $(M-H)^-$ $(ES^-)$. $^1H$ NMR (400 MHz, DMSO-$d_6$) δ: 12.03 (s, 1H), 7.42-7.30 (m, 10H), 5.02 (dd, J=8.4, 1.0 Hz, 4H), 3.74 (t, J=6.5 Hz, 2H), 2.12-2.03 (tt, J=12.3, 3.5 Hz, 1H), 1.91-1.81 (m, 2H), 1.71-1.61 (m, 2H), 1.54-1.41 (m, 1H), 1.24 (ddd, J=3.3, 13.1, 16.3 Hz, 2H), 0.92 (ddd, J=3.3, 13.1, 16.3 Hz, 2H).

Step (iii): (1R,1'R,4R,4'R)-2,5-Bis(dimethylcarbamoyl)-1-(4-methoxyphenyl)-1H-pyrrole-3,4-diyl bis(4-(((bis(benzyloxy)phosphoryl)oxy)methyl)cyclohexanecarboxylate) (69)

PS-DCC (2.3 mmol/g, 1.25 g, 17.6 mmol) was added to a solution of 3,4-dihydroxy-1-(4-methoxyphenyl)-$N^2,N^2,N^5$,$N^5$-tetramethyl-1H-pyrrole-2,5-dicarboxamide (UL1-005) (200 mg, 0.58 mmol), DMAP (0.028 g, 0.230 mmol) and (1R,4R)-4-(((bis(benzyloxy)phosphoryl)oxy)methyl)cyclohexanecarboxylic acid (68) (578 mg, 1.38 mmol) in THF (20 mL) and the reaction mixture was shaken at RT for 96 h.

The reaction mixture was diluted with EtOAc (50 mL) and washed with 1 M HCl (aq.) (50 mL), sat. $NaHCO_3$ (aq.) (50 mL), brine (50 mL), dried ($MgSO_4$), filtered and concentrated in vacuo. The product was purified by silica gel chromatography (12 g, 0-3% MeOH in DCM) to afford (1R,1'R,4R,4'R)-2,5-bis(dimethylcarbamoyl)-1-(4-methoxyphenyl)-1H-pyrrole-3,4-diyl bis(4-(((bis(benzyloxy)phosphoryl)oxy)methyl)cyclohexanecarboxylate) (69) (325 mg, 49%) as a yellow oil: m/z not observed. $^1H$ NMR (400 MHz, DMSO-$d_6$) δ: 7.41-7.32 (m, 20H), 7.11-7.07 (m, 2H), 6.97-6.92 (m, 2H), 5.07-4.98 (m, 8H), 3.77 (s, 3H), 3.75 (d, J=6.2 Hz, 4H), 2.83 (br s, 6H), 2.75 (br s, 6H), 2.44 (tt, J=3.5, 12.2 Hz, 2H), 1.96-1.87 (m, 4H), 1.75-1.65 (m, 4H), 1.59-1.46 (m, 2H), 1.33 (ddd, J=3.4, 13.1, 16.2 Hz, 4H), 1.01 (ddd, J=3.4, 13.1, 16.2 Hz, 4H).

Step (iv): (1R,1'R,4R,4'R)-2,5-Bis(dimethylcarbamoyl)-1-(4-methoxyphenyl)-1H-pyrrole-3,4-diyl bis(4-((phosphonooxy)methyl)cyclohexanecarboxylate) (UL1-126)

A solution of (1R,1'R,4R,4'R)-2,5-bis(dimethylcarbamoyl)-1-(4-methoxyphenyl)-1H-pyrrole-3,4-diyl bis(4-(((bis(benzyloxy)phosphoryl)oxy)methyl)cyclohexanecarboxylate) (69) (323 mg, 0.28 mmol) in MeOH (8 mL) was passed through a Thales 'H-cube' cartridge (10% Pd/C) at a flow rate of 1 mL/min at 50° C. under $H_2$ (full $H_2$ mode). The output was concentrated in vacuo, and a solid was collected by filtration after trituration with EtOAc (5 mL) to afford (1R, 1'R,4R,4'R)-2,5-bis(dimethylcarbamoyl)-1-(4-methoxyphenyl)-1H-pyrrole-3,4-diyl bis(4-((phosphonooxy)methyl)cyclohexanecarboxylate) (UL1-126) (121 mg, 43%) as a pale yellow solid: m/z 788 $(M+H)^+$ $(ES^+)$; 786 $(M-H)^-$ $(ES^-)$. $^1H$ NMR (400 MHz, DMSO-d$_6$) δ: 10.90 (br s, 2H), 7.12-7.06 (m, 2H), 6.97-6.92 (m, 2H), 3.77 (s, 3H), 3.63 (t, J=6.4 Hz, 4H), 2.83 (br s, 6H), 2.75 (br s, 6H), 2.50-2.45 (m, 2H), 2.00-1.93 (m, 4H), 1.84-1.76 (m, 4H), 1.63-1.51 (m, 2H), 1.38 (ddd, 3.1, 12.7, 16.0 Hz, 4H), 1.05 (ddd, 3.1, 12.7, 16.0 Hz, 4H).

The following Examples in Table 1 were prepared using the general methods outlined above:

TABLE 1

| Entry | Structure | Compound name | ID | IC$_{50}$ | $^1$H NMR Data (DMSO-d$_6$) | Ionisation | Preparation |
|---|---|---|---|---|---|---|---|
| 1 | 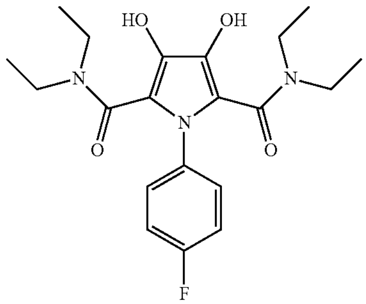 [SMILES: CCN(CC)C(=O)c1c(O)c(O)c(C(=O)N(CC)CC)n1-c1ccc(F)cc1] | N$^2$,N$^2$,N$^5$,N$^5$-tetraethyl-1-(4-fluorophenyl)-3,4-dihydroxy-1H-pyrrole-2,5-dicarboxamide | UL1-001 | +++ | δ: 8.37 (s, 2H), 7.19-7.08 (m, 2H), 7.05-6.95 (m, 2H), 3.29 (q, J = 7.1 Hz, 8H), 0.98 (t, J = 7.1 Hz, 12H). | m/z 392 (M + H)$^+$ (ES$^+$), 390 (M − H)$^−$ (ES$^−$) | As example A except diethyl 3,4-bis(benzyloxy)-1-(4-fluorophenyl)-1H-pyrrole-2,5-dicarboxylate used in step (i) |
| 2 | 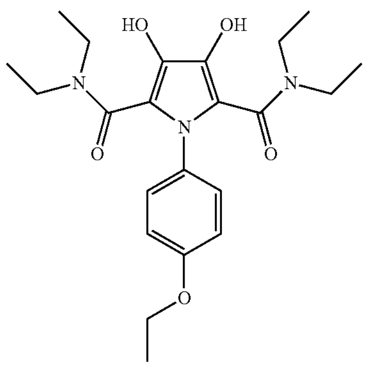 [SMILES: CCOc1ccc(-n2c(C(=O)N(CC)CC)c(O)c(O)c2C(=O)N(CC)CC)cc1] | 1-(4-ethoxyphenyl)-N$^2$,N$^2$,N$^5$,N$^5$-tetraethyl-3,4-dihydroxy-1H-pyrrole-2,5-dicarboxamide | UL1-002 | +++ | δ: 8.23 (s, 2H), 6.94-6.88 (m, 2H), 6.85-6.79 (m, 2H), 3.98 (q, J = 7.0 Hz, 2H), 3.27 (q, J = 7.0 Hz, 8H), 1.30 (t, J = 7.0 Hz, 3H), 0.95 (t, J = 7.0 Hz, 12H). | m/z 418 (M + H)$^+$ (ES$^+$), 416 (M − H)$^−$ (ES$^−$) | As example A except diethyl 3,4-bis(benzyloxy)-1-(4-ethoxyphenyl)-1H-pyrrole-2,5-dicarboxylate was used in step (i) |
| 3 | 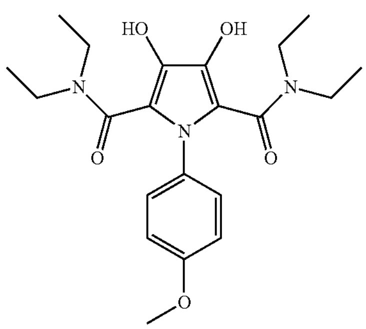 [SMILES: CCN(CC)C(=O)c1c(O)c(O)c(C(=O)N(CC)CC)n1-c1ccc(OC)cc1] | N$^2$,N$^2$,N$^5$,N$^5$-tetraethyl-3,4-dihydroxy-1-(4-methoxyphenyl)-1H-pyrrole-2,5-dicarboxamide | UL1-003 | +++ | δ: 8.26 (s, 2H), 6.96-6.88 (m, 2H), 6.87-6.81 (m, 2H), 3.72 (s, 3H), 3.27 (q, J = 7.1 Hz, 8H), 0.96 (t, J = 7.0 Hz, 12H). | m/z 404 (M + H)$^+$ (ES$^+$), 402 (M − H)$^−$ (ES$^−$) | Example A |
| 4 | 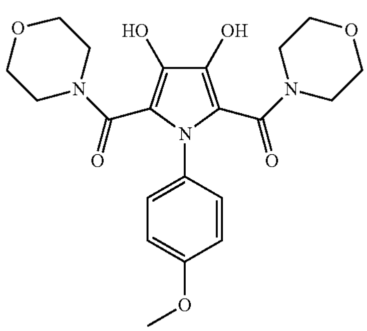 [SMILES: COc1ccc(-n2c(C(=O)N3CCOCC3)c(O)c(O)c2C(=O)N2CCOCC2)cc1] | (3,4-dihydroxy-1-(4-methoxyphenyl)-1H-pyrrole-2,5-diyl)bis(morpholinomethanone) | UL1-004 | +++ | δ: 8.51 (s, 2H), 7.00-6.98 (m, 2H), 6.91-6.83 (m, 2H), 3.75 (s, 3H), 3.50-3.37 (m, 16H). | m/z 432 (M + H)$^+$ (ES$^+$); 430 (M − H)$^−$ (ES$^−$) | As example A except morpholine used in step (ii) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 5 | 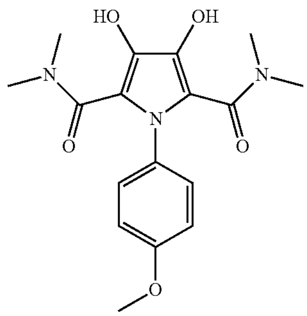 | 3,4-dihydroxy-1-(4-methoxyphenyl)-N$^2$,N$^2$,N$^5$,N$^5$-tetramethyl-1H-pyrrole-2,5-dicarboxamide | UL1-005 | +++ | δ: 8.38 (s, 2H), 6.96-6.87 (m, 2H), 6.86-5.79 (m, 2H), 3.73 (s, 3H), 2.88 (br s, 12H). | m/z 348, (M + H)$^+$ (ES$^+$), 346 (M − H)$^−$ (ES$^−$) | As example A except dimethylamine hydrochloride used in step (ii) |
| 6 | 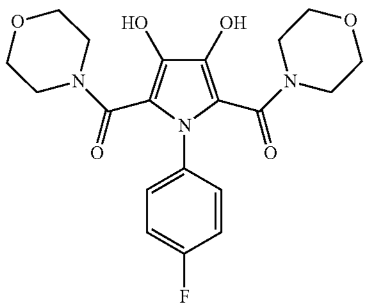 [SMILES: O=C(c1c(O)c(O)c(C(=O)N2CCOCC2)n1-c1ccc(F)cc1)N1CCOCC1] | (1-(4-fluorophenyl)-3,4-dihydroxy-1H-pyrrole-2,5-diyl)bis(morpholinomethanone) | UL1-006 | +++ | δ: 8.60 (s, 2H), 7.20-7.12 (m, 2H), 7.10-7.03 (m, 2H), 3.52-3.39 (m, 16H). | m/z 420 (M + H)$^+$ (ES$^+$), 418 (M − H)$^−$ (ES$^−$) | As example A except diethyl 3,4-bis(benzyloxy)-1-(4-fluorophenyl)-1H-pyrrole-2,5-dicarboxylate used in step (i) and morpholine used in step (ii). |
| 7 | 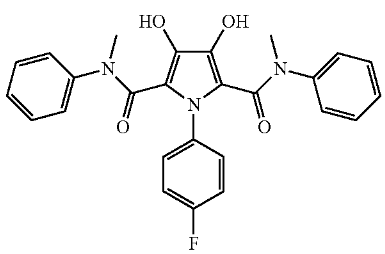 [SMILES: CN(C(=O)c1c(O)c(O)c(C(=O)N(C)c2ccccc2)n1-c1ccc(F)cc1)c1ccccc1] | 1-(4-fluorophenyl)-3,4-dihydroxy-N$^2$,N$^5$-dimethyl-N$^2$,N$^5$-diphenyl-1H-pyrrole-2,5-dicarboxamide | UL1-007 | + | δ: 8.34 (s, 2H), 7.24-7.06 (m, 8H), 6.79-6.70 (m, 4H), 6.86-6.60 (m, 2H), 3.12 (s, 6H). | m/z 460 (M + H)$^+$ (ES$^+$), 458 (M − H)$^−$ (ES$^−$) | As example A except diethyl 3,4-bis(benzyloxy)-1-(4-fluorophenyl)-1H-pyrrole-2,5-dicarboxylate used in step (i) and N-methylaniline used in step (ii). |
| 8 | 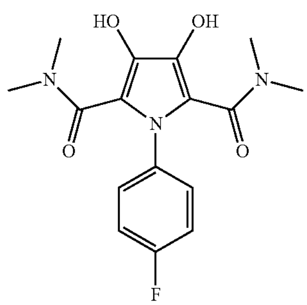 | 1-(4-fluorophenyl)-3,4-dihydroxy-N$^2$,N$^2$,N$^5$,N$^5$-tetramethyl-1H-pyrrole-2,5-dicarboxamide | ULI-008 | +++ | δ: 8.48 (s, 2H), 7.16-7.07 (m, 2H), 7.06-6.96 (m, 2H), 2.90 (s, 12H). | m/z 336 (M + H)$^+$ (ES$^+$), 334 (M − H)$^−$ (ES$^−$) | As example A except diethyl 3,4-bis(benzyloxy)-1-(4-fluorophenyl)-1H-pyrrole-2,5-dicarboxylate used in step (i) and dimethylamine hydrochloride used in step (ii). |
| 9 | 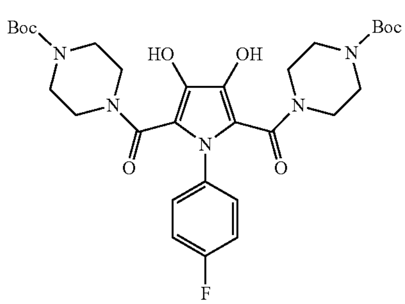 [SMILES: CC(C)(C)OC(=O)N1CCN(C(=O)c2c(O)c(O)c(C(=O)N3CCN(C(=O)OC(C)(C)C)CC3)n2-c2ccc(F)cc2)CC1] | di-tert-butyl 4,4'-(1-(4-fluorophenyl)-3,4-dihydroxy-1H-pyrrole-2,5-dicarbonyl)bis(piperazine-1-carboxylate) | UL1-009 | +++ | δ: 8.62 (s, 2H), 7.17-7.10 (m, 2H), 7.08-7.02 (m, 2H), 3.47-3.36 (m, 8H), 3.29-3.22 (m, 8H), 1.40 (s, 18H). | m/z 618 (M + H)$^+$ (ES$^+$), 616 (M − H)$^−$ (ES$^−$) | As example A except diethyl 3,4-bis(benzyloxy)-1-(4-fluorophenyl)-1H-pyrrole-2,5-dicarboxylate used in step (i) and tert-butyl piperazine-1-carboxylate used in step (ii). |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 10 | 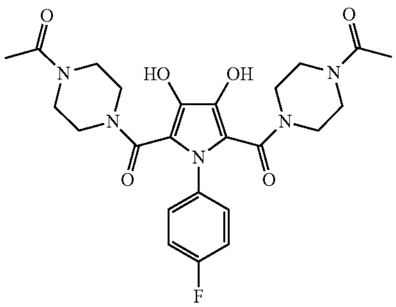 [SMILES: CC(=O)N1CCN(C(=O)c2c(O)c(O)c(C(=O)N3CCN(C(C)=O)CC3)n2-c2ccc(F)cc2)CC1] | 1,1'-(4,4'-(1-(4-fluorophenyl)-3,4-dihydroxy-1H-pyrrole-2,5-dicarbonyl)bis(piperazine-4,1-diyl))diethanone | UL1-010 | +++ | δ: 8.66 (s, 2H), 7.17-7.10 (m, 2H), 7.09-7.02 (m, 2H), 3.51-3.44 (m, 4H), 3.43-3.35 (m, 12H), 1.40 (s, 6H). | m/z 502 (M + H)$^+$ (ES$^+$), 500 (M − H)$^−$ (ES$^−$) | As example A except diethyl 3,4-bis(benzyloxy)-1-(4-fluorophenyl)-1H-pyrrole-2,5-dicarboxylate used in step (i) and 1-(piperazin-1-yl)ethanone used in step (ii). |
| 11 | 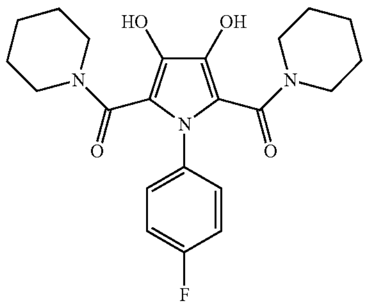 [SMILES: O=C(c1c(O)c(O)c(C(=O)N2CCCCC2)n1-c1ccc(F)cc1)N1CCCCC1] | (1-(4-fluorophenyl)-3,4-dihydroxy-1H-pyrrole-2,5-diyl)bis(piperidin-1-ylmethanone) | UL1-011 | +++ | δ: 8.42 (s, 2H), 7.22-7.10 (m, 2H), 7.05-6.96 (m, 2H), 3.45-3.33 (m, 8H), 1.60-1.47 (m, 4H), 1.44-1.29 (m, 8H). | m/z 416 (M + H)$^+$ (ES$^+$), 414 (M − H)$^−$ (ES$^−$) | As example A except diethyl 3,4-bis(benzyloxy)-1-(4-fluorophenyl)-1H-pyrrole-2,5-dicarboxylate used in step (i) and piperidine used in step (ii). |
| 12 | 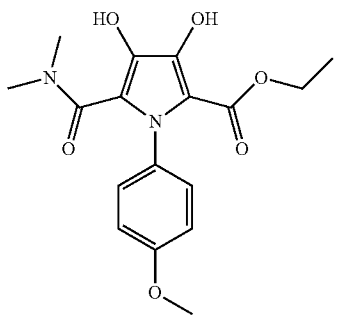 [SMILES: CCOC(=O)c1c(O)c(O)c(C(=O)N(C)C)n1-c1ccc(OC)cc1] | ethyl 5-(dimethylcarbamoyl)-3,4-dihydroxy-1-(4-methoxyphenyl)-1H-pyrrole-2-carboxylate | UL1-012 | +++ | δ: 8.60 (s, 1H), 8.46 (s, 1H), 7.08-7.01 (m, 2H), 6.90-6.82 (m, 2H), 4.00 (q, J = 7.0 Hz, 2H), 3.76 (s, 3H), 2.83 (br s, 6H), 0.99 (t, J = 7.1 Hz, 6H). | m/z 349 (M + H)$^+$ (ES$^+$), 347 (M − H)$^−$ (ES$^−$) | Example B |
| 13 | 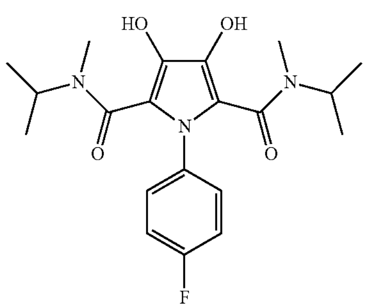 [SMILES: CC(C)N(C)C(=O)c1c(O)c(O)c(C(=O)N(C)C(C)C)n1-c1ccc(F)cc1] | 1-(4-fluorophenyl)-3,4-dihydroxy-N$^2$,N$^5$-diisopropyl-N$^2$,N$^5$-dimethyl-1H-pyrrole-2,5-dicarboxamide | UL1-013 | +++ | δ: 8.40 (s, 2H), 7.19-7.10 (m, 2H), 7.02-6.94 (m, 2H), 4.28 (m, 2H), 2.71 (s, 6H), 0.99 (d, J = 6.7 Hz, 12H). | m/z 392 (M + H)$^+$ (ES$^+$), 390 (M − H)$^−$ (ES$^−$) | As example A except diethyl 3,4-bis(benzyloxy)-1-(4-fluorophenyl)-1H-pyrrole-2,5-dicarboxylate used in step (i) and N-methylpropan-2-amine used in step (ii). |
| 14 | 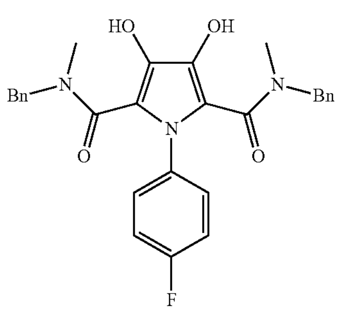 [SMILES: CN(Cc1ccccc1)C(=O)c1c(O)c(O)c(C(=O)N(C)Cc2ccccc2)n1-c1ccc(F)cc1] | N$^2$,N$^5$-dibenzyl-1-(4-fluorophenyl)-3,4-dihydroxy-N$^2$,N$^5$-dimethyl-1H-pyrrole-2,5-dicarboxamide | UL1-014 | +++ | δ: 8.17 (s, 2H), 7.30-7.19 (m, 6H), 7.11-7.04 (m, 8H), 4.50 (s, 4H), 2.85 (s, 6H). | m/z 488 (M + H)$^+$ (ES$^+$), 486 (M − H)$^−$ (ES$^−$) | As example A except diethyl 3,4-bis(benzyloxy)-1-(4-fluorophenyl)-1H-pyrrole-2,5-dicarboxylate used in step (i) and N-methyl-1-phenylmethanamine used in step (ii). |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 15 | (structure) | di-tert-butyl 4,4'-(3,4-dihydroxy-1-(4-methoxyphenyl)-1H-pyrrole-2,5-dicarbonyl)bis(piperazine-1-carboxylate) | UL1-015 | +++ | δ: 8.49 (s, 2H), 6.99-6.91 (m, 2H), 6.89-6.81 (m, 2H), 3.73 (s, 3H), 3.47-3.35 (m, 8H), 3.30-3.14 (m, 8H), 1.40 (br s, 18H). | m/z 630 (M + H)$^+$ (ES$^+$), 628 (M − H)$^−$ (ES$^−$) | As example A except tert-butyl piperazine-1-carboxylate used in step (ii) |
| 16 | (structure) | (3,4-dihydroxy-1-(4-methoxyphenyl)-1H-pyrrole-2,5-diyl)bis(piperazin-1-ylmethanone) | UL1-016 | +++ | δ: 8.86-8.64 (m, 6H), 7.06-6.95 (m, 2H), 6.89-6.80 (m, 2H), 3.75 (s, 3H), 3.67-3.54 (m, 8H), 3.11-2.96 (m, 8H). | m/z 430 (M + H)$^+$ (ES$^+$), 428 (M − H)$^−$ (ES$^−$) | Obtained as the di-TFA salt from TFA mediated Boc-deprotection of UL1-015 |
| 17 | (structure) | 1-(4-fluorophenyl)-3,4-dihydroxy-N$^2$,N$^2$,N$^5$,N$^5$-tetraisopropyl-1H-pyrrole-2,5-dicarboxamide | UL1-017 | +++ | δ: 8.16 (s, 2H), 7.23-7.12 (m, 2H), 7.09-6.97 (m, 2H), 3.89-3.51 (m, 4H), 1.22-0.98 (m, 4H). | m/z 448 (M + H)$^+$ (ES$^+$), 446 (M − H)$^−$ (ES$^−$) | As example A except diethyl 3,4-bis(benzyloxy)-1-(4-fluorophenyl)-1H-pyrrole-2,5-dicarboxylate used in step (i) and diisopropylamine used in step (ii) |
| 18 | (structure) | (3,4-dihydroxy-1-(4-methoxyphenyl)-1H-pyrrole-2,5-diyl)bis(piperidin-1-ylmethanone) | UL1-018 | +++ | δ: 8.30 (s, 2H), 6.95-6.89 (m, 2H), 6.88-6.83 (m, 2H), 3.74 (s, 3H), 3.39-3.33 (m, 8H), 1.57-1.47 (m, 4H), 1.40-1.32 (m, 8H). | m/z 428 (M + H)$^+$ (ES$^+$), 426 (M − H)$^−$ (ES$^−$) | As example A except piperidine used in step (ii) |
| 19 | (structure) | 3,4-dihydroxy-1-(2-methoxyphenyl)-N$^2$,N$^2$,N$^5$,N$^5$-tetramethyl-1H-pyrrole-2,5-dicarboxamide | UL1-019 | +++ | δ: 8.29 (s, 2H), 7.19-7.10 (m, 1H), 6.99-6.92 (m, 1H), 6.91-6.79 (m, 2H), 3.63 (s, 3H), 2.90 (s, 12H). | m/z 348 (M + H)$^+$ (ES$^+$), 346 (M − H)$^−$ (ES$^−$) | As example A except diethyl 3,4-bis(benzyloxy)-1-(2-methoxyphenyl)-1H-pyrrole-2,5-dicarboxylate used in step (i) and dimethylamine hydrochloride used in step (ii) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 20 | 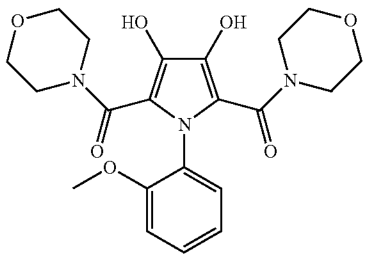 [SMILES: COc1ccccc1-n1c(C(=O)N2CCOCC2)c(O)c(O)c1C(=O)N1CCOCC1] | (3,4-dihydroxy-1-(2-methoxyphenyl)-1H-pyrrole-2,5-diyl)bis(morpholinomethanone) | UL1-020 | +++ | δ: 8.42 (s, 2H), 7.25-7.13 (m, 1H), 7.02-6.93 (m, 2H), 6.92-6.83 (m, 1H), 3.67 (s, 3H), 3.54-3.35 (m, 16H). | m/z 432 (M + H)$^+$ (ES$^+$), 430 (M − H)$^−$ (ES$^−$) | As example A except diethyl 3,4-bis(benzyloxy)-1-(2-methoxyphenyl)-1H-pyrrole-2,5-dicarboxylate used in step (i) and morpholine used in step (ii) |
| 21 | 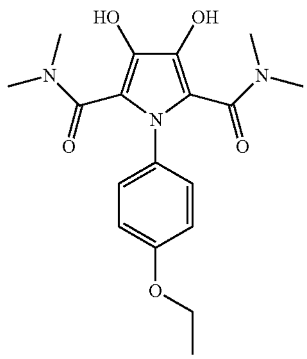 | 1-(4-ethoxyphenyl)-3,4-dihydroxy-N$^2$,N$^2$,N$^5$,N$^5$-tetramethyl-1H-pyrrole-2,5-dicarboxamide | UL1-021 | +++ | δ: 8.35 (s, 2H), 6.94-6.86 (m, 2H), 6.84-6.77 (m, 2H), 3.99 (q, J = 7.0 Hz, 2H), 2.87 (br s, 12H), 1.32 (t, J = 7.0 Hz, 3H). | m/z 362 (M + H)$^+$ (ES$^+$), 360 (M − H)$^−$ (ES$^−$) | As example A except diethyl 3,4-bis(benzyloxy)-1-(4-ethoxyphenyl)-1H-pyrrole-2,5-dicarboxylate was used in step (i) and dimethylamine hydrochloride used in step (ii) |
| 22 | 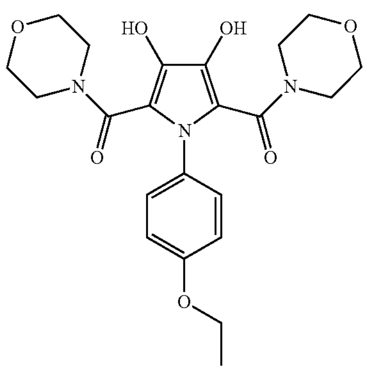 [SMILES: CCOc1ccc(-n2c(C(=O)N3CCOCC3)c(O)c(O)c2C(=O)N2CCOCC2)cc1] | (1-(4-ethoxyphenyl)-3,4-dihydroxy-1H-pyrrole-2,5-diyl)bis(morpholinomethanone) | UL1-022 | +++ | δ: 8.47 (s, 2H), 6.98-6.91 (m, 2H), 6.90-6.81 (m, 2H), 4.01 (q, J = 7.0 Hz, 2H), 3.51-3.35 (m, 16H), 1.32 (t, J = 7.0 Hz, 3H). | m/z 446 (M + H)$^+$ (ES$^+$), 444 (M − H)$^−$ (ES$^−$) | As example A except diethyl 3,4-bis(benzyloxy)-1-(4-ethoxyphenyl)-1H-pyrrole-2,5-dicarboxylate was used in step (i) and dimethylamine hydrochloride used in step (ii) |
| 23 | 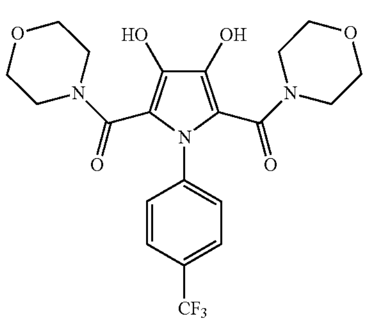 [SMILES: O=C(c1c(O)c(O)c(C(=O)N2CCOCC2)n1-c1ccc(C(F)(F)F)cc1)N1CCOCC1] | (3,4-dihydroxy-1-(4-(trifluoromethyl)phenyl)-1H-pyrrole-2,5-diyl)bis(morpholinomethanone) | UL1-023 | +++ | δ: 8.84 (s, 2H), 7.73-7.67 (m, 2H), 7.24-7.19 (m, 2H), 3.60-3.44 (m, 16H). | m/z 470 (M + H)$^+$ (ES$^+$), 468 (M − H)$^−$ (ES$^−$) | As example A except diethyl 3,4-bis(benzyloxy)-1-(4-(trifluoromethyl)phenyl)-1H-pyrrole-2,5-dicarboxylate was used in step (i) and morpholine used in step (ii) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 24 | 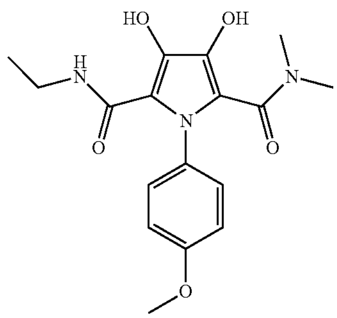 [SMILES: CCNC(=O)c1c(O)c(O)c(C(=O)N(C)C)n1-c1ccc(OC)cc1] | N$^2$-ethyl-3,4-dihydroxy-1-(4-methoxyphenyl)-N$^5$,N$^5$-dimethyl-1H-pyrrole-2,5-dicarboxamide | UL1-024 | +++ | δ: 9.44 (s, 1H), 8.42 (s, 1H), 7.10-7.03 (m, 1H), 7.02-6.97 (m, 2H), 6.86-6.77 (m, 2H), 3.75 (s, 3H), 3.14-3.06 (m, 2H), 2.81 (br s, 6H), 0.97 (t, J = 7.2 Hz, 3H). | m/z 348 (M + H)$^+$ (ES$^+$), 346 (M − H)$^-$ (ES$^-$) | Example C |
| 25 | 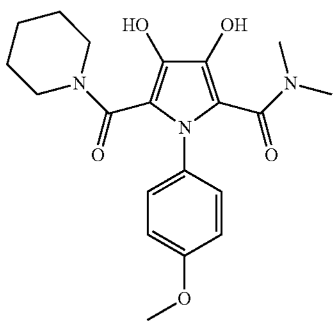 [SMILES: COc1ccc(-n2c(C(=O)N(C)C)c(O)c(O)c2C(=O)N2CCCCC2)cc1] | 3,4-dihydroxy-1-(4-methoxyphenyl)-N,N-dimethyl-5-(piperidine-1-carbonyl)-1H-pyrrole-2-carboxamide | UL1-025 | +++ | δ: 8.40 (s, 1H), 8.32 (s, 1H), 6.94-6.88 (m, 2H), 6.87-6.80 (m, 2H), 3.73 (s, 3H), 3.39-3.35 (m, 4H), 2.88 (br s, 6H), 1.59-1.47 (m, 2H), 1.45-1.25 (m, 4H). | m/z 388 (M + H)$^+$ (ES$^+$), 386 (M − H)$^-$ (ES$^-$) | As example C except piperidine used in step (i) |
| 26 | 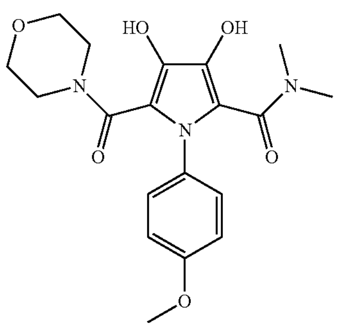 [SMILES: COc1ccc(-n2c(C(=O)N(C)C)c(O)c(O)c2C(=O)N2CCOCC2)cc1] | 3,4-dihydroxy-1-(4-methoxyphenyl)-N,N-dimethyl-5-(morpholine-4-carbonyl)-1H-pyrrole-2-carboxamide | UL1-026 | +++ | δ: 8.48 (s, 1H), 8.42 (s, 1H), 6.97-6.91 (m, 2H), 6.89-6.83 (m, 2H), 3.75 (s, 3H), 3.51-3.38 (m, 8H), 2.88 (br s, 6H). | m/z 390 (M + H)$^+$ (ES$^+$), 388 (M − H)$^-$ (ES$^-$) | As example C except morpholine used in step (i) |
| 27 | 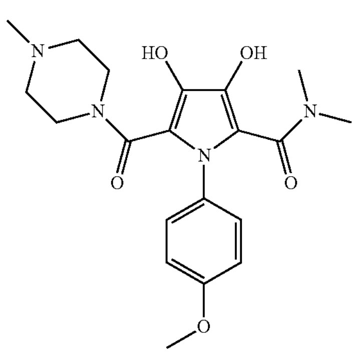 | 3,4-dihydroxy-1-(4-methoxyphenyl)-N,N-dimethyl-5-(4-methylpiperazine-1-carbonyl)-1H-pyrrole-2-carboxamide | UL1-027 | +++ | δ: 8.46 (br s, 2H), 6.98-6.90 (m, 2H), 6.89-6.80 (m, 2H), 3.75 (s, 3H), 3.48-3.37 (m, 4H), 2.88 (br s, 6H), 2.26-2.18 (m, 4H), 1.91 (s, 3H). | m/z 403 (M + H)$^+$ (ES$^+$), 401 (M − H)$^-$ (ES$^-$) | As example C except 1-methylpiperazine used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 28 | 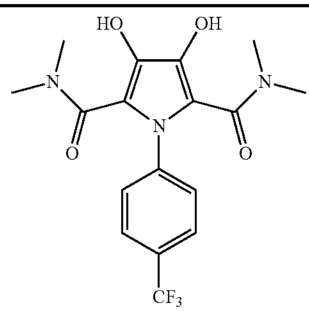 | 3,4-dihydroxy-N$^2$,N$^2$,N$^5$,N$^5$-tetramethyl-1-(4-(trifluoromethyl)phenyl)-1H-pyrrole-2,5-dicarboxamide | UL1-028 | +++ | δ: 8.68 (s, 2H), 7.69-7.60 (m, 2H), 7.18-7.11 (m, 2H), 2.96 (m, 12H). | m/z 386 (M + H)$^+$ (ES$^+$), 384 (M − H)$^−$ (ES$^−$) | As example A except diethyl 3,4-bis(benzyloxy)-1-(4-(trifluoromethyl)phenyl)-1H-pyrrole-2,5-dicarboxylate was used in step (i) and dimethylamine hydrochloride used in step (ii) |
| 29 | 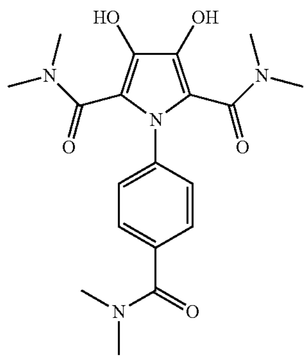 | 1-(4-(dimethylcarbamoyl)phenyl)-3,4-dihydroxy-N$^2$,N$^2$,N$^5$,N$^5$-tetramethyl-1H-pyrrole-2,5-dicarboxamide | UL1-029 | +++ | δ: 8.57 (s, 2H), 7.36-7.29 (m, 2H), 7.03-6.96 (m, 2H), 3.01-2.85 (m, 12H). | m/z 389 (M + H)$^+$ (ES$^+$), 387 (M − H)$^−$ (ES$^−$) | As example A except 1-(4-carboxyphenyl)-3,4-dihydroxy-1H-pyrrole-2,5-dicarboxylic acid and dimethylamine hydrochloride used in step (ii) |
| 30 | 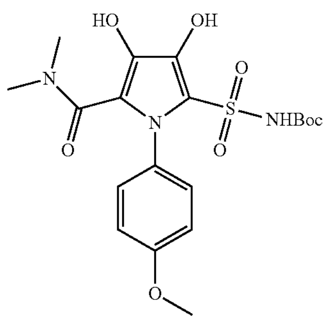 [SMILES: COc1ccc(-n2c(C(=O)N(C)C)c(O)c(O)c2S(=O)(=O)NC(=O)OC(C)(C)C)cc1] | tert-butyl (5-(dimethylcarbamoyl)-3,4-dihydroxy-1-(4-methoxyphenyl)-1H-pyrrol-2-yl)sulfonylcarbamate | UL1-030 | + | δ: 11.04 (s, 1H), 8.75 (s, 1H), 8.35 (s, 1H), 7.07-7.00 (m, 2H), 6.92-6.86 (m, 2H), 3.77 (s, 3H), 2.80 (br s, 6H), 1.35 (s, 9H). | m/z 456 (M + H)$^+$ (ES$^+$), 454 (M − H)$^−$ (ES$^−$) | Example E |
| 31 | 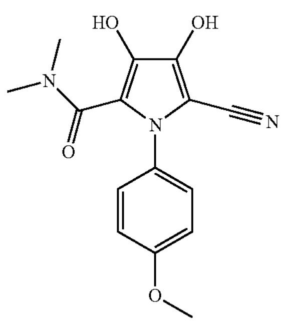 [SMILES: COc1ccc(-n2c(C#N)c(O)c(O)c2C(=O)N(C)C)cc1] | 5-cyano-3,4-dihydroxy-1-(4-methoxyphenyl)-N,N-dimethyl-1H-pyrrole-2-carboxamide | UL1-031 | +++ | δ: 9.80 (s, 1H), 8.80 (s, 1H), 7.21-7.11 (m, 2H), 7.03-6.93 (m, 2H), 3.79 (s, 3H), 2.88 (br s, 6H). | m/z 302 (M + H)$^+$ (ES$^+$), 300 (M − H)$^−$ (ES$^−$) | Example F |
| 32 | 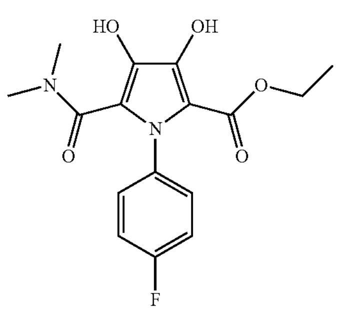 [SMILES: CCOC(=O)c1c(O)c(O)c(C(=O)N(C)C)n1-c1ccc(F)cc1] | ethyl 5-(dimethylcarbamoyl)-1-(4-fluorophenyl)-3,4-dihydroxy-1H-pyrrole-2-carboxylate | UL1-032 | +++ | δ: 8.70 (s, 1H), 8.55 (s, 1H), 7.32-7.10 (m, 4H), 4.00 (q, J = 7.1 Hz, 4H), 2.85 (br s, 6H), 0.99 (t, J = 7.1 Hz, 3H). | m/z 337 (M + H)$^+$ (ES$^+$), 335 (M − H)$^−$ (ES$^−$) | As example B except 4-fluoroaniline used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 33 | 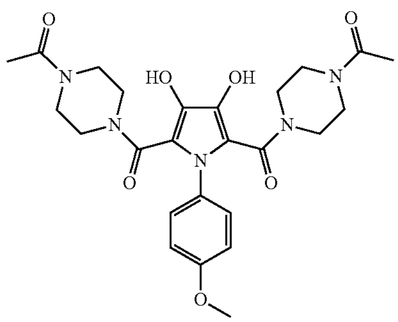 [SMILES: COc1ccc(-n2c(C(=O)N3CCN(C(C)=O)CC3)c(O)c(O)c2C(=O)N2CCN(C(C)=O)CC2)cc1] | 1,1'-(4,4'-(3,4-dihydroxy-1-(4-methoxyphenyl)-1H-pyrrole-2,5-dicarbonyl)bis(piperazine-4,1-diyl))diethanone | UL1-033 | +++ | δ: 8.59 (s, 2H), 7.00-6.92 (m, 2H), 6.90-6.83 (m, 2H), 3.73 (s, 3H), 3.51-3.41 (m, 4H), 3.40-3.35 (m, 12H), 2.01 (s, 6H). | m/z 514 (M + H)$^+$ (ES$^+$), 512 (M − H)$^−$ (ES$^−$) | As example A except 1-(piperazin-1-yl)ethanone used in step (ii). |
| 34 | 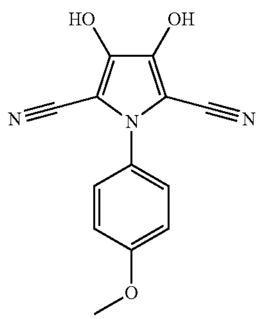 [SMILES: COc1ccc(-n2c(C#N)c(O)c(O)c2C#N)cc1] | 3,4-dihydroxy-1-(4-methoxyphenyl)-1H-pyrrole-2,5-dicarbonitrile | UL1-034 | + | δ: 7.44-7.36 (m, 2H), 7.14-7.05 (m, 2H). | m/z 254 (M − H)$^−$ (ES$^−$) | Example G |
| 35 | 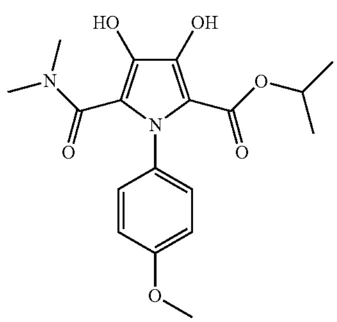 [SMILES: COc1ccc(-n2c(C(=O)OC(C)C)c(O)c(O)c2C(=O)N(C)C)cc1] | isopropyl 5-(dimethylcarbamoyl)-3,4-dihydroxy-1-(4-methoxyphenyl)-1H-pyrrole-2-carboxylate | UL1-035 | +++ | δ: 8.60 (s, 1H), 8.42 (s, 1H), 7.10-6.99 (m, 2H), 6.91-6.82 (m, 2H), 4.83 (sept., J = 6.2 Hz, 1H), 3.77 (s, 3H), 2.83 (br s, 6H), 0.96 (d, J = 6.2 Hz, 6H). | m/z 363 (M + H)$^+$ (ES$^+$), 361 (M − H)$^−$ (ES$^−$) | Example D |
| 36 | 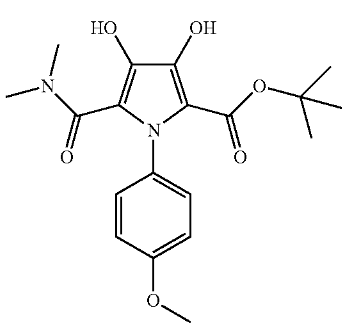 [SMILES: COc1ccc(-n2c(C(=O)OC(C)(C)C)c(O)c(O)c2C(=O)N(C)C)cc1] | tert-butyl 5-(dimethylcarbamoyl)-3,4-dihydroxy-1-(4-methoxyphenyl)-1H-pyrrole-2-carboxylate | UL1-036 | +++ | δ: 8.62 (s, 1H), 8.45 (s, 1H), 7.12-6.99 (m, 2H), 6.94-6.81 (m, 2H), 3.76 (s, 3H), 2.83 (br s, 6H), 1.17 (s, 9H). | m/z 377 (M + H)$^+$ (ES$^+$), 375 (M − H)$^−$ (ES$^−$) | Example I |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 37 | 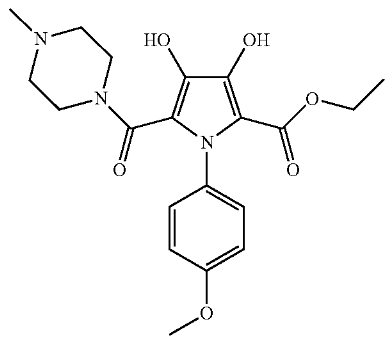 [SMILES: CCOC(=O)c1c(O)c(O)c(C(=O)N2CCN(C)CC2)n1-c1ccc(OC)cc1] | ethyl 3,4-dihydroxy-1-(4-methoxyphenyl)-5-(4-methylpiperazine-1-carbonyl)-1H-pyrrole-2-carboxylate | UL1-037 | +++ | δ: 8.60 (s, 1H), 8.46 (s, 1H), 7.08-7.01 (m, 2H), 6.90-6.82 (m, 2H), 4.00 (q, J = 7.0 Hz, 2H), 3.76 (s, 3H), 3.45-3.29 (m, 4H), 2.34-1.97 (m, 7H), 0.99 (t, J = 7.1 Hz, 3H). | m/z 404 (M + H)$^+$ (ES$^+$), 402 (M − H)$^-$ (ES$^-$) | As example B except 1-methylpiperazine used in step (v) |
| 38 | 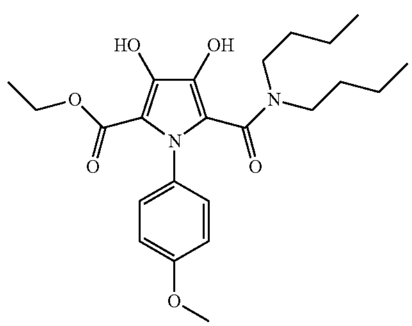 [SMILES: CCCCN(CCCC)C(=O)c1c(O)c(O)c(C(=O)OCC)n1-c1ccc(OC)cc1] | ethyl 5-(dibutyl-carbamoyl)-3,4-dihydroxy-1-(4-methoxyphenyl)-1H-pyrrole-2-carboxylate | UL1-038 | +++ | δ: 8.18-7.96 (m, 2H), 7.11-7.02 (m, 2H), 6.90-6.82 (m, 2H), 4.01 (q, J = 7.0 Hz, 2H), 3.78 (s, 3H), 3.16 (t, J = 7.4 Hz, 4H), 1.29 (quin., J = 7.6 Hz, 4H), 1.12 (sext., J = 7.4 Hz, 4H), 1.29 (t, J = 7.1 Hz, 3H), 0.81 (t, J = 7.3 Hz, 6H). | m/z 433 (M + H)$^+$ (ES$^+$), 431 (M − H)$^-$ (ES$^-$) | As example B except dibutylamine used in step (v) |
| 39 | 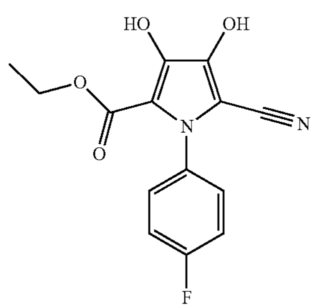 [SMILES: CCOC(=O)c1c(O)c(O)c(C#N)n1-c1ccc(F)cc1] | ethyl 5-cyano-1-(4-fluorophenyl)-3,4-dihydroxy-1H-pyrrole-2-carboxylate | UL1-039 | + | δ: 10.14 (s, 1H), 8.99 (s, 1H), 7.44-7.36 (m, 2H), 7.35-7.26 (m, 2H), 4.05 (q, J = 7.1 Hz, 2H), 1.01 (t, J = 7.1 Hz, 3H). | m/z 291 (M + H)$^+$ (ES$^+$), 289 (M − H)$^-$ (ES$^-$) | Example H |
| 40 | 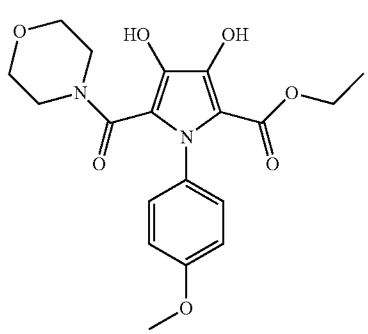 [SMILES: CCOC(=O)c1c(O)c(O)c(C(=O)N2CCOCC2)n1-c1ccc(OC)cc1] | ethyl 3,4-dihydroxy-1-(4-methoxyphenyl)-5-(morpholine-4-carbonyl)-1H-pyrrole-2-carboxylate | UL1-040 | +++ | δ: 8.65 (s, 1H), 8.47 (s, 1H), 7.11-7.01 (m, 2H), 6.91-6.83 (m, 2H), 4.00 (q, J = 7.1 Hz, 2H), 3.76 (s, 3H), 3.50-3.32 (m, 8H), 0.99 (t, J = 7.1 Hz, 3H). | m/z 391 (M + H)$^+$ (ES$^+$), 389 (M − H)$^-$ (ES$^-$) | As example B except morpholine used in step (v) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 41 | 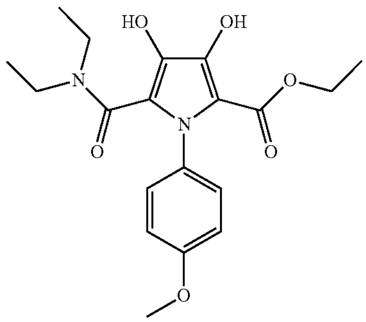 [SMILES: CCOC(=O)c1c(O)c(O)c(C(=O)N(CC)CC)n1-c1ccc(OC)cc1] | ethyl 5-(diethyl-carbamoyl)-3,4-dihydroxy-1-(4-methoxyphenyl)-1H-pyrrole-2-carboxylate | UL1-041 | +++ | δ: 8.08 (br s, 2H), 7.10-7.01 (m, 2H), 6.92-6.79 (m, 2H), 4.03 (q, J = 7.0 Hz, 2H), 3.22 (q, J = 7.0 Hz, 4H), 3.77 (s, 3H), 1.01 (t, J = 7.0 Hz, 3H), 0.92 (t, J = 7.1 Hz, 6H). | m/z 377 (M + H)$^+$ (ES$^+$), 375 (M − H)$^−$ (ES$^−$) | As example B except diethylamine used in step (v) |
| 42 | 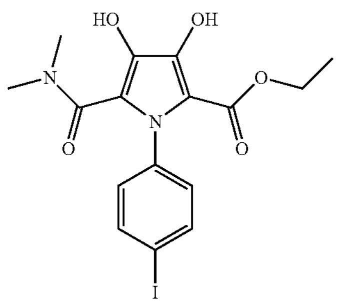 [SMILES: CCOC(=O)c1c(O)c(O)c(C(=O)N(C)C)n1-c1ccc(I)cc1] | ethyl 5-(dimethyl-carbamoyl)-3,4-dihydroxy-1-(4-iodophenyl)-1H-pyrrole-2-carboxylate | UL1-042 | +++ | δ: 8.75 (s, 1H), 8.59 (s, 1H), 7.69-7.63 (m, 2H), 6.95-6.89 (m, 2H), 4.01 (q, J = 7.1 Hz, 2H), 2.85 (br s, 6H), 1.00 (t, J = 7.1 Hz, 3H). | m/z 445 (M + H)$^+$ (ES$^+$), 443 (M − H)$^−$ (ES$^−$) | As example B except 4-iodoaniline used in step (i) |
| 43 | 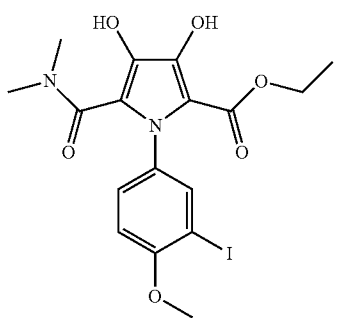 [SMILES: CCOC(=O)c1c(O)c(O)c(C(=O)N(C)C)n1-c1ccc(OC)c(I)c1] | ethyl 5-(dimethyl-carbamoyl)-3,4-dihydroxy-1-(3-iodo-4-methoxyphenyl)-1H-pyrrole-2-carboxylate | UL1-043 | +++ | δ: 8.70 (s, 1H), 8.53 (s, 1H), 7.52 (d, J = 2.5 Hz, 1H), 7.11 (dd, J = 8.7, 2.5 Hz, 1H), 6.92 (d, J = 8.7 Hz, 1H), 4.00 (q, J = 7.1 Hz, 2H), 3.83 (s, 3H), 2.85 (br s, 6H), 1.01 (t, J = 7.1 Hz, 3H). | m/z 475 (M + H)$^+$ (ES$^+$); 472 (M − H)$^−$ (ES$^−$) | As example B except 3-iodo-4-methoxyaniline used in step (i) |
| 44 | 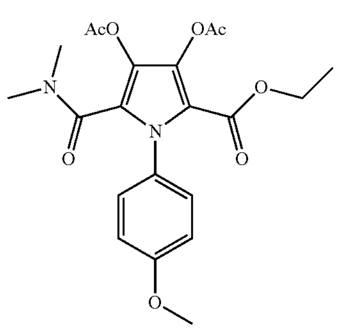 [SMILES: CCOC(=O)c1c(OC(C)=O)c(OC(C)=O)c(C(=O)N(C)C)n1-c1ccc(OC)cc1] | 2-(dimethyl-carbamoyl)-5-(ethoxycarbonyl)-1-(4-methoxyphenyl)-1H-pyrrole-3,4-diyl diacetate | UL1-044* | +++ | δ: 7.27-7.11 (2H, m), 7.00-6.88 (2H, m), 4.00 (q, J = 7.1 Hz, 2H), 3.79 (s, 3H), 2.79 (s, 3H), 2.71 (s, 3H), 2.26 (s, 6H) 1.05 (t, J = 7.1 Hz, 3H). | m/z 433 (M + H)$^+$ (ES$^+$) | Example J |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 45 | 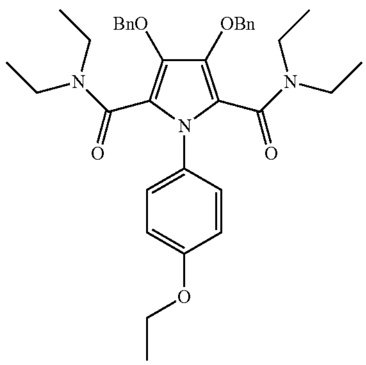 [SMILES: CCOc1ccc(-n2c(C(=O)N(CC)CC)c(OCc3ccccc3)c(OCc3ccccc3)c2C(=O)N(CC)CC)cc1] | 3,4-bis(benzyloxy)-1-(4-ethoxyphenyl)-N$^2$,N$^2$,N$^5$,N$^5$-tetraethyl-1H-pyrrole-2,5-dicarboxamide | UL1-045 | +++ | δ: 7.43-7.26 (m, 10H), 7.05-6.99 (m, 2H), 6.93-6.84 (m, 2H), 4.97 (s, 4H), 4.00 (t, J = 6.9 Hz, 2H), 3.29-3.19 (m, 4H), 3.18-3.07 (m, 4H), 1.31 (t, J = 6.9 Hz, 3H), 0.95-0.79 (m, 12H). | m/z 598 (M + H)$^+$ (ES$^+$) | UL1-002 |
| 46 | 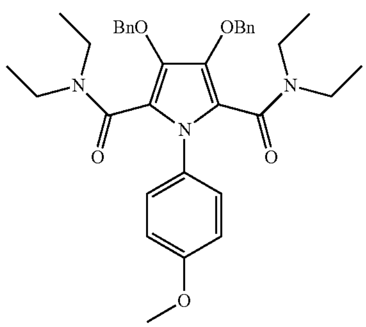 [SMILES: CCN(CC)C(=O)c1c(OCc2ccccc2)c(OCc2ccccc2)c(C(=O)N(CC)CC)n1-c1ccc(OC)cc1] | 3,4-bis(benzyloxy)-N$^2$,N$^2$,N$^5$,N$^5$-tetraethyl-1-(4-methoxyphenyl)-1H-pyrrole-2,5-dicarboxamide | UL1-046 | +++ | δ: 7.40-7.28 (m, 10H), 7.07-7.00 (m, 2H), 6.95-6.87 (m, 2H), 4.97 (s, 4H), 3.74 (s, 3H), 3.29-3.20 (m, 4H), 3.19-3.11 (m, 4H), 0.95-0.79 (m, 12H). | m/z 584 (M + H)$^+$ (ES$^+$) | Example A |
| 47 | 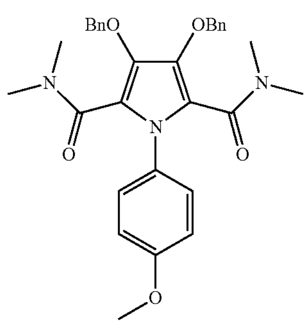 | 3,4-bis(benzyloxy)-1-(4-methoxyphenyl)-N$^2$,N$^2$,N$^5$,N$^5$-tetramethyl-1H-pyrrole-2,5-dicarboxamide | UL1-047 | ++ | (CDCl$_3$) δ: 7.40-7.27 (m, 10H), 7.17-7.04 (m, 2H), 6.88-6.75 (m, 2H), 5.08 (s, 4H), 3.78 (s, 3H), 2.81 (s, 6H), 2.65 (s, 6H). | m/z 529 (M + H)$^+$ (ES$^+$) | UL1-005 |
| 48 | 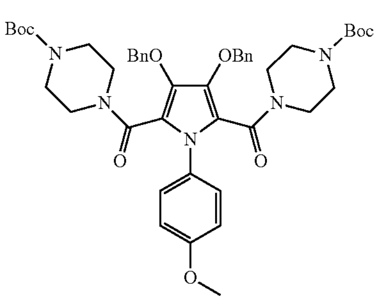 [SMILES: COc1ccc(-n2c(C(=O)N3CCN(C(=O)OC(C)(C)C)CC3)c(OCc3ccccc3)c(OCc3ccccc3)c2C(=O)N2CCN(C(=O)OC(C)(C)C)CC2)cc1] | di-tert-butyl 4,4'-(3,4-bis(benzyloxy)-1-(4-methoxyphenyl)-1H-pyrrole-2,5-dicarbonyl)bis(piperazine-1-carboxylate) | UL1-048 | +++ | δ: 7.47-7.26 (m, 10H),7.10-7.00 (m, 2H), 6.97-6.87 (m, 2H), 5.01 (s, 4H), 3.75 (s, 3H), 5.09-4.95 (m, 16H), 1.39 (s, 18H). | m/z 810 (M + H)$^+$ (ES$^+$) | UL1-015 |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 49 | 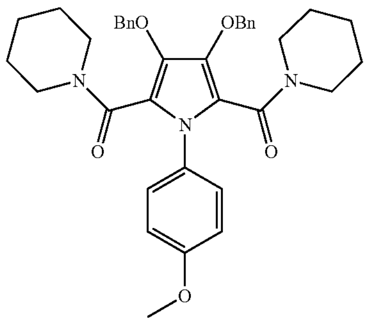 [SMILES: COc1ccc(-n2c(C(=O)N3CCCCC3)c(OCc3ccccc3)c(OCc3ccccc3)c2C(=O)N2CCCCC2)cc1] | (3,4-bis(benzyloxy)-1-(4-methoxyphenyl)-1H-pyrrole-2,5-diyl)bis(piperidin-1-ylmethanone) | UL1-049 | +++ | δ: 7.42-7.27 (m, 10H), 7.03-6.98 (m, 2H), 6.97-6.90 (m, 2H), 4.98 (s, 4H), 3.75 (s, 3H), 3.42-3.28 (m, 4H), 3.20-3.07 (m, 4H), 1.48-1.39 (m, 4H), 1.38-1.06 (m, 8H). | m/z 608 (M + H)$^+$ (ES$^+$) | UL1-018 |
| 50 | 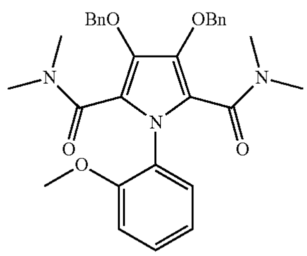 | 3,4-bis(benzyloxy)-1-(2-methoxyphenyl)-N$^2$,N$^2$,N$^5$,N$^5$-tetramethyl-1H-pyrrole-2,5-dicarboxamide | UL1-050 | ++ | δ: 7.43-7.28 (m, 10H), 7.28-7.20 (m, 1H), 7.06-6.94 (m, 2H), 6.93-6.86 (m. 1H), 5.08-4.88 (m, 4H), 3.66 (s, 3H), 2.87 (s, 6H), 2.75 (s, 6H). | m/z 528 (M + H)$^+$ (ES$^+$) | UL1-019 |
| 51 | 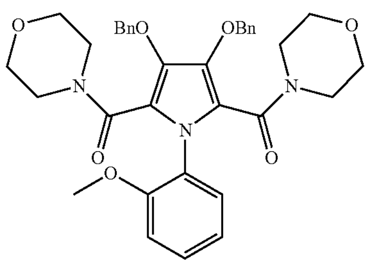 [SMILES: COc1ccccc1-n1c(C(=O)N2CCOCC2)c(OCc2ccccc2)c(OCc2ccccc2)c1C(=O)N1CCOCC1] | (3,4-bis(benzyloxy)-1-(2-methoxyphenyl)-1H-pyrrole-2,5-diyl)bis(morpholinomethanone) | UL1-051 | + | δ: 7.42-7.24 (m, 11H), 7.08-7.00 (m, 2H), 6.98-6.91 (m, 1H), 5.07-4.95 (m, 4H), 3.69 (s, 3H), 3.47-3.05 (m, 16H). | m/z 612 (M + H)$^+$ (ES$^+$) | UL1-020 |
| 52 | 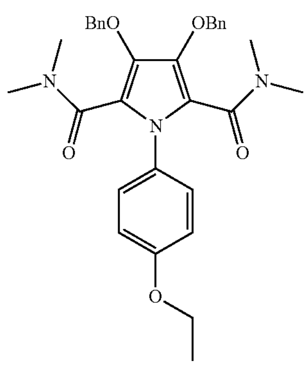 | 3,4-bis(benzyloxy)-1-(4-ethoxyphenyl)-N$^2$,N$^2$,N$^5$,N$^5$-tetramethyl-1H-pyrrole-2,5-dicarboxamide | UL1-052 | +++ | δ: 7.42-7.27 (m, 10H), 7.01-6.94 (m, 2H), 6.91-6.84 (m, 2H), 5.00 (s, 4H), 4.00 (q, J = 6.9 Hz, 2H), 2.76-2.67 (m, 12H), 1.32 (t, J = 6.9 Hz, 3H). | m/z 542 (M + H)$^+$ (ES$^+$) | UL1-021 |
| 53 | 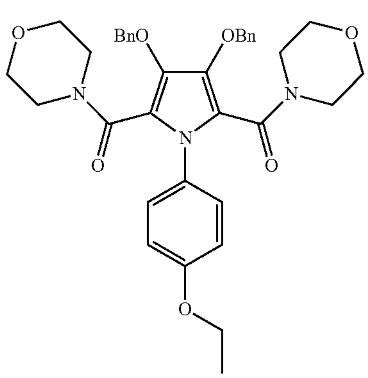 [SMILES: CCOc1ccc(-n2c(C(=O)N3CCOCC3)c(OCc3ccccc3)c(OCc3ccccc3)c2C(=O)N2CCOCC2)cc1] | (3,4-bis(benzyloxy)-1-(4-ethoxyphenyl)-1H-pyrrole-2,5-diyl)bis(morpholinomethanone) | UL1-053 | ++ | δ: 7.42-7.29 (m, 10H), 7.05-6.99 (m, 2H), 6.97-6.90 (m, 2H), 5.01 (s, 4H), 4.01 (q, J = 7.0 Hz, 2H), 3.42-3.33 (m, 8H), 3.25-3.10 (m, 8H), 1.32 (t, J = 7.0 Hz, 3H). | m/z 626 (M + H)$^+$ (ES$^+$) | UL1-022 |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 54 | 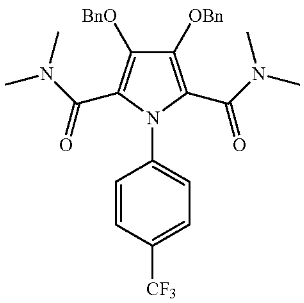 | 3,4-bis(benzyloxy)-N$^2$,N$^2$,N$^5$,N$^5$-tetramethyl-1-(4-(trifluoromethyl)phenyl)-1H-pyrrole-2,5-dicarboxamide | UL1-054 | ++ | δ: 7.78-7.69 (m, 2H), 7.42-7.30 (m, 10H), 7.29-7.23 (m, 2H), 5.03 (s, 4H), 2.89 (s, 6H), 2.79 (s, 6H). | m/z 566 (M + H)$^+$ (ES$^+$) | UL1-028 |
| 55 | 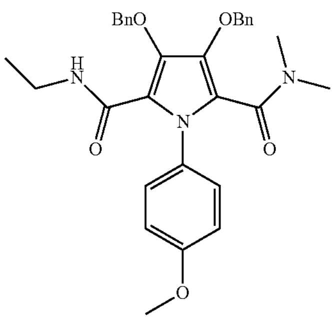 [SMILES: CCNC(=O)c1c(OCc2ccccc2)c(OCc2ccccc2)c(C(=O)N(C)C)n1-c1ccc(OC)cc1] | 3,4-bis(benzyloxy)-N$^2$-ethyl-1-(4-methoxyphenyl)-N$^5$,N$^5$-dimethyl-1H-pyrrole-2,5-dicarboxamide | UL1-055 | ++ | (CDCl$_3$) δ: 7.42-7.30 (m, 10H), 7.20-7.09 (m, 2H), 7.06-6.96 (m, 1H), 6.89-6.80 (m, 2H), 5.20 (s, 2H), 5.07 (s, 2H), 3.79 (s, 3H), 3.25-3.13 (m, 2H), 2.79 (s, 3H), 2.72 (s, 3H), 0.97 (t, J = 7.3 Hz, 3H). | m/z 528 (M + H)$^+$ (ES$^+$) | Example C |
| 56 | 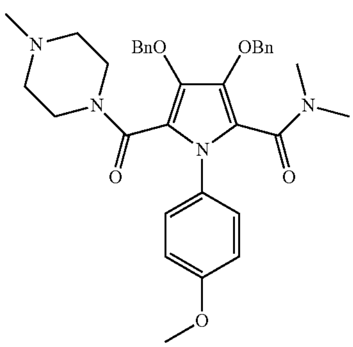 | 3,4-bis(benzyloxy)-1-(4-methoxyphenyl)-N,N-dimethyl-5-(4-methylpiperazine-1-carbonyl)-1H-pyrrole-2-carboxamide | UL1-056 | ++ | (CDCl$_3$) δ: 7.42-7.26 (m, 10H), 7.15-7.06 (m, 2H), 6.88-6.79 (m, 2H), 5.07 (s, 4H), 3.78 (s, 3H), 3.53 (br s, 2H), 3.30-3.18 (m, 2H), 2.83 (s, 3H), 2.70 (s, 3H), 2.21 (br s, 2H), 2.17 (s, 3H), 2.02 (br s, 2H). | m/z 583 (M + H)$^+$ (ES$^+$) | UL1-027 |
| 57 | 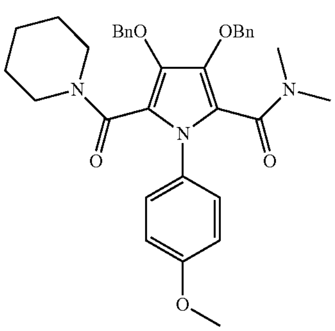 [SMILES: COc1ccc(-n2c(C(=O)N(C)C)c(OCc3ccccc3)c(OCc3ccccc3)c2C(=O)N2CCCCC2)cc1] | 3,4-bis(benzyloxy)-1-(4-methoxyphenyl)-N,N-dimethyl-5-(piperidine-1-carbonyl)-1H-pyrrole-2-carboxamide | UL1-057 | +++ | (CDCl$_3$) δ: 7.45-7.26 (m, 10H), 7.19-7.06 (m, 2H), 6.90-6.77 (m, 2H), 5.07 (s, 4H), 3.78 (s, 3H), 3.46 (br s, 2H), 3.21-3.05 (m, 2H), 2.82 (s, 3H), 2.68 (s, 3H), 1.56-1.31 (m, 4H), 1.21 (br s, 2H). | m/z 568 (M + H)$^+$ (ES$^+$) | UL1-025 |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 58 | 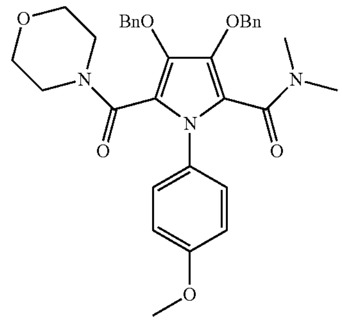 [SMILES: COc1ccc(-n2c(C(=O)N(C)C)c(OCc3ccccc3)c(OCc3ccccc3)c2C(=O)N2CCOCC2)cc1] | 3,4-bis(benzyloxy)-1-(4-methoxyphenyl)-N,N-dimethyl-5-(morpholine-4-carbonyl)-1H-pyrrole-2-carboxamide | UL1-058 | + | (CDCl$_3$) δ: 7.42-7.27 (m, 10H), 7.15-7.06 (m, 2H), 6.89-6.80 (m, 2H), 5.13-5.03 (m, 4H), 3.79 (s, 3H), 3.56-3.37 (m, 4H), 3.32-3.09 (m, 4H), 2.82 (s, 3H), 2.69 (s, 3H). | m/z 570 (M + H)$^+$ (ES$^+$) | UL1-026 |
| 59 | 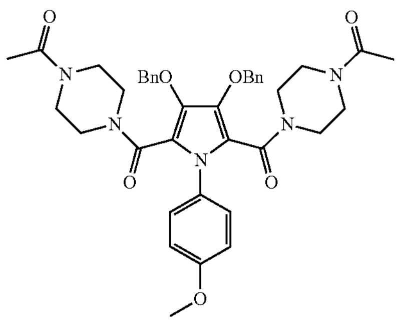 [SMILES: COc1ccc(-n2c(C(=O)N3CCN(C(C)=O)CC3)c(OCc3ccccc3)c(OCc3ccccc3)c2C(=O)N2CCN(C(C)=O)CC2)cc1] | 1,1'-(4,4'-(3,4-bis(benzyloxy)-1-(4-methoxyphenyl)-1H-pyrrole-2,5-dicarbonyl)bis(piperazine-4,1-diyl))diethanone | UL1-059 | + | δ: 7.42-7.27 (m, 10H), 7.11-7.02 (m, 2H), 6.97-6.88 (m, 2H), 5.02 (s, 4H), 3.77 (s, 3H), 3.41-3.17 (m, 16H), 1.96 (s, 6H). | m/z 694 (M + H)$^+$ (ES$^+$) | UL1-033 |
| 60 | 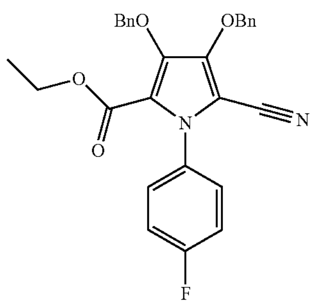 [SMILES: CCOC(=O)c1c(OCc2ccccc2)c(OCc2ccccc2)c(C#N)n1-c1ccc(F)cc1] | ethyl 3,4-bis(benzyloxy)-5-cyano-1-(4-fluorophenyl)-1H-pyrrole-2-carboxylate | UL1-060 | + | δ: 7.51-7.32 (m, 14H), 5.27 (s, 2H), 5.11 (s, 2H), 4.05 (q, J = 7.1 Hz, 2H), 1.00 (t, J = 7.1 Hz, 3H). | m/z 471 (M + H)$^+$ (ES$^+$) | Example H |
| 61 | 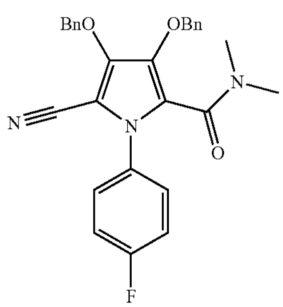 [SMILES: CN(C)C(=O)c1c(OCc2ccccc2)c(OCc2ccccc2)c(C#N)n1-c1ccc(F)cc1] | 3,4-bis(benzyloxy)-5-cyano-1-(4-fluorophenyl)-N,N-dimethyl-1H-pyrrole-2-carboxamide | UL1-061 | +++ | δ: 7.49-7.30 (m, 14H), 5.30 (s, 2H), 5.00 (s, 2H), 2.79-2.74 (m, 6H). | m/z 470 (M + H)$^+$ (ES$^+$) | As example F except triethylammonium 3,4-bis(benzyloxy)-5-(dimethylcarbamoyl)-1-(4-fluorophenyl)-1H-pyrrole-2-carboxylate used in step (i) |
| 62 | 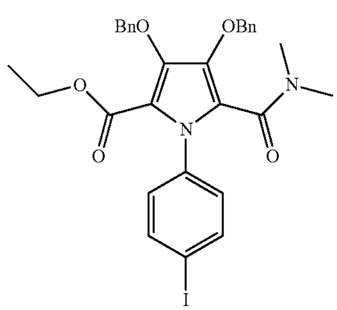 [SMILES: CCOC(=O)c1c(OCc2ccccc2)c(OCc2ccccc2)c(C(=O)N(C)C)n1-c1ccc(I)cc1] | ethyl 3,4-bis(benzyloxy)-5-(dimethylcarbamoyl)-1-(4-iodophenyl)-1H-pyrrole-2-carboxylate | UL1-062 | +++ | δ: 7.76-7.68 (m, 2H), 7.47-7.42 (m, 2H), 7.41-7.29 (m, 8H), 7.03-6.96 (m, 2H), 5.13 (s, 2H), 4.97 (s, 2H), 4.01 (q, J = 7.1 Hz, 2H), 2.77 (s, 3H), 2.73 (s, 3H), 1.01 (t, J = 7.1 Hz, 3H). | m/z 625 (M + H)$^+$ (ES$^+$) | UL1-042 |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 63 | 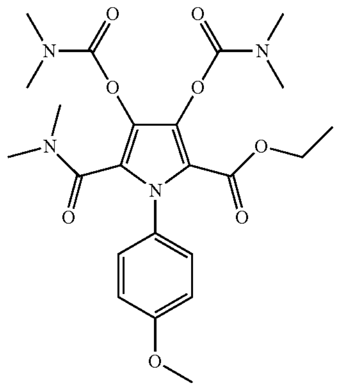 [SMILES: CCOC(=O)c1c(OC(=O)N(C)C)c(OC(=O)N(C)C)c(C(=O)N(C)C)n1-c1ccc(OC)cc1] | ethyl 5-(dimethyl-carbamoyl)-3,4-bis((dimethyl-carbamoyl)oxy)-1-(4-methoxyphenyl)-1H-pyrrole-2-carboxylate | UL1-063* | – | δ: 7.21-7.11 (m, 2H), 6.98-6.88 (m, 2H), 4.00 (q, J = 7.1 Hz, 2H), 3.79 (s, 3H), 3.01 (s, 3H), 2.96 (s, 3H), 2.90 (s, 3H), 2.88 (s, 3H), 2.80 (s, 3H), 2.70 (s, 3H) 1.05 (t, J = 7.1 Hz, 3H). | m/z 491 (M + H)$^+$ (ES$^+$) | Example O |
| 64 | 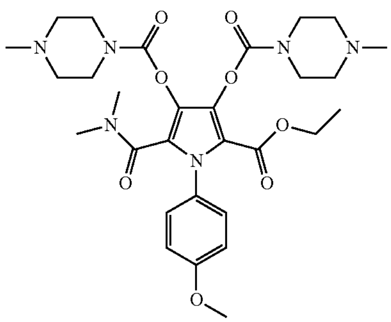 | 2-(dimethyl-carbamoyl)-5-(ethoxycarbonyl)-1-(4-methoxyphenyl)-1H-pyrrole-3,4-diyl bis(4-methylpiperazine-1-carboxylate) | UL1-064* | – | δ: 7.20-7.14 (m, 2H), 6.96-6.91 (m, 2H), 4.01 (q, J = 7.1 Hz, 2H), 3.79 (s, 3H), 3.60-3.36 (br m, 8H), 2.82 (s, 3H), 2.72 (s, 3H), 2.40-2.29 (br m, 8H), 2.23 (s, 3H), 2.22 (s, 3H) 1.07 (t, J = 7.1 Hz, 3H). | m/z 301 (M + H)$^+$ (ES$^+$) | As example O except 4-methylpiperazine-1-carbonyl chloride used |
| 65 | 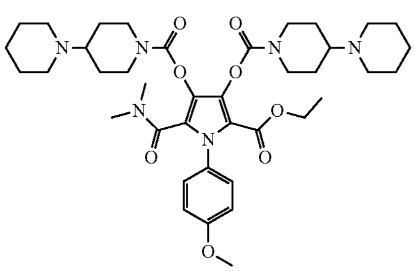 [SMILES: CCOC(=O)c1c(OC(=O)N2CCC(N3CCCCC3)CC2)c(OC(=O)N2CCC(N3CCCCC3)CC2)c(C(=O)N(C)C)n1-c1ccc(OC)cc1] | 2-(dimethyl-carbamoyl)-5-(ethoxycarbonyl)-1-(4-methoxyphenyl)-1H-pyrrole-3,4-diyl bis([1,4'-bipiperidine]-1'-carboxylate) | UL1-065* | – | δ: 7.18-7.14 (m, 2H), 6.95-6.91 (m, 2H), 4.14-3.94 (m, 6H), 3.79 (s, 3H) 3.01-2.80 (m, 7H), 2.71 (s, 3H) 2.45-2.44 (br m, 10H) 1.78-1.75 (m, 4H) 1.48-1.26 (m, 16H) 1.05 (t, J = 7.1 Hz, 3H). | m/z 369 (M + H)$^+$ (ES$^+$) | As example O except [1,4'-bipiperidine]-1'-carbonyl chloride used |
| 66 | 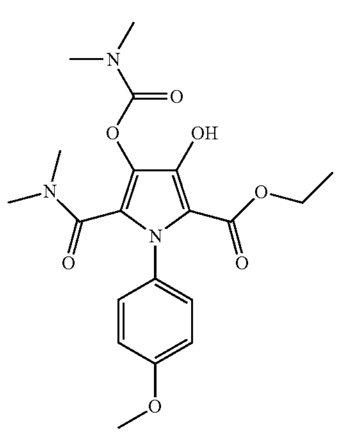 [SMILES: CCOC(=O)c1c(O)c(OC(=O)N(C)C)c(C(=O)N(C)C)n1-c1ccc(OC)cc1] | ethyl 5-(dimethyl-carbamoyl)-4-((dimethyl-carbamoyl)oxy)-3-hydroxy-1-(4-methoxyphenyl)-1H-pyrrole-2-carboxylate | UL1-066* | +++ | δ: 8.85 (s, 1H), 7.16-7.06 (m, 2H), 6.95-6.86 (m, 2H), 4.00 (q, J = 7.1 Hz, 2H), 3.77 (s, 3H), 2.98 (s, 3H), 2.88 (s, 3H), 2.78 (s, 3H), 2.69 (s, 3H), 1.00 (t, J = 7.1 Hz, 3H). | m/z 420 (M + H)$^+$ (ES$^+$) | Example P |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 67 | 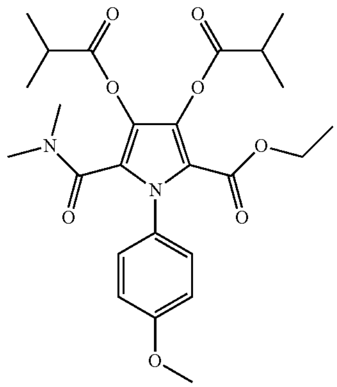 [SMILES: CCOC(=O)c1c(OC(=O)C(C)C)c(OC(=O)C(C)C)c(C(=O)N(C)C)n1-c1ccc(OC)cc1] | 2-(dimethyl-carbamoyl)-5-(ethoxycarbonyl)-1-(4-methoxyphenyl)-1H-pyrrole-3,4-diyl bis(2-methylpropanoate) | UL1-067* | + | δ: 7.23-7.16 (m, 2H), 6.95-6.86 (m, 2H), 4.00 (q, J = 7.1 Hz, 2H), 3.79 (s, 3H), 2.83-2.74 (s, 5H), 2.71 (s, 3H), 1.20 (d, J = 7.0 Hz, 6H), 1.20 (d, J = 7.0 Hz, 6H), 1.03 (t, J = 7.1 Hz, 3H). | m/z 489 (M + H)$^+$ (ES$^+$) | As example J except isobutyryl chloride used |
| 68 | 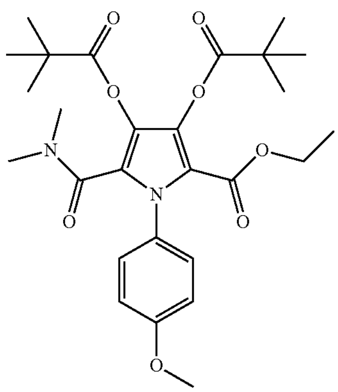 [SMILES: CCOC(=O)c1c(OC(=O)C(C)(C)C)c(OC(=O)C(C)(C)C)c(C(=O)N(C)C)n1-c1ccc(OC)cc1] | 2-(dimethyl-carbamoyl)-5-(ethoxycarbonyl)-1-(4-methoxyphenyl)-1H-pyrrole-3,4-diyl bis(2,2-dimethyl-propanoate) | UL1-068* | − | δ: 7.23-7.17 (m, 2H), 6.97-6.91 (m, 2H), 4.00 (q, J = 7.1 Hz, 2H), 3.79 (s, 3H), 2.82 (s, 3H), 2.71 (s, 3H), 1.27 (s, 9H), 1.21 (s, 9H), 1.02 (t, J = 7.1 Hz, 3H). | m/z 517 (M + H)$^+$ (ES$^+$) | As example J except pivaloyl chloride used |
| 69 | 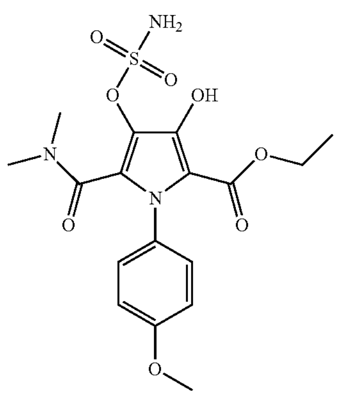 [SMILES: CCOC(=O)c1c(O)c(OS(N)(=O)=O)c(C(=O)N(C)C)n1-c1ccc(OC)cc1] | ethyl 5-(dimethyl-carbamoyl)-3-hydroxy-1-(4-methoxyphenyl)-4-(sulfamoyloxy)-1H-pyrrole-2-carboxylate | UL1-069* | +++ | δ: 8.87 (s, 1H), 7.92 (s, 2H), 7.16-7.08 (m, 2H), 6.96-6.88 (m, 2H), 4.03 (q, J = 7.1 Hz, 2H), 3.79 (s, 3H), 2.75 (s, 3H), 2.67 (s, 3H), 1.02 (t, J = 7.1 Hz, 3H). | m/z 428 (M + H)$^+$ (ES$^+$), 426 (M − H)$^−$ (ES$^−$) | As example Q |
| 70 | 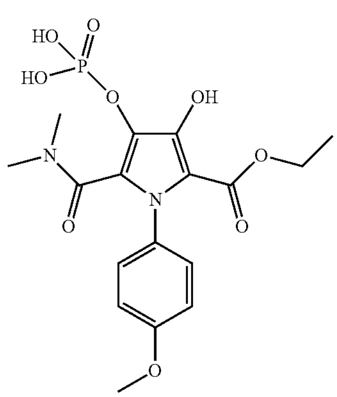 [SMILES: CCOC(=O)c1c(O)c(OP(=O)(O)O)c(C(=O)N(C)C)n1-c1ccc(OC)cc1] | ethyl 5-(dimethyl-carbamoyl)-3-hydroxy-1-(4-methoxyphenyl)-4-(phosphonooxy)-1H-pyrrole-2-carboxylate | UL1-070* | + | δ: 7.11-7.03 (m, 2H), 6.93-6.85 (m, 2H), 3.99 (q, J = 7.1 Hz, 2H), 3.77 (s, 3H), 2.82 (s, 3H), 2.71 (s, 3H), 1.02 (t, J = 7.1 Hz, 3H). | m/z 429 (M + H)$^+$ (ES$^+$), 427 (M − H)$^−$ (ES$^−$) | Example R |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 71 | 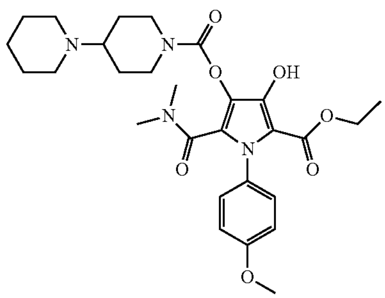 [SMILES: CCOC(=O)c1c(O)c(OC(=O)N2CCC(N3CCCCC3)CC2)c(C(=O)N(C)C)n1-c1ccc(OC)cc1] | 2-(dimethylcarbamoyl)-5-(ethoxycarbonyl)-4-hydroxy-1-(4-methoxyphenyl)-1H-pyrrol-3-yl [1,4'-bipiperidine]-1'-carboxylate | UL1-071* | + | δ: 8.86 (s, 1H), 7.17-7.05 (m, 2H), 6.95-6.85 (m, 2H), 4.15-3.91 (m, 4H), 3.77 (s, 3H), 3.04-2.89 (m, 1H), 2.89-2.75 (m, 4H), 2.69 (s, 3H), 2.44 (br s, 5H), 1.75-1.73 (br m, 2H), 1.54-1.43 (br m, 4H), 1.43-1.29 (br m, 2H), 1.01 (t, J = 7.1 Hz, 3H). | m/z 543 (M + H)$^+$ (ES$^+$), 541 (M − H)$^−$ (ES$^−$) | As example P except [1,4'-bipiperidine]-1'-carbonyl chloride used |
| 72 | 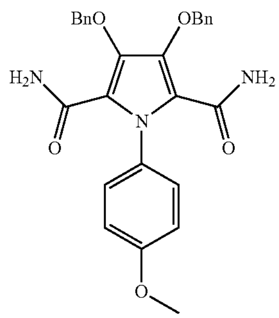 [SMILES: COc1ccc(-n2c(C(N)=O)c(OCc3ccccc3)c(OCc3ccccc3)c2C(N)=O)cc1] | 3,4-bis(benzyloxy)-1-(4-methoxyphenyl)-1H-pyrrole-2,5-dicarboxamide | UL1-072 | + | δ: 7.49-7.33 (m, 10H), 7.28 (s, 2H), 7.13 (s, 2H), 7.09-7.03 (m, 2H), 6.88-6.81 (m, 2H), 5.13 (s, 4H), 3.77 (s, 3H). | m/z 472 (M + H)$^+$ (ES$^+$) | As Example A except ammonium chloride used in step (ii) |
| 73 | 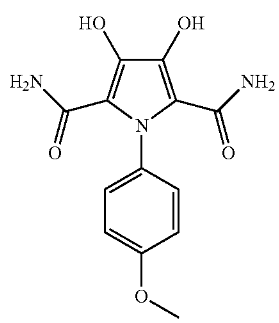 [SMILES: COc1ccc(-n2c(C(N)=O)c(O)c(O)c2C(N)=O)cc1] | 3,4-dihydroxy-1-(4-methoxyphenyl)-1H-pyrrole-2,5-dicarboxamide | UL1-073 | +++ | δ: 9.72 (s, 2H), 7.16-7.10 (m, 2H), 6.93-6.68 (m, 2H), 3.79 (s, 3H). | m/z 292 (M + H)$^+$ (ES$^+$), 290 (M − H)$^−$ (ES$^−$) | As Example A except ammonium chloride used in step (ii) |
| 74 | 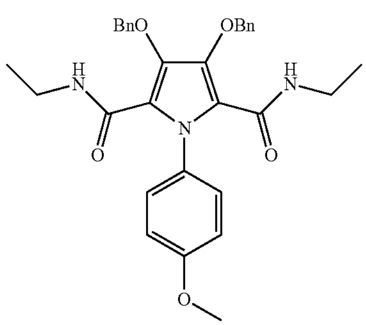 [SMILES: CCNC(=O)c1c(OCc2ccccc2)c(OCc2ccccc2)c(C(=O)NCC)n1-c1ccc(OC)cc1] | 3,4-bis(benzyloxy)-N2,N5-diethyl-1-(4-methoxyphenyl)-1H-pyrrole-2,5-dicarboxamide | UL1-074 | + | δ: 7.67 (t, J = 5.7 Hz, 2H), 7.48-7.32 (m, 10H), 7.08-6.99 (m, 2H), 6.88-6.80 (m, 2H), 5.11 (s, 4H), 3.76 (s, 3H), 3.08-2.96 (m, 4H), 0.87 (t, J = 7.2 Hz, 6H). | m/z 528 (M + H)$^+$ (ES$^+$) | As Example A except ethylamine used in step (ii) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 75 | (structure: 3,4-bis(benzyloxy)-1-(4-fluorophenyl)-1H-pyrrole-2,5-dicarboxamide) | 3,4-bis(benzyloxy)-1-(4-fluorophenyl)-1H-pyrrole-2,5-dicarboxamide | UL1-075 | + | δ: 7.48-7.34 (m, 10H), 7.32 (br s, 2H), 7.20-7.09 (m, 6H), 5.15 (s, 4H). | m/z 460 (M + H)$^+$ (ES$^+$) | As Example A except diethyl 3,4-bis(benzyloxy)-1-(4-fluorophenyl)-1H-pyrrole-2,5-dicarboxylate used in step (i) and ammonium chloride used in step (ii) |
| 76 | (structure: 1-(4-fluorophenyl)-3,4-dihydroxy-1H-pyrrole-2,5-dicarboxamide) | 1-(4-fluorophenyl)-3,4-dihydroxy-1H-pyrrole-2,5-dicarboxamide | UL1-076 | ++ | δ: 9.54 (s, 2H), 7.20-7.09 (m, 4H), 6.87 (br s, 4H). | m/z 280 (M + H)$^+$ (ES$^+$), 278 (M − H)$^-$ (ES$^-$) | As Example A except diethyl 3,4-bis(benzyloxy)-1-(4-fluorophenyl)-1H-pyrrole-2,5-dicarboxylate used in step (i) and ammonium chloride used in step (ii) |
| 77 | (structure: 1-(4-ethoxyphenyl)-3,4-dihydroxy-1H-pyrrole-2,5-dicarboxamide) | 1-(4-ethoxyphenyl)-3,4-dihydroxy-1H-pyrrole-2,5-dicarboxamide | UL1-077 | + | δ: 9.72 (s, 2H), 7.15-7.09 (m, 2H), 6.92-6.86 (m, 2H), 4.05 (q, J = 7.0 Hz, 2H), 1.35 (t, J = 7.0 Hz, 3H). | m/z 306 (M + H)$^+$ (ES$^+$), 304 (M − H)$^-$ (ES$^-$) | As Example A except diethyl 3,4-bis(benzyloxy)-1-(4-ethoxyphenyl)-1H-pyrrole-2,5-dicarboxylate used in step (i) and ammonium chloride used in step (ii) |
| 78 | (structure: 1-(4-ethoxyphenyl)-N2,N5-diethyl-3,4-dihydroxy-1H-pyrrole-2,5-dicarboxamide) | 1-(4-ethoxyphenyl)-N2,N5-diethyl-3,4-dihydroxy-1H-pyrrole-2,5-dicarboxamide | UL1-078 | +++ | δ: 9.46 (s, 2H), 7.08-7.02 (m, 2H), 7.01-6.93 (m, 2H), 6.87-6.80 (m, 2H), 4.04 (q, J = 7.0 Hz, 2H), 3.12-2.99 (m, 4H), 1.34 (t, J = 7.0 Hz, 3H), 0.92 (t, J = 7.2 Hz, 6H). | m/z 362 (M + H)$^+$ (ES$^+$), 360 (M − H)$^-$ (ES$^-$) | As Example A except diethyl 3,4-bis(benzyloxy)-1-(4-ethoxyphenyl)-1H-pyrrole-2,5-dicarboxylate used in step (i) and ethylamine used in step (ii) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 79 | 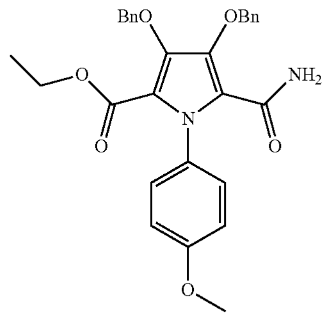 [SMILES: CCOC(=O)c1c(OCc2ccccc2)c(OCc2ccccc2)c(C(N)=O)n1-c1ccc(OC)cc1] | ethyl 3,4-bis (benzyloxy)-5-carbamoyl-1-(4-methoxyphenyl)-1H-pyrrole-2-carboxylate | UL1-079 | +++ | δ: 7.52-7.24 (m, 12H), 7.16-7.03 (m, 2H), 6.95-6.82 (m, 2H), 5.12 (s, 2H), 5.10 (s, 2H), 3.97 (q, J = 7.1 Hz, 2H), 3.78 (s, 3H), 0.97 (t, J = 7.1 Hz, 3H). | m/z 501 (M + H)$^+$ (ES$^+$) | As Example B except ammonium chloride used in step (v) |
| 80 | 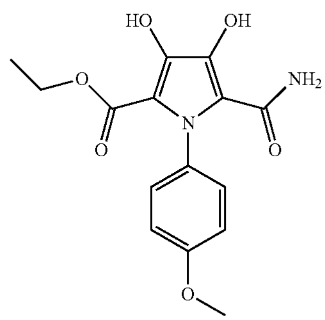 [SMILES: CCOC(=O)c1c(O)c(O)c(C(N)=O)n1-c1ccc(OC)cc1] | ethyl 5-carbamoyl-3,4-dihydroxy-1-(4-methoxyphenyl)-1H-pyrrole-2-carboxylate | UL1-080 | +++ | δ: 9.67 (s, 1H), 8.54 (s, 1H), 7.07-7.03 (m, 2H), 6.87-6.84 (m, 2H), 3.96 (t, J = 7.1 Hz, 2H), 3.77 (s, 3H), 0.95 (t, J = 7.1 Hz, 3H). | m/z 321 (M + H)$^+$ (ES$^+$), 319 (M − H)$^-$ (ES$^-$) | As Example B except ammonium chloride used in step (v) |
| 81 | 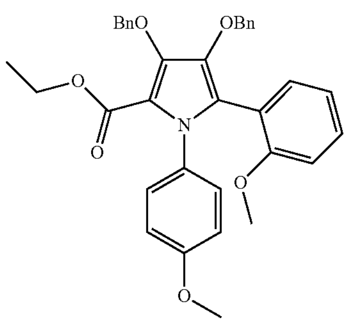 [SMILES: CCOC(=O)c1c(OCc2ccccc2)c(OCc2ccccc2)c(-c2ccccc2OC)n1-c1ccc(OC)cc1] | ethyl 3,4-bis (benzyloxy)-5-(2-methoxyphenyl)-1-(4-methoxyphenyl)-1H-pyrrole-2-carboxylate | UL1-081 | + | δ: 7.52-7.46 (m, 2H), 7.43-7.31 (m, 3H), 7.31-7.22 (m, 4H), 7.16-7.11 (m, 2H), 7.10-7.05 (m, 1H), 7.02-6.92 (m, 2H), 6.91-6.82 (m, 2H), 6.77-6.69 (m, 2H), 5.19-5.09 (m, 2H), 4.88-4.74 (m, 2H), 3.99 (q, J = 7.1 Hz, 2H), 3.68 (s, 3H), 3.56 (s, 3H), 1.00 (t, J = 7.1 Hz, 3H). | m/z 564 (M + H)$^+$ (ES$^+$) | As example S except (2-methoxyphenyl) boronic acid and PdCl$_2$(dppf) used in step (ii) |
| 82 | 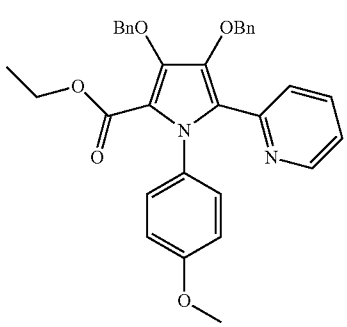 [SMILES: CCOC(=O)c1c(OCc2ccccc2)c(OCc2ccccc2)c(-c2ccccn2)n1-c1ccc(OC)cc1] | ethyl 3,4-bis (benzyloxy)-1-(4-methoxyphenyl)-5-(pyridin-2-yl)-1H-pyrrole-2-carboxylate | UL1-082 | ++ | δ: 8.47-8.40 (m, 1H), 7.71-7.63 (m, 1H), 7.54-7.47 (m, 2H), 7.45-7.16 (m, 10H), 7.12-7.03 (m, 2H), 6.83-6.76 (m, 2H), 5.18 (s, 2H), 4.96 (s, 2H), 4.02 (q, J = 7.1 Hz, 2H), 3.72 (s, 3H), 1.03 (t, J = 7.1 Hz, 3H). | m/z 535 (M + H)$^+$ (ES$^+$) | Example S |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 83 | 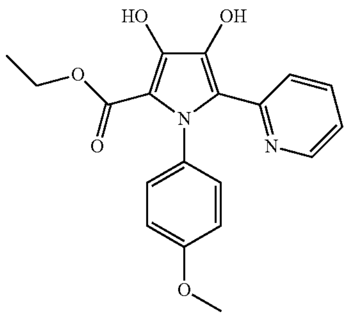 [SMILES: CCOC(=O)c1c(O)c(O)c(-c2ccccn2)n1-c1ccc(OC)cc1] | ethyl 3,4-dihydroxy-1-(4-methoxyphenyl)-5-(pyridin-2-yl)-1H-pyrrole-2-carboxylate | UL1-083 | +++ | δ: 10.84 (s, 1H), 8.62 (s, 1H), 8.56-8.47 (m, 1H), 7.67-7.55 (m, 1H), 7.26-7.12 (m, 3H), 7.01-6.89 (m, 2H), 6.62-6.49 (m, 1H), 4.01 (q, J = 7.1 Hz, 2H), 3.80 (s, 3H), 1.02 (t, J = 7.1 Hz, 3H). | m/z 355 (M + H)$^+$ (ES$^+$), 353 (M − H)$^−$ (ES$^−$) | Example S |
| 84 | 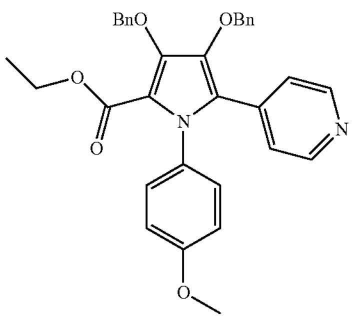 [SMILES: CCOC(=O)c1c(OCc2ccccc2)c(OCc2ccccc2)c(-c2ccncc2)n1-c1ccc(OC)cc1] | ethyl 3,4-bis(benzyloxy)-1-(4-methoxyphenyl)-5-(pyridin-4-yl)-1H-pyrrole-2-carboxylate | UL1-084 | +++ | δ: 8.39-8.33 (m, 1H), 8.28-8.24 (m, 1H), 7.54-7.48 (m, 2H), 7.45-7.33 (m, 4H), 7.30-7.21 (m, 4H), 7.19-7.14 (m, 2H), 7.14-7.07 (m, 2H), 6.87-6.80 (m, 2H), 5.20 (s, 2H), 4.91 (s, 2H), 4.02 (q, J = 7.1 Hz, 2H), 3.73 (s, 3H) 1.02 (t, J = 7.1 Hz, 3H). | m/z 535 (M + H)$^+$ (ES$^+$) | As example S except pyridin-4-ylboronic acid and PdCl$_2$(dppf) used in step (ii) |
| 85 | 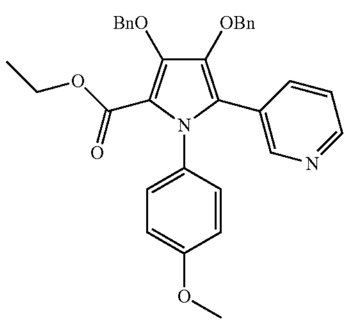 [SMILES: CCOC(=O)c1c(OCc2ccccc2)c(OCc2ccccc2)c(-c2cccnc2)n1-c1ccc(OC)cc1] | ethyl 3,4-bis(benzyloxy)-1-(4-methoxyphenyl)-5-(pyridin-3-yl)-1H-pyrrole-2-carboxylate | UL1-085 | +++ | δ: 8.42-8.37 (m, 2H), 7.54-7.47 (m, 2H), 7.46-7.33 (m, 2H), 7.32-7.26 (m, 3H), 7.25-7.18 (m, 2H), 7.16-7.09 (m, 2H), 7.05-7.00 (m, 2H), 6.92-6.83 (m, 2H), 5.19 (s, 2H), 4.74 (s, 2H), 4.03 (q, J = 7.1 Hz, 2H), 3.75 (s, 3H), 1.03 (t, J = 7.1 Hz, 3H). | m/z 535 (M + H)$^+$ (ES$^+$) | As example S except pyridin-3-ylboronic acid and PdCl$_2$(dppf) used in step (ii) |
| 86 | 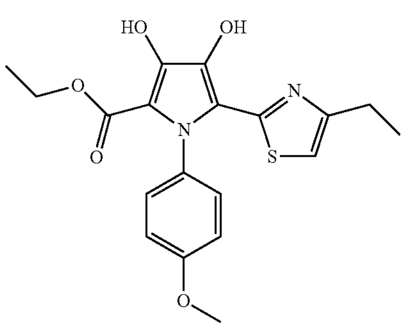 [SMILES: CCOC(=O)c1c(O)c(O)c(-c2nc(CC)cs2)n1-c1ccc(OC)cc1] | ethyl 5-(4-ethylthiazol-2-yl)-3,4-dihydroxy-1-(4-methoxyphenyl)-1H-pyrrole-2-carboxylate | UL1-086 | +++ | δ: 9.82 (s, 1H), 8.68 (s, 1H), 7.28-7.19 (m, 2H), 7.06-7.03 (m, 1H), 7.03-6.97 (m, 2H), 4.00 (q, J = 7.1 Hz, 2H), 3.82 (s, 3H), 2.67 (q, J = 7.5 Hz, 2H), 1.16 (t, J = 7.5 Hz, 3H), 0.99 (t, J = 7.1 Hz, 3H). | m/z 389 (M + H)$^+$ (ES$^+$) | Example T |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 87 | 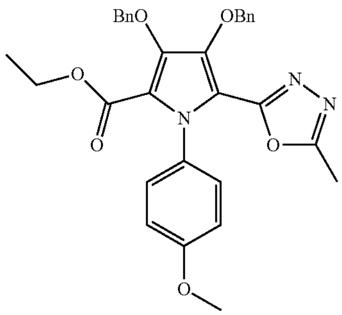 [SMILES: CCOC(=O)c1c(OCc2ccccc2)c(OCc2ccccc2)c(-c2nnc(C)o2)n1-c1ccc(OC)cc1] | ethyl 3,4-bis(benzyloxy)-1-(4-methoxyphenyl)-5-(5-methyl-1,3,4-oxadiazol-2-yl)-1H-pyrrole-2-carboxylate | UL1-087 | +++ | δ: 7.51-7.46 (m, 2H), 7.43-7.31 (m, 8H), 7.18-7.12 (m, 2H), 6.93-6.87 (m, 2H), 5.17 (s, 2H), 5.07 (s, 2H), 4.02 (q, J = 7.1 Hz, 2H), 3.78 (s, 3H), 2.35 (s, 3H), 1.01 (t, J = 7.1 Hz, 3H). | m/z 540 (M + H)$^+$ (ES$^+$) | Example U |
| 88 | 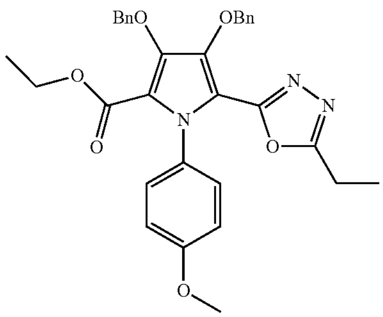 [SMILES: CCOC(=O)c1c(OCc2ccccc2)c(OCc2ccccc2)c(-c2nnc(CC)o2)n1-c1ccc(OC)cc1] | ethyl 3,4-bis(benzyloxy)-5-(5-ethyl-1,3,4-oxadiazol-2-yl)-1-(4-methoxyphenyl)-1H-pyrrole-2-carboxylate | UL1-088 | ++ | δ: 7.51-7.45 (m, 2H), 7.44-7.31 (m, 8H), 7.19-7.13 (m, 2H), 6.95-6.88 (m, 2H), 5.17 (s, 2H), 5.09 (s, 2H), 4.02 (q, J = 7.1 Hz, 2H), 3.78 (s, 3H), 2.69 (q, J = 7.6 Hz, 2H), 1.04 (t, J = 7.6 Hz, 3H), 1.01 (t, J = 7.1 Hz, 3H). | m/z 554 (M + H)$^+$ (ES$^+$) | As example U except propionohydrazide used in step (i) |
| 89 | 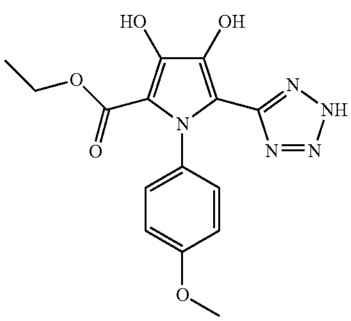 [SMILES: CCOC(=O)c1c(O)c(O)c(-c2nn[nH]n2)n1-c1ccc(OC)cc1] | ethyl 3,4-dihydroxy-1-(4-methoxyphenyl)-5-(2H-tetrazol-5-yl)-1H-pyrrole-2-carboxylate | UL1-089 | +++ | δ: 9.30 (br s, 1H), 8.67 (s, 1H), 7.10-7.05 (m, 2H), 6.87-6.81 (m, 2H), 4.02 (q, J = 7.1 Hz, 2H), 3.76 (s, 3H), 0.99 (t, J = 7.1 Hz, 3H). | m/z 346 (M + H)$^+$ (ES$^+$), 344 (M − H)$^−$ (ES$^−$) | Example V |
| 90 | 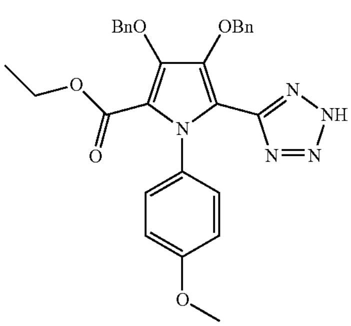 [SMILES: CCOC(=O)c1c(OCc2ccccc2)c(OCc2ccccc2)c(-c2nn[nH]n2)n1-c1ccc(OC)cc1] | ethyl 3,4-bis(benzyloxy)-1-(4-methoxyphenyl)-5-(2H-tetrazol-5-yl)-1H-pyrrole-2-carboxylate | UL1-090 | +++ | δ: 7.51-7.45 (m, 2H), 7.42-7.25 (m, 8H), 7.10-7.03 (m, 2H), 6.83-6.76 (m, 2H), 5.15 (s, 2H), 4.95 (s, 2H), 4.00 (q, J = 7.1 Hz, 2H), 3.74 (s, 3H), 1.00 (t, J = 7.1 Hz, 3H). | m/z 526 (M + H)$^+$ (ES$^+$), 524 (M − H)$^−$ (ES$^−$) | Example V |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 91 | 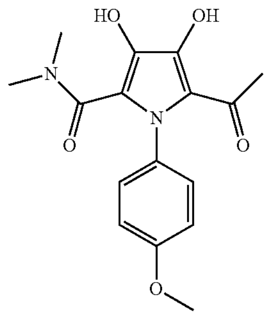 [SMILES: COc1ccc(-n2c(C(C)=O)c(O)c(O)c2C(=O)N(C)C)cc1] | 5-acetyl-3,4-dihydroxy-1-(4-methoxyphenyl)-N,N-dimethyl-1H-pyrrole-2-carboxamide | UL1-091 | +++ | δ: 9.77 (s, 1H), 8.57 (s, 1H), 7.09-7.07 (m, 2H), 6.88-6.86 (m, 2H), 3.77 (s, 3H), 2.81 (br s, 6H), 2.05 (s, 3H). | m/z 319 (M + H)$^+$ (ES$^+$), 317 (M − H)$^−$ (ES$^−$) | Example W |
| 92 | 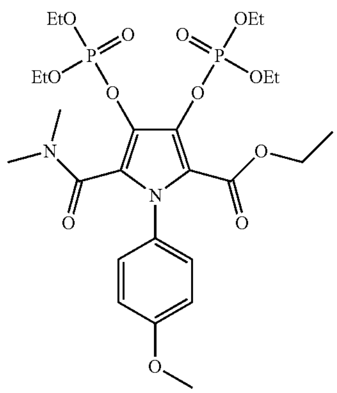 [SMILES: CCOC(=O)c1c(OP(=O)(OCC)OCC)c(OP(=O)(OCC)OCC)c(C(=O)N(C)C)n1-c1ccc(OC)cc1] | ethyl 3,4-bis((diethoxy-phosphoryl)oxy)-5-(dimethyl-carbamoyl)-1-(4-methoxyphenyl)-1H-pyrrole-2-carboxylate | UL1-092* | − | δ: 7.18-7.15 (m, 2H), 6.97-6.94 (m, 2H), 4.22-4.02 (m, 10H), 3.79 (s, 3H), 2.75 (s, 3H), 2.71 (s, 3H), 1.31-1.24 (m, 12H), 1.07 (t, J = 7.2 Hz, 3H). | m/z 621 (M + H)$^+$ (ES$^+$) | Example X |
| 93 | 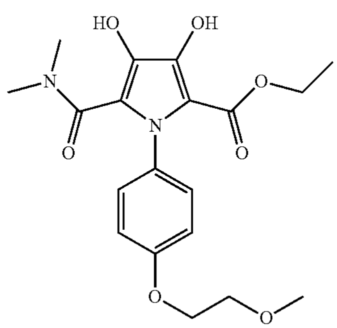 [SMILES: CCOC(=O)c1c(O)c(O)c(C(=O)N(C)C)n1-c1ccc(OCCOC)cc1] | ethyl 5-(dimethyl-carbamoyl)-3,4-dihydroxy-1-(4-(2-methoxyethoxy)phenyl)-1H-pyrrole-2-carboxylate | UL1-093 | +++ | δ: 8.58 (s, 1H), 8.44 (s, 1H), 7.07-6.98 (m, 2H), 6.89-6.81 (m, 2H), 4.12-4.05 (m, 2H), 3.29 (q, J = 7.1 Hz, 2H), 3.69-3.63 (m, 2H), 3.31 (s, 3H), 2.82 (br s, 6H), 0.98 (t, J = 7.1 Hz, 3H). | m/z 393 (M + H)$^+$ (ES$^+$); 391 (M − H)$^−$ (ES$^−$) | As example B except 4-(2-methoxyethoxy)aniline used in step (i) |
| 94 | 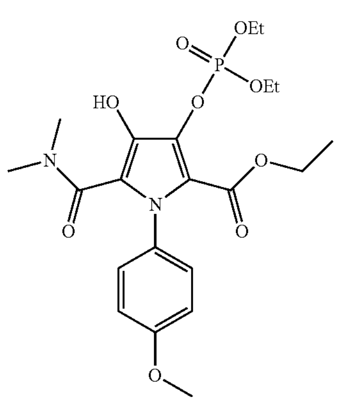 [SMILES: CCOC(=O)c1c(OP(=O)(OCC)OCC)c(O)c(C(=O)N(C)C)n1-c1ccc(OC)cc1] | ethyl 3-((diethoxy-phosphoryl)oxy)-5-(dimethyl-carbamoyl)-4-hydroxy-1-(4-methoxyphenyl)-1H-pyrrole-2-carboxylate | UL1-094* | + | δ: 8.95 (s,1H), 7.08-7.10 (m, 2H), 6.89-6.91 (m, 2H), 4.15-4.25 (m, 4H), 4.00 (q, J = 7.1 Hz, 2H), 3.78 (s, 3H), 2.84 (br s, 6H), 1.28 (dt, J = 7.1, 1.1 Hz, 6H), 1.02 (t, J = 7.1 Hz, 3H). | m/z 485 (M + H)$^+$ (ES$^+$); 482 (M − H)$^−$ (ES$^−$) | As example R, step (i) except using diethyl phosphite |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 95 | 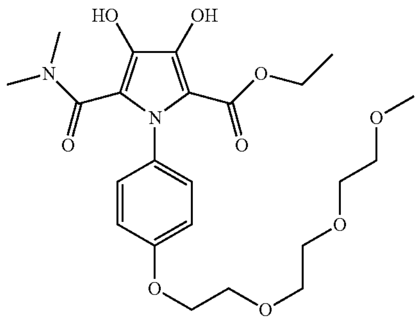 | ethyl 5-(dimethyl-carbamoyl)-3,4-dihydroxy-1-(4-(2-(2-(2-methoxyethoxy)ethoxy)ethoxy)phenyl)-1H-pyrrole-2-carboxylate | UL1-095 | +++ | δ: 8.60 (s, 1H), 8.47 (s, 1H), 7.06-6.99 (m, 2H), 6.89-6.82 (m, 2H), 4.10-4.05 (m, 2H), 3.99 (q, J = 7.0 Hz, 2H), 3.78-3.70 (m, 2H), 3.62-3.57 (m, 2H), 3.55-3.49 (m, 4H), 3.45-3.40 (m, 2H), 3.23 (s, 3H), 2.81 (br s, 6H), 0.98 (t, J = 7.0 Hz, 3H). | m/z 481 (M + H)$^+$ (ES$^+$); 479 (M − H)$^−$ (ES$^−$) | As example B except 4-(2-(2-(2-methoxyethoxy)ethoxy)ethoxy)aniline used in step (i) |
| 96 | 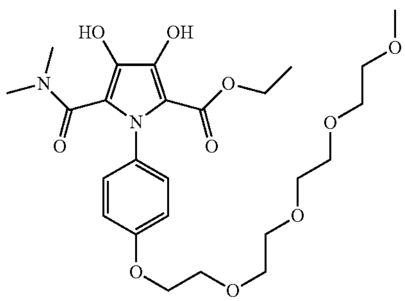 | ethyl 1-(4-(2,5,8,11-tetraoxatridecan-13-yloxy)phenyl)-5-(dimethyl-carbamoyl)-3,4-dihydroxy-1H-pyrrole-2-carboxylate | UL1-096 | +++ | δ: 8.60 (s, 1H), 8.46 (s, 1H), 7.05-7.00 (m, 2H), 6.89-6.83 (m, 2H), 4.11-4.05 (m, 2H), 3.99 (q, J = 7.0 Hz, 2H), 3.76-3.72 (m, 2H), 3.61-3.56 (m, 2H), 3.55-3.48 (m, 8H), 3.44-3.39 (m, 2H), 3.23 (s, 3H), 2.81 (br s, 6H), 0.98 (t, J = 7.1 Hz, 3H). | m/z 525 (M + H)$^+$ (ES$^+$); 523 (M − H)$^−$ (ES$^−$) | As example B except 4-(2,5,8,11-tetraoxatridecan-13-yloxy)aniline used in step (i) |
| 97 | 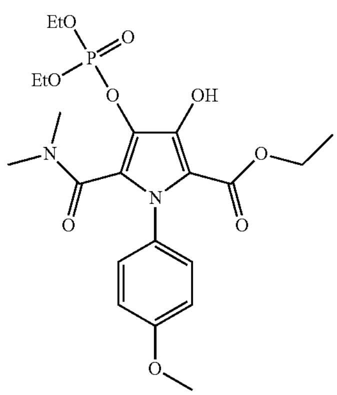 [SMILES: CCOC(=O)c1c(O)c(OP(=O)(OCC)OCC)c(C(=O)N(C)C)n1-c1ccc(OC)cc1] | ethyl 4-((diethoxy-phosphoryl)oxy)-5-(dimethyl-carbamoyl)-3-hydroxy-1-(4-methoxyphenyl)-1H-pyrrole-2-carboxylate | UL1-097* | − | δ: 8.87 (s, 1H), 7.16-7.09 (m, 2H), 6.93-6.87 (m, 2H), 4.22-4.07 (m, 2H), 4.05-3.98 (m, 2H), 3.77 (s, 3H), 2.78 (s, 3H), 2.70 (s, 3H), 1.29-1.20 (m, 6H), 1.05-0.97 (m, 3H). | m/z 485 (M + H)$^+$ (ES$^+$); 483 (M − H)$^−$ (ES$^−$) | As example R, step (i) except using diethyl phosphite |
| 98 | 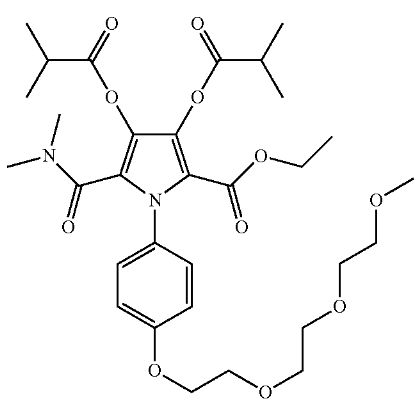 | 2-(dimethyl-carbamoyl)-5-(ethoxycarbonyl)-1-(4-(2-(2-(2-methoxyethoxy)ethoxy)ethoxy)phenyl)-1H-pyrrole-3,4-diyl bis(2-methylpropanoate) | UL1-098* | − | δ: 7.22 (m, 2H), 6.98-6.92 (m, 2H), 4.15-4.09 (m, 2H), 4.01 (q, J = 7.2 Hz, 2H), 3.75-3.77 (m, 2H), 3.59-3.61 (m, 2H), 3.52-3.55 (m, 4H), 3.42-3.45 (m, 2H), 3.24 (s, 3H), 2.75-2.82 (m, 5H), 2.71 (s, 3H), 1.21 (d, J = 6.8 Hz, 6H), 1.16 (d, J = 6.8 Hz, 6H), 1.03 (t, J = 7.2 Hz, 3H). | m/z 621 (M + H)$^+$ (ES$^+$) | As Example J, except isobutyryl chloride and UL1-095 used in step (i). |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 99 | 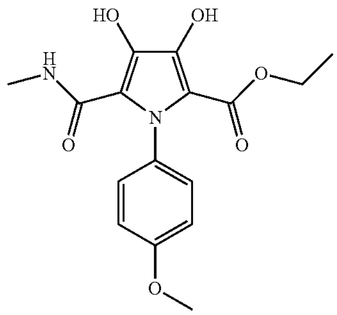 [SMILES: CCOC(=O)c1c(O)c(O)c(C(=O)NC)n1-c1ccc(OC)cc1] | ethyl 3,4-dihydroxy-1-(4-methoxyphenyl)-5-(methyl-carbamoyl)-1H-pyrrole-2-carboxylate | UL1-099 | +++ | δ: 9.56 (s, 1H), 8.51 (s, 1H), 7.51-7.48 (m, 1H), 7.04-7.00 (m, 2H), 6.86-6.82 (m, 2H), 3.96 (q, J = 7.2 Hz, 2H), 3.77 (s, 3H), 2.61 (d, J = 4.7 Hz, 3H), 0.95 (t, J = 7.2 Hz, 3H). | m/z 335 (M + H)$^+$ (ES$^+$); 333 (M − H)$^−$ (ES$^−$) | As example B except methylamine used in step (v) |
| 100 | 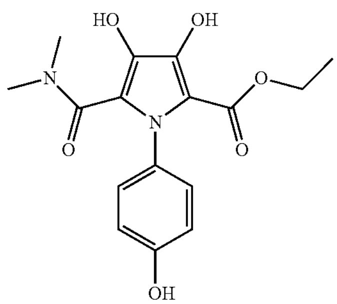 [SMILES: CCOC(=O)c1c(O)c(O)c(C(=O)N(C)C)n1-c1ccc(O)cc1] | ethyl 5-(dimethyl-carbamoyl)-3,4-dihydroxy-1-(4-hydroxyphenyl)-1H-pyrrole-2-carboxylate | UL1-100 | +++ | δ: 9.50 (s, 1H), 8.54 (s, 1H), 8.42 (s, 1H), 6.94-6.86 (m, 2H), 6.69-6.62 (m, 2H), 3.99 (q, J = 7.0 Hz, 2H), 2.81 (br s, 6H), 0.98 (t J = 7.0 Hz, 3H). | m/z 335 (M + H)$^+$ (ES$^+$); 333 (M − H)$^−$ (ES$^−$) | Example Y |
| 101 | 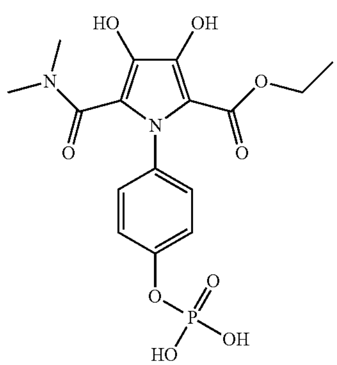 [SMILES: CCOC(=O)c1c(O)c(O)c(C(=O)N(C)C)n1-c1ccc(OP(=O)(O)O)cc1] | ethyl 5-(dimethyl-carbamoyl)-3,4-dihydroxy-1-(4-(phosphonooxy)phenyl)-1H-pyrrole-2-carboxylate | UL1-101 | +++ | δ: 8.66 (br s, 2H), 8.50 (br s, 1H), 7.09 (s, 4H), 4.00 (q, J = 7.1 Hz, 2H), 2.85 (br s, 6H), 0.99 (t, J = 7.1 Hz, 3H). | m/z 415 (M + H)$^+$ (ES$^+$); 413 (M − H)$^−$ (ES$^−$) | As example R except 36 used in step (i) |
| 102 | 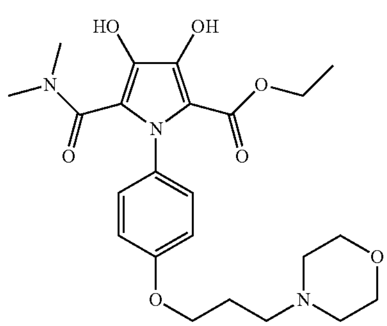 [SMILES: CCOC(=O)c1c(O)c(O)c(C(=O)N(C)C)n1-c1ccc(OCCCN2CCOCC2)cc1] | ethyl 5-(dimethyl-carbamoyl)-3,4-dihydroxy-1-(4-(3-morpholino-propoxy)phenyl)-1H-pyrrole-2-carboxylate | UL1-102 | +++ | δ: 8.58 (s, 1H), 8.44 (s, 1H), 7.05-6.99 (m, 2H), 6.86-6.82 (m, 2H), 4.03-3.95 (m, 4H), 3.61-3.53 (m, 4H), 2.82 (br s, 6H), 2.45-2.34 (m, 6H), 1.93-1.81 (m, 2H), 0.98 (t, J = 7.0 Hz, 3H). | m/z 462 (M + H)$^+$ (ES$^+$); 460 (M − H)$^−$ (ES$^−$) | Example Z |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 103 | 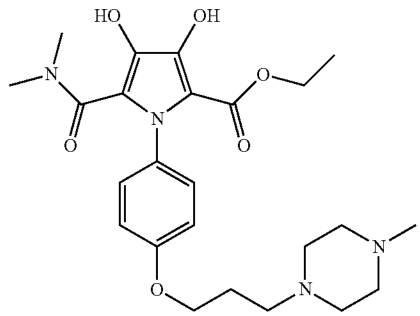 | ethyl 5-(dimethyl-carbamoyl)-3,4-dihydroxy-1-(4-(3-(4-methylpiperazin-1-yl)propoxy)phenyl)-1H-pyrrole-2-carboxylate | UL1-103 | +++ | δ: 8.59 (s, 1H), 8.45 (s, 1H), 7.06-6.99 (m, 2H), 6.86-6.81 (m, 2H), 4.02-3.94 (m, 4H), 2.82 (br s, 6H), 2.46-2.33 (m, 10H), 2.17 (s, 3H), 1.92-1.79 (m, 2H), 0.98 (t, J = 7.1 Hz, 3H). | m/z 475 (M + H)$^+$ (ES$^+$); 473 (M − H)$^-$ (ES$^-$) | As example Z except 1-(3-chloropropyl)-4-methylpiperazine dihydrochloride used in step (i) |
| 104 | 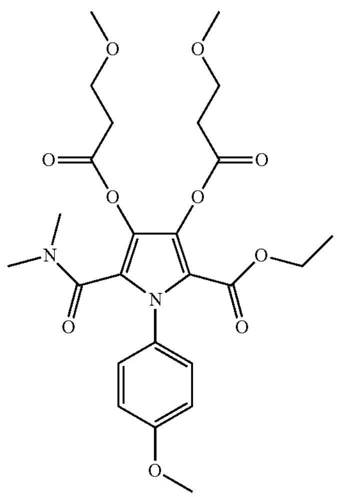 [SMILES: CCOC(=O)c1c(OC(=O)CCOC)c(OC(=O)CCOC)c(C(=O)N(C)C)n1-c1ccc(OC)cc1] | 2-(dimethyl-carbamoyl)-5-(ethoxycarbonyl)-1-(4-methoxyphenyl)-1H-pyrrole-3,4-diyl bis(3-methoxy-propanoate) | UL1-104* | +++ | δ: 7.24-7.15 (m, 2H), 6.98-6.89 (m, 2H), 4.00 (q, J = 7.1 Hz, 2H), 3.79 (s, 3H), 3.65-3.59 (m, 4H), 3.27 (s, 3H), 3.25 (s, 3H), 2.82 (s, 3H), 2.78 (t, J = 6.0 Hz, 4H), 2.71 (s, 3H), 1.05 (t, J = 7.1 Hz, 3H). | m/z 521 (M + H)$^+$ (ES$^+$) | Example A1 |
| 105 | 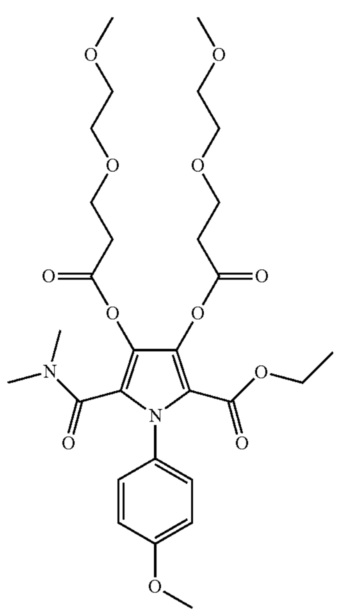 [SMILES: CCOC(=O)c1c(OC(=O)CCOCCOC)c(OC(=O)CCOCCOC)c(C(=O)N(C)C)n1-c1ccc(OC)cc1] | 2-(dimethyl-carbamoyl)-5-(ethoxycarbonyl)-1-(4-methoxyphenyl)-1H-pyrrole-3,4-diyl bis(3-(2-methoxyethoxy)propanoate) | UL1-105* | +++ | δ: 7.23-7.17 (m, 2H), 6.98-6.92 (m, 2H), 4.01 (q, J = 7.0 Hz, 2H), 3.79 (s, 3H), 3.73-3.68 (m, 4H), 3.45-3.42 (m, 4H), 3.45-3.42 (m, 4H), 3.24 (s, 6H), 3.82 (s, 3H), 2.80 (t, J = 6.2 Hz, 4H), 2.71 (s, 3H), 1.05 (t, J = 7.0 Hz, 3H). | m/z 609 (M + H)$^+$ (ES$^+$) | As Example A1 except 3-(2-methoxyethoxy)propanoic acid used. |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 106 | 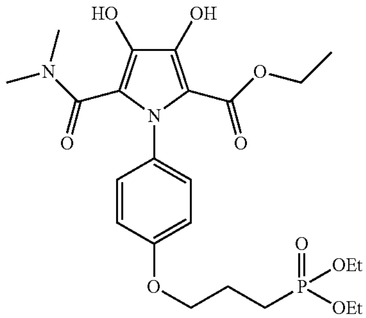 [SMILES: CCOC(=O)c1c(O)c(O)c(C(=O)N(C)C)n1-c1ccc(OCCCP(=O)(OCC)OCC)cc1] | ethyl 1-(4-(3-(diethoxyphosphoryl)propoxy)phenyl)-5-(dimethylcarbamoyl)-3,4-dihydroxy-1H-pyrrole-2-carboxylate | UL1-106 | +++ | δ: 8.58 (s, 1H), 8.44 (s, 1H), 7.05-7.00 (m, 2H), 6.87-6.81 (m, 2H), 4.06-3.91 (m, 8H), 2.82 (br s, 6H), 1.97-1.80 (m, 4H), 1.23 (t, J = 7.0 Hz, 6H), 0.98 (t, J = 7.0 Hz, 3H). | m/z 513 (M + H)$^+$ (ES$^+$); 511 (M − H)$^−$ (ES$^−$) | As Example Z except diethyl (3-bromopropyl)phosphonate used in step (i) |
| 107 | 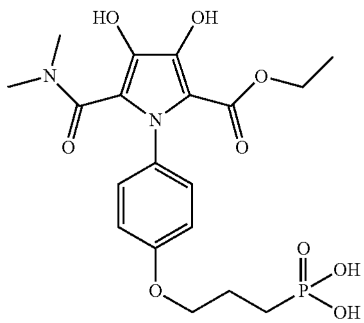 [SMILES: CCOC(=O)c1c(O)c(O)c(C(=O)N(C)C)n1-c1ccc(OCCCP(=O)(O)O)cc1] | (3-(4-(2-(dimethylcarbamoyl)-5-(ethoxycarbonyl)-3,4-dihydroxy-1H-pyrrol-1-yl)phenoxy)propyl)phosphonic acid | UL1-107 | +++ | δ: 8.70-8.23 (m, 1H), 7.06-6.99 (m, 2H), 6.86-6.81 (m, 2H), 4.05-3.95 (m, 5H), 2.82 (br s, 6H), 1.95-1.84 (m, 2H), 1.72-1.60 (m, 2H), 0.99 (t, J = 7.0 Hz, 3H). | m/z 456 (M + H)$^+$ (ES$^+$); 455 (M − H)$^−$ (ES$^−$) | Synthesised by standard TMSBr/DCM mediated hydrolysis of UL1-106 |
| 108 | 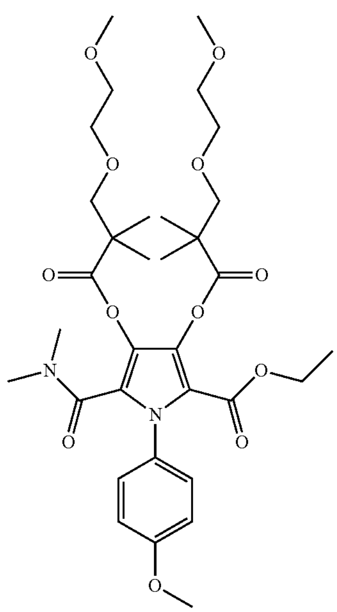 [SMILES: CCOC(=O)c1c(OC(=O)C(C)(C)COCCOC)c(OC(=O)C(C)(C)COCCOC)c(C(=O)N(C)C)n1-c1ccc(OC)cc1] | 2-(dimethylcarbamoyl)-5-(ethoxycarbonyl)-1-(4-methoxyphenyl)-1H-pyrrole-3,4-diyl bis(3-(2-methoxyethoxy)-2,2-dimethylpropanoate) | UL1-108* | ++ | δ: 7.23-7.15 (m, 2H), 6.98-6.89 (m, 2H), 4.02 (q, J = 7.2 Hz, 2H), 3.79 (s, 3H), 3.58-3.39 (m, 12H), 3.24 (s, 3H), 3.23 (s, 3H), 2.81 (s, 3H), 2.70 (s, 3H), 1.25 (s, 6H), 1.19 (s, 6H), 1.05 (t, J = 7.2 Hz, 3H). | m/z 665 (M + H)$^+$ (ES$^+$) | Example B1 |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 109 | 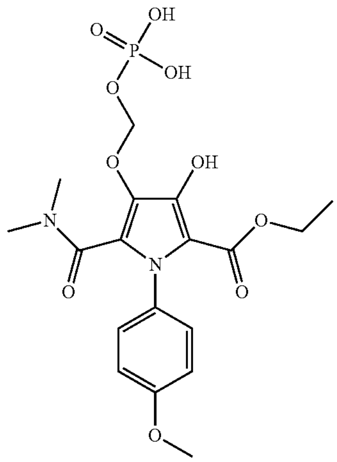 [SMILES: CCOC(=O)c1c(O)c(OCOP(=O)(O)O)c(C(=O)N(C)C)n1-c1ccc(OC)cc1] | ethyl 5-(dimethyl-carbamoyl)-3-hydroxy-1-(4-methoxyphenyl)-4-((phosphonooxy)methoxy)-1H-pyrrole-2-carboxylate | UL1-109* | – | δ: 7.14-7.05 (m, 2H), 6.93-6.85 (m, 2H), 5.35-5.23 (br m, 2H), 3.99 (q, J = 7.2 Hz, 2H), 3.77 (s, 3H), 2.73 (s, 3H), 2.70 (s, 3H), 1.02 (t, J = 7.2 Hz, 3H). | m/z 459 (M + H)$^+$ (ES$^+$) | Example C1 |
| 110 | 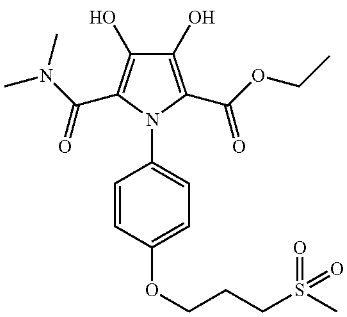 [SMILES: CCOC(=O)c1c(O)c(O)c(C(=O)N(C)C)n1-c1ccc(OCCCS(C)(=O)=O)cc1] | ethyl 5-(dimethyl-carbamoyl)-3,4-dihydroxy-1-(4-(3-(methylsulfonyl)propoxy)phenyl)-1H-pyrrole-2-carboxylate | UL1-110 | +++ | δ: 8.58 (s, 1H), 8.45 (s, 1H), 7.07-7.02 (m, 2H), 6.89-6.84 (m, 2H), 4.08 (t, J = 7.2 Hz, 2H), 3.99 (q, J = 7.1 Hz, 2H), 3.29-3.25 (m, 2H), 3.02 (s, 3H), 2.92-2.71 (br s, 6H), 2.21-2.07 (m, 2H), 0.99 (t, J = 7.1 Hz, 3H). | m/z 455 (M + H)$^+$ (ES$^+$); 453 (M – H)$^-$ (ES$^-$) | Example D1 |
| 111 | 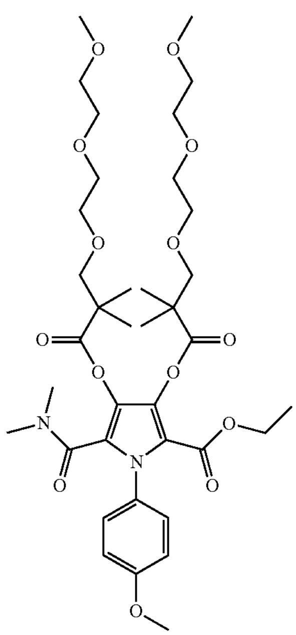 [SMILES: CCOC(=O)c1c(OC(=O)C(C)(C)COCCOCCOC)c(OC(=O)C(C)(C)COCCOCCOC)c(C(=O)N(C)C)n1-c1ccc(OC)cc1] | 2-(dimethyl-carbamoyl)-5-(ethoxycarbonyl)-1-(4-methoxyphenyl)-1H-pyrrole-3,4-diyl bis(3-(2-(2-methoxyethoxy)ethoxy)-2,2-dimethyl-propanoate) | UL1-111* | +++ | δ: 7.21-7.18 (m, 2H), 6.96-6.94 (m, 2H), 4.02 (q, J = 7.1 Hz, 2H), 3.79 (s, 3H), 3.56-3.48 (m, 16H), 3.43-3.41 (m, 4H), 3.24 (s, 3H), 3.23 (s, 3H), 2.82 (s, 3H), 3.27 (s, 3H), 1.26 (s, 6H), 1.19 (s, 6H), 1.02 (t, J = 7.1 Hz, 3H). | m/z 753 (M + H)$^+$ (ES$^+$) | As example B1 except 1-bromo-2-(2-methoxyethoxy)ethane used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 112 | 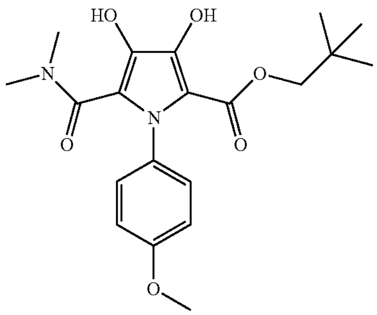 [SMILES: COc1ccc(-n2c(C(=O)OCC(C)(C)C)c(O)c(O)c2C(=O)N(C)C)cc1] | neopentyl 5-(dimethyl-carbamoyl)-3,4-dihydroxy-1-(4-methoxyphenyl)-1H-pyrrole-2-carboxylate | UL1-112 | +++ | δ: 8.63 (s, 1H), 8.62 (s, 1H), 7.11-7.08 (m, 2H), 6.89-6.86 (m, 2H), 3.74 (s, 3H), 3.67 (s, 2H), 3.00-2.55 (br s, 6H), 0.64 (s, 9H). | m/z 391 (M + H)$^+$ (ES$^+$) | As Example D, except 1-iodo-2,2-dimethylpropane used in step (i) |
| 113 | 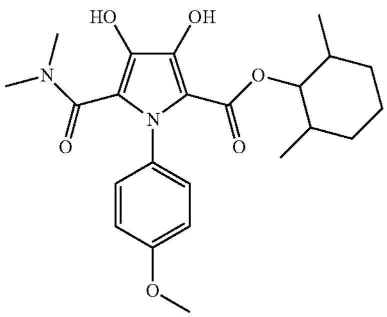 [SMILES: COc1ccc(-n2c(C(=O)OC3C(C)CCCC3C)c(O)c(O)c2C(=O)N(C)C)cc1] | 2,6-dimethyl-cyclohexyl 5-(dimethyl-carbamoyl)-3,4-dihydroxy-1-(4-methoxyphenyl)-1H-pyrrole-2-carboxylate | UL1-113 | +++ | δ: 8.67-8.40 (m, 2H), 7.15-7.05 (m, 2H), 6.91-6.85 (m, 2H), 5.05 (br s, 1H), 3.76-3.75 (m, 3H), 2.82 (br s, 6H), 1.64-0.94 (m, 6H), 0.74-0.57 (m, 6H), 0.57-0.40 (m, 2H). | m/z 431 (M + H)$^+$ (ES$^+$); 429 (M − H)$^-$ (ES$^-$) | Example E1 |
| 114 | 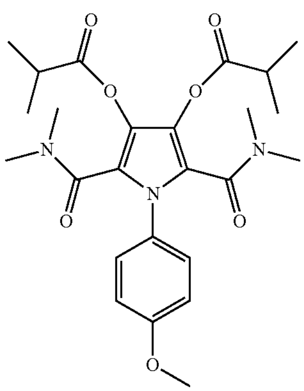 | 2,5-bis(dimethyl-carbamoyl)-1-(4-methoxyphenyl)-1H-pyrrole-3,4-diyl bis(2-methylpropanoate) | UL1-114* | ++ | δ: 7.12-7.08 (m, 2H), 6.97-6.93 (m, 2H), 3.77 (s, 3H), 2.85 (br s, 6H), 2.79-2.72 (m, 8H), 1.15 (d, J = 7.0 Hz, 12 H). | m/z 488 (M + H)$^+$ (ES$^+$) | As Example J, except UL1-005 used in step (i). |
| 115 | 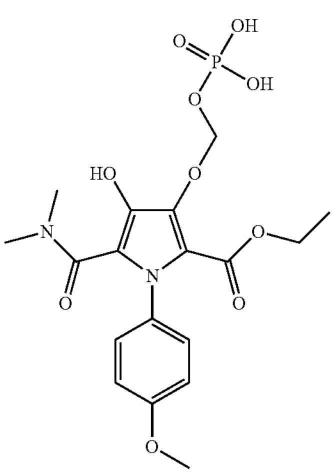 [SMILES: CCOC(=O)c1c(OCOP(=O)(O)O)c(O)c(C(=O)N(C)C)n1-c1ccc(OC)cc1] | ethyl 5-(dimethyl-carbamoyl)-4-hydroxy-1-(4-methoxyphenyl)-3-((phosphonooxy)methoxy)-1H-pyrrole-2-carboxylate | UL1-115* | + | δ: 7.11-7.05 (m, 2H), 6.91-6.84 (m, 2H), 5.45 (d, J = 16 Hz, 2H), 3.98 (q, J = 7.1 Hz, 2H), 3.77 (s, 3H), 2.98 (br s, 3H) 2.74 (br s, 3H), 1.01 (t, J = 7.0 Hz, 3H). | m/z 459 (M + H)$^+$ (ES$^+$); 457 (M − H)$^-$ (ES$^-$) | Example H1 |

| Entry | Structure | Compound name | ID | IC$_{50}$ | $^1$H NMR Data (DMSO-d$_6$) | Ionisation | Preparation |
|---|---|---|---|---|---|---|---|
| 116 | 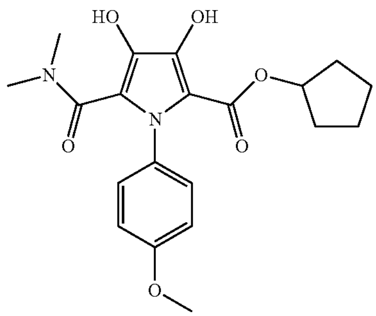 [SMILES: COc1ccc(-n2c(C(=O)OC3CCCC3)c(O)c(O)c2C(=O)N(C)C)cc1] | cyclopentyl 5-(dimethylcarbamoyl)-3,4-dihydroxy-1-(4-methoxyphenyl)-1H-pyrrole-2-carboxylate | UL1-116 | +++ | δ: 8.65 (s, 1H), 8.51 (s, 1H), 7.09-7.03 (m, 2H), 6.89-6.84 (m, 2H), 5.07-5.01 (m, 1H), 3.75 (s, 3H), 2.82 (br s, 6H), 1.66-1.52 (m, 2H), 1.40-1.17 (m, 6H). | m/z 389 (M + H)$^+$ (ES$^+$), 387 (M − H)$^−$ (ES$^−$) | As Example D, except bromocyclopentane used in step (i) |
| 117 | 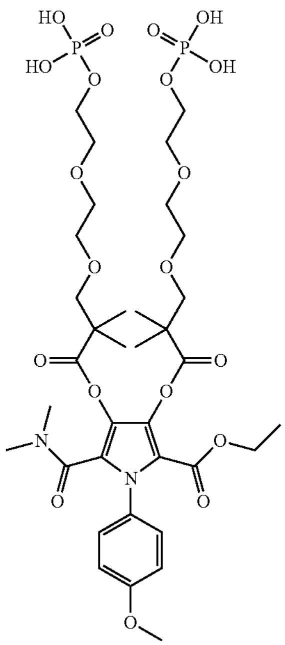 | 2-(dimethylcarbamoyl)-5-(ethoxycarbonyl)-1-(4-methoxyphenyl)-1H-pyrrole-3,4-diyl bis(2,2-dimethyl-3-(2-(2-(phosphonooxy)ethoxy)ethoxy)propanoate) | UL1-117* | ++ | (CDCl$_3$) δ 7.25-7.15 (m, 2H, m), 6.91-6.86 (m, 2H), 4.20-4.02 (m, 6H), 3.82 (s, 3H), 3.75-3.50 (m, 16H), 2.83 (s, 3H), 2.77 (s, 3H), 2.69 (br s, 4H), 1.35 (s, 6H), 1.28 (s, 6H), 1.08 (t, J = 7.2 Hz, 3H). | m/z 885 (M + H)$^+$ (ES$^+$); 883 (M − H)$^−$ (ES$^−$) | Example F1 |
| 118 | 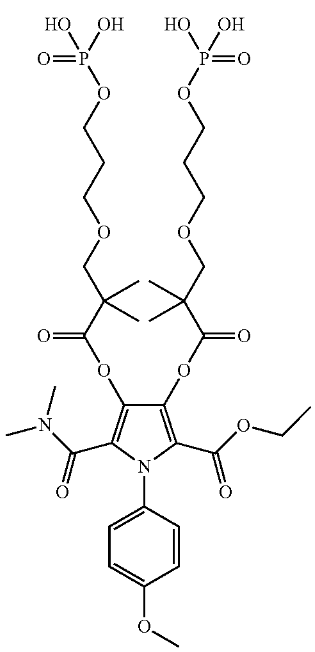 [SMILES: CCOC(=O)c1c(OC(=O)C(C)(C)COCCCOP(=O)(O)O)c(OC(=O)C(C)(C)COCCCOP(=O)(O)O)c(C(=O)N(C)C)n1-c1ccc(OC)cc1] | 2-(dimethylcarbamoyl)-5-(ethoxycarbonyl)-1-(4-methoxyphenyl)-1H-pyrrole-3,4-diyl bis(2,2-dimethyl-3-(3-(phosphonooxy)propoxy)propanoate) | UL1-118* | +++ | δ: 7.24-7.16 (m, 2H), 6.98-6.91 (m, 2H), 4.01 (q, J = 7.1 Hz, 2H), 3.90-3.81 (m, 4H), 3.79 (s, 3H), 3.51-3.43 (m, 8H), 2.82 (s, 3H), 2.70 (s, 3H), 1.86-1.73 (m, 4H), 1.25 (s, 6H), 1.19 (s, 6H), 1.01 (t, J = 7.1 Hz, 3H). | m/z 825 (M + H)$^+$ (ES$^+$); 823 (M − H)$^−$ (ES$^−$) | Example G1 |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 119 | 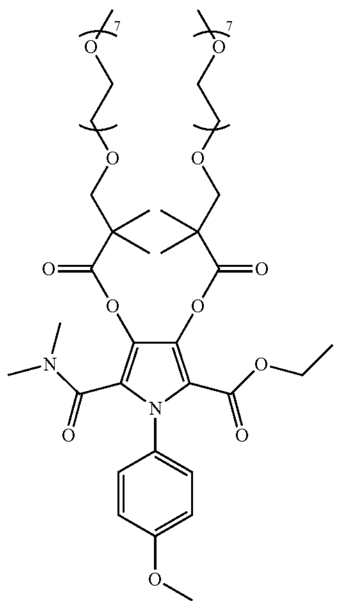 | 2-(dimethyl-carbamoyl)-5-(ethoxycarbonyl)-1-(4-methoxyphenyl)-1H-pyrrole-3,4-diyl bis(25,25-dimethyl-2,5,8,11,14,17,20,23-octaoxahexacosan-26-oate) | UL1-119* | +++ | δ: 7.21-7.16 (m, 2H), 6.96-6.92 (m, 2H), 4.02 (q, J = 7.1 Hz, 2H), 3.79 (s, 3H), 3.58-3.46 (m, 56H), 3.43-3.40 (m, 4H), 3.23 (s, 6H), 2.82 (s, 3H), 2.70 (s, 3H), 1.25 (s, 6H), 1.19 (s, 6H), 1.02 (t, J = 7.1 Hz, 3H). | m/z 1193 (M + H)$^+$ (ES$^+$) | Example I1 |
| 120 | 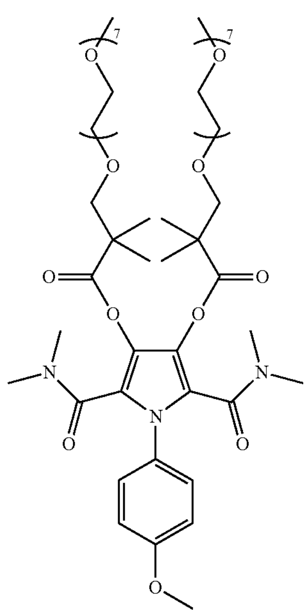 | 2,5-bis(dimethyl-carbamoyl)-1-(4-methoxyphenyl)-1H-pyrrole-3,4-diyl bis(25,25-dimethyl-2,5,8,11,14,17,20,23-octaoxahexacosan-26-oate) | UL1-120* | ++ | δ: 7.12-7.07 (m, 2H), 6.97-6.93 (m, 2H), 3.77 (s, 3H), 3.52-3.47 (m, 56H), 3.44-3.40 (m, 4H), 3.23 (s, 6H), 2.87 (s, 6H), 2.75 (s, 6H), 1.18 (s, 12H). | m/z 1193 (M + H)$^+$ (ES$^+$) | As example H1 except UL1-005 used in step (iii) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 121 | 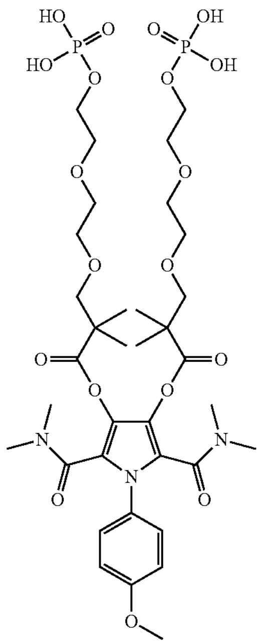 | 2,5-bis(dimethyl-carbamoyl)-1-(4-methoxyphenyl)-1H-pyrrole-3,4-diyl bis(2,2-dimethyl-3-(2-(2-(phosphonooxy)ethoxy)ethoxy)propanoate) | UL1-121* | ++ | δ: 7.11-7.09 (m, 2H), 6.97-6.95 (m, 2H), 3.91-3.87 (m, 4H), 3.78 (s, 3H), 3.58-3.50 (m, 16H), 2.89 (s, 6H), 2.76 (s, 6H), 1.19 (s, 12H). | m/z 884 (M + H)$^+$ (ES$^+$); 882 (M − H)$^−$ (ES$^−$) | Example J1 |
| 122 | 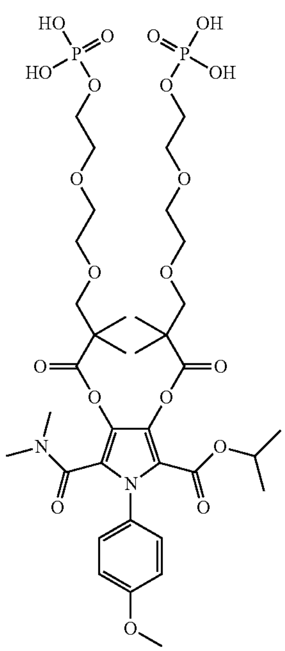 [SMILES: COc1ccc(-n2c(C(=O)OC(C)C)c(OC(=O)C(C)(C)COCCOCCOP(=O)(O)O)c(OC(=O)C(C)(C)COCCOCCOP(=O)(O)O)c2C(=O)N(C)C)cc1] | 2-(dimethyl-carbamoyl)-5-(isopropoxy-carbonyl)-1-(4-methoxyphenyl)-1H-pyrrole-3,4-diyl bis(2,2-dimethyl-3-(2-(2-(phosphonooxy)ethoxy)ethoxy)propanoate) | UL1-122* | +++ | δ: 7.21-7.18 (m, 2H), 6.97-6.92 (m, 2H), 4.83 (sept, J = 6.3 Hz, 1H), 3.92-3.85 (m, 4H), 3.79 (s, 3H), 3.59-3.48 (m, 16H), 2.82 (s, 3H), 2.70 (s, 3H), 1.26 (s, 6H), 1.19 (s, 6H), 0.98 (d, J = 6.3 Hz, 6H). | m/z 889 (M + H)$^+$ (ES$^+$); 897 (M − H)$^−$ (ES$^−$) | As Example J1 but UL1-035 used in step (i) |

TABLE 1-continued

| Entry | Structure | Compound name | ID | IC$_{50}$ | $^{1}$H NMR Data (DMSO-d$_6$) | Ionisation | Preparation |
|---|---|---|---|---|---|---|---|
| 123 | 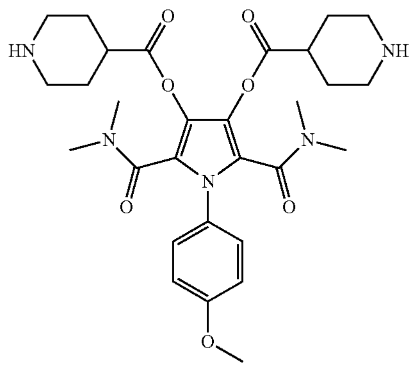 [SMILES: COc1ccc(-n2c(C(=O)N(C)C)c(OC(=O)C3CCNCC3)c(OC(=O)C3CCNCC3)c2C(=O)N(C)C)cc1] | 2,5-bis(dimethyl-carbamoyl)-1-(4-methoxyphenyl)-1H-pyrrole-3,4-diyl bis(piperidine-4-carboxylate) | UL1-123* | +++ | δ: 8.71-8.61 (br m, 2H), 8.49-8.36 (br m, 2H), 7.13-7.08 (m, 2H), 7.00-6.95 (m, 2H), 3.78 (s, 3H), 3.33-3.25 (br m, 4H), 3.05-2.92 (m, 6H), 2.79 (br s, 6H), 2.75 (br s, 6H), 2.08-2.00 (br m, 4H), 1.82-1.69 (m, 4H). | m/z 570 (M + H)$^+$ (ES$^+$) | Example K1 isolated as the di-TFA salt |
| 124 | 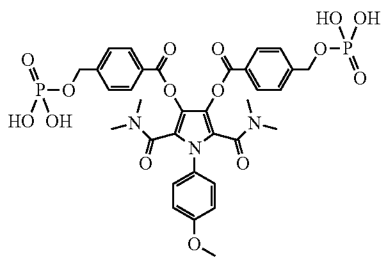 [SMILES: COc1ccc(-n2c(C(=O)N(C)C)c(OC(=O)c3ccc(COP(=O)(O)O)cc3)c(OC(=O)c3ccc(COP(=O)(O)O)cc3)c2C(=O)N(C)C)cc1] | 2,5-bis(dimethyl-carbamoyl)-1-(4-methoxyphenyl)-1H-pyrrole-3,4-diyl bis(4-((phosphonooxy)methyl)benzoate) | UL1-124* | +++ | δ: 8.00-7.98 (m, 4H), 7.54-7.52 (m, 4H), 7.20-7.18 (m, 2H), 7.00-6.98 (m, 2H), 4.98-4.96 (d, 4H), 3.79 (s, 3H), 2.89 (s, 6H), 2.74 (s, 6H). | m/z 776 (M + H)$^+$ (ES$^+$); 774 (M − H)$^-$ (ES$^-$) | Example L1 |
| 125 | 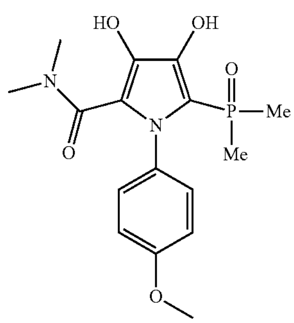 [SMILES: COc1ccc(-n2c(C(=O)N(C)C)c(O)c(O)c2P(C)(C)=O)cc1] | 5-(dimethylphosphoryl)-3,4-dihydroxy-1-(4-methoxyphenyl)-N,N-dimethyl-1H-pyrrole-2-carboxamide | UL1-125 | +++ | δ: 9.35 (s, 1H), 8.55 (s, 1H), 7.23-7.14 (m, 2H), 6.96-6.88 (m, 2H), 3.77 (s, 3H), 2.86 (br s, 6H), 1.33 (s, 3H), 1.30 (s, 3H). | m/z 353 (M + H)$^+$ (ES$^+$), 351 (M − H)$^-$ (ES$^-$) | Example M1 |
| 126 | 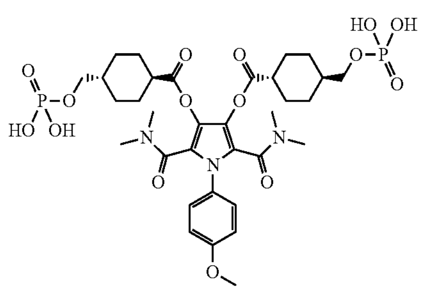 [SMILES: COc1ccc(-n2c(C(=O)N(C)C)c(OC(=O)[C@H]3CC[C@H](COP(=O)(O)O)CC3)c(OC(=O)[C@H]3CC[C@H](COP(=O)(O)O)CC3)c2C(=O)N(C)C)cc1] | (1R,1'R,4R,4'R)-2,5-bis(dimethyl-carbamoyl)-1-(4-methoxyphenyl)-1H-pyrrole-3,4-diyl bis(4-((phosphonooxy)methyl)cyclohexane-carboxylate) | UL1-126* | +++ | δ: 10.90 (br. s, 2H), 7.12-7.06 (m, 2H), 6.97-6.92 (m, 2H), 3.77 (s, 3H), 3.63 (t, J = 6.4 Hz, 4H), 2.83 (br.s, 6H), 2.75 (br.s, 6H), 2.50-2.45 (m, 2H), 2.00-1.93 (m, 4H), 1.84-1.76 (m, 4H), 1.63-1.51 (m, 2H), 1.38 (ddd, 3.1, 12.7, 16.0 Hz, 4H), 1.05 (ddd, 3.1, 12.7, 16.0 Hz, 4H). | m/z 788 (M + H)$^+$ (ES$^+$), 786 (M − H)$^-$ (ES$^-$) | Example N1 |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 127 | 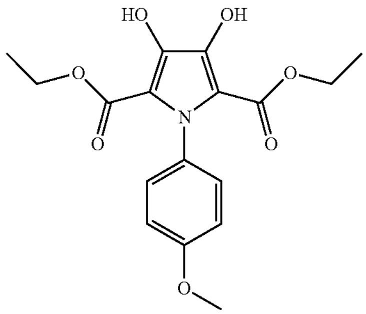 [SMILES: CCOC(=O)c1c(O)c(O)c(C(=O)OCC)n1-c1ccc(OC)cc1] | diethyl 3,4-dihydroxy-1-(4-methoxyphenyl)-1H-pyrrole-2,5-dicarboxylate | UL2-001 | +++ | δ: 8.64 (s, 2H), 7.13-7.01 (m, 2H), 6.92-6.81 (m, 2H), 3.99 (q, J = 7.1 Hz, 4H), 3.78 (s, 3H), 0.99 (t, J = 7.1 Hz, 6H). | m/z 350 (M + H)$^+$ (ES$^+$), 348 (M − H)$^−$ (ES$^−$) | UL1-012 |
| 128 | 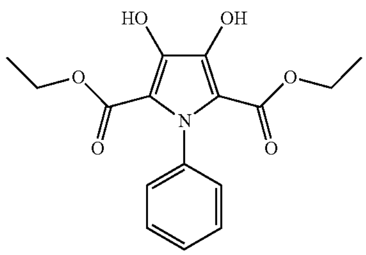 [SMILES: CCOC(=O)c1c(O)c(O)c(C(=O)OCC)n1-c1ccccc1] | diethyl 3,4-dihydroxy-1-phenyl-1H-pyrrole-2,5-dicarboxylate | UL2-002 | +++ | δ: 8.72 (s, 2H), 7.39-7.27 (m, 3H), 7.20-7.09 (m, 2H), 3.95 (q, J = 7.1 Hz, 4H), 0.92 (t, J = 7.1 Hz, 6H). | m/z 320 (M + H)$^+$ (ES$^+$), 318 (M − H)$^−$ (ES$^−$) | As UL1-012 except aniline used in step (i) |
| 129 | 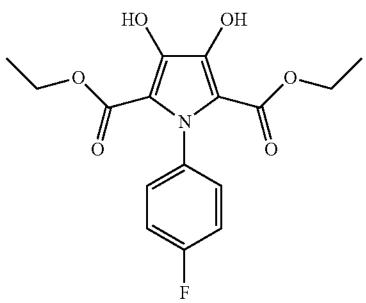 [SMILES: CCOC(=O)c1c(O)c(O)c(C(=O)OCC)n1-c1ccc(F)cc1] | diethyl 1-(4-fluorophenyl)-3,4-dihydroxy-1H-pyrrole-2,5-dicarboxylate | UL2-003 | ++ | δ: 7.88 (s, 2H), 7.20-7.14 (m, 2H), 7.09-7.01 (m, 2H), 4.09 (q, J = 7.1 Hz, 4H), 0.99 (t, J = 7.1 Hz, 6H). | m/z 338 (M + H)$^+$ (ES$^+$), 336 (M − H)$^−$ (ES$^−$) | As UL1-012 except 4-fluoroaniline used in step (i) |
| 130 | 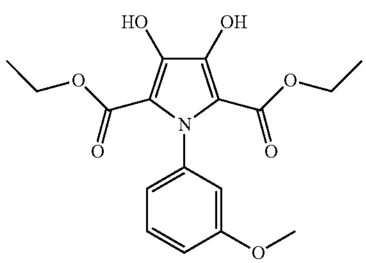 [SMILES: CCOC(=O)c1c(O)c(O)c(C(=O)OCC)n1-c1cccc(OC)c1] | diethyl 3,4-dihydroxy-1-(3-methoxyphenyl)-1H-pyrrole-2,5-dicarboxylate | UL2-004 | ++ | δ: 8.75 (br s, 2H), 7.22 (t, J = 8.0 Hz, 1H), 6.95-6.88 (m, 1H), 6.76-6.73 (m, 1H), 6.72-6.69 (m, 1H), 3.73 (s, 3H), 3.98 (q, J = 7.1 Hz, 4H), 0.95 (t, J = 7.1 Hz, 6H). | m/z 350 (M + H)$^+$ (ES$^+$), 348 (M − H)$^−$ (ES$^−$) | As UL1-012 except 3-methoxyaniline used in step (i) |
| 131 | 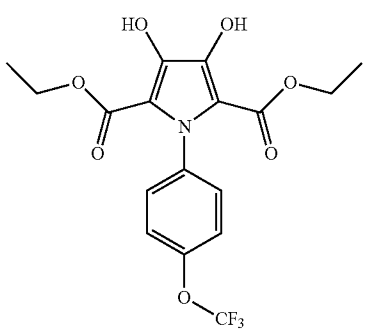 [SMILES: CCOC(=O)c1c(O)c(O)c(C(=O)OCC)n1-c1ccc(OC(F)(F)F)cc1] | diethyl 3,4-dihydroxy-1-(4-(trifluoromethoxy)phenyl)-1H-pyrrole-2,5-dicarboxylate | UL2-005 | +++ | δ: 8.82 (br s, 2H), 7.38-7.24 (m, 4H), 3.97 (q, J = 7.1 Hz, 4H), 0.93 (t, J = 7.1 Hz, 6H). | m/z 404 (M + H)$^+$ (ES$^+$), 402 (M − H)$^−$ (ES$^−$) | As UL1-012 except 4-(trifluoromethoxy) aniline used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 132 | 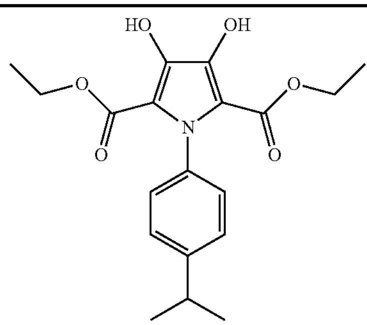 | diethyl 3,4-dihydroxy-1-(4-isopropylphenyl)-1H-pyrrole-2,5-dicarboxylate | UL2-006 | +++ | δ: 8.68 (br s, 2H), 7.22-7.15 (m, 2H), 7.08-7.01 (m, 2H), 3.95 (q, J = 7.1 Hz, 4H), 2.93 (sept., J = 6.9 Hz, 1H), 1.22 (d, J = 6.9 Hz, 6H), 0.89 (t, J = 7.1 Hz, 6H). | m/z 362 (M + H)$^+$ (ES$^+$), 360 (M − H)$^−$ (ES$^−$) | As UL1-012 except 4-isopropylaniline used in step (i) |
| 133 | 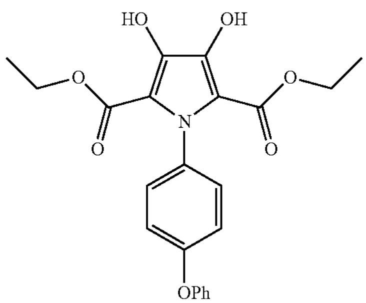 [SMILES: CCOC(=O)c1c(O)c(O)c(C(=O)OCC)n1-c1ccc(Oc2ccccc2)cc1] | diethyl 3,4-dihydroxy-1-(4-phenoxyphenyl)-1H-pyrrole-2,5-dicarboxylate | UL2-007 | +++ | δ: 8.73 (s, 2H), 7.46-7.39 (m, 2H), 7.20-7.13 (m, 3H), 7.06-7.00 (m, 2H), 6.97-6.91 (m, 2H), 4.01 (q, J = 7.1 Hz, 4H), 1.00 (t, J = 7.1 Hz, 6H). | m/z 412 (M + H)$^+$ (ES$^+$) | As UL1-012 except 4-phenoxyaniline used in step (i) |
| 134 | 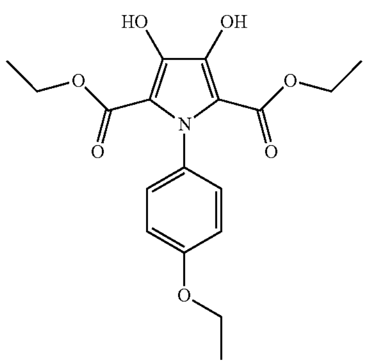 [SMILES: CCOC(=O)c1c(O)c(O)c(C(=O)OCC)n1-c1ccc(OCC)cc1] | diethyl 1-(4-ethoxyphenyl)-3,4-dihydroxy-1H-pyrrole-2,5-dicarboxylate | UL2-008 | +++ | δ: 8.65 (s, 2H), 7.07-6.99 (m, 2H), 6.88-6.80 (m, 2H), 4.03 (q, J = 7.0 Hz, 2H), 3.97 (q, J = 7.1 Hz, 4H), 1.34 (t, J = 7.0 Hz, 3H), 0.97 (t, J = 7.1 Hz, 6H). | m/z 364 (M + H)$^+$ (ES$^+$), 362 (M − H)$^−$ (ES$^−$) | As UL1-012 except 4-ethoxyaniline used in step (i) |
| 135 | 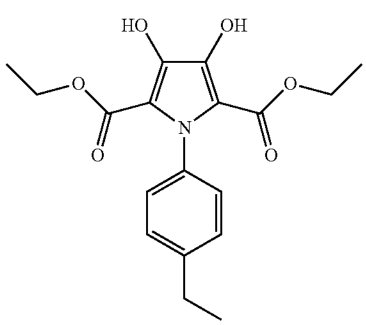 [SMILES: CCOC(=O)c1c(O)c(O)c(C(=O)OCC)n1-c1ccc(CC)cc1] | diethyl 1-(4-ethylphenyl)-3,4-dihydroxy-1H-pyrrole-2,5-dicarboxylate | UL2-009 | +++ | δ: 8.67 (s, 2H), 7.19-7.11 (m, 2H), 7.08-6.99 (m, 2H), 3.95 (q, J = 7.1 Hz, 4H), 2.63 (q, J = 7.6 Hz, 2H), 1.19 (t, J = 7.6 Hz, 3H), 0.92 (t, J = 7.1 Hz, 6H). | m/z 348 (M + H)$^+$ (ES$^+$), 346 (M − H)$^−$ (ES$^−$) | As UL1-012 except 4-ethylaniline used in step (i) |
| 136 | 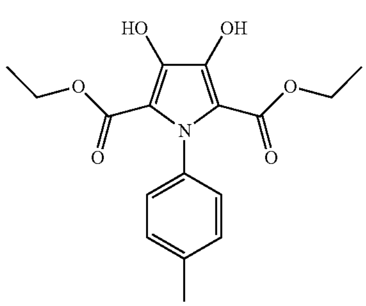 [SMILES: CCOC(=O)c1c(O)c(O)c(C(=O)OCC)n1-c1ccc(C)cc1] | diethyl 3,4-dihydroxy-1-(p-tolyl)-1H-pyrrole-2,5-dicarboxylate | UL2-010 | +++ | δ: 8.67 (s, 2H), 7.15-7.09 (m, 2H), 7.04-6.98 (m, 2H), 3.97 (q, J = 7.1 Hz, 4H), 2.33 (s, 3H), 0.96 (t, J = 7.1 Hz, 6H). | m/z 334 (M + H)$^+$ (ES$^+$), 332 (M − H)$^−$ (ES$^−$) | As UL1-012 except p-toluidine used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 137 | 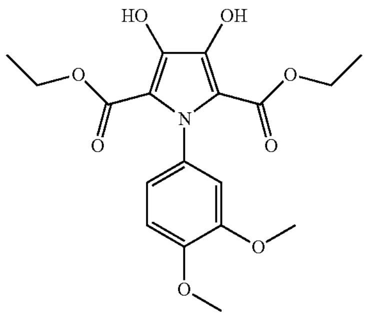 [SMILES: CCOC(=O)c1c(O)c(O)c(C(=O)OCC)n1-c1ccc(OC)c(OC)c1] | diethyl 1-(3,4-dimethoxyphenyl)-3,4-dihydroxy-1H-pyrrole-2,5-dicarboxylate | UL2-011 | +++ | δ: 8.65 (s, 2H), 6.89-6.83 (m, 1H), 6.81-6.77 (m, 1H), 6.68-6.61 (m, 1H), 3.99 (q, J = 7.1 Hz, 4H), 3.77 (s, 3H), 3.69 (s, 3H), 0.97 (t, J = 7.1 Hz, 6H). | m/z 380 (M + H)$^+$ (ES$^+$) | As UL1-012 except 3,4-dimethoxyaniline used in step (i) |
| 138 | 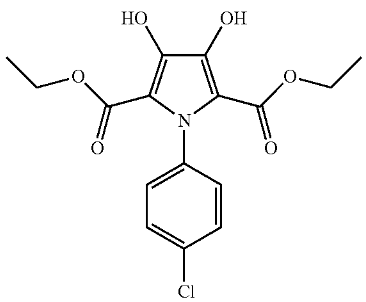 [SMILES: CCOC(=O)c1c(O)c(O)c(C(=O)OCC)n1-c1ccc(Cl)cc1] | diethyl 1-(4-chlorophenyl)-3,4-dihydroxy-1H-pyrrole-2,5-dicarboxylate | UL2-012 | +++ | (CDCl$_3$) δ: 7.85 (s, 2H), 7.36-7.31 (m, 2H), 7.15-7.10 (m, 2H), 4.10 (q, J = 7.1 Hz, 4H), 1.00 (t, J = 7.1 Hz, 6H). | m/z 354 (M + H)$^+$ (ES$^+$), 352 (M − H)$^−$ (ES$^−$) | As UL1-012 except 4-chloroaniline used in step (i) |
| 139 | 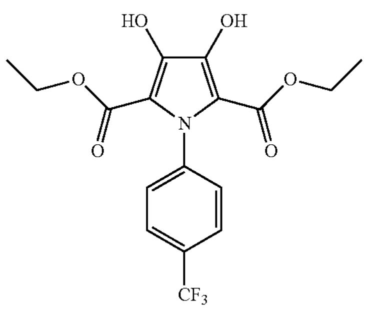 [SMILES: CCOC(=O)c1c(O)c(O)c(C(=O)OCC)n1-c1ccc(C(F)(F)F)cc1] | diethyl 3,4-dihydroxy-1-(4-(trifluoromethyl)phenyl)-1H-pyrrole-2,5-dicarboxylate | UL2-013 | +++ | (CDCl$_3$) δ: 7.88 (s, 2H), 7.67-7.61 (m, 2H), 7.36-7.31 (m, 2H), 4.08 (q, J = 7.1 Hz, 4H), 0.93 (t, J = 7.1 Hz, 6H). | m/z 388 (M + H)$^+$ (ES$^+$), 386 (M − H)$^−$ (ES$^−$) | As UL1-012 except 4-(trifluoromethyl)aniline used in step (i) |
| 140 | 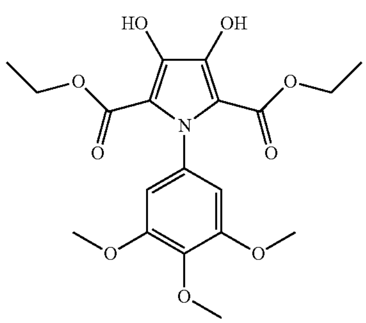 [SMILES: CCOC(=O)c1c(O)c(O)c(C(=O)OCC)n1-c1cc(OC)c(OC)c(OC)c1] | diethyl 3,4-dihydroxy-1-(3,4,5-trimethoxyphenyl)-1H-pyrrole-2,5-dicarboxylate | UL2-014 | +++ | (CDCl$_3$) δ: 7.94 (s, 2H), 6.44 (s, 2H), 4.11 (q, J = 7.1 Hz, 4H), 3.88 (s, 3H), 3.82 (s, 6H), 1.01 (t, J = 7.1 Hz, 6H). | m/z 410 (M + H)$^+$ (ES$^+$), 408 (M − H)$^−$ (ES$^−$) | As UL1-012 except 3,4,5-trimethoxyaniline used in step (i) |
| 141 | 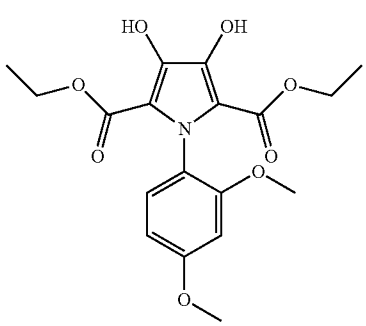 [SMILES: CCOC(=O)c1c(O)c(O)c(C(=O)OCC)n1-c1ccc(OC)cc1OC] | diethyl 1-(2,4-dimethoxyphenyl)-3,4-dihydroxy-1H-pyrrole-2,5-dicarboxylate | UL2-015 | +++ | (CDCl$_3$) δ: 7.79 (s, 2H), 7.04-6.98 (m, 1H), 6.51-6.40 (m, 2H), 4.19-4.01 (m, 4H), 3.84 (s, 3H), 3.70 (s, 3H), 1.01 (t, J = 7.1 Hz, 6H). | m/z 380 (M + H)$^+$ (ES$^+$), 378 (M − H)$^−$ (ES$^−$) | As UL1-012 except 2,4-dimethoxyaniline used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 142 | 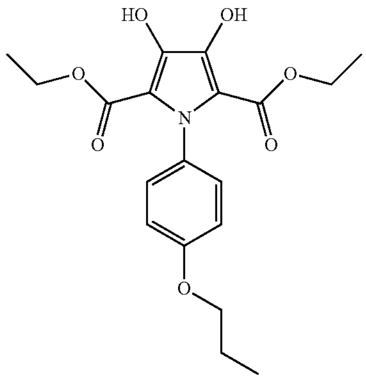 [SMILES: CCCOc1ccc(-n2c(C(=O)OCC)c(O)c(O)c2C(=O)OCC)cc1] | diethyl 3,4-dihydroxy-1-(4-propoxyphenyl)-1H-pyrrole-2,5-dicarboxylate | UL2-016 | +++ | (CDCl$_3$) δ: 7.85 (s, 2H), 7.10-7.03 (m, 2H), 6.88-6.81 (m, 2H), 4.09 (q, J = 7.1 Hz, 4H), 3.95 (t, J = 6.6 Hz, 2H), 1.82 (sext., J = 7.4 Hz, 2H), 1.05 (t, J = 7.4 Hz, 3H), 1.00 (t, J = 7.1 Hz, 6H). | m/z 378 (M + H)$^+$ (ES$^+$), 376 (M − H)$^−$ (ES$^−$) | As UL1-012 except 4-propoxyaniline used in step (i) |
| 143 | 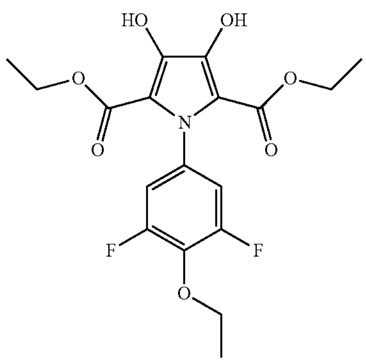 [SMILES: CCOC(=O)c1c(O)c(O)c(C(=O)OCC)n1-c1cc(F)c(OCC)c(F)c1] | diethyl 1-(4-ethoxy-3,5-difluorophenyl)-3,4-dihydroxy-1H-pyrrole-2,5-dicarboxylate | UL2-017 | +++ | (CDCl$_3$) δ: 7.91 (s, 2H), 6.85-6.76 (m, 2H), 4.25 (q, J = 7.1 Hz, 2H), 4.14 (q, J = 7.1 Hz, 4H), 1.43 (t, J = 7.1 Hz, 2H), 1.07 (t, J = 7.1 Hz, 6H). | m/z 400 (M + H)$^+$ (ES$^+$), 398 (M − H)$^−$ (ES$^−$) | As UL1-012 except 4-ethoxy-3,5-difluoroaniline used in step (i) |
| 144 | 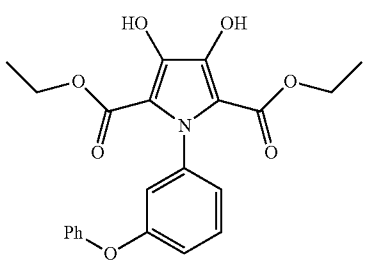 [SMILES: CCOC(=O)c1c(O)c(O)c(C(=O)OCC)n1-c1cccc(Oc2ccccc2)c1] | diethyl 3,4-dihydroxy-1-(3-phenoxyphenyl)-1H-pyrrole-2,5-dicarboxylate | UL2-018 | +++ | (CDCl$_3$) δ: 7.88 (s, 2H), 7.38-7.27 (m, 3H), 7.15-7.09 (m, 1H), 7.08-7.04 (m, 1H), 7.03-6.97 (m, 2H), 6.95-6.91 (m, 1H), 6.89-6.85 (m, 1H), 4.12 (q, J = 7.1 Hz, 4H), 1.04 (t, J = 7.1 Hz, 6H). | m/z 412 (M + H)$^+$ (ES$^+$), 410 (M − H)$^−$ (ES$^−$) | As UL1-012 except 3-phenoxyaniline used in step (i) |
| 145 | 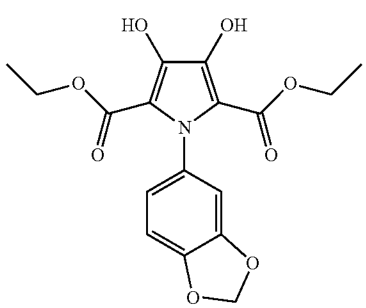 [SMILES: CCOC(=O)c1c(O)c(O)c(C(=O)OCC)n1-c1ccc2c(c1)OCO2] | diethyl 1-(benzo[d][1,3]dioxol-5-yl)-3,4-dihydroxy-1H-pyrrole-2,5-dicarboxylate | UL2-019 | + | (CDCl$_3$) δ: 7.82 (s, 2H), 6.79-6.74 (m, 1H), 6.71-6.62 (m, 2H), 6.02 (s, 2H), 4.13 (q, J =7.1 Hz, 4H), 1.06 (t, J = 7.1 Hz, 6H). | m/z 364 (M + H)$^+$ (ES$^+$), 362 (M − H)$^−$ (ES$^−$) | As UL1-012 except benzo[d][1,3]dioxol-5-amine used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 146 | 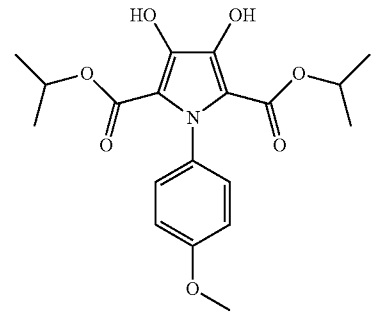 [SMILES: COc1ccc(-n2c(C(=O)OC(C)C)c(O)c(O)c2C(=O)OC(C)C)cc1] | diisopropyl 3,4-dihydroxy-1-(4-methoxyphenyl)-1H-pyrrole-2,5-dicarboxylate | UL2-020 | +++ | δ: 8.62 (s, 2H), 7.12-7.01 (m, 2H), 6.93-6.84 (m, 2H), 4.80 (sept., J = 6.3 Hz, 2H), 3.78 (s, 3H), 0.95 (d, J = 6.2 Hz, 12H). | m/z 378 (M + H)$^+$ (ES$^+$) | Example L |
| 147 | 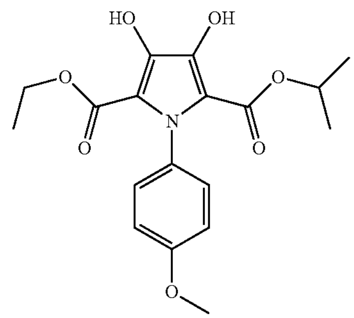 [SMILES: CCOC(=O)c1c(O)c(O)c(C(=O)OC(C)C)n1-c1ccc(OC)cc1] | 2-ethyl 5-isopropyl 3,4-dihydroxy-1-(4-methoxyphenyl)-1H-pyrrole-2,5-dicarboxylate | UL2-021 | +++ | δ: 8.66 (s, 1H), 8.62 (s, 1H), 7.09-7.03 (m, 2H), 6.90-6.85 (m, 2H), 4.80 (sept., J = 6.2 Hz, 1H), 3.98 (q, J = 7.1 Hz, 2H), 3.77 (s, 3H), 1.00 (t, J = 7.1 Hz, 3H), 0.93 (d, J = 6.2 Hz, 6H). | m/z 364 (M + H)$^+$ (ES$^+$) | Example L |
| 148 | 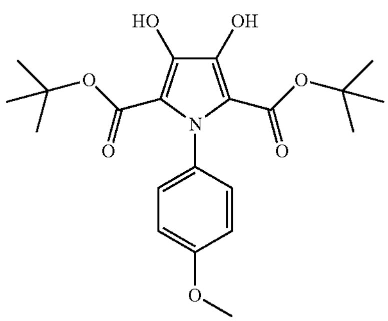 [SMILES: COc1ccc(-n2c(C(=O)OC(C)(C)C)c(O)c(O)c2C(=O)OC(C)(C)C)cc1] | di-tert-butyl 3,4-dihydroxy-1-(4-methoxyphenyl)-1H-pyrrole-2,5-dicarboxylate | UL2-022 | +++ | (CDCl$_3$) δ: 8.12 (s, 2H), 7.10-7.02 (m, 2H), 6.89-6.82 (m, 2H), 3.83 (s, 3H), 1.22 (s, 18H). | m/z 404 (M − H)$^−$ (ES$^−$) | As example B except tert-butyl 2-bromoacetate used in step (i) and di-tert-butyl oxalate and KO$^t$-Bu/$^t$BuOH used in step (iii) |
| 149 | 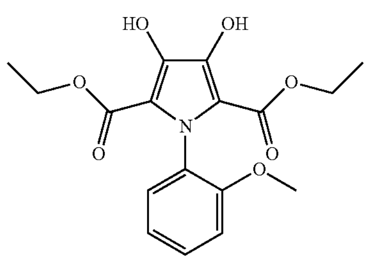 [SMILES: CCOC(=O)c1c(O)c(O)c(C(=O)OCC)n1-c1ccccc1OC] | diethyl 3,4-dihydroxy-1-(2-methoxyphenyl)-1H-pyrrole-2,5-dicarboxylate | UL2-023 | + | (CDCl$_3$) δ: 7.83 (s, 2H), 7.38-7.30 (m, 1H), 7.14-7.08 (m, 1H), 6.96-6.87 (m, 2H), 4.16-3.97 (m, 4H), 3.73 (s, 3H), 0.94 (t, J = 7.1 Hz, 6H). | m/z 350 (M + H)$^+$ (ES$^+$) | As UL1-012 except 2-methoxyaniline used in step (i) |
| 150 | 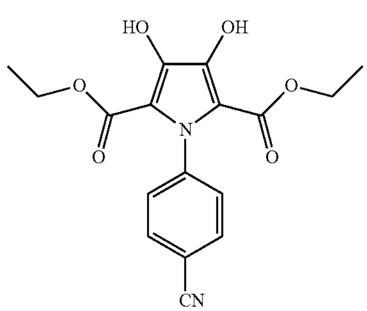 [SMILES: CCOC(=O)c1c(O)c(O)c(C(=O)OCC)n1-c1ccc(C#N)cc1] | diethyl 1-(4-cyanophenyl)-3,4-dihydroxy-1H-pyrrole-2,5-dicarboxylate | UL2-024 | ++ | δ: 8.91 (s, 2H), 7.86-7.80 (m, 2H), 7.44-7.37 (m, 2H), 4.00 (t, J = 7.1 Hz, 4H), 0.98 (t, J = 7.1 Hz, 6H). | m/z 345 (M + H)$^+$ (ES$^+$), 343 (M − H)$^−$ (ES$^−$) | As UL1-012 except 4-aminobenzonitrile used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 151 | 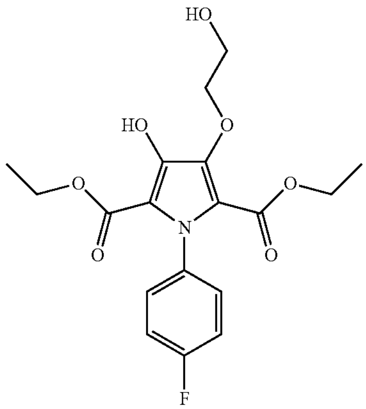 [SMILES: CCOC(=O)c1c(O)c(OCCO)c(C(=O)OCC)n1-c1ccc(F)cc1] | diethyl 1-(4-fluorophenyl)-3-hydroxy-4-(2-hydroxyethoxy)-1H-pyrrole-2,5-dicarboxylate | UL2-025 | + | δ: 8.94 (br s, 1H), 7.29-7.22 (m, 2H), 7.21-7.14 (m, 2H), 5.01 (br s, 1H), 4.08-3.97 (m, 6H), 3.73-3.65 (m, 2H), 1.02 (t, J = 7.1 Hz, 3H), 0.99 (t, J = 7.1 Hz, 3H). | m/z 382 (M + H)$^+$ (ES$^+$), 380 (M − H)$^−$ (ES$^−$) | Example M |
| 152 | 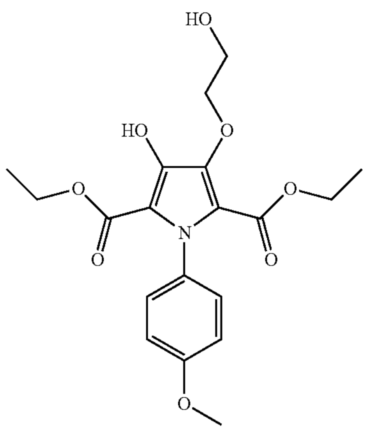 [SMILES: CCOC(=O)c1c(O)c(OCCO)c(C(=O)OCC)n1-c1ccc(OC)cc1] | diethyl 3-hydroxy-4-(2-hydroxyethoxy)-1-(4-methoxyphenyl)-1H-pyrrole-2,5-dicarboxylate | UL2-026 | + | (CDCl$_3$) δ: 8.11 (br s, 1H), 7.13-7.02 (m, 2H), 6.92-6.79 (m, 2H), 4.33-4.28 (m, 2H), 4.10-4.01 (m, 4H), 3.85-3.80 (m, 5H), 3.26 (br s, 2H), 1.03 (t, J = 7.1 Hz, 3H), 0.98 (t, J = 7.1 Hz, 3H). | m/z 394 (M + H)$^+$ (ES$^+$), 392 (M − H)$^−$ (ES$^−$) | As example M except UL2-001 used in step (i) |
| 153 | 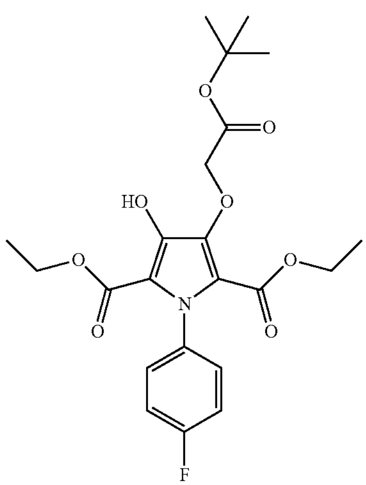 [SMILES: CCOC(=O)c1c(O)c(OCC(=O)OC(C)(C)C)c(C(=O)OCC)n1-c1ccc(F)cc1] | diethyl 3-(2-(tert-butoxy)-2-oxoethoxy)-1-(4-fluorophenyl)-4-hydroxy-1H-pyrrole-2,5-dicarboxylate | UL2-027 | ++ | δ: 8.92 (s, 1H) 7.28-7.14 (m, 4H), 4.60 (s, 2H), 4.03-3.94 (m, 4H), 1.45 (s, 9H), 1.03-0.94 (m, 6H). | m/z 396 (M + H − CH$_2$C(CH$_3$)$_2$)$^+$ (ES$^+$) | As example N except UL2-003 used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 154 | 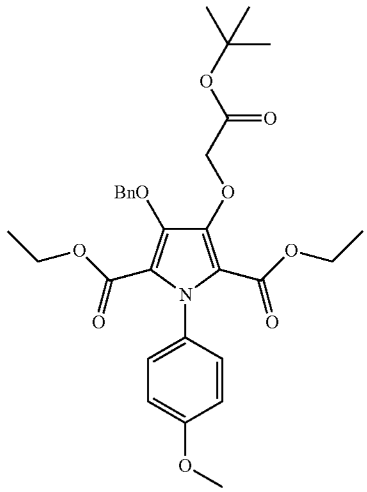 [SMILES: CCOC(=O)c1c(OCC(=O)OC(C)(C)C)c(OCc2ccccc2)c(C(=O)OCC)n1-c1ccc(OC)cc1] | diethyl 3-(benzyloxy)-4-(2-(tert-butoxy)-2-oxoethoxy)-1-(4-methoxyphenyl)-1H-pyrrole-2,5-dicarboxylate | UL2-028 | + | δ: 7.49-7.44 (m, 2H), 7.43-7.31 (m, 3H), 7.15-7.08 (m, 2H), 6.94-6.88 (m, 2H), 5.12 (s, 2H), 4.59 (s, 2H), 4.02-3.94 (m, 4H), 3.79 (s, 3H), 1.40 (s, 9H), 1.03-0.93 (m, 6H). | m/z 554 (M + H)$^+$ (ES$^+$) | Example N |
| 155 | 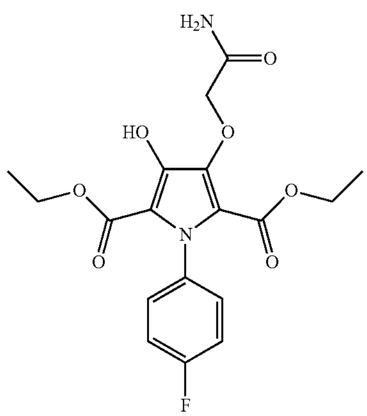 [SMILES: CCOC(=O)c1c(O)c(OCC(N)=O)c(C(=O)OCC)n1-c1ccc(F)cc1] | diethyl 3-(2-amino-2-oxoethoxy)-1-(4-fluorophenyl)-4-hydroxy-1H-pyrrole-2,5-dicarboxylate | UL2-029 | + | δ: 9.72 (s, 1H), 7.80-7.67 (m, 2H), 7.31-7.23 (m, 2H), 7.22-7.14 (m, 2H), 4.50 (s, 2H), 4.04-3.94 (m, 4H), 1.04-0.97 (m, 6H). | m/z 395 (M + H)$^+$ (ES$^+$), 393 (M − H)$^-$ (ES$^-$) | As example N except UL2-003 used in step (i) |
| 156 | 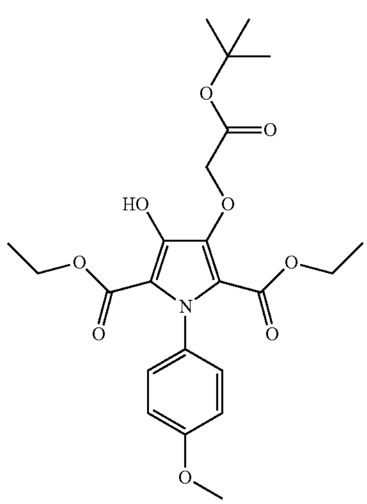 [SMILES: CCOC(=O)c1c(O)c(OCC(=O)OC(C)(C)C)c(C(=O)OCC)n1-c1ccc(OC)cc1] | diethyl 3-(2-(tert-butoxy)-2-oxoethoxy)-4-hydroxy-1-(4-methoxyphenyl)-1H-pyrrole-2,5-dicarboxylate | UL2-030 | ++ | δ: 8.85 (s, 1H), 7.14-7.06 (m, 2H), 6.93-6.86 (m, 2H), 4.59 (s, 2H), 4.02-3.93 (m, 4H), 3.78 (s, 3H), 1.44 (s, 9H), 1.03-0.92 (m, 6H). | m/z 408 (M + H − CH$_2$C(CH$_3$)$_2$)$^+$ (ES$^+$) | Prepared from standard Pd/C hydrogenation of UL2-028 |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 157 | 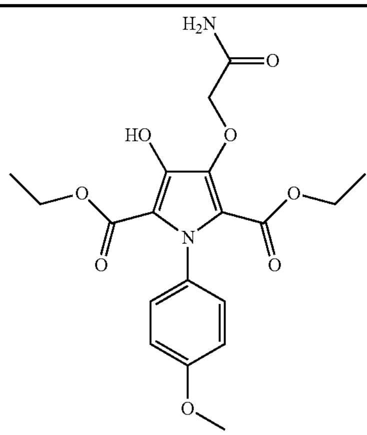 | diethyl 3-(2-amino-2-oxoethoxy)-4-hydroxy-1-(4-methoxyphenyl)-1H-pyrrole-2,5-dicarboxylate | UL2-031 | + | δ: 9.61 (s, 1H), 7.82-7.63 (m, 2H), 7.10-7.06 (m, 2H), 6.93-6.84 (m, 2H), 4.49 (s, 2H), 4.03-3.93 (m, 4H), 3.79 (s, 3H), 1.05-0.94 (m, 6H). | m/z 407 (M + H)$^+$ (ES$^+$), 405 (M − H)$^-$ (ES$^-$) | Example N |
| 158 | 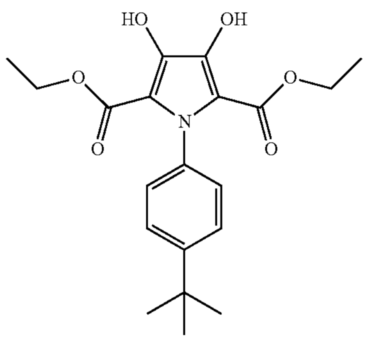 [SMILES: CCOC(=O)c1c(O)c(O)c(C(=O)OCC)n1-c1ccc(C(C)(C)C)cc1] | diethyl 1-(4-(tert-butyl)phenyl)-3,4-dihydroxy-1H-pyrrole-2,5-dicarboxylate | UL2-032 | +++ | δ: 8.68 (s, 2H), 7.36-7.31 (m, 2H), 7.08-7.03 (m, 2H), 3.94 (q, J = 7.1 Hz, 4H), 1.30 (s, 9H), 0.88 (t, J = 7.1 Hz, 6H). | m/z 376 (M + H)$^+$ (ES$^+$) | As UL1-012 except 4-(tert-butyl)aniline used in step (i) |
| 159 | 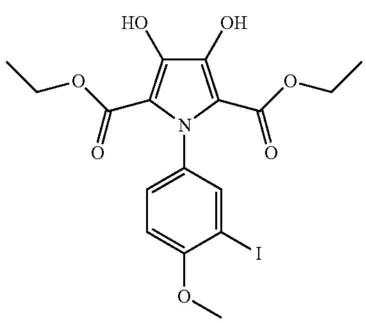 [SMILES: CCOC(=O)c1c(O)c(O)c(C(=O)OCC)n1-c1ccc(OC)c(I)c1] | diethyl 3,4-dihydroxy-1-(3-iodo-4-methoxyphenyl)-1H-pyrrole-2,5-dicarboxylate | UL2-033 | +++ | δ: 8.75 (s, 2H), 7.59-7.53 (m, 1H), 7.15-7.08 (m, 1H), 6.96-6.88 (m, 1H), 4.00 (t, J = 7.1 Hz, 4H), 3.84 (s, 3H), 0.99 (t, J = 7.1 Hz, 6H). | m/z 476 (M + H)$^+$ (ES$^+$), 473 (M − H)$^-$ (ES$^-$) | As UL1-012 except 3-iodo-4-methoxyaniline used in step (i) |
| 160 | 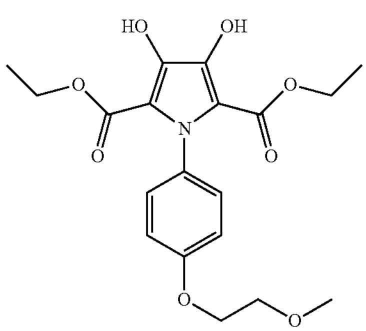 [SMILES: CCOC(=O)c1c(O)c(O)c(C(=O)OCC)n1-c1ccc(OCCOC)cc1] | diethyl 3,4-dihydroxy-1-(4-(2-methoxyethoxy)phenyl)-1H-pyrrole-2,5-dicarboxylate | UL2-034 | +++ | δ: 8.63 (s, 2H), 7.07-7.00 (m, 2H), 6.90-6.83 (m, 2H), 4.13-4.06 (m, 2H), 3.97 (q, J = 7.1 Hz, 4H), 3.71-3.63 (m, 2H), 3.32 (s, 3H), 0.97 (t, J = 7.1 Hz, 6H). | m/z 394 (M + H)$^+$ (ES$^+$); 392 (M − H)$^-$ (ES$^-$) | As example B except 4-(2-methoxyethoxy)aniline used in step (i) |

TABLE 1-continued

| Entry | Structure | Compound name | ID | IC$_{50}$ | $^1$H NMR Data (DMSO-d$_6$) | Ionisation | Preparation |
|---|---|---|---|---|---|---|---|
| 161 | 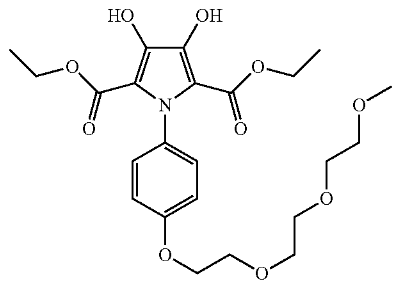 [SMILES: CCOC(=O)c1c(O)c(O)c(C(=O)OCC)n1-c1ccc(OCCOCCOCCOC)cc1] | diethyl 3,4-dihydroxy-1-(4-(2-(2-(2-methoxyethoxy)ethoxy)ethoxy)phenyl)-1H-pyrrole-2,5-dicarboxylate | UL2-035 | +++ | δ: 8.64 (m, 2H), 7.04-7.07 (m, 2H), 6.86-6.90 (m, 2H), 4.10-4.12 (m, 2H), 3.99 (q, J = 7.0 Hz, 4H), 3.75-3.77 (m, 2H), 3.59-3.62 (m, 2H), 3.52-3.56 (m, 4H), 3.43-3.45 (m, 2H), 3.25 (s, 3H), 0.98 (t, J = 7.0 Hz, 6H). | m/z 482 (M + H)$^+$ (ES$^+$); 480 (M − H)$^−$ (ES$^−$) | As example B except 4-(2-(2-(2-methoxyethoxy)ethoxy)ethoxy)aniline used in step (i) |
| 162 | 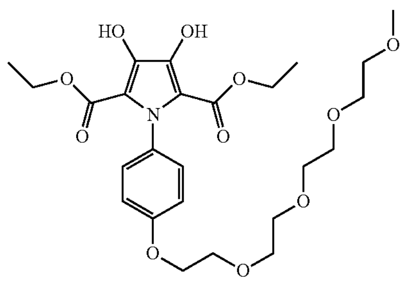 [SMILES: CCOC(=O)c1c(O)c(O)c(C(=O)OCC)n1-c1ccc(OCCOCCOCCOCCOC)cc1] | diethyl 1-(4-(2,5,8,11-tetraoxatridecan-13-yloxy)phenyl)-3,4-dihydroxy-1H-pyrrole-2,5-dicarboxylate | UL2-036 | +++ | δ: 8.63 (s, 2H), 7.03-7.07 (m, 2H), 6.86-6.90 (m, 2H), 4.10-4.12 (m, 2H), 3.98 (q, J = 7.1 Hz, 4H), 3.75-3.77 (m, 2H), 3.59-3.62 (m, 2H), 3.51-3.57 (m, 8H), 3.42-3.44 (m, 2H), 3.24 (s, 3H), 0.98 (t, J = 7.0 Hz, 6H). | m/z 526 (M + H)$^+$ (ES$^+$); 524 (M − H)$^−$ (ES$^−$) | As example B except 4-(2,5,8,11-tetraoxatridecan-13-yloxy)aniline used in step (i) |
| 163 | 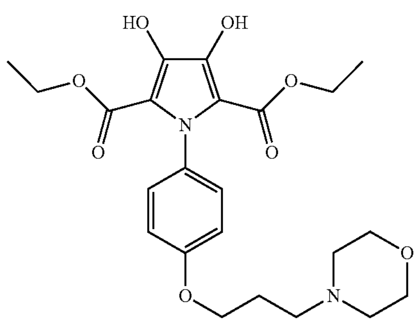 [SMILES: CCOC(=O)c1c(O)c(O)c(C(=O)OCC)n1-c1ccc(OCCCN2CCOCC2)cc1] | diethyl 3,4-dihydroxy-1-(4-(3-morpholinopropoxy)phenyl)-1H-pyrrole-2,5-dicarboxylate | UL2-037 | +++ | δ: 8.67 (s, 2H), 7.07-7.01 (m, 2H), 6.88-6.82 (m, 2H), 4.05-3.93 (m, 6H), 3.59 (br s, 4H), 2.48-2.34 (6H, br m), 1.96-1.84 (m, 2H), 0.97 (t, J = 7.1 Hz, 6H). | m/z 463 (M + H)$^+$ (ES$^+$); 461 (M − H)$^−$ (ES$^−$) | As example B except 4-(3-morpholinopropoxy)aniline used in step (i) |
| 164 | 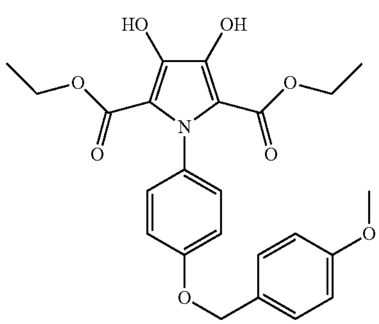 [SMILES: CCOC(=O)c1c(O)c(O)c(C(=O)OCC)n1-c1ccc(OCc2ccc(OC)cc2)cc1] | diethyl 3,4-dihydroxy-1-(4-((4-methoxybenzyl)oxy)phenyl)-1H-pyrrole-2,5-dicarboxylate | UL2-038 | +++ | δ: 8.66 (br s, 2H), 7.41-7.36 (m, 2H), 7.06-7.01 (m, 2H), 6.97-6.89 (m, 4H), 5.04 (s, 2H), 3.97 (q, J = 7.2 Hz, 4H), 3.75 (s, 3H), 0.94 (t, J = 7.2 Hz, 6H). | m/z 456 (M + H)$^+$ (ES$^+$) | As example B except 4-((4-methoxybenzyl)oxy)aniline used in step (i) |

*compounds are prodrug derivatives of UL1-012

Biological Testing

There is provided below a summary of the primary in vitro assay performed with all the compounds of the invention, and further assays performed with the compounds UL1-012 and UL2-001 as representatives for the biological activity of the compounds of the invention.

A. Primary In Vitro Assay: Inhibition of the Haemolytic Activity of PNEUMOLYSIN

Rationale

The basis of this assay is that when pneumolysin is added to red blood cells, it induces their lysis and leads to the release of haemoglobin. In the presence of an inhibitory compound, pneumolysin-induced lysis is abolished, the red blood cells pellet at the bottom of the microtitre plate well and the supernatant is clear. However, if the compound is not inhibitory, the red blood cells are lysed and haemoglobin is released into the supernatant.

Experimental Procedure

Test compound solutions (typically at 5 mM in DMSO) were diluted 1:1 in 100% DMSO. The compounds were then two-fold serially diluted in 100% DMSO across 11 wells of 96-well round-bottomed microtitre plate. PBS was then added to all the wells to achieve a 1:10 (v/v) dilution of the compound in PBS. Pneumolysin was then added at a concentration equal to its LD100. Plates were then incubated at 37° C. for 30-40 min. After the incubation period, an equal volume of 4% (v/v) sheep erythrocyte suspension was added to each well and the plates incubated again at 37° C., for at least 30 min. Controls with only erythrocytes in PBS (control for no lysis) or erythrocytes plus pneumolysin (control for lysis) were prepared following the same procedure. Following the incubation with the erythrocytes, the Absorbance at 595 nm of each well was measured and the data used to determine the $IC_{50}$ for each test compound. The $IC_{50}$ values were determined using non-linear regression curve fitting. For that, the Log of the concentrations of the test compound was plotted against the percentage inhibition, estimated from the $A_{595}$ values, followed by fitting a Hill Slope to the data.

Results $IC_{50}$ values for compounds of the invention generated in this assay are shown in Table 1 as follows: +++=$IC_{50}$<10 μM; ++=$IC_{50}$ 10 to <20 μM; +=$IC_{50}$ 20 to <60 μM.

Specific $IC_{50}$ values for representative compounds of the invention are:

UL1-004: $IC_{50}$ 0.17 μM; UL1-012: $IC_{50}$ 0.15 μM; UL1-024: $IC_{50}$ 0.182 μM; UL1-028: $IC_{50}$ 0.068 μM; UL1-049: $IC_{50}$ 0.479 μM; UL2-001: $IC_{50}$ 0.3 μM; UL1-005: $IC_{50}$ 0.15 μM; UL1-035: $IC_{50}$ 0.15 μM; UL1-089: $IC_{50}$ 0.4 μM; UL1-106: $IC_{50}$ 0.17 μM; UL1-116: $IC_{50}$ 0.18 μM.

B. Primary In Vitro Assay: Inhibition of the Haemolytic Activity of Other Cholesterol Dependent Cytolysins Compounds UL1-012 and UL2-001 were tested for their ability to inhibit the haemolytic activity of Streptolysin O (SLO), Perfringolysin O (PFO), Listeriolysin O (LLO), Anthrolysin O (ALO) and Suilysin (SLY) using the assay protocol outlined in the above Section A. Inhibition of haemolysis of these toxins was obtained with $IC_{50}$ as indicated in the table below (Table 2).

TABLE 2

| Toxin | $IC_{50}$ for UL1-012 | $IC_{50}$ for UL2-001 |
|---|---|---|
| SLO | +++ | + |
| PFO | +++ | +++ |
| LLO | +++ | +++ |
| ALO | +++ | +++ |
| SLY | +++ | +++ |

+++ = $IC_{50}$ < 10 μM;
++ = IC50 10 to < 20 μM;
+ = IC50 20 to < 60 μM

C. Secondary In Vitro Assay: Inhibition of Pneumolysin-Induced Lactate Dehydrogenase Release Rationale Pneumolysin induces the release of lactate dehydrogenase (LDH) from human monocytes and lung epithelial cells: a phenomenon that is indicative of plasma membrane damage or rupture [Infect. Immun. (2002) 70 1017-1022]. The LDH assay was applied to demonstrate the ability of the disclosed compounds to inhibit the cytotoxic effect of pneumolysin on human lung epithelial cells in culture. The use of this assay can provide two main pieces of information on (1) Activity, to demonstrate the inhibition of LDH release from cells exposed to pneumolysin in the presence of inhibitory compounds versus the LDH release from cells exposed to pneumolysin alone, (2) Compound toxicity, the assay format was designed so it allows, in the control wells, the testing of the LDH release from cells exposed to the compound only.

Experimental Procedure

Human lung epithelial cells (A549) were seeded in flat-bottomed 96-well tissue culture plates and grown in RPMI 1640 medium supplemented with Glutamine, at 37° C., 5% $CO_2$, for 24 h. Before use, the cells were washed with PBS. Test compound dilutions were incubated with pneumolysin as described in Section A, then transferred to wells containing the human lung epithelial cells and the plates were incubated at 37° C., 5% $CO_2$, for 30 min. The following controls were included on the plate (1) Negative controls, called low control (PBS only) to measure the natural release of LDH from the cells in culture, (2) positive controls (1% (v/v) Triton-X in PBS) to measure the maximum release of LDH from the cells (3) Pneumolysin solution only to measure pneumolysin-induced LDH release, (4) Test compound solution to assess the toxicity of the compound alone. After incubation, the supernatant was transferred to the wells of round-bottomed 96-well microtitre plates containing a double volume of lactate dehydrogenase assay mixture (TOX7, Sigma) prepared according to manufacturer's instructions. Incubation in a light-proof chamber at RT for 5-10 min was followed by the addition of 1N HCl to all wells. Absorbance at 490 nm and 655 nm was then measured. The percentage of LDH release induced by pneumolysin in the presence and absence of test compounds was plotted against the Log of the concentration of the compound and the $IC_{50}$ was determined, as described above in the inhibition of haemolysis assay, Section A.

Results

UL1-012 was tested in the LDH assay in triplicate over a range of concentration from 62.5 μM to 0.49 μM. The results obtained are shown in FIG. 1.

In FIG. 1: (1) The horizontal dotted line at 100%, PLY control (O), indicates the maximum release of LDH from the cells under the effect of pneumolysin, as opposed to the horizontal solid line at 0% (low control), which corresponds to the supernatant of cells exposed to the assay buffer alone that shows the natural LDH release under the assay conditions. (2) The grey solid line ( ⊙ ) shows that the LDH release from cells exposed to pneumolysin was significantly reduced in the presence of UL1-012, in a dose response manner, when compared to the PLY control. This demonstrates that UL1-

012 prevents pneumolysin from damaging the human lung epithelial cells in culture, with an $IC_{50}<0.4$ μM. (3) The dotted black line (x) shows that UL1-012 does not exhibit cytotoxicity at the concentrations tested, up to approximately 150 times the therapeutic $IC_{50}$ value.

Conclusion

UL1-012 inhibits the damaging activity of pneumolysin on human lung epithelial cells in culture. UL1-012 did not exhibit cytotoxic effects on the human lung epithelial cells at 150 times the therapeutic $IC_{50}$ value.

D. Ex Vivo Assay: Inhibition of the Effect of Pneumolysin on the Ciliary Function of Cultured Ependymal Cells Rationale The ependymal ciliated cells line the cerebral ventricles of the brain and the central canal of the spinal cord and are covered with cilia responsible for the circulation of the cerebrospinal fluid (CSF) around the central nervous system. This layer acts as a selective brain barrier to and from the cerebrospinal fluid and plays a role in controlling the CSF volume. Long standing research in this field in the laboratory of the inventors resulted in the development of a rat ex vivo model of meningitis that was proven to predict the in vivo situation during meningitis. This model is based on culturing and differentiating ciliated ependymal cells from neonate rat brains, which recreate the in vivo situation, where cells lining the brain ventricles, are exposed to S. pneumoniae and its toxic products.

The use of the ex vivo model of meningitis constitutes a powerful means to predict the ability of a compound to prevent pneumolysin from causing damage in vivo.

Experimental Procedure

Ependymal cell cultures were prepared by the method previously described [Microb. Pathog. (1999) 27 303-309]. Tissue culture trays were coated with bovine fibronectin and incubated at 37° C. in 5% (v/v) $CO_2$ for 2 h before use. The growth medium was minimum essential medium (MEM) with added penicillin (100 IU/ml), streptomycin (100 μg/ml), fungizone (2.5 μg/ml), BSA (5 μg/ml), insulin (5 μg/ml), transferrin (10 μg/ml) and selenium (5 μg/ml). Neo-natal (0-1 day old) rats were killed by cervical dislocation, and their brains were removed. The cerebellum was removed along with edge regions of the left and right cortical hemispheres and the frontal cortex. The remaining brain areas were mechanically dissociated in 4 ml of growth medium. The dissociated tissue from one or two brains was added to the wells of the tissue culture trays (500 μl/well), each containing 2.5 ml of growth medium. The cells then were incubated at 37° C. in 5% (v/v) $CO_2$. The medium was replaced after three days and thereafter the ependymal cells were fed every two days with 2 ml of fresh growth medium supplemented with thrombin.

After approximately two weeks, the cells were fully ciliated and ready for experiments. For experiments, the growth medium replaced with 1 ml of medium MEM containing 25 mM HEPES, pH 7.4. The tissue culture trays were placed inside a thermostatically controlled incubation chamber surrounding the stage of an inverted light microscope. The cell cultures were allowed to equilibrate until the temperature of the assay medium was 37° C. At this point, either recombinant purified pneumolysin or S. pneumoniae cell lysate containing native pneumolysin—obtained following the lytic effect of the antibiotic Penicillin—with and without test compound, pre-incubated in 1 ml of medium MEM at 37° C. for 40 min, were added to the wells containing the ciliated cells. To the control cells, 1 ml of MEM medium was added. Beating cilia were recorded before and after exposure over 30 min, with a digital high-speed video camera at a rate of 500 frames/s. The recorded video sequences were played back at reduced frame rates and the ciliary beat frequency (CBF) was determined by the following equation:

$$CBF\ (Hz) = \frac{500\ \text{frames/s}}{(\text{frames elapsed for 5 ciliary beat cycles})} \times 5 (\text{conversion per beat cycle}).$$

Results

Figure 2A:
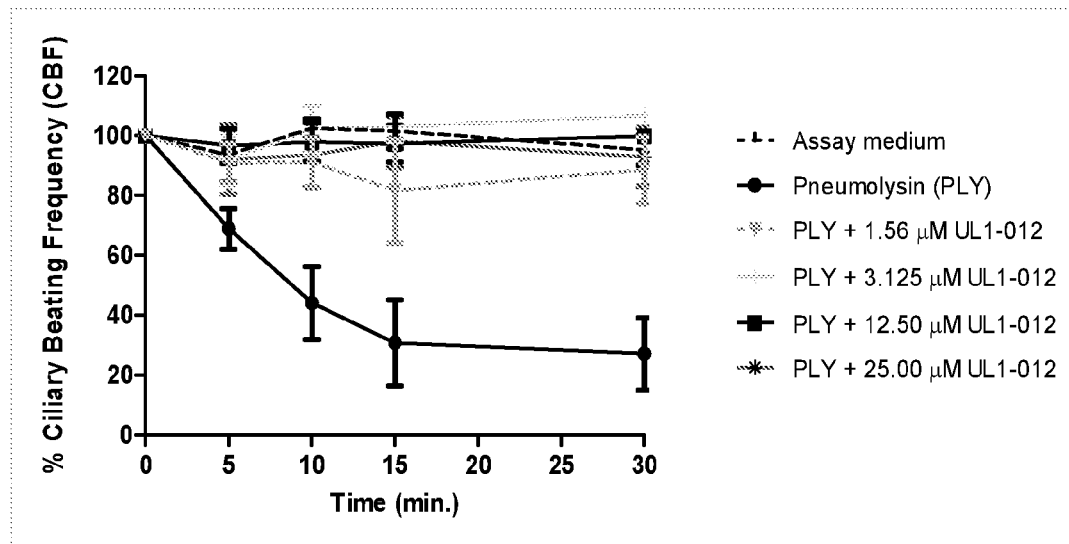
FIG. 2A shows the effect of the compound UL1-012 in inhibiting pneumolysin from damaging the ciliary function of ependymal cells in an ex vivo meningitis efficacy assay.
Figure 2B:
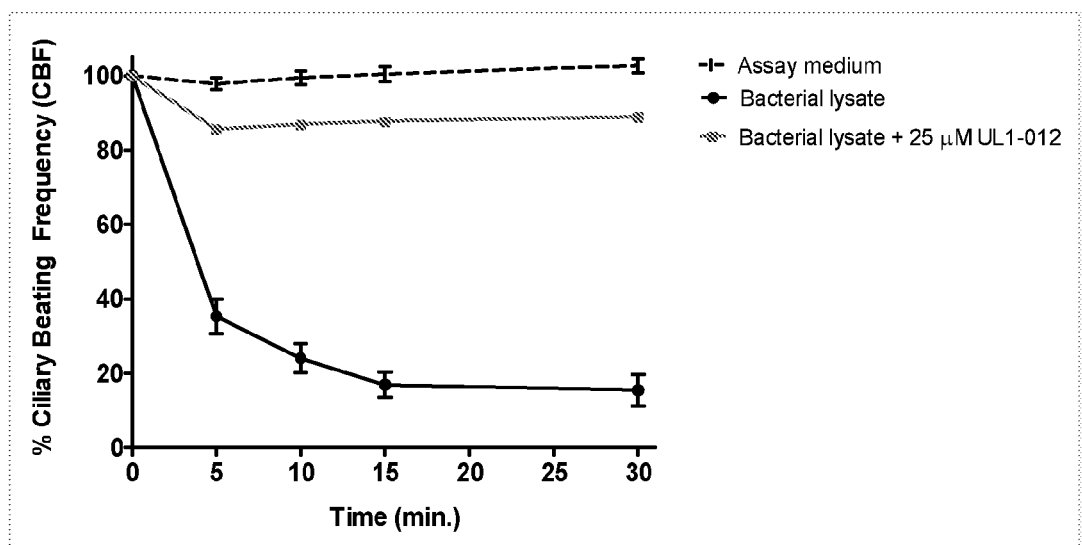
FIG. 2B shows the effect of the compound UL1-012 in inhibiting a bacterial lysate from damaging the ciliary function of ependymal cells in an ex vivo meningitis efficacy assay.
Figure 3:
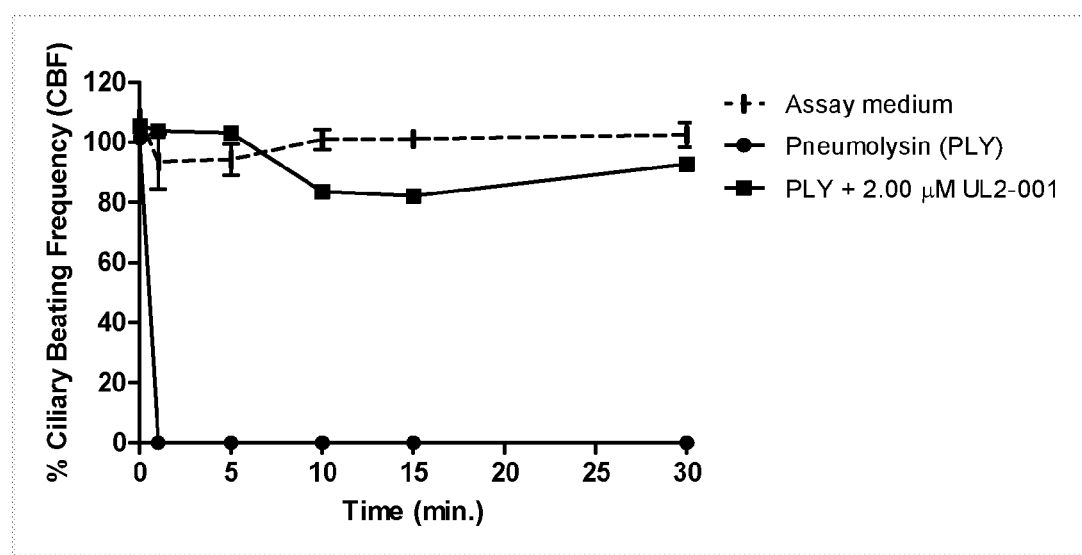
FIG. 3 shows the effect of the compound UL2-001 in inhibiting pneumolysin from damaging the ciliary function of ependymal cells in an ex vivo meningitis efficacy assay.

The parameter measured was the ciliary beating frequency (CBF). Pneumolysin or bacterial lysate, added to ciliated cells in culture induces a severe or total loss of ciliary beating. UL1-012 and UL2-001 inhibited this damaging effect induced by pneumolysin on the ciliary function of ependymal cells in culture (FIG. 2.A and FIG. 3, respectively). Furthermore, UL1-012 was also shown to inhibit the detrimental effect caused by a bacterial lysate, using the same ex vivo model (FIG. 2.B).

In FIG. 2.A: Each time point represents the normalised mean±SD of ciliary beating frequency (CBF) measurements of four individual cilia from each well, in three independent experiments. (1) Control 1, assay medium only: the symbol (-|-) represents measurements of the CBF in the assay medium which was used as a reference for the normal cilia beating. No damaging effect on the CBF was seen throughout the recording. (2) Control 2, pneumolysin only: The symbol (◆) represents measurements of the CBF in the wells where pneumolysin was added. A progressive drop in the CBF to 27% of the original frequency was observed. (3) Treatment with UL1-012: Symbols ( ; ■; ✴ ) represent the measurements of the CBF in the presence of pneumolysin and UL1-012 (1.56 μM-25 μM). No significant loss of the CBF was seen, showing that UL1-012 inhibits pneumolysin-induced damage on the ciliary beating frequency of the brain ependymal cells. There was no statistical difference between the CBF of Control 1 (medium only) and the CBF in the presence of the treatment ( ; ■; ✴ ), indicating that the inhibition of the damaging effect of pneumolysin by UL1-012 was achieved to an extent comparable to the control medium alone.

In FIG. 2.B: Each time point represents the normalised mean±SD of ciliary beating frequency (CBF) measurements of four individual cilia from each well, in three independent experiments. (1) Control 1, assay medium only: the symbol (-|-) represents measurements of the CBF in the assay medium which was used as a reference for the normal cilia beating. No damaging effect on the CBF was seen throughout the recording. (2) Control 2, bacterial lysate: the symbol (◆) represents measurements of the CBF in the wells where the bacterial lysate obtained from penicillin-lysed S. pneumoniae induced a significant reduction in the CBF within the first five minutes of the recording, to 16% of the original frequency. (3) Treatment with UL1-012: the symbol (※) represents the measurements of the CBF in the presence of treatment UL1-012 and bacterial lysate obtained from penicillin-lysed S. pneumoniae. UL1-012 significantly prevented the drop of the CBF, indicating that UL1-012 inhibits pneumolysin released from penicillin-lysed bacteria, to a similar extent of the control 1 (-|-); healthy cilia in the presence of the assay medium.

In FIG. 3: Each time point represents the normalised mean±SD of ciliary beating frequency (CBF) measurements of four individual cilia from each well, in three independent experiments. (1) Control 1, assay medium only: the symbol (-|-) represents measurements of the CBF in the assay medium which was used as a reference for the normal cilia beating. No damaging effect on the CBF was seen throughout the recording (2) Control 2, pneumolysin only: The symbol (♦) represents measurements of the CBF in the wells where pneumolysin was added. A rapid drop in the CBF, with complete inhibition by 1 minute after the addition of pneumolysin was observed (3) Treatment with UL2-001: Symbol (-■-) represent the measurements of the CBF in the presence of pneumolysin and UL2-001 (2.00 µM). No significant loss of the CBF was seen, showing that UL2-001 inhibits pneumolysin-induced damage on the ciliary beating frequency of the brain ependymal cells. There was no statistical difference between the CBF of Control 1 (medium only) and the CBF in the presence of the treatment, indicating that the inhibition of the damaging effect of pneumolysin by UL2-001 was achieved to an extent comparable to the control medium alone.

Conclusion

UL1-012 and UL2-001 inhibit the damaging effect that pneumolysin induces on the brain ependymal ciliated cells in culture which predicts its ability to prevent pneumolysin from causing damage in vivo. In addition, UL1-012 demonstrated the ability to also inhibit the native pneumolysin, released by pneumococcus following antibiotic-mediated lysis. It is remarkable that the inhibition of pneumolysin only, amongst all other bacterial products present in *S. pneumoniae* bacterial lysate, was sufficient to abolish the damaging effect of the whole bacterial lysate, which highlights again the substantial involvement of pneumolysin in the damaging effect of antibiotic lysed bacteria.

These findings support the use of this novel-approach as an adjunctive therapy in patients.

E. In Vivo Efficacy Assay Using a Mouse Pneumonia Model

Rationale

This model has been long developed and well established in the laboratory of the inventors and has become adapted by other research groups working in this field. Using this model, pneumolysin was shown to be essential for the pathogenesis of *S. pneumoniae* and for its survival in vivo. With this disease model, mice infected with a strain of *S. pneumoniae* mutant deficient in pneumolysin (PLN-A), exhibited (1) a significant increase in the survival, (2) significant delay and attenuation of the signs of the disease and (3) substantial decrease in the pulmonary inflammation and less bacteraemia (infiltration of the bacteria from the lungs to the circulation). Therefore, this in vivo disease model constitutes a powerful tool to study the disease progression of mice infected with wild-type *S. pneumoniae* and treated with pneumolysin inhibitors. To assess the severity of the disease, the parameters that are followed are the survival and the disease score.

Experimental Procedures: Infection, Treatment and Disease Signs Scoring

Outbred MF1 female mice, 8 weeks old or more and weighing 25-30 g were used. The animals were maintained under controlled conditions of temperature, humidity and day length. They had free access to tap water and pelleted food. The in vivo experiments were performed using two control groups: Control 1 (infected and not treated), Control 2 (not infected and treated) and one Treatment group (infected and treated). Mice in control group 1 and in the treatment group were infected intranasally with *Streptococcus pneumoniae* strain D39 (procedure described below). After completing the infections, the viable count of the given dose was determined (as described below). Subsequently, every six hours, animals in the Treatment group and in Control group 2, received the test compound intravenously or intranasally as appropriate while excipient alone was administered to Control group 1. The progress of the signs of disease (Table 3) was assessed every 6 h based on the scheme of Morton and Griffiths [Veterinary Record. (1985) 111, 431-436].

Animals were killed if they became 2+ lethargic and the time was recorded. After approximately 72 h the experiment was ended. The survival rates of control and test groups were compared with a log-rank test, while the signs of disease were compared with the Mann-Whitney test.

TABLE 3

Scoring scheme of the disease signs

| Sign | Description | Score |
| --- | --- | --- |
| Normal | Healthy appearance. Highly active. | 0 |
| 1+/2+ Hunched | Slight (1+) or pronounced (2+) convex curvature of the upper spine. | 1; 2 |
| 1+/2+ Starey coat (Piloerection) | Slight (1+) or pronounced (2+) piloerection of the coat. | 3; 4 |
| 1+/2+ Lethargic | Pronounced hunching and piloerection accompanied by a considerable (1+) or severe (2+) reduction of activity. | 5; 6 |
| Moribund | Complete inertia. Drastic reduction of breathing rate. Drop of the body temperature. | N/A |

N/A - Not applicable

The administration of *S. pneumoniae*/Treatment and the determination of the bacterial viable counts mentioned in the above procedure are detailed as follows:

—Intranasal Administration

Mice were lightly anaesthetised with 2.5% (v/v) isoflurane over 1.6-1.8 L $O_2$/min. The confirmation of effective anaesthesia was made by observation of no pedal reflex. A mouse was held by the scruff of the neck in a vertical position with its nose upward. The dose was then administered in sterile PBS, given drop by drop into the nostrils, allowing the animal to inhale it in between drops. Once the dose was given, the mouse was returned to its cage, placed on its back to recover from the effects of anaesthetic.

—Intravenous Administration

Mice were placed in a cage inside an incubator at 37° C., for 20 min, to dilate their veins. After incubation, the cage was brought outside and the mice were kept warm under an infrared (IR) lamp. A mouse was then placed inside a restrainer, leaving the tail of the animal exposed. The tail was disinfected with 10% (v/v) Microsol in water. The dose was then gently administered intravenously using a 0.5 mL insulin syringe inserted carefully into one of the tail lateral veins.

—Determination of Viable Counts

Viable counting was performed by the method of Miles and Misra [J. Hyg. (1938) 38 732-749). 20 µl of the sample were serially diluted in 180 µl PBS in round-bottomed 96-wells microtitre plates, up to a dilution of $10^6$. Blood agar plates were divided into six sectors and 60 µl of each dilution plated onto an individual sector. The plates were incubated in $CO_2$ gas jars overnight at 37° C. The following day, colonies were counted in the sector where 30-300 colonies were visible. The concentration of colony forming units (CFU) per millilitre was determined by using the following equation:

$$CFU \text{ per ml} = \frac{\text{Number of colonies in sector}}{60 \, \mu l} \times \text{Dilution} \times 1000 (\text{conversion factor}).$$

Results of the In Vivo Efficacy Assay Obtained with Example UL1-012

—Experimental Design

Figure 4:
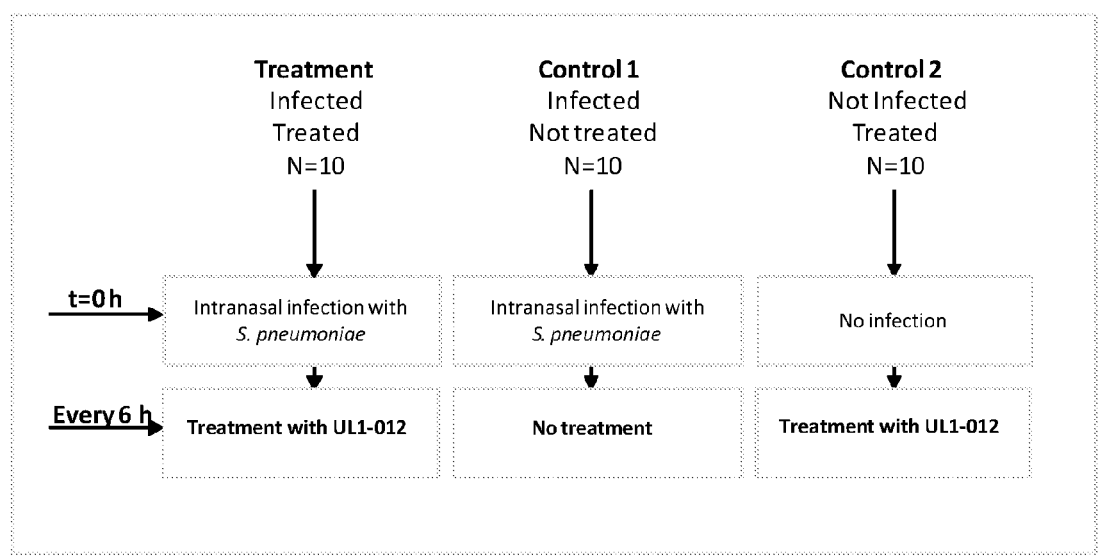
FIG. 4 shows the experimental design for an in vivo mouse pneumonia model efficacy assay using the compound UL1-012.

The experimental design is shown in FIG. 4. The treatment with UL1-012 was administered intravenously every 6 h. Based on the $IC_{100}$ concentration seen in the primary assay, the amount of compound required to neutralise pneumolysin released in vivo during the most severe phase of infection, was calculated. A dose of 4 mg/kg prepared in 2% (v/v) DMSO in PBS was given. This proved effective. In subsequent PD experiments, 16 mg/kg prepared in 4% (v/v) DMSO in PBS was also used. The doses were prepared freshly and administered intravenously to the animals.

Figure 5:
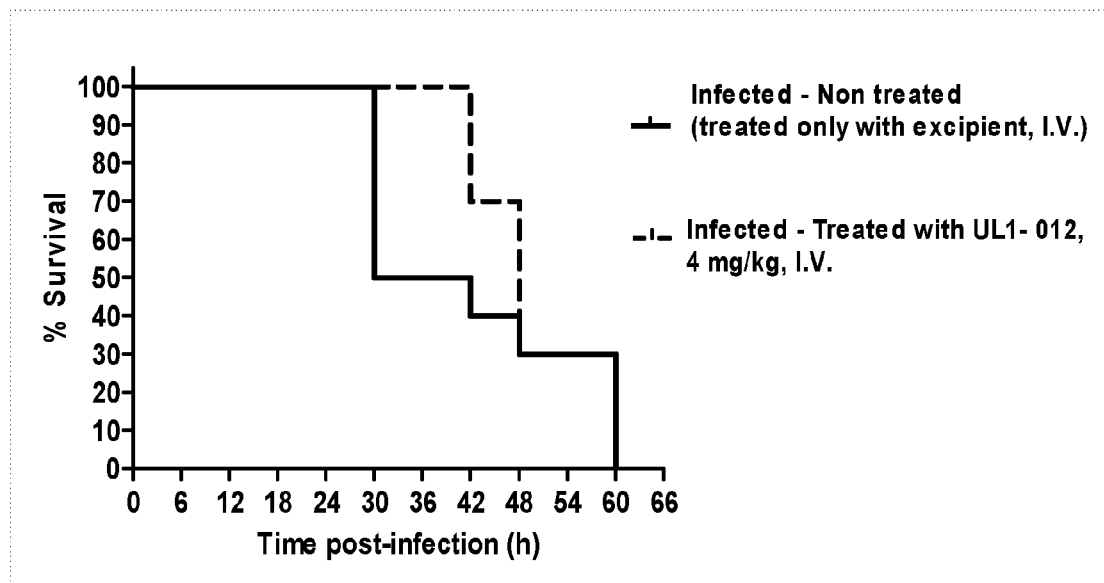
FIG. 5 shows the survival of infected control mice and treated groups administered with 4 mg/kg of the compound UL1-012 in an in vivo mouse pneumonia model efficacy assay.

—Survival Results 4 mg/kg of body weight of UL1-012 was administered intravenously every 6 h to mice infected with *S. pneumoniae* and the outcome compared against a control group of infected mice, which had not received the compound (only the excipient). The p-value was calculated by means of the log-rank (Mantel-Cox) test (n=10/group). The survival curves of the control (solid line) and treatment (dotted line) groups obtained with this experiment are presented in FIG. 5. Up to approximately 40 h after infection, there was a significant improvement in the survival of the treatment group over the control group ($p<0.05$). 4 mg/kg of UL1-012 produced a good outcome with a significant increase of the survival at critical time points where we usually see a rapid disease progression of untreated animals ($p<0.05$).

Figure 6:
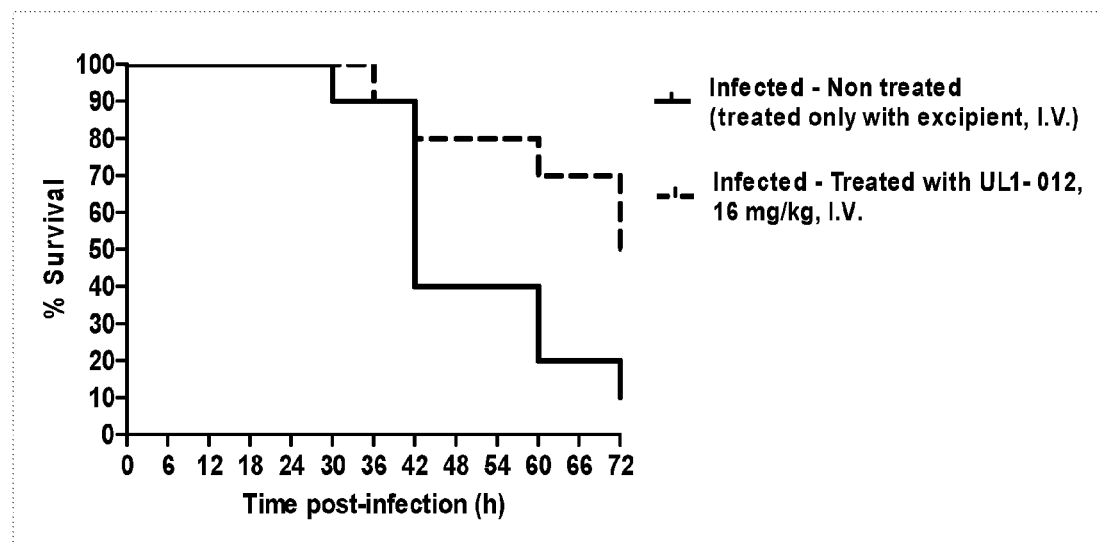
FIG. 6 shows the survival of infected control mice and treated groups administered with 16 mg/kg of the compound UL1-012 in an in vivo mouse pneumonia model efficacy assay.

16 mg/kg of body weight of UL1-012 was used. Six hours post infection with wild-type *S. pneumoniae*, animals received intravenously UL1-012 (16 mg/kg) and every 6 h thereafter. The p-value was calculated by means of the log-rank (Mantel-Cox) test (n=10/group). This was performed to test if protection could be enhanced but also to test if a higher dose is as tolerated. As shown in FIG. 6, a significant increase in the survival was seen with 50% of mice surviving at the endpoint of the experiment at 72 h post infection ($p<0.05$).

—Disease Score Results

During the course of the experiment, the signs of the disease were assessed at least every 6 h and disease scores were noted for each mouse. At various time points of the experiment, infected/non-treated mice exhibited pronounced signs of the disease, reflected by their hunched spine, piloerect coat and reduction in their activity. On the other hand, a significantly higher number of infected mice that received the treatment with UL1-012 had a healthy appearance (spine not hunched, coat not standing) and were highly active, exploring the cage surroundings.

Figure 7:
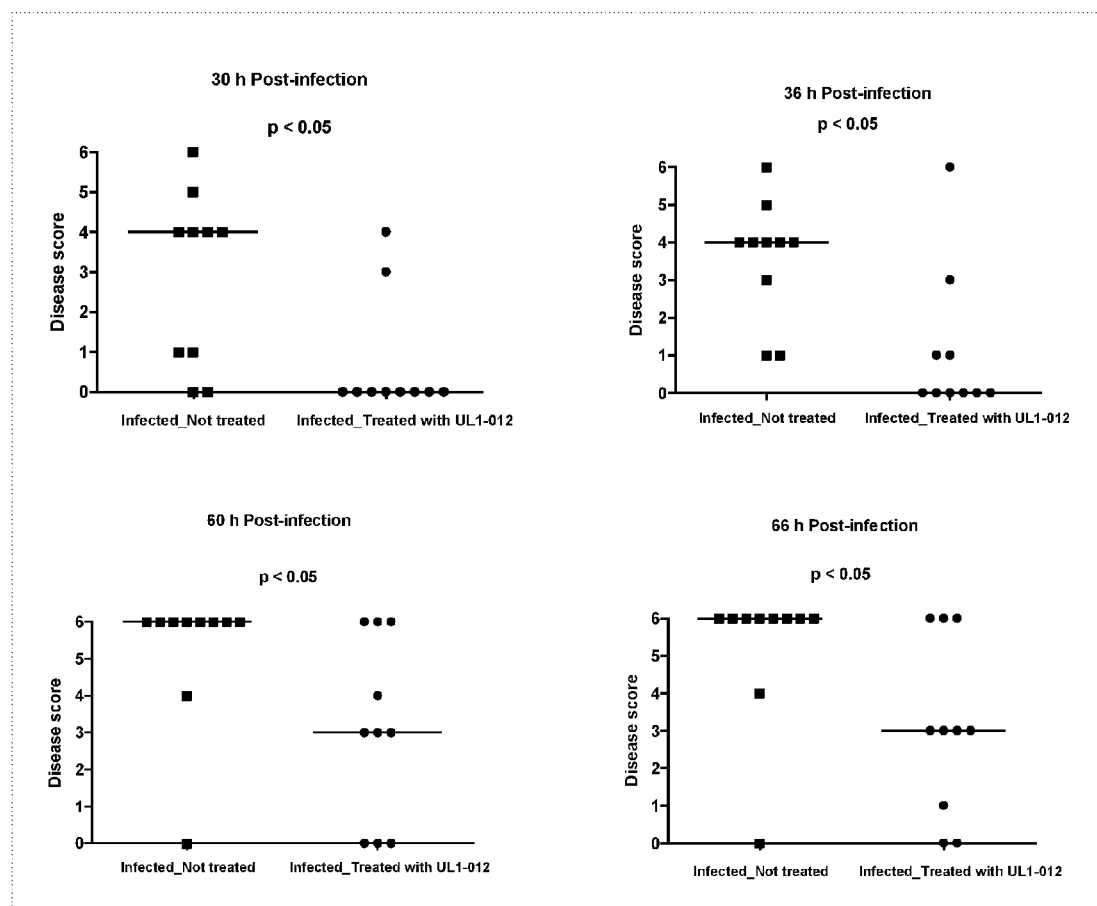
FIG. 7 shows a comparison of the signs of disease between an infected/non-treated control group and an infected/treated group that received 16 mg/kg of the compound UL1-012 in an in vivo mouse pneumonia model efficacy assay.

Disease scoring with 16 mg/kg of UL1-012 recorded at multiple time points during the course of the experiment is shown in FIG. 7. Each symbol (■;●) represents an individual mouse in the control and treatment group, respectively; horizontal lines represent medians; p-values were calculated by using a Mann-Whitney test. A delay in the onset of the signs of the disease for the group that was treated with UL1-012 was obtained. The difference in the disease scoring between the two groups was statistically significant ($p<0.05$) at 30 h, 36 h, 60 h and 66 h post-infection. The results indicate a delay in the onset of the disease and a significant attenuation of the signs of the disease.

—Conclusion (1) In vivo protection was obtained with UL1-012 at both dosing regimen tested. (2) Higher dose of UL1-012 provided an enhanced protection showing that there is a dose dependent response. (3) Protection is seen even in the absence of an antibiotic, which is a remarkable outcome, suggesting that the neutralisation of pneumolysin alone, without the killing of the bacterium, is providing protection to the animals. This is consistent with the disease profile obtained with *S. pneumoniae* deficient in pneumolysin (PLN-A). (4) Even at the highest concentration of UL1-012, no visible adverse effects were seen in the control group of mice receiving the compound alone.

Results of the In Vivo Efficacy Assay Obtained with Example UL2-001

—Experimental Set Up

Figure 8:
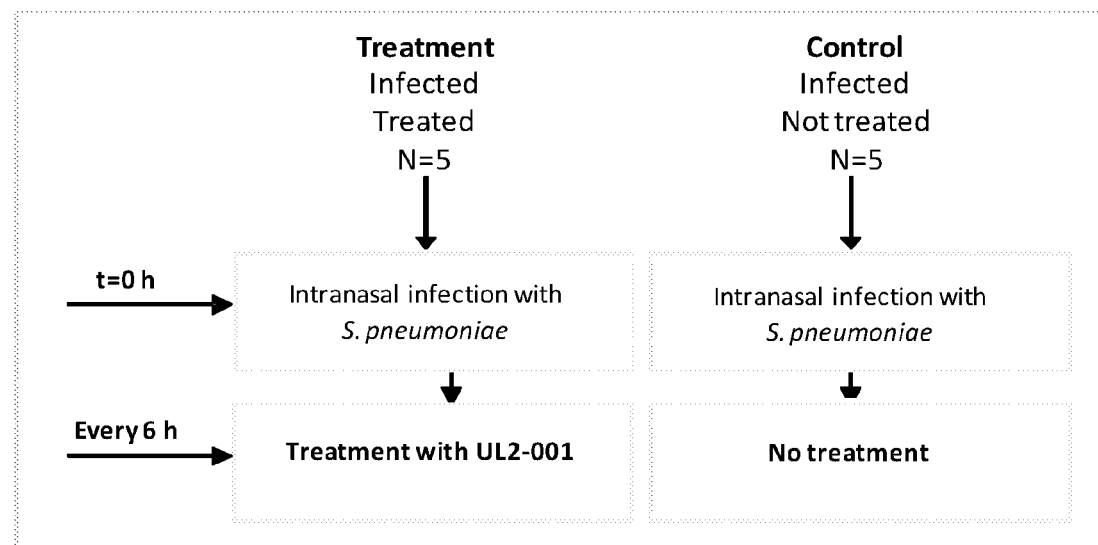
FIG. 8 shows the experimental design for an in vivo mouse pneumonia model efficacy assay using the compound UL2-001.

The in vivo efficacy of Example UL2-001 was tested using a pneumonia model. The experimental design is shown in FIG. 8. The treatment with UL2-001 was administered intranasally every 6 h. Based on the $IC_{100}$ concentration seen in the primary assay, the amount of compound required to neutralise pneumolysin released in vivo during the most severe phase of infection, was calculated. A dose of 0.8 mg/kg prepared in 2% (v/v) DMSO in PBS was given. This proved effective. The doses were prepared freshly and administered intranasally to the animals.

Figure 9:
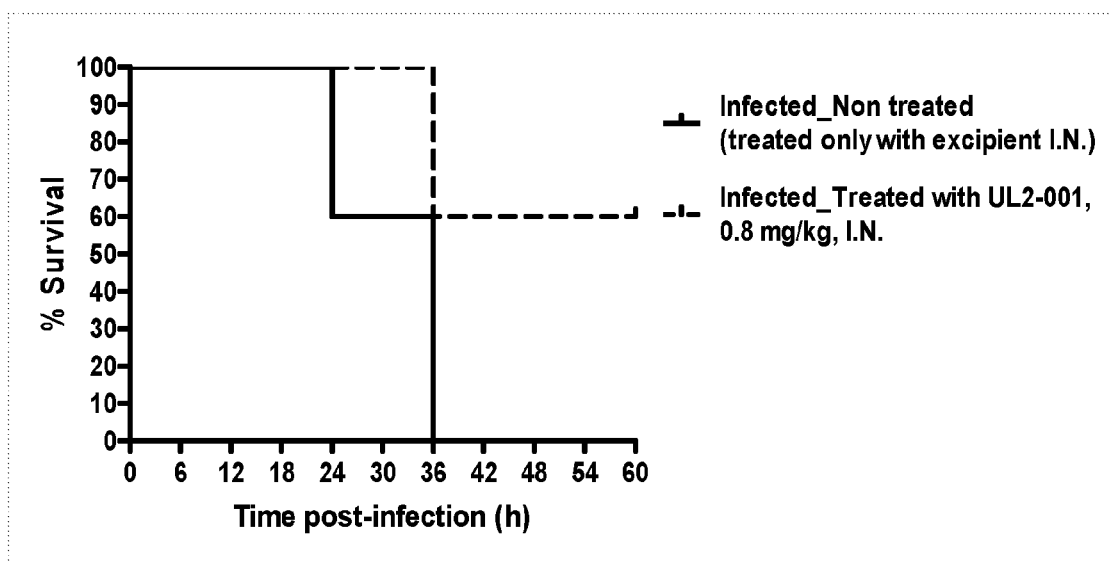
FIG. 9 shows the survival of infected control mice and treated groups administered with 8 mg/kg of the compound UL2-001 in an in vivo mouse pneumonia model efficacy assay.

—Survival Results 0.8 mg/kg of body weight of UL2-001 was administered intranasally every 6 h to mice infected intranasally with *S. pneumoniae* and the outcome compared against a control group of infected mice, which had not received the compound (only the excipient). The p-value was calculated by means of the log-rank (Mantel-Cox) test (n=5/group). The survival curves of the control (solid line) and treatment (dotted line) groups obtained with this experiment are presented in FIG. 9. 36 hours post-infection infection, all mice in the control group had died. At this time-point, the percentage of survival of the treatment group had dropped to 60%, and then remained constant until the endpoint of the experiment at 60 hours post-infection. This experimental outcome has shown a significant improvement in the survival of the treatment group over the control group ($p<0.05$).

—Conclusion (1) In vivo protection was obtained with UL2-001 following intranasal administration. (2) Protection is seen even in the absence of an antibiotic, suggesting that the neutralisation of pneumolysin alone, without the killing of the bacterium, is providing protection to the animals. This is consistent with the disease profile obtained with *S. pneumoniae* deficient in pneumolysin (PLN-A).

F. Conversion of Prodrug Derivatives to Active Inhibitors in Mouse and Human Plasma Rationale To demonstrate that the prodrug derivatives are converted to the active ingredient in the presence of plasma enzymes, a prodrug derivative was incubated with mouse and human plasma at 37° C. at 5 time points over a 2 h period. The samples were then analysed by LC-MS/MS to obtain the amount of active compound appearing and prodrug derivative remaining over time. The mouse plasma assay system is considered to be a good model for human behaviour. Nevertheless data obtained in a human plasma assay system was obtained in some cases.

Experimental Procedure

Prodrug derivatives were assessed in the mouse and human plasma stability assay at a concentration of 10 µM. Test compounds were diluted in DMSO to a final stock concentration of 10 mM. For the purpose of the assay, the stocks prepared were further diluted in DMSO to a concentration of 400 µM and 5 were added to 195 µl of mouse or human plasma (pH 7.4) and then incubated at 37° C. The final concentration of DMSO in the plate was 2.5% (v/v). Reactions were terminated at 0, 15, 30, 60 and 120 min after incubation by adding 400 µl of acetonitrile containing 0.55 µM metoprolol and 1%

(v/v) formic acid. The plate was then centrifuged at 3000 rpm, for 45 min, at 4° C. 80 µl of supernatant were transferred into a conical bottom 96 well glass coated plate. 40 µl of water were added prior to analysis for prodrug derivative and active species by LC-MS/MS. This assay was performed by a contract research organisation, Cyprotex Discovery Limited, UK, at the request of the inventors at Leicester.

Results

The quantification of the parent compound (prodrug derivative) remaining and the active ingredient appearing was performed as follows:

(1) The active compound was quantified using a 6 point calibration curve prepared in deactivated mouse and human plasma. (2) The percentage of parent compound remaining at each time point relative to 0 min sample was calculated from LC-MS/MS peak area ratios (compound peak area/internal standard peak area). This percentage was then used to determine the concentration of the parent compound at each time point in reference to the starting concentration (10 µM) at time 0 min.

A summary of the conversion of the prodrug derivatives to active inhibitors is shown Table 4.

Conclusion

The results presented in Table 4 clearly indicate the therapeutic benefits of the prodrugs of the invention, which is demonstrated by their conversion in plasma into the pharmacologically active ingredient. The rate of conversion of the prodrug derivatives to the active ingredients is variable amongst the prodrug derivatives. This offers a range of different therapeutic strategies ranging from immediate to slow release, in order to achieve the desired therapeutic benefits.

TABLE 4

| Prodrug ID | Prodrug/Active* | [ ] (µM) $t_{0\ min.}$ | [ ] (µM) $t_{15\ min.}$ | [ ] (µM) $t_{30\ min.}$ | [ ] (µM) $t_{60\ min.}$ | [ ] (µM) $t_{120\ min.}$ |
|---|---|---|---|---|---|---|
| UL1-044 | Prodrug (UL1-044) | 10 | 0 | 0 | 0 | 0 |
|  | Active (UL1-012) | 0 | 9 | 11 | 11 | 13 |
| UL1-063 | Prodrug (UL1-063) | 10 | 10 | 9.20 | 9.40 | 8.50 |
|  | Active (UL1-012) | 0 | 0 | 0.02 | 0.03 | 0.05 |
| UL1-064 | Prodrug (UL1-064) | 10 | 3.10 | 7.00 | 5.00 | 2.20 |
|  | Active (UL1-012) | 0 | 0.02 | 0.11 | 0.24 | 0.37 |
| UL1-065 | Prodrug (UL1-065) | 10 | 4.21 | 3.72 | 2.57 | 1.14 |
|  | Active (UL1-012) | 0 | 0.05 | 0.07 | 0.12 | 0.19 |
| UL1-066 | Prodrug (UL1-066) | 10 | 9.90 | 10.00 | 9.78 | 9.50 |
|  | Active (UL1-012) | 0 | 0.23 | 0.23 | 0.21 | 0.20 |
| UL1-067 | Prodrug (UL1-067) | 10 | 0 | 0 | 0 | 0 |
|  | Active (UL1-012) | 0 | 10.40 | 10.60 | 10.10 | 10.80 |
| UL1-068 | Prodrug (UL1-068) | 10 | 3.02 | 1.00 | 0.136 | 0 |
|  | Active (UL1-012) | 0 | 6.12 | 8.98 | 9.00 | 9.00 |
| UL1-069 | Prodrug (UL1-069) | 10 | 9.90 | 9.70 | 9.60 | 9.90 |
|  | Active (UL1-012) | 0 | 0.44 | 0.42 | 0.40 | 0.40 |
| UL1-070 | Prodrug (Mouse plasma) (UL1-070) | 10 | 6.40 | 4.73 | 2.43 | 0.93 |
|  | Active (Mouse plasma) (UL1-012) | 0 | 3.22 | 5.85 | 7.72 | 8.71 |
|  | Prodrug (Human) (UL1-070) | 10 | 8.02 | 8.28 | 7.70 | 7.48 |
|  | Active (Human) (UL1-012) | 0 | 0.25 | 0.45 | 0.78 | 1.29 |
| UL1-071 | Prodrug (UL1-071) | 10 | 9.50 | 9.00 | 8.72 | 7.39 |
|  | Active (UL1-012) | 0 | 0.47 | 0.87 | 1.65 | 2.56 |
| UL1-092 | Prodrug (UL1-092) | 10 | 5.12 | 4.67 | 4.59 | 3.70 |
|  | Active (UL1-012) | 0 | 0.01 | 0.01 | 0.01 | 0.012 |
| UL1-094 | Prodrug (UL1-094) | 10 | 9.99 | 9.22 | 8.78 | 8.49 |

TABLE 4-continued

| Prodrug ID | Prodrug/Active* | [ ] (µM) t$_{0\ min.}$ | [ ] (µM) t$_{15\ min.}$ | [ ] (µM) t$_{30\ min.}$ | [ ] (µM) t$_{60\ min.}$ | [ ] (µM) t$_{120\ min.}$ |
|---|---|---|---|---|---|---|
| | Active (UL1-012) | 0.059 | 0.01 | 0.01 | 0.03 | 0.05 |
| UL1-098 | Prodrug (Mouse) (UL1-098) | 10 | 0 | 0 | 0 | 0 |
| | Active (Mouse) (UL1-095) | 0 | 10.40 | 11.00 | 11.40 | 11.40 |
| | Prodrug (Human) (UL1-098) | 10 | 5.42 | 3.45 | 1.76 | 0.65 |
| | Active (Human) (UL1-095) | 0 | 4.45 | 6.84 | 8.93 | 10 |
| UL1-105 | Prodrug (UL1-105) | 10 | 0 | 0 | 0 | 0 |
| | Active (UL1-012) | 0.22 | 14.50 | 12.83 | 13.60 | 13.83 |
| UL1-109 | Prodrug (Mouse) (UL1-109) | 10 | 6.87 | 4.84 | 2.45 | 0.73 |
| | Active (Mouse) (UL1-012) | 0.06 | 3.47 | 6.01 | 8.40 | 9.92 |
| | Prodrug (Human) (UL1-109) | 10 | 6.22 | 5.37 | 3.39 | 1.72 |
| | Active (Human) (UL1-012) | 0 | 1.96 | 3.31 | 5.81 | 8.71 |
| UL1-111 | Prodrug (Mouse) (UL1-111) | 10 | 4.74 | 2.47 | 1.16 | 0.47 |
| | Active (Mouse) (UL1-012) | 0.22 | 6.31 | 8.55 | 10.45 | 13.8 |
| | Prodrug (Human) (UL1-111) | 10 | 2.84 | 0.80 | 0.09 | 0.00 |
| | Active (Human) (UL1-012) | <LOQ | 6.98 | 9.01 | 9.23 | 9.23 |
| UL1-114 | Prodrug (Mouse) (UL1-114) | 10 | 0 | 0 | 0 | 0 |
| | Active (Mouse) (UL1-005) | 0 | 14.14 | 14.16 | 13.14 | 10.85 |
| | Prodrug (Human) (UL1-114) | 10 | 9.53 | 9.48 | 8.22 | 7.22 |
| | Active (Human) (UL1-005) | 0 | 1.72 | 3.11 | 4.96 | 7.62 |
| UL1-115 | Prodrug (Mouse) (UL1-115) | 10 | 7.56 | 4.04 | 1.54 | 0.38 |
| | Active (Mouse) (UL1-012) | 0 | 4.16 | 6.22 | 8.41 | 9.65 |
| | Prodrug (Human) (UL1-115) | 10 | 10.8 | 9.41 | 6.69 | 2.98 |
| | Active (Human) (UL1-012) | 0 | 2.36 | 4.41 | 6.55 | 8.84 |
| UL1-117 | Prodrug (Mouse) (UL1-117) | 10 | 5.92 | 4.26 | 1.41 | 0.21 |
| | Active (Mouse) (UL1-012) | 0 | 0.76 | 1.26 | 3.17 | 5.95 |
| | Prodrug (Human) (UL1-117) | 10 | 14.9 | 10.1 | 4.28 | 1.12 |
| | Active (Human) (UL1-012) | 0.17 | 1.94 | 3.60 | 5.86 | 8.88 |

TABLE 4-continued

| Prodrug ID | Prodrug/Active* | [ ] (µM) $t_{0\,min}$ | [ ] (µM) $t_{15\,min}$ | [ ] (µM) $t_{30\,min}$ | [ ] (µM) $t_{60\,min}$ | [ ] (µM) $t_{120\,min}$ |
|---|---|---|---|---|---|---|
| UL1-118 | Prodrug (Mouse) (UL1-118) | 10 | 6.04 | 4.00 | 1.68 | 0.23 |
|  | Active (Mouse) (UL1-012) | 0 | 1.04 | 1.63 | 3.44 | 6.32 |

*If the species is not specified in the table it is referring to mouse.

A set of clauses defining certain aspects of the invention is as follows:

1. A compound of formula (I):

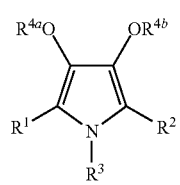

wherein:

$R^1$ and $R^2$ are independently selected from —C(O)NR$^5$R$^6$, —C(O)OR$^7$, CN, —C(O)R$^7$, —C(O)NHC(O)R$^7$, —NO$_2$, —SO$_3$R$^7$, —SO$_2$R$^7$, —SO$_2$NR$^5$R$^6$, —SOR$^7$, —SO$_2$NH—C(O)OR$^8$ and optionally substituted phenyl or heteroaryl;

$R^3$ is optionally substituted phenyl;

$R^{4a}$ and $R^{4b}$ are independently selected from hydrogen, $C_1$-$C_6$ alkyl which alkyl group may optionally be substituted by hydroxyl, COOR$^{12}$ or CONR$^{13}$R$^{14}$, aryl and —C$_1$-C$_3$ alkylaryl in which said aryl groups may be optionally substituted;

$R^5$ and $R^6$ are independently selected from:

(a) hydrogen, (b) $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —C$_1$-C$_3$ alkyl-C$_3$-C$_{10}$ cycloalkyl, —C$_1$-C$_3$ alkyl-C$_5$-C$_{10}$ cycloalkenyl or —C$_1$-C$_3$ alkylheterocyclyl, or R$^5$ and R$^6$ together with the N to which they are attached may form a 5- or 6-membered heterocyclic ring optionally containing a further heteroatom selected from O, S and NR$^9$, in which any of the aforementioned R$^5$ and R$^6$ groups may be optionally substituted by a group selected from cyano, $C_1$-$C_6$ alkoxy, $C_1$-$C_6$ fluoroalkoxy, $C_1$-$C_6$ alkyl, $C_1$-$C_6$ fluoroalkyl and —C(O)NR$^a$R$^b$, where R$^a$ and R$^b$ are independently selected from hydrogen and $C_1$-$C_6$ alkyl, and any of the aforementioned R$^5$ and R$^6$ groups may be optionally substituted by one or more halogen atoms, and (c) aryl, heteroaryl, $C_1$-$C_3$ alkylaryl and —C$_1$-C$_3$ alkylheteroaryl, said aryl and heteroaryl groups being optionally substituted;

$R^7$ is selected from:

(a) $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —C$_1$-C$_3$ alkyl-C$_3$-C$_{10}$ cycloalkyl, —C$_1$-C$_3$ alkyl-C$_5$-C$_{10}$ cycloalkenyl or —C$_1$-C$_3$ alkylheterocyclyl, in which any of the aforementioned R$^7$ groups may be optionally substituted by a group selected from cyano, $C_1$-$C_6$ alkoxy, $C_1$-$C_6$ fluoroalkoxy, $C_1$-$C_6$ alkyl, $C_1$-$C_6$ fluoroalkyl and —C(O)NR$^a$R$^b$, where R$^a$ and R$^b$ are independently selected from hydrogen and $C_1$-$C_6$ alkyl, and any of the aforementioned R$^7$ groups may be optionally substituted by one or more halogen atoms, and (b) aryl, heteroaryl, $C_1$-$C_3$ alkylaryl and —C$_1$-C$_3$ alkylheteroaryl, said aryl and heteroaryl groups being optionally substituted;

$R^8$ is $C_1$-$C_6$ alkyl;

$R^9$ is hydrogen, $C_1$-$C_6$ alkyl; —C(O)R$^{10}$ or —C(O)OR$^{11}$;

$R^{10}$ is $C_1$-$C_6$ alkyl;

$R^{11}$ is $C_1$-$C_6$ alkyl;

$R^{12}$ is $C_1$-$C_6$ alkyl;

$R^{13}$ is hydrogen or $C_1$-$C_6$ alkyl; and $R^{14}$ is hydrogen or $C_1$-$C_6$ alkyl;

or a pharmaceutically acceptable prodrug derivative thereof, or a pharmaceutically acceptable salt or solvate thereof;

provided that the compound is not:

a) diethyl 3,4-dihydroxy-1-(4-methoxyphenyl)-1H-pyrrole-2,5-dicarboxylate;

b) diethyl 3,4-dihydroxy-1-phenyl-1H-pyrrole-2,5-dicarboxylate;

c) dimethyl 3,4-dihydroxy-1-(4-bromophenyl)-1H-pyrrole-2,5-dicarboxylate;

d) dimethyl 3,4-dihydroxy-1-(4-chlorophenyl)-1H-pyrrole-2,5-dicarboxylate;

e) di-tert-butyl 3,4-dihydroxy-1-(4-nitrophenyl)-1H-pyrrole-2,5-dicarboxylate;

f) dimethyl 3,4-dihydroxy-1-(4-methoxyphenyl)-1H-pyrrole-2,5-dicarboxylate;

g) dimethyl 3,4-dihydroxy-1-phenyl-1H-pyrrole-2,5-dicarboxylate;

h) diethyl 3,4-bis(acetyloxy)-1-phenyl-1H-pyrrole-2,5-dicarboxylate; or i) dimethyl 3,4-bis(acetyloxy)-1-phenyl-1H-pyrrole-2,5-dicarboxylate.

2. A compound according to clause 1 wherein $R^1$ and $R^2$ are independently selected from —C(O)NR$^5$R$^6$, —C(O)OR$^7$ and CN.

3. A compound according to clause 1 wherein (i) $R^1$ is —C(O)NR$^5$R$^6$ and $R^2$ is —C(O)NR$^5$R$^6$ or (ii) $R^1$ is —C(O)NR$^5$R$^6$ and $R^2$ is —C(O)OR$^7$.

4. A compound according to clause 1 wherein $R^1$ is —C(O)OR$^7$ and $R^2$ is —C(O)OR$^7$.

5. A compound according to any one of the preceding clauses wherein $R^3$ is substituted phenyl.

6. A compound according to clause 5 wherein $R^3$ is phenyl substituted by 1, 2 or 3 substituents selected from halo, cyano, $C_1$-$C_6$ alkoxy, $C_1$-$C_6$ fluoroalkoxy, $C_1$-$C_6$ alkyl, $C_1$-$C_6$ fluoroalkyl and —C(O)NR$^a$R$^b$, where R$^a$ and R$^b$ are independently selected from hydrogen and $C_1$-$C_6$ alkyl.

7. A compound according to clause 5 or 6 wherein $R^3$ is phenyl having a substituent in the meta or para positions relative to the pyrrole ring.

8. A compound according to any one of the preceding clauses wherein $R^{4a}$ and $R^{4b}$ are hydrogen or —C$_1$-C$_3$ alkylaryl.

9. A compound according to clause 8 wherein $R^{4a}$ and $R^{4b}$ are hydrogen.

10. A compound according to any one of the preceding clauses wherein $R^5$ and $R^6$ are independently selected from hydrogen, $C_1$-$C_6$ alkyl, aryl or $C_1$-$C_3$ alkylaryl in which said aryl may be optionally substituted, or $R^5$ and $R^6$ together with the N to which they are attached form a 5- or 6-membered heterocyclic ring optionally containing a further heteroatom selected from O, S and $NR^9$.

11. A compound according to clause 10 wherein $R^5$ and $R^6$ are not both hydrogen.

12. A compound according to any one of the preceding clauses wherein $R^7$ is $C_1$-$C_6$ alkyl.

13. A compound according to clause 1 which is selected from:

$N^2,N^2,N^5,N^5$-tetraethyl-1-(4-fluorophenyl)-3,4-dihydroxy-1H-pyrrole-2,5-dicarboxamide;

1-(4-ethoxyphenyl)-$N^2,N^2,N^5,N^5$-tetraethyl-3,4-dihydroxy-1H-pyrrole-2,5-dicarboxamide;

$N^2,N^2,N^5,N^5$-tetraethyl-3,4-dihydroxy-1-(4-methoxyphenyl)-1H-pyrrole-2,5-dicarboxamide;

(3,4-dihydroxy-1-(4-methoxyphenyl)-1H-pyrrole-2,5-diyl)bis(morpholinomethanone);

3,4-dihydroxy-1-(4-methoxyphenyl)-$N^2,N^2,N^5,N^5$-tetramethyl-1H-pyrrole-2,5-dicarboxamide;

(1-(4-fluorophenyl)-3,4-dihydroxy-1H-pyrrole-2,5-diyl)bis(morpholinomethanone);

1-(4-fluorophenyl)-3,4-dihydroxy-$N^2,N^5$-dimethyl-$N^2,N^5$-diphenyl-1H-pyrrole-2,5-dicarboxamide;

1-(4-fluorophenyl)-3,4-dihydroxy-$N^2,N^2,N^5,N^5$-tetramethyl-1H-pyrrole-2,5-dicarboxamide;

di-tert-butyl 4,4'-(1-(4-fluorophenyl)-3,4-dihydroxy-1H-pyrrole-2,5-dicarbonyl)bis(piperazine-1-carboxylate);

1,1'-(4,4'-(1-(4-fluorophenyl)-3,4-dihydroxy-1H-pyrrole-2,5-dicarbonyl)bis(piperazine-4,1-diyl))diethanone;

(1-(4-fluorophenyl)-3,4-dihydroxy-1H-pyrrole-2,5-diyl)bis(piperidin-1-ylmethanone);

ethyl 5-(dimethylcarbamoyl)-3,4-dihydroxy-1-(4-methoxyphenyl)-1H-pyrrole-2-carboxylate;

1-(4-fluorophenyl)-3,4-dihydroxy-$N^2,N^5$-diisopropyl-$N^2,N^5$-dimethyl-1H-pyrrole-2,5-dicarboxamide;

$N^2,N^5$-dibenzyl-1-(4-fluorophenyl)-3,4-dihydroxy-$N^2,N^5$-dimethyl-1H-pyrrole-2,5-dicarboxamide;

di-tert-butyl 4,4'-(3,4-dihydroxy-1-(4-methoxyphenyl)-1H-pyrrole-2,5-dicarbonyl)bis(piperazine-1-carboxylate);

(3,4-dihydroxy-1-(4-methoxyphenyl)-1H-pyrrole-2,5-diyl)bis(piperazin-1-ylmethanone);

1-(4-fluorophenyl)-3,4-dihydroxy-$N^2,N^2,N^5,N^5$-tetraisopropyl-1H-pyrrole-2,5-dicarboxamide;

(3,4-dihydroxy-1-(4-methoxyphenyl)-1H-pyrrole-2,5-diyl)bis(piperidin-1-ylmethanone);

3,4-dihydroxy-1-(2-methoxyphenyl)-$N^2,N^2,N^5,N^5$-tetramethyl-1H-pyrrole-2,5-dicarboxamide;

(3,4-dihydroxy-1-(2-methoxyphenyl)-1H-pyrrole-2,5-diyl)bis(morpholinomethanone);

1-(4-ethoxyphenyl)-3,4-dihydroxy-$N^2,N^2,N^5,N^5$-tetramethyl-1H-pyrrole-2,5-dicarboxamide;

(1-(4-ethoxyphenyl)-3,4-dihydroxy-1H-pyrrole-2,5-diyl)bis(morpholinomethanone);

(3,4-dihydroxy-1-(4-(trifluoromethyl)phenyl)-1H-pyrrole-2,5-diyl)bis(morpholinomethanone);

$N^2$-ethyl-3,4-dihydroxy-1-(4-methoxyphenyl)-$N^5,N^5$-dimethyl-1H-pyrrole-2,5-dicarboxamide;

3,4-dihydroxy-1-(4-methoxyphenyl)-N,N-dimethyl-5-(piperidine-1-carbonyl)-1H-pyrrole-2-carboxamide;

3,4-dihydroxy-1-(4-methoxyphenyl)-N,N-dimethyl-5-(morpholine-4-carbonyl)-1H-pyrrole-2-carboxamide;

3,4-dihydroxy-1-(4-methoxyphenyl)-N,N-dimethyl-5-(4-methylpiperazine-1-carbonyl)-1H-pyrrole-2-carboxamide;

3,4-dihydroxy-$N^2,N^2,N^5,N^5$-tetramethyl-1-(4-(trifluoromethyl)phenyl)-1H-pyrrole-2,5-dicarboxamide;

1-(4-(dimethylcarbamoyl)phenyl)-3,4-dihydroxy-$N^2,N^2,N^5,N^5$-tetramethyl-1H-pyrrole-2,5-dicarboxamide;

tert-butyl (5-(dimethylcarbamoyl)-3,4-dihydroxy-1-(4-methoxyphenyl)-1H-pyrrol-2-yl)sulfonylcarbamate;

5-cyano-3,4-dihydroxy-1-(4-methoxyphenyl)-N,N-dimethyl-1H-pyrrole-2-carboxamide;

ethyl 5-(dimethylcarbamoyl)-1-(4-fluorophenyl)-3,4-dihydroxy-1H-pyrrole-2-carboxylate;

1,1'-(4,4'-(3,4-dihydroxy-1-(4-methoxyphenyl)-1H-pyrrole-2,5-dicarbonyl)bis(piperazine-4,1-diyl))diethanone;

3,4-dihydroxy-1-(4-methoxyphenyl)-1H-pyrrole-2,5-dicarbonitrile;

isopropyl 5-(dimethylcarbamoyl)-3,4-dihydroxy-1-(4-methoxyphenyl)-1H-pyrrole-2-carboxylate;

tert-butyl 5-(dimethylcarbamoyl)-3,4-dihydroxy-1-(4-methoxyphenyl)-1H-pyrrole-2-carboxylate;

ethyl 3,4-dihydroxy-1-(4-methoxyphenyl)-5-(4-methylpiperazine-1-carbonyl)-1H-pyrrole-2-carboxylate;

ethyl 5-(dibutylcarbamoyl)-3,4-dihydroxy-1-(4-methoxyphenyl)-1H-pyrrole-2-carboxylate;

ethyl 5-cyano-1-(4-fluorophenyl)-3,4-dihydroxy-1H-pyrrole-2-carboxylate;

ethyl 3,4-dihydroxy-1-(4-methoxyphenyl)-5-(morpholine-4-carbonyl)-1H-pyrrole-2-carboxylate;

ethyl 5-(diethylcarbamoyl)-3,4-dihydroxy-1-(4-methoxyphenyl)-1H-pyrrole-2-carboxylate;

ethyl 5-(dimethylcarbamoyl)-3,4-dihydroxy-1-(4-iodophenyl)-1H-pyrrole-2-carboxylate;

ethyl 5-(dimethylcarbamoyl)-3,4-dihydroxy-1-(3-iodo-4-methoxyphenyl)-1H-pyrrole-2-carboxylate;

3,4-bis(benzyloxy)-1-(4-ethoxyphenyl)-$N^2, N^2, N^5, N^5$-tetraethyl-1H-pyrrole-2,5-dicarboxamide;

3,4-bis(benzyloxy)-$N^2, N^2, N^5, N^5$-tetraethyl-1-(4-methoxyphenyl)-1H-pyrrole-2,5-dicarboxamide;

3,4-bis(benzyloxy)-1-(4-methoxyphenyl)-$N^2, N^2, N^5, N^5$-tetramethyl-1H-pyrrole-2,5-dicarboxamide;

di-tert-butyl 4,4'-(3,4-bis(benzyloxy)-1-(4-methoxyphenyl)-1H-pyrrole-2,5-dicarbonyl)bis(piperazine-1-carboxylate);

(3,4-bis(benzyloxy)-1-(4-methoxyphenyl)-1H-pyrrole-2,5-diyl)bis(piperidin-1-ylmethanone);

3,4-bis(benzyloxy)-1-(2-methoxyphenyl)-$N^2, N^2, N^5, N^5$-tetramethyl-1H-pyrrole-2,5-dicarboxamide;

(3,4-bis(benzyloxy)-1-(2-methoxyphenyl)-1H-pyrrole-2,5-diyl)bis(morpholinomethanone);

3,4-bis(benzyloxy)-1-(4-ethoxyphenyl)-$N^2, N^2, N^5, N^5$-tetramethyl-1H-pyrrole-2,5-dicarboxamide;

(3,4-bis(benzyloxy)-1-(4-ethoxyphenyl)-1H-pyrrole-2,5-diyl)bis(morpholinomethanone);

3,4-bis(benzyloxy)-$N^2, N^2, N^5, N^5$-tetramethyl-1-(4-(trifluoromethyl)phenyl)-1H-pyrrole-2,5-dicarboxamide;

3,4-bis(benzyloxy)-$N^2$-ethyl-1-(4-methoxyphenyl)-$N^5,N^5$-dimethyl-1H-pyrrole-2,5-dicarboxamide;

3,4-bis(benzyloxy)-1-(4-methoxyphenyl)-N,N-dimethyl-5-(4-methylpiperazine-1-carbonyl)-1H-pyrrole-2-carboxamide;

3,4-bis(benzyloxy)-1-(4-methoxyphenyl)-N,N-dimethyl-5-(piperidine-1-carbonyl)-1H-pyrrole-2-carboxamide;

3,4-bis(benzyloxy)-1-(4-methoxyphenyl)-N,N-dimethyl-5-(morpholine-4-carbonyl)-1H-pyrrole-2-carboxamide;

1,1'-(4,4'-(3,4-bis(benzyloxy)-1-(4-methoxyphenyl)-1H-pyrrole-2,5-dicarbonyl)bis(piperazine-4,1-diyl))diethanone;

ethyl 3,4-bis(benzyloxy)-5-cyano-1-(4-fluorophenyl)-1H-pyrrole-2-carboxylate;

3,4-bis(benzyloxy)-5-cyano-1-(4-fluorophenyl)-N,N-dimethyl-1H-pyrrole-2-carboxamide;
ethyl 3,4-bis(benzyloxy)-5-(dimethylcarbamoyl)-1-(4-iodophenyl)-1H-pyrrole-2-carboxylate;
3,4-bis(benzyloxy)-1-(4-methoxyphenyl)-1H-pyrrole-2,5-dicarboxamide;
3,4-dihydroxy-1-(4-methoxyphenyl)-1H-pyrrole-2,5-dicarboxamide;
3,4-bis(benzyloxy)-$N^2,N^5$-diethyl-1-(4-methoxyphenyl)-1H-pyrrole-2,5-dicarboxamide;
3,4-bis(benzyloxy)-1-(4-fluorophenyl)-1H-pyrrole-2,5-dicarboxamide;
1-(4-fluorophenyl)-3,4-dihydroxy-1H-pyrrole-2,5-dicarboxamide;
1-(4-ethoxyphenyl)-3,4-dihydroxy-1H-pyrrole-2,5-dicarboxamide;
1-(4-ethoxyphenyl)-$N^2,N^5$-diethyl-3,4-dihydroxy-1H-pyrrole-2,5-dicarboxamide;
ethyl 3,4-bis(benzyloxy)-5-carbamoyl-1-(4-methoxyphenyl)-1H-pyrrole-2-carboxylate;
ethyl 5-carbamoyl-3,4-dihydroxy-1-(4-methoxyphenyl)-1H-pyrrole-2-carboxylate;
ethyl 3,4-bis(benzyloxy)-5-(2-methoxyphenyl)-1-(4-methoxyphenyl)-1H-pyrrole-2-carboxylate;
ethyl 3,4-bis(benzyloxy)-1-(4-methoxyphenyl)-5-(pyridin-2-yl)-1H-pyrrole-2-carboxylate;
ethyl 3,4-dihydroxy-1-(4-methoxyphenyl)-5-(pyridin-2-yl)-1H-pyrrole-2-carboxylate;
ethyl 3,4-bis(benzyloxy)-1-(4-methoxyphenyl)-5-(pyridin-4-yl)-1H-pyrrole-2-carboxylate;
ethyl 3,4-bis(benzyloxy)-1-(4-methoxyphenyl)-5-(pyridin-3-yl)-1H-pyrrole-2-carboxylate;
ethyl 5-(4-ethylthiazol-2-yl)-3,4-dihydroxy-1-(4-methoxyphenyl)-1H-pyrrole-2-carboxylate;
ethyl 3,4-bis(benzyloxy)-1-(4-methoxyphenyl)-5-(5-methyl-1,3,4-oxadiazol-2-yl)-1H-pyrrole-2-carboxylate;
ethyl 3,4-bis(benzyloxy)-5-(5-ethyl-1,3,4-oxadiazol-2-yl)-1-(4-methoxyphenyl)-1H-pyrrole-2-carboxylate;
ethyl 3,4-dihydroxy-1-(4-methoxyphenyl)-5-(2H-tetrazol-5-yl)-1H-pyrrole-2-carboxylate;
ethyl 3,4-bis(benzyloxy)-1-(4-methoxyphenyl)-5-(2H-tetrazol-5-yl)-1H-pyrrole-2-carboxylate;
diethyl 1-(4-fluorophenyl)-3,4-dihydroxy-1H-pyrrole-2,5-dicarboxylate;
diethyl 3,4-dihydroxy-1-(3-methoxyphenyl)-1H-pyrrole-2,5-dicarboxylate;
diethyl 3,4-dihydroxy-1-(4-(trifluoromethoxy)phenyl)-1H-pyrrole-2,5-dicarboxylate;
diethyl 3,4-dihydroxy-1-(4-isopropylphenyl)-1H-pyrrole-2,5-dicarboxylate;
diethyl 3,4-dihydroxy-1-(4-phenoxyphenyl)-1H-pyrrole-2,5-dicarboxylate;
diethyl 1-(4-ethoxyphenyl)-3,4-dihydroxy-1H-pyrrole-2,5-dicarboxylate;
diethyl 1-(4-ethylphenyl)-3,4-dihydroxy-1H-pyrrole-2,5-dicarboxylate;
diethyl 3,4-dihydroxy-1-(p-tolyl)-1H-pyrrole-2,5-dicarboxylate;
diethyl 1-(3,4-dimethoxyphenyl)-3,4-dihydroxy-1H-pyrrole-2,5-dicarboxylate;
diethyl 1-(4-chlorophenyl)-3,4-dihydroxy-1H-pyrrole-2,5-dicarboxylate;
diethyl 3,4-dihydroxy-1-(4-(trifluoromethyl)phenyl)-1H-pyrrole-2,5-dicarboxylate;
diethyl 3,4-dihydroxy-1-(3,4,5-trimethoxyphenyl)-1H-pyrrole-2,5-dicarboxylate;
diethyl 1-(2,4-dimethoxyphenyl)-3,4-dihydroxy-1H-pyrrole-2,5-dicarboxylate;
diethyl 3,4-dihydroxy-1-(4-propoxyphenyl)-1H-pyrrole-2,5-dicarboxylate;
diethyl 1-(4-ethoxy-3,5-difluorophenyl)-3,4-dihydroxy-1H-pyrrole-2,5-dicarboxylate;
diethyl 3,4-dihydroxy-1-(3-phenoxyphenyl)-1H-pyrrole-2,5-dicarboxylate;
diethyl 1-(benzo[d][1,3]dioxol-5-yl)-3,4-dihydroxy-1H-pyrrole-2,5-dicarboxylate;
diisopropyl 3,4-dihydroxy-1-(4-methoxyphenyl)-1H-pyrrole-2,5-dicarboxylate;
2-ethyl 5-isopropyl 3,4-dihydroxy-1-(4-methoxyphenyl)-1H-pyrrole-2,5-dicarboxylate;
di-tert-butyl 3,4-dihydroxy-1-(4-methoxyphenyl)-1H-pyrrole-2,5-dicarboxylate;
diethyl 3,4-dihydroxy-1-(2-methoxyphenyl)-1H-pyrrole-2,5-dicarboxylate;
diethyl 1-(4-cyanophenyl)-3,4-dihydroxy-1H-pyrrole-2,5-dicarboxylate;
diethyl 1-(4-fluorophenyl)-3-hydroxy-4-(2-hydroxyethoxy)-1H-pyrrole-2,5-dicarboxylate;
diethyl 3-hydroxy-4-(2-hydroxyethoxy)-1-(4-methoxyphenyl)-1H-pyrrole-2,5-dicarboxylate;
diethyl 3-(2-(tert-butoxy)-2-oxoethoxy)-1-(4-fluorophenyl)-4-hydroxy-1H-pyrrole-2,5-dicarboxylate;
diethyl 3-(benzyloxy)-4-(2-(tert-butoxy)-2-oxoethoxy)-1-(4-methoxyphenyl)-1H-pyrrole-2,5-dicarboxylate;
diethyl 3-(2-amino-2-oxoethoxy)-1-(4-fluorophenyl)-4-hydroxy-1H-pyrrole-2,5-dicarboxylate;
diethyl 3-(2-(tert-butoxy)-2-oxoethoxy)-4-hydroxy-1-(4-methoxyphenyl)-1H-pyrrole-2,5-dicarboxylate;
diethyl 3-(2-amino-2-oxoethoxy)-4-hydroxy-1-(4-methoxyphenyl)-1H-pyrrole-2,5-dicarboxylate;
diethyl 1-(4-(tert-butyl)phenyl)-3,4-dihydroxy-1H-pyrrole-2,5-dicarboxylate; and
diethyl 3,4-dihydroxy-1-(3-iodo-4-methoxyphenyl)-1H-pyrrole-2,5-dicarboxylate; or a pharmaceutically acceptable prodrug derivative of any one thereof, or a pharmaceutically acceptable salt or solvate of any one thereof.

14. A compound according to any one of clauses 1 to 13 in the form of a prodrug derivative.

15. A compound according to clause 14 wherein the prodrug derivative is selected from carboxylate ester, sulfamate ester, phosphate ester and carbamate ester derivatives.

16. A compound according to clause 14 wherein one or both of $R^{4a}$ and $R^{4b}$ are independently selected from —C(O)$R^{16}$, —SO$_2$NH$_2$, —PO(O$R^{19}$)(O$R^{20}$) and —C(O)N$R^{17}R^{18}$, wherein
$R^{16}, R^{17}, R^{18}, R^{19}$ and $R^{20}$ are independently selected from
(a) $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —$C_1$-$C_3$ alkyl-$C_3$-$C_{10}$ cycloalkyl, —$C_1$-$C_3$ alkyl-$C_5$-$C_{10}$ cycloalkenyl or —$C_1$-$C_3$ alkylheterocyclyl, in which any of the aforementioned $R^{16}, R^{17}$ or $R^{18}$ groups may be optionally substituted by a group selected from cyano, $C_1$-$C_6$ alkoxy, $C_1$-$C_6$ fluoroalkoxy, $C_1$-$C_6$ alkyl, $C_1$-$C_6$ fluoroalkyl and —C(O)N$R^aR^b$, where $R^a$ and $R^b$ are independently selected from hydrogen and $C_1$-$C_6$ alkyl, and any of the aforementioned $R^{16}, R^{17}$ or $R^{18}$ groups may be optionally substituted by one or more halogen atoms, and
(b) aryl, heteroaryl, $C_1$-$C_3$ alkylaryl and —$C_1$-$C_3$ alkylheteroaryl, said aryl and heteroaryl groups being optionally substituted;
or $R^{18}, R^{19}$ and $R^{20}$ may independently represent hydrogen.

17. A compound according to clause 14 selected from:
2-(dimethylcarbamoyl)-5-(ethoxycarbonyl)-1-(4-methoxyphenyl)-1H-pyrrole-3,4-diyl diacetate;
ethyl 5-(dimethylcarbamoyl)-3,4-bis((dimethylcarbamoyl)oxy)-1-(4-methoxyphenyl)-1H-pyrrole-2-carboxylate;
2-(dimethylcarbamoyl)-5-(ethoxycarbonyl)-1-(4-methoxyphenyl)-1H-pyrrole-3,4-diyl bis(4-methylpiperazine-1-carboxylate);
2-(dimethylcarbamoyl)-5-(ethoxycarbonyl)-1-(4-methoxyphenyl)-1H-pyrrole-3,4-diyl bis([1,4'-bipiperidine]-1'-carboxylate);
ethyl 5-(dimethylcarbamoyl)-4-((dimethylcarbamoyl)oxy)-3-hydroxy-1-(4-methoxyphenyl)-1H-pyrrole-2-carboxylate;
2-(dimethylcarbamoyl)-5-(ethoxycarbonyl)-1-(4-methoxyphenyl)-1H-pyrrole-3,4-diyl bis(2-methylpropanoate);
2-(dimethylcarbamoyl)-5-(ethoxycarbonyl)-1-(4-methoxyphenyl)-1H-pyrrole-3,4-diyl bis(2,2-dimethylpropanoate);
ethyl 5-(dimethylcarbamoyl)-3-hydroxy-1-(4-methoxyphenyl)-4-(sulfamoyloxy)-1H-pyrrole-2-carboxylate;
ethyl 5-(dimethylcarbamoyl)-3-hydroxy-1-(4-methoxyphenyl)-4-(phosphonooxy)-1H-pyrrole-2-carboxylate; and
2-(dimethylcarbamoyl)-5-(ethoxycarbonyl)-4-hydroxy-1-(4-methoxyphenyl)-1H-pyrrol-3-yl [1,4'-bipiperidine]-1'-carboxylate;
or a pharmaceutically acceptable salt or solvate of any one thereof.

18. A compound according to clause 1 which is ethyl 5-(dimethylcarbamoyl)-3,4-dihydroxy-1-(4-methoxyphenyl)-1H-pyrrole-2-carboxylate, or a pharmaceutically acceptable prodrug derivative, or a pharmaceutically acceptable salt or solvate thereof.

19. A pharmaceutical composition comprising a compound according to any one of clauses 1 to 18, without provisos a) to i), optionally in combination with one or more pharmaceutically acceptable diluents or carriers.

20. A pharmaceutical composition according to clause 19 comprising one or more other therapeutically active ingredients.

21. A compound according to any one of clauses 1 to 18 without proviso a) to i) for use as a medicament.

22. A compound according to clause 21 for use as a medicament which is diethyl 3,4-dihydroxy-1-(4-methoxyphenyl)-1H-pyrrole-2,5-dicarboxylate or a pharmaceutically acceptable prodrug derivative thereof, or a pharmaceutically acceptable salt or solvate thereof.

23. A compound according to any one of clauses 1 to 18, 21 and 22 without provisos a) to i) for use in the treatment of bacterial infections caused by bacteria producing pore-forming toxins, such as cholesterol dependent cytolysins.

24. A compound for use according to clause 23 wherein the bacterial infection is caused by *Streptococcus* spp. (e.g. *Streptococcus pneumoniae*, Group A Streptococci or *Streptococcus suis*), *Clostridium* spp. (e.g. *Clostridium perfringens*), *Listeria* spp. (e.g. *Listeria monocytogenes*) or *Bacillus* spp. (e.g. *Bacillus anthracis*).

25. A compound for use according to clause 24 for the treatment of bacterial infection which is caused by *Streptococcus pneumoniae*.

26. A compound for use according to clause 25 for the treatment of pneumococcal pneumonia, pneumococcal meningitis, pneumococcal septicaemia/bacteraemia, pneumococcal keratitis or pneumococcal otitis media.

27. A compound for use according to clause 24 for the treatment of conditions selected from gas gangrene, gastrointestinal anthrax, inhalational anthrax, porcine meningitis, encephalitis, septicaemia/bacteraemia and pneumonia which are caused by bacteria other than pneumococcus.

28. A compound for use according to any one of clauses 21 to 27 wherein the compound is administered in combination with one or more other therapeutically active ingredients (e.g. one or more antibiotic agents).

29. A method of treatment of bacterial infections caused by bacteria producing pore-forming toxins, such as cholesterol dependent cytolysins which comprises administering to a subject in need thereof an effective amount of a compound according to any one of clauses 1 to 18, 21 and 22 without provisos a) to i).

30. A compound of formula (II):

$$R^1 \diagup N \diagdown R^2$$
$$|$$
$$R^3$$

(II)

wherein $R^1$, $R^2$ and $R^3$ are as defined in clause 1 for the compounds of formula (I), or a salt or protected derivative thereof;
provided that when $R^5$ or $R^6$ is optionally substituted aryl it is optionally substituted by 1, 2 or 3 groups selected from hydroxyl, halo, cyano, $C_1$-$C_6$ alkoxy or $C_1$-$C_6$ fluoroalkoxy, $C_1$-$C_6$ alkyl or $C_1$-$C_6$ fluoroalkyl, and —C(O)NR$^a$R$^b$, where R$^a$ and R$^b$ are independently selected from hydrogen and $C_1$-$C_6$ alkyl; or when two adjacent hydroxyl substituents are present they may optionally be connected by a methylene group to form an acetal;
and provided that the compound is not:
a) methyl 2-((2-oxo-2-(phenylamino)ethyl)(phenyl)amino)acetate;
b) methyl 2-((4-methoxyphenyl)(2-oxo-2-(phenylamino)ethyl)amino)acetate;
c) ethyl 2-(phenyl(tosylmethyl)amino)acetate;
d) ethyl 2-((cyanomethyl)(3,4-dichlorophenyl)amino)acetate;
e) methyl 2-((cyanomethyl)(p-tolyl)amino)acetate; or
f) ethyl 2-(mesityl(2-oxopropyl)amino)acetate.

31. A compound of formula (II) according to clause 30 wherein $R^1$ is —C(O)NR$^5$R$^6$ and $R^2$ is —C(O)NR$^5$R$^6$ or wherein $R^1$ is —C(O)NR$^5$R$^6$ and $R^2$ is —C(O)OR$^7$.

32. A process for preparing compounds of formula (I) as defined in any one of clauses 1 to 18 in which R$^{4a}$ and R$^{4b}$ represent H which comprises reacting a compound of formula (II) as defined in clause 30 with a compound of formula R$^x$OCOCOOR$^x$ in which R$^x$ represents $C_1$-$C_6$ alkyl.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:
1. A compound of formula (I):

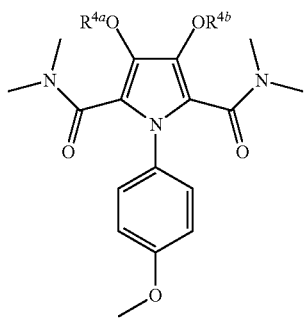

(I)

wherein $R^{4a}$ and $R^{4b}$ are hydrogen;
or a pharmaceutically acceptable prodrug thereof, or a pharmaceutically acceptable salt or solvate thereof.

2. The compound according to claim 1, in the form of a prodrug.

3. The compound according to claim 2, wherein the prodrug is selected from the group consisting of carboxylate ester, sulfamate ester, phosphate ester and carbamate ester derivatives.

4. The compound according to claim 2, wherein the prodrug is a carboxylate ester derivative.

5. The compound according to claim 2, wherein one or both of $R^{4a}$ and $R^{4b}$ are independently selected from the group consisting of —C(O)$R^{16}$, —SO$_2$NH$_2$, —PO(O$R^{19}$)(O$R^{20}$), —CH$R^{26}$—OPO(O$R^{19}$)(O$R^{20}$) where $R^{26}$ is hydrogen or $C_1$-$C_6$ alkyl, and —C(O)N$R^{17}R^{18}$, wherein $R^{16}$, $R^{17}$, $R^{18}$, $R^{19}$ and $R^{20}$ are independently selected from:

$C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —$C_1$-$C_3$ alkyl-$C_3$-$C_{10}$ cycloalkyl, —$C_1$-$C_3$ alkyl-$C_5$-$C_{10}$ cycloalkenyl or —$C_1$-$C_3$ alkylheterocyclyl, or $R^{17}$ and $R^{18}$ together with the N to which they are attached may form a 5- or 6-membered heterocyclic ring optionally containing a further heteroatom selected from O, S and N$R^{25a}R^{25b}$ where $R^{25a}$ is hydrogen, $C_1$-$C_6$ alkyl, —CH$_2$—OPO(O$R^{19}$)(O$R^{20}$) or a 5- or 6-membered heterocyclic ring, and $R^{25b}$ is absent or $C_1$-$C_6$ alkyl; and in which any of the aforementioned $R^{16}$, $R^{17}$ or $R^{18}$ groups may be optionally substituted by one or more groups selected from cyano, —OPO(O$R^{19}$)(O$R^{20}$), —(O(CH$_2$)$_z$)$_r$O$R^{24}$, wherein each z, which may be the same or different, represents 2 or 3, r represents an integer selected from 1 to 20, and $R^{24}$ is hydrogen, $C_1$-$C_3$ alkyl or —PO(O$R^{19}$)(O$R^{20}$), $C_1$-$C_6$ alkoxy, $C_1$-$C_6$ fluoroalkoxy, $C_1$-$C_6$ alkyl, $C_1$-$C_6$ fluoroalkyl and —C(O)N$R^aR^b$, where $R^a$ and $R^b$ are independently selected from hydrogen and $C_1$-$C_6$ alkyl, and any of the aforementioned $R^{16}$, $R^{17}$ or $R^{18}$ groups may be optionally substituted by one or more halogen atoms; and aryl, heteroaryl, $C_1$-$C_3$ alkylaryl and —$C_1$-$C_3$ alkylheteroaryl, said aryl and heteroaryl groups being optionally substituted;

or $R^{18}$, $R^{19}$ and $R^{20}$ may independently represent hydrogen.

6. The compound according to claim 2, wherein one or both of $R^{4a}$ and $R^{4b}$ are independently selected from the group consisting of —C(O)$R^{16}$, —SO$_2$NH$_2$, —PO(O$R^{19}$)(O$R^{20}$) and —C(O)N$R^{17}R^{18}$, wherein $R^{16}$, $R^{17}$, $R^{18}$, $R^{19}$ and $R^{20}$ are independently selected from $C_1$-$C_6$ alkyl, $C_2$-$C_6$ alkenyl, $C_2$-$C_6$ alkynyl, $C_3$-$C_{10}$ cycloalkyl, $C_5$-$C_{10}$ cycloalkenyl, heterocyclyl, —$C_1$-$C_3$ alkyl-$C_3$-$C_{10}$ cycloalkyl, —$C_1$-$C_3$ alkyl-$C_5$-$C_{10}$ cycloalkenyl or —$C_1$-$C_3$ alkylheterocyclyl, in which any of the aforementioned $R^{16}$, $R^{17}$, or $R^{18}$ groups may be optionally substituted by a group selected from cyano, $C_1$-$C_6$ alkoxy, $C_1$-$C_6$ fluoroalkoxy, $C_1$-$C_6$ alkyl, $C_1$-$C_6$ fluoroalkyl and —C(O)N$R^aR^b$, where $R^a$ and $R^b$ are independently selected from hydrogen and $C_1$-$C_6$ alkyl, and any of the aforementioned $R^{16}$, $R^{17}$ or $R^{18}$ groups may be optionally substituted by one or more halogen atoms, and aryl, heteroaryl, $C_1$-$C_3$ alkylaryl and —$C_1$-$C_3$ alkylheteroaryl, said aryl and heteroaryl groups being optionally substituted;

or $R^{18}$, $R^{19}$ and $R^{20}$ may independently represent hydrogen.

7. The compound according to claim 5, wherein both of $R^{4a}$ and $R^{4b}$ are independently selected from the group consisting of —C(O)$R^{16}$, —SO$_2$NH$_2$, —PO(O$R^{19}$)(O$R^{20}$), —CH$R^{26}$—OPO(O$R^{19}$)(O$R^{20}$) where $R^{26}$ is hydrogen or $C_1$-$C_6$ alkyl, and —C(O)N$R^{17}R^{18}$.

8. The compound according to claim 5, wherein one of $R^{4a}$ and $R^{4b}$ is selected from the group consisting of —C(O)$R^{16}$, —SO$_2$NH$_2$, —PO(O$R^{19}$)(O$R^{20}$), —CH$R^{26}$—OPO(O$R^{19}$)(O$R^{20}$) where $R^{26}$ is hydrogen or $C_1$-$C_6$ alkyl, and —C(O)N$R^{17}R^{18}$; and the other of $R^{4a}$ and $R^{4b}$ is hydrogen.

9. The compound according to claim 5, wherein one or both of $R^{4a}$ and $R^{4b}$ are independently selected from —C(O)$R^{16}$.

10. The compound according to claim 9, wherein $R^{16}$ is $C_1$-$C_6$ alkyl or $C_3$-$C_{10}$ cycloalkyl in which either of the aforementioned groups may be optionally substituted by a group selected from —OPO(O$R^{19}$)(O$R^{20}$) and —(O(CH$_2$)$_z$)$_r$O$R^{24}$, where each z, which may be the same or different, represents 2 or 3, r represents an integer selected from 1 to 20, and $R^{24}$ is hydrogen, $C_1$-$C_3$ alkyl or —PO(O$R^{19}$)(O$R^{20}$) or $R^{16}$ is phenyl optionally substituted by —(CH$R^{26}$)$_q$—OPO(O$R^{19}$)(O$R^{20}$) wherein q represents 0 or 1.

11. A compound of the formula:

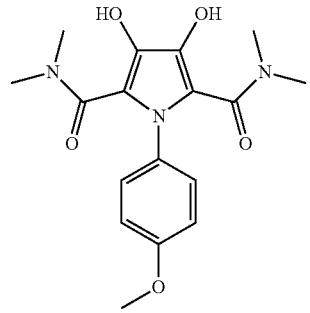

or a pharmaceutically acceptable salt or solvate thereof.

12. A compound of the formula:

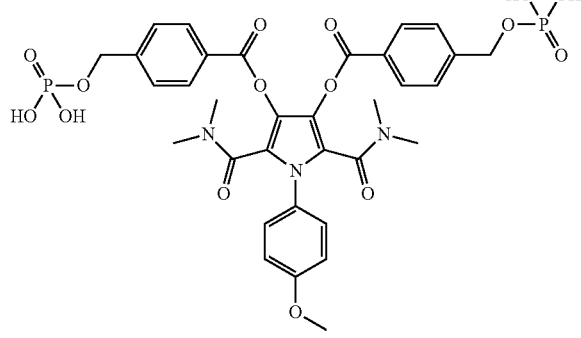

or a pharmaceutically acceptable salt or solvate thereof.

13. A pharmaceutical composition comprising a compound according to claim 1 or a pharmaceutically acceptable prodrug thereof, or a pharmaceutically acceptable salt or solvate thereof, in combination with one or more pharmaceutically acceptable diluents or carriers.

14. The pharmaceutical composition according to claim 13, comprising one or more other therapeutically active ingredients.

15. A method of treatment of bacterial infections caused by bacteria producing pore-forming toxins, which comprises administering to a subject in need thereof an effective amount of a compound according to claim 1 or a pharmaceutically acceptable prodrug thereof, or a pharmaceutically acceptable salt or solvate thereof.

16. The compound according to claim 15, wherein the bacterial infection is caused by *Streptococcus* spp., *Clostridium* spp., *Listeria* spp. or *Bacillus* spp.

17. The compound according to claim 15, wherein the bacterial infection is caused by *Streptococcus pneumoniae.*

18. The compound according to claim 15, wherein the infection is selected from the group consisting of pneumococcal pneumonia, pneumococcal meningitis, pneumococcal septicaemia/bacteraemia, pneumococcal keratitis and pneumococcal otitis media.

19. The compound according to claim 15, wherein the infection is selected from the group consisting of gas gangrene, gastrointestinal anthrax, inhalational anthrax, porcine meningitis, encephalitis, septicaemia/bacteraemia and pneumonia.

20. The compound according to claim 15, wherein the compound is administered to the subject in combination with one or more other therapeutically active ingredients.

21. The compound according to claim 20, wherein the compound and the one or more other therapeutically active ingredients are administered to the subject in separate formulations.

22. The compound according to claim 20, wherein the one or more other therapeutically active ingredients is one or more antimicrobial or immunomodulatory agents.

23. The compound according to claim 20, wherein the compound is administered to the subject in combination with one or more antibiotic agents selected from the group consisting of a β-lactam, a β-lactam in combination with a β-lactamase inhibitor, a cephalosporin a fluoroquinolone, a tetracycline, a macrolide antibiotic a lipopeptide antibiotic an aminoglycoside antibiotic, a glycopeptide antibiotic, a lincosamide antibiotic and a rifamycin.

24. The compound according to claim 15, wherein the subject is a human.

* * * * *